United States Patent [19]
Farrell et al.

[11] Patent Number: 5,934,885
[45] Date of Patent: Aug. 10, 1999

[54] REAGENT PUMP ASSEMBLY

[75] Inventors: Gregory A. Farrell, Ridgewood; Bruce E. Behringer, Park Ridge, both of N.J.; John W. Nelson, Wappingers Falls; Joseph Raneri, West Harrision, both of N.Y.

[73] Assignee: Bayer Corporation, Tarrytown, N.Y.

[21] Appl. No.: 08/688,547

[22] Filed: Jul. 30, 1996

Related U.S. Application Data

[63] Continuation-in-part of application No. 08/549,958, Oct. 30, 1995, Pat. No. 5,669,764, which is a continuation-in-part of application No. 08/319,856, Oct. 7, 1994, abandoned, and application No. 08/319,858, Oct. 7, 1994, abandoned.

[51] Int. Cl.$^6$ ................................................. F04B 17/00
[52] U.S. Cl. .................... 417/392; 417/393; 417/395; 417/250; 417/251
[58] Field of Search .................................. 417/392, 393, 417/395, 563, 250, 251

[56] References Cited

U.S. PATENT DOCUMENTS

| | | | |
|---|---|---|---|
| 3,000,320 | 9/1961 | Ring | 417/395 |
| 3,668,756 | 6/1972 | Wieme | 29/157 R |
| 3,741,687 | 6/1973 | Nystroem | 417/317 |
| 3,997,386 | 12/1976 | Oshida et al. | 156/306 |
| 4,430,048 | 2/1984 | Fritsch | 417/395 |
| 4,583,920 | 4/1986 | Linder | 417/395 |
| 4,875,956 | 10/1989 | Brackett | 156/84 |
| 5,018,949 | 5/1991 | Götz | 417/395 |
| 5,041,181 | 8/1991 | Brackett et al. | 156/84 |
| 5,259,352 | 11/1993 | Gerhardy | 417/395 |
| 5,669,764 | 9/1997 | Behringer | 417/395 |

OTHER PUBLICATIONS

"High Technology Machined Acrylics," Eastern Plastics Inc. date unknown.
"Technicon ™ Diaphragm Pump Assy," drawing No. 113–B461.
"Technicon ™ Reagent Pump Assy," drawing No. 113–B632.
"Technicon ™ Syringe Reagent Pump Assy," drawing No. 113–B205.
"Technicon H*3 RTX™ Hydraulic Interconnect Diagram," publication No. TU9–3823–10.

*Primary Examiner*—Bibhu Mohanty
*Attorney, Agent, or Firm*—Orrick, Herrington & Sutcliffe

[57] ABSTRACT

A reagent pump assembly for metering precise volumes of fluids, such as reagent, for an analytical instrument, such as a clinical hematology or flow cytometer instrument. The assembly includes a multilayer block having a plurality of diaphragm pumps interposed between two of the layers, controlled by application of one of vacuum or pressure, in sequence, to fill the reservoirs and expel the contents of the pump. One-way check valves are used to control the fluid flow from the reservoirs of fluids to the fluid outlet ports. The fluid outlet ports may be directly coupled to fluid inlet ports of a compatible unified flow circuit, which contains reaction chambers and a plurality of sample aliquots. Thus, the reagent pump assembly can be used to combine and mix a sample aliquots with a precise amount of reagent in a reaction chamber, preparatory for analyzing the reaction mixture.

7 Claims, 83 Drawing Sheets

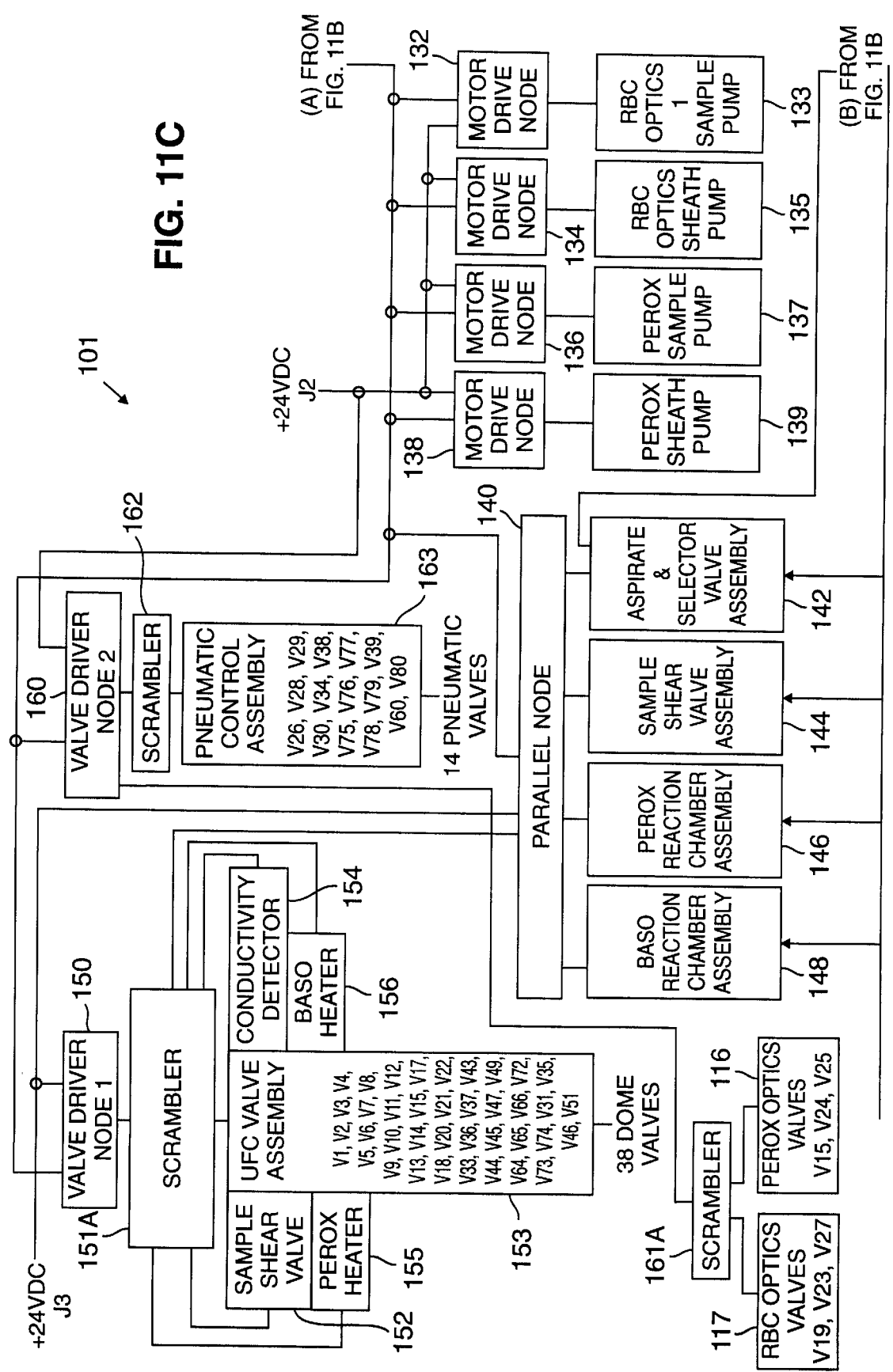

PRESSURE/SWITCH NODE

HGB NODE

PUMP NODE

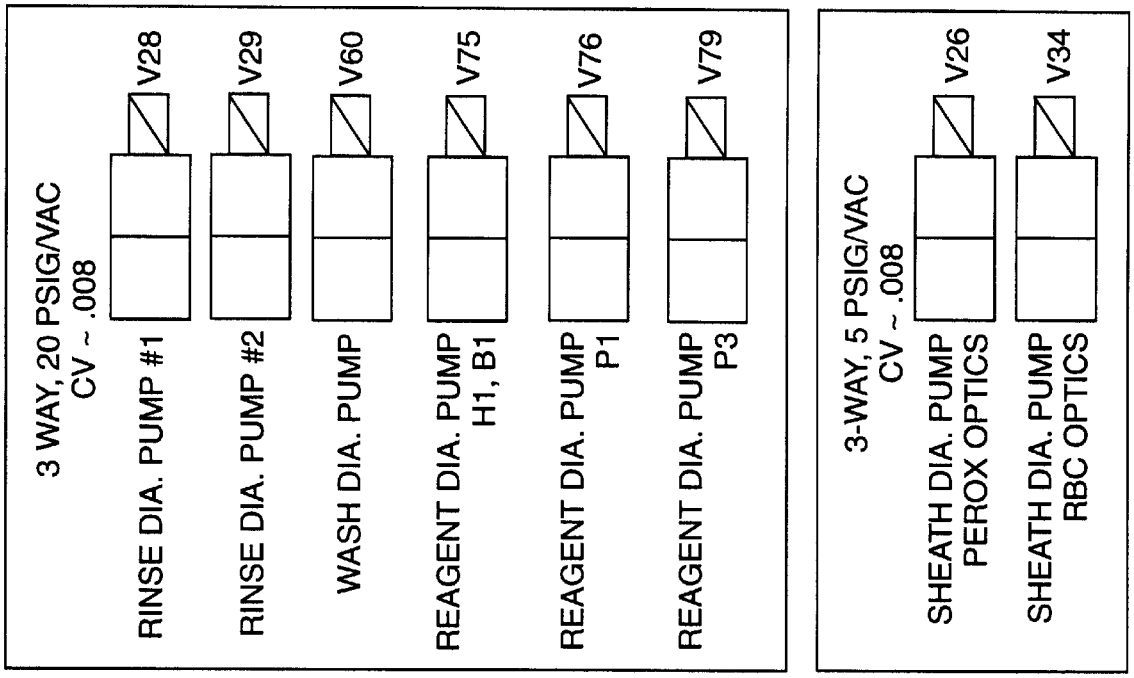
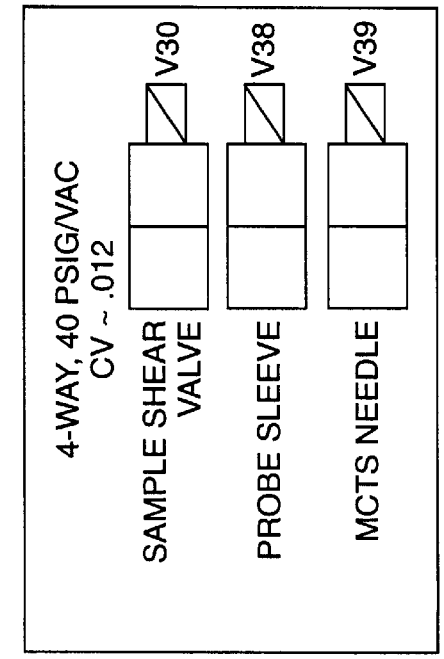
FIG. 46

CONDITIONS AT THE LAST
STEP OF RINSE FLOW

CONDITIONS AT END OF RINSING
BEFORE NEXT SAMPLE TYPE IS KNOWN

BLOOD FLOW - CBC ONLY

CONDITIONS RIGHT BEFORE CBC + DIFF SAMPLE TYPE IS ASPIRATED

BLOOD FLOW - CBC + DIFF

CONDITIONS RIGHT BEFORE CBC + DIFF + RETIC SAMPLE TYPE IS ASPIRATED

BLOOD FLOW -
CBC + DIFF + RETIC 5,934,885

REAGENT PUMP ASSEMBLY

CROSS REFERENCE TO RELATED APPLICATIONS

This is a continuation-in-part of application Ser. No. 08/549,958 filed Oct. 30, 1995 for "Pneumatic Diaphragm Pump", now U.S. Pat. No. 5,669,764, which is a continuation-in-part of application Ser. No. 319,856, filed Oct. 7, 1994, and Ser. No. 319,858, filed Oct. 7, 1994, both abandoned. The disclosures of the aforementioned applications are hereby incorporated herein by reference in their entirety.

This application is related to U.S. Pat. No. 5,496,009, the disclosure of which is hereby incorporated herein by reference.

FIELD OF THE INVENTION

The present invention relates to improvements in analytic instruments for performing analyses on test samples, in particular to instruments for performing a series of tests using different reagents and aliquots of a particular sample. Such instruments include, for example, and without limitation, immunoassay analyzers, clinical hematology analyzers, flow cytometers, and chemistry analyzers.

BACKGROUND OF THE INVENTION

Analytical instruments are well known. They have been commercially used for many years in different constructions and for performing different test analyses by various methods.

In general, these instruments provide for receiving one sample at a time, and more preferably a series of samples, dividing each sample into a plurality of aliquots, and performing one or more tests by combining each aliquot with one or more reagents. The reaction mixtures thus formed are then analyzed in a usual manner. For example, a calorimeter or similar measurement may be made on one reaction mixture. One or more other reaction mixtures may be suspended in a sheath and passed through a flow cell, substantially one particle at a time, and illuminated in the flow cell such that optical interactions can be detected. These interactions may include scatter and absorption of the incident light or a fluorescent response to the incident light. The detected interactions can then be qualitatively and/or quantitatively evaluated to characterize the sample aliquot under examination. The results of the interactions on all of different reactions performed on the sample can be evaluated to characterize the sample.

These instruments typically include numerous hydraulic lines, mixing chambers, valves and control systems to select the samples and reagents to be combined to form the reaction mixtures, and to perform the interactions to collect data. The result is a complicated, sophisticated machine that requires precise timing and fluid controls to process samples in large volumes. One of the problems with these instruments is that, because of their complexity, they may require frequent service, calibration and maintenance. They also are subject to breakdown, which often requires a field service visit. Instruments being out of service until repairs can be made results in significant lost business, particularly in the case of laboratories which perform a large number of test analyses.

It is therefore, an object of the present invention to provide an analytical instrument having improved component construction and operation, which results in fewer parts, fewer service calls, and improved durability and reliability, as compared to the known instruments.

It is another object to provide an improved analytical instrument that is comprised of subcomponents and modules which are applicable to a broad range of analyzer types.

SUMMARY OF THE INVENTION

Broadly, the present invention is directed to a reagent pump assembly for a metering precise volumes of fluids, such as reagents, for an analytical instrument, such as a clinical instrument for an immunoassay, hematology, chemistry or flow cytometry instrument. The assembly includes a multilayer block having a plurality of diaphragm pumps interposed between two of the layers, controlled by application of one of vacuum or pressure, in sequence, to fill the pump and expel the contents of the pump. One-way check valves are used to control the fluid flow from the reservoirs of fluids to the fluid outlet ports. The reagent/fluid supplies are connected to the pump assembly by hydraulic lines.

Preferably, the fluid outlet ports may be directly coupled to corresponding fluid inlet ports of a compatible unified flow circuit, which contains a sample shear valve and a plurality of reaction chambers and sample aliquots. Thus, the reagent pump assembly can be used to pump sample aliquots out of the shear valve by expelling reagent from the pump into the unified flow circuit through the shear valve, and then to mix the sample aliquot with a precise amount of reagent in a reaction chamber, preparatory for analyzing the reaction mixture.

One aspect of the invention is directed to a reagent pump assembly for an analytical instrument in which precise amounts of reagents are to be mixed with precise sample volumes for analysis of a sample. One such embodiment includes:

a top layer having a top surface and a bottom surface;
a middle layer having a top surface and a bottom surface;
a bottom layer having a top surface and a bottom surface;
a plurality of diaphragm pumps formed at a plurality of locations in an interface between the middle layer bottom surface and the bottom layer top surface, each diaphragm pump having a valve chamber and a pump chamber demarcated by a flexible membrane, each diaphragm pump having a first state corresponding to a filled pump containing a predetermined precision volume and a second state corresponding to an empty pump containing substantially no volume;
a plurality of pressure control lines in said bottom plate, each pressure control line extending through said bottom plate to control the state of the diaphragm pump between said first and second states;
a plurality of fluid input lines connecting said plurality of pump chambers to a like plurality of fluid supplies, wherein each fluid input line further comprises a first passage through said top layer, a second passage through said middle layer, and a first one-way valve interposed between said first and second passages, wherein the first and second passages and first one-way valve provide for flow of one of said fluid supplies into said pump chamber in response to the diaphragm pump changing from said second state to said first state, and no flow from said pump chamber to said fluid supply in response to the diaphragm pump changing from the first state to the second state, each diaphragm pump having an input line; and
a plurality of fluid output lines connecting said plurality of pump chambers to a like plurality of output ports, wherein, for a given diaphragm pump, each fluid outlet line further comprises a third passage extending through said top layer, a fourth passage extending from the top of the middle layer and connecting to said second passage between said first one-way valve and said pump chamber and a second one-way valve interposed between said third and fourth passages, wherein the third and fourth passages and second one-way valve provide for flow of a precise fluid volume in said pump chamber to said output port in response to the diaphragm pump changing from said first state to said second state, and no flow from said pump chamber to said outlet port in response to the diaphragm pump changing from the second state to the first state.

The reagent pump assembly may have in the bottom layer top surface a plurality of receptacles wherein the plurality of first one-way check valves are inserted in said plurality of receptacles. Further, the middle layer bottom surface may have a plurality of receptacles wherein the plurality of second one-way valves are inserted in said plurality of receptacles. Alternatively, the check valves may be in the other of the aforementioned surfaces.

In a preferred embodiment, the top, middle, and bottom layers are fused together so that the opposing top and bottom surfaces are molecularly bonded together. Alternatively, the top, middle, and bottom layers may be bolted together in a fluid tight arrangement.

BRIEF DESCRIPTION OF THE DRAWINGS

Further features and advantages of the invention will become apparent from the drawings and the following detailed description of the inventions, in which like reference characters refer to like elements, and in which:

FIGS. 11A–11E are schematic block diagram of the electronic architecture of a preferred embodiment of the present invention;

FIG. 46 is a block diagram of the pneumatic control assemblies of FIGS. 11C and 37–44;

FIGS. 53A, 52B, and 53C are right side, left side, and bottom views of the UFC of FIG. 51;

DETAILED DESCRIPTION OF THE DRAWINGS

Figure 1:
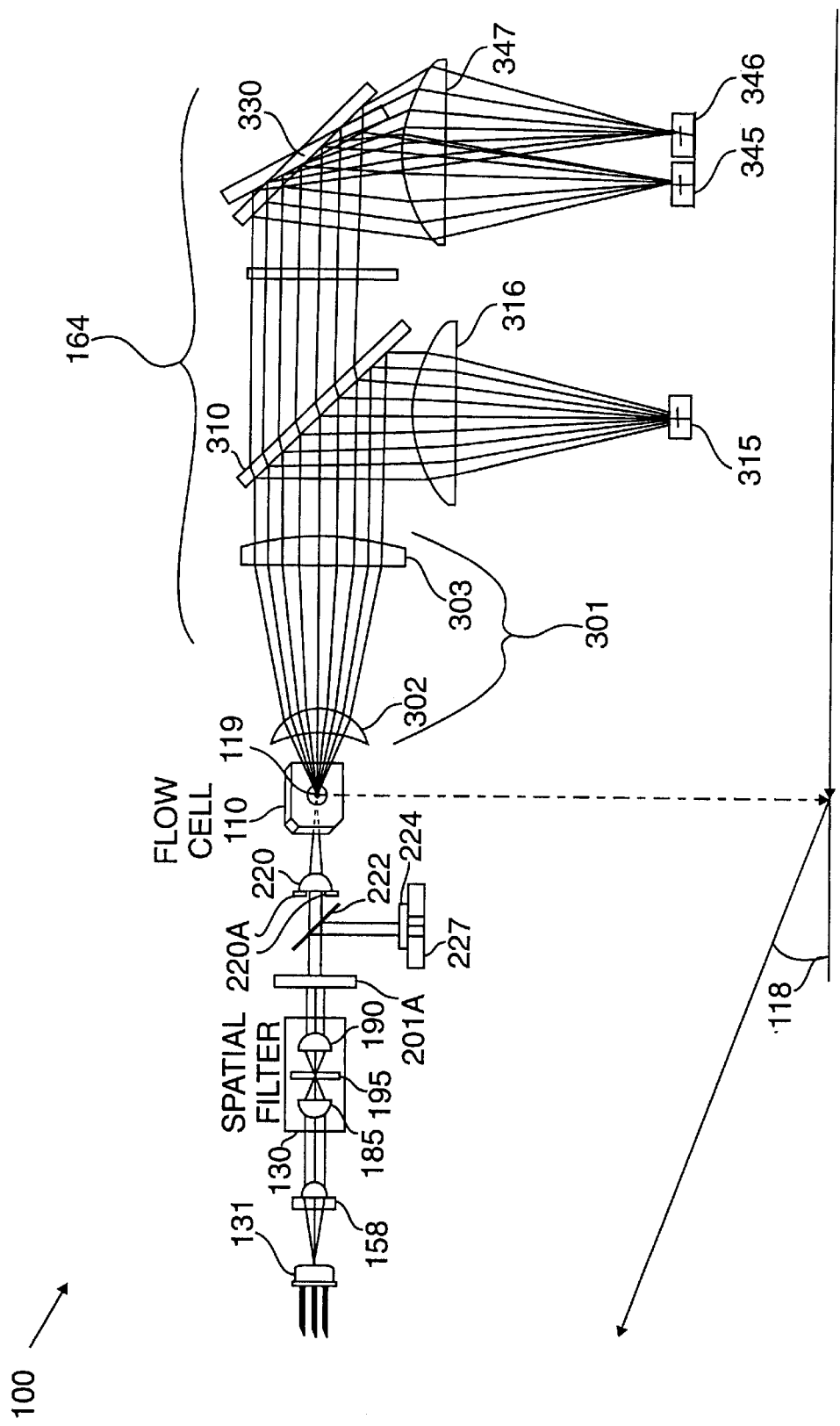
FIG. 1 is a schematic diagram of a laser optical bench and detectors for use in a preferred embodiment of a red and white blood cell analysis channel in a device in accordance with the present invention.

Referring to FIGS. 11A–11D, 39–42, 49 and 51, blood samples for analysis in the flow cytometer instrument of the present invention are aspirated by vacuum into a sample input port 541 of a unified flow circuit (UFC) assembly 508. In the UFC assembly 508, the blood sample is separated into one or more predetermined aliquots by a shear valve 503, the different aliquots are then mixed with one or more reagents in different reaction chambers, to prepare the aliquots for different analyses. The reacted mixtures are then analyzed in one or more of an REC/BASO/RETIC optical bench 117, a PEROX optics bench 116, or the HGB calorimeter 121. As will be discussed in more detail below, these analyses are performed independently under the control of a System Controller 105, which is preferably in turn controlled by an operator using a computer workstation 103. As a result, more than one reacted mixture may be formed from different aliquots of the same blood sample and examined in the same flow cell 110 (or flow cell 110A) to obtain different scatter and absorption data from the same blood sample under different reactions at different times.

I. HYDRAULIC SYSTEM

A. Sample Aspiration

Figure 37:
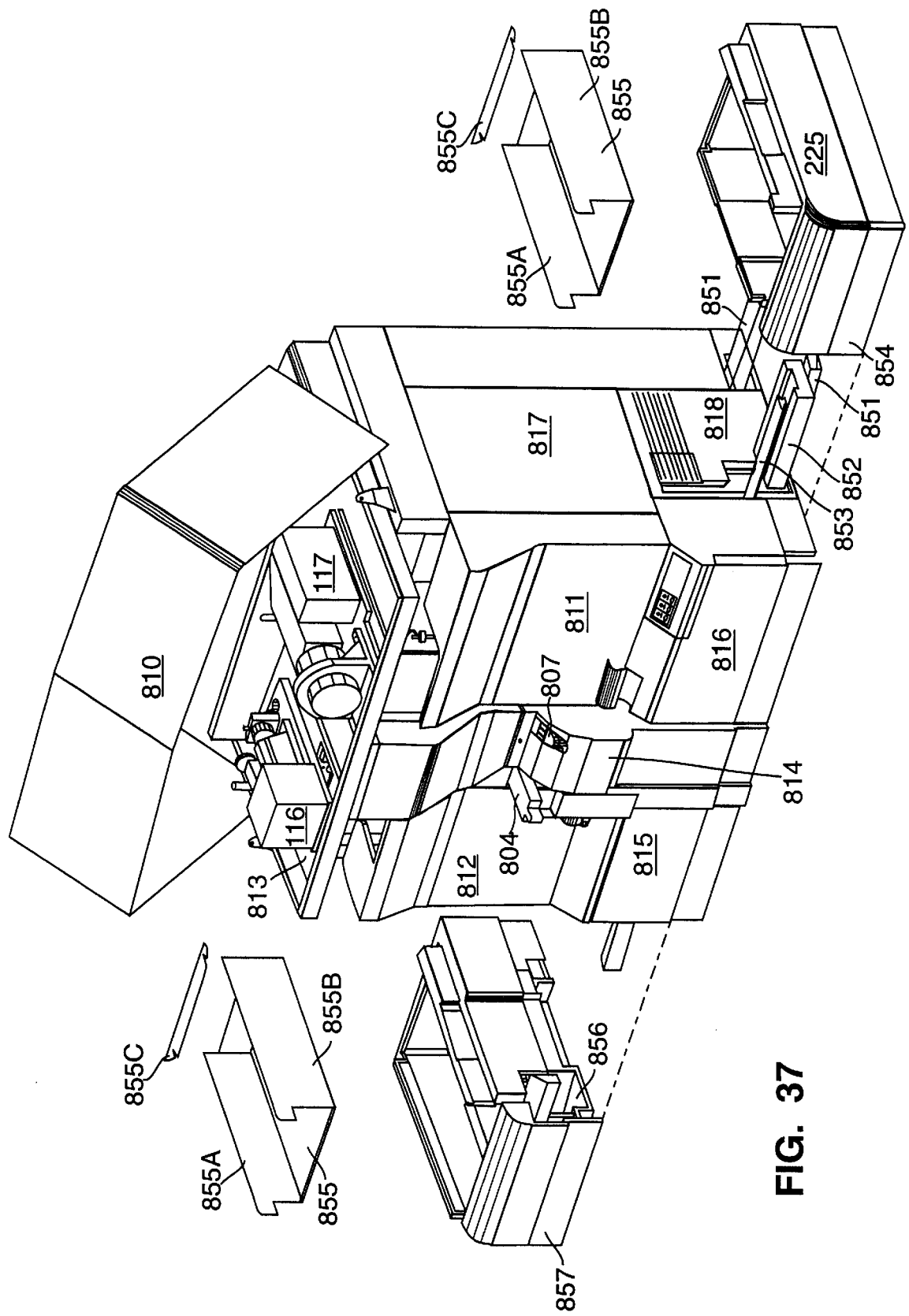
FIG. 37 is an elevated perspective view of an apparatus in accordance with a preferred embodiment of the present invention, shown in partial exploded view.
Figure 39:
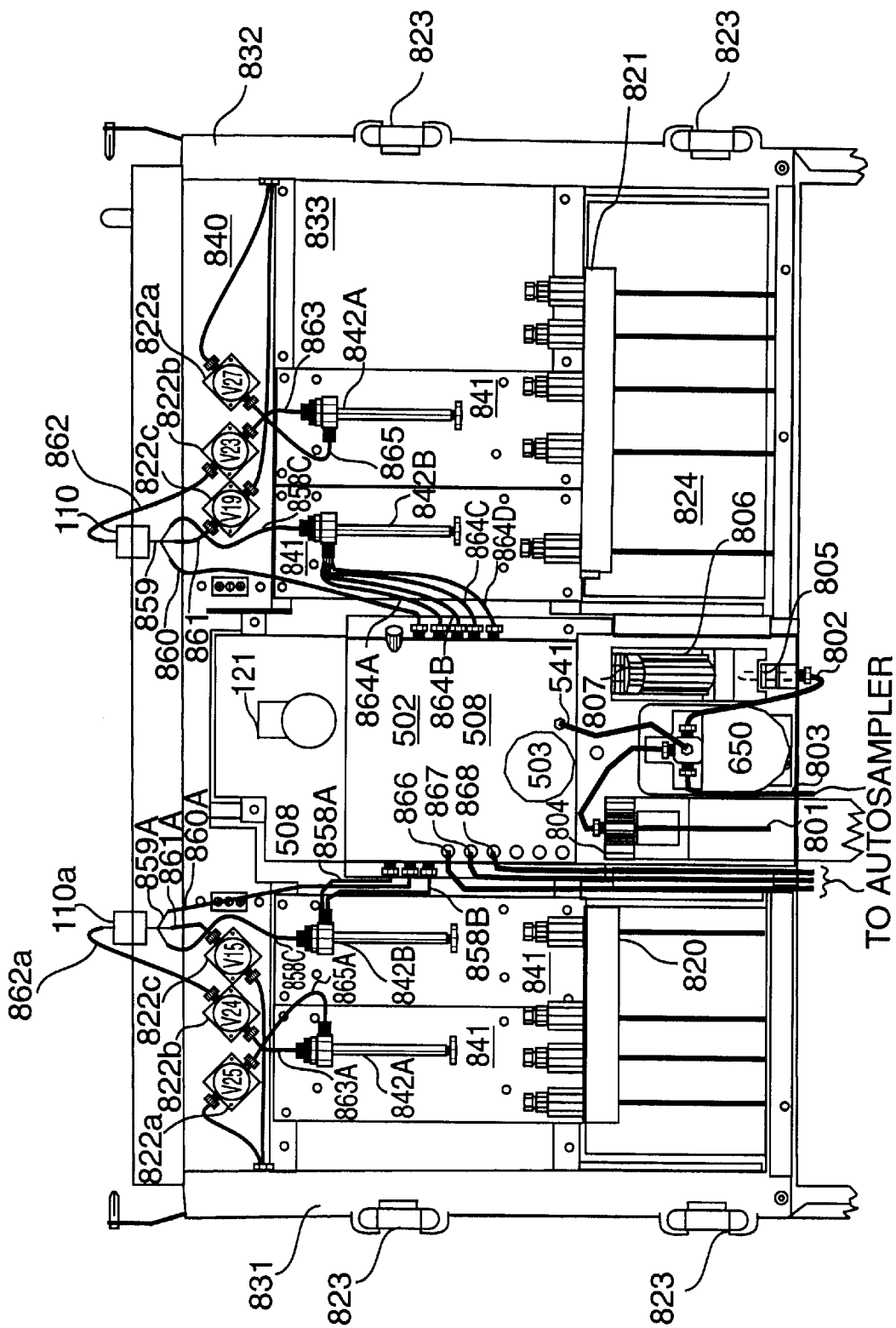
FIGS. 39 and 40 are respectively front views of the hydraulic and fluid portion of FIG. 38 for sample aspiration and pumping.

Referring to FIGS. 37 and 39, a blood sample may be aspirated from one of three sources: a manual open tube sampler 801, a manual closed tube sampler 802 and an automatic closed tube sampler 803, which is part of an Autosampler 818. The manual open tube sampler 801 is a piece of tubing that can be inserted into an open test tube containing a blood (or other fluid) sample. The tube, preferably made of a flexible, medical grade material, extends downwardly from a mounting 804 that protrudes from the front of the instrument. Between manual aspiration of samples, there is a rinse, followed by a dry cycle, for the outside of the manual open tube sampler. For all three samplers, there is a complete internal backflush (combination of rinse and drying).

The manual closed tube sampler 802 includes a needle 805 (shown in phantom in FIG. 39) that is suitable for penetrating the typical rubber or elastomeric seal on a closed blood sample tube, to extract a blood sample volume from the tube. Preferably, the needle 805 projects upwardly into a receptacle 806 (only the outer housing of the receptacle is shown) into which the sample tube is inserted with the seal downwardly. Pushing the tube downwardly inside the receptacle 806 operates a pneumatic drive which causes the sample tube to move relative to the needle 805, so that the needle penetrates the seal. The length of the needle 805 is limited so that it will not pass above the typical level of fluid in the inverted sample tube, and an appropriate volume may be extracted by the vacuum. The other sampler 803 is that of the Autosampler 818, which is similar in construction and orientation to the manual closed tube sampler 802 except that the tube sampling process is automated. The Autosampler 818 is a mechanism that permits automatically feeding a succession of sample tubes through the instrument, without operator attendance required. Although it forms no part of the present invention, in that the invention can be used with any manual or automatic sample tube feeding mechanism, portions of a useful prototype feeding mechanism are nevertheless disclosed.

Figure 38:
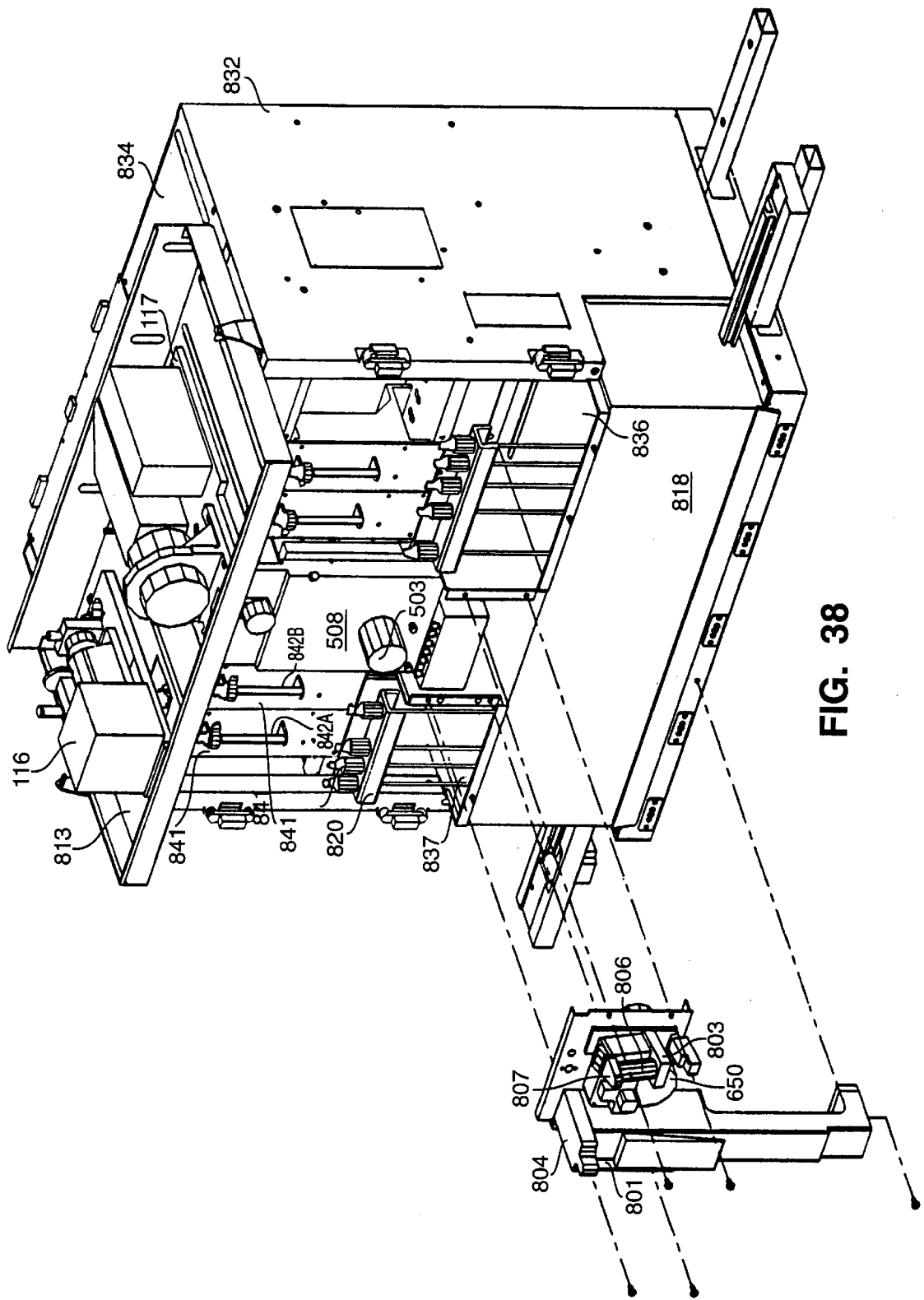
FIG. 38 is a partial exploded and disassembled view of the instrument of FIG. 37.

A three-way selector valve 650, shown in FIGS. 38, 39 and 65, selectively connects the input port 541 with one of the three samplers 801, 802, 803 under automatic control as is described below.

Figure 66A:
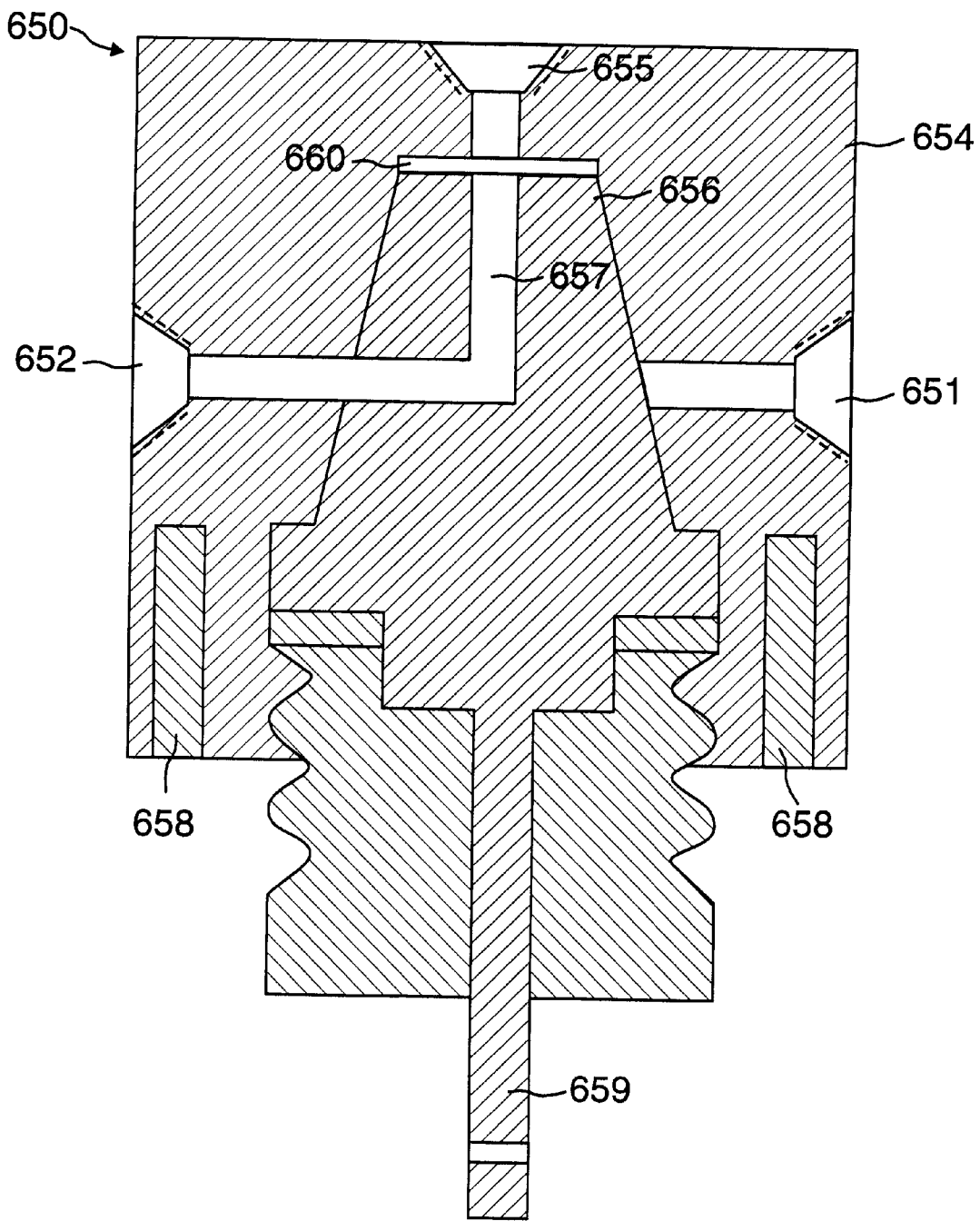
FIG. 66A is a side sectional view of the selector valve of FIG. 65 taken along line 66A—66A.

The selector valve 650, also shown in section in FIG. 66A, has three inlets 651, 652, 653 (only 651, 652 shown) connected by tubing to the three sample sources 801, 802, 803. The inlets are arranged radially in the valve housing 654 at 90° intervals. The inlets communicate, one at a time, through a single passage 657 in a tapered, rotatable valve spool 656, to a common axial outlet port 655 in the valve housing. A minimal axial clearance 660 is provided between the valve spool 656 and the housing 654 in order to assure proper seating of the tapered surface of the valve spool. The clearance 660 is part of the axial common port exposed to each blood sample as it is aspirated; it must therefore be rinsed with the selector valve during each sampler rinse cycle.

The valve housing and spool are preferably constructed of an inert fluorocarbon, e.g., a TEFLON brand material. TEFLON is a trademark of Du Pont.

The valve spool has an extension 659 on the end opposite the common outlet port 655 for turning the valve spool. In order to use one of the three sample sources in the instrument, the valve spool is turned by turning the extension 659 until the single passage 657 in the spool is aligned with a corresponding one of the three inlets 651, 652, 653 in the housing 654.

Figure 66B:
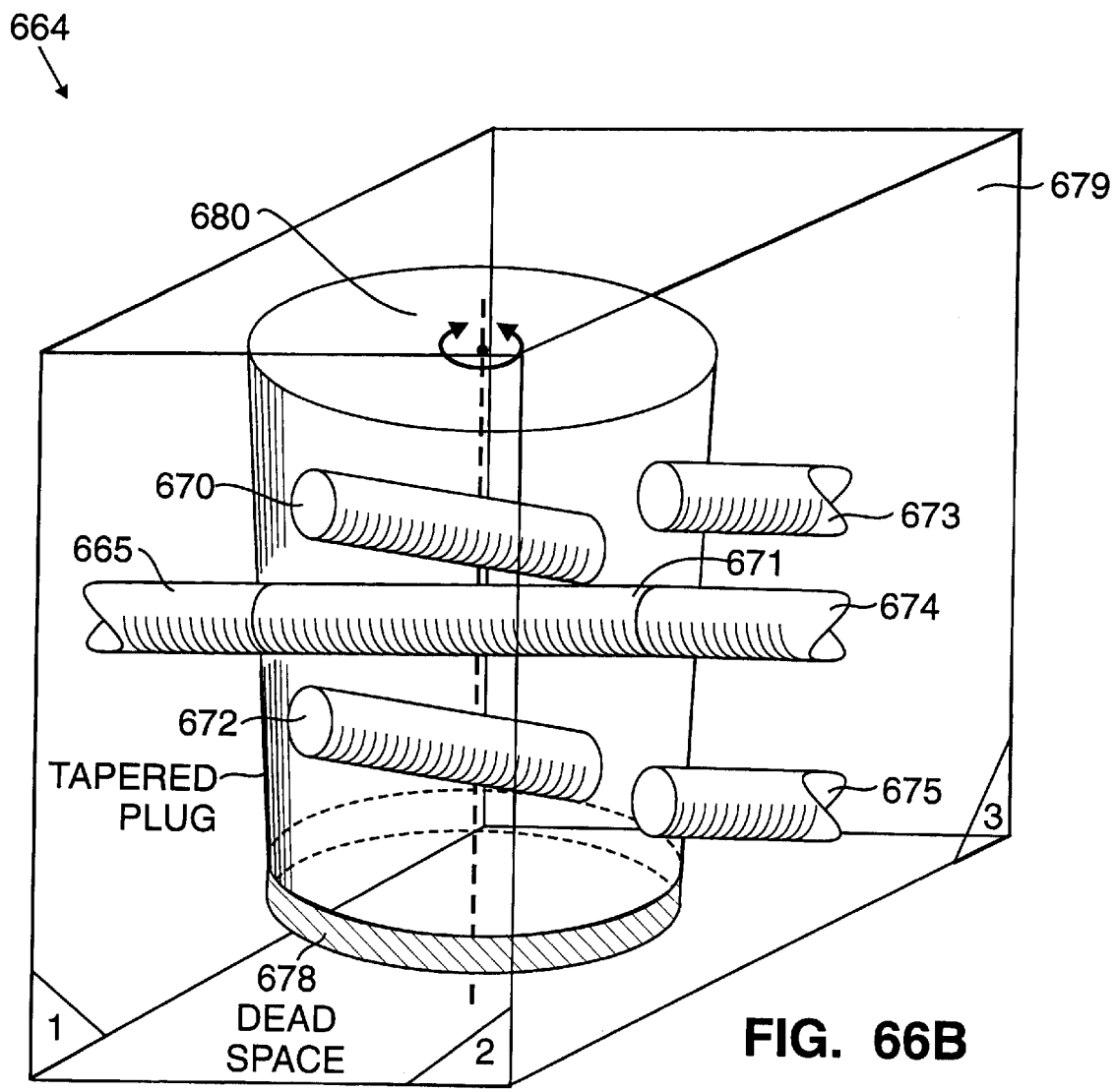
FIG. 66B is an elevated, three dimensional transparent view of an alternate embodiment of a selector valve for use in the present invention.

In an alternative embodiment, selector valve 664, shown in FIG. 66B, has a tapered, rotatable valve spool 680 having three separate, unconnected passages 670, 671, 672. These passages are drilled at different orientations through the valve spool. Each of the passages has an opening that may be aligned with a common radial outlet port 665 in the housing 679. The spool 680 has a first rotational position, shown in FIG. 66B, such that the passage 670 provides communication between the common port 665 and an inlet port 673. In a second spool position, the passage 671 provides communication between the common port 665 and an inlet port 674. In a third position, the passage 672 provides communication between the common port 665 and an inlet port 675.

In each of the three positions, the two inactive passageways in the spool 680 do not communicate with any of the inlet ports or the outlet port. The tapered surface of the spool 680 effectively seals the passages from each other. After a passage is used during aspiration of a blood sample, the passage is rinsed and dried as part of a "sample" rinse cycle (the internal backflush described above), namely a rinse cycle that rinses the sample aspiration portion of the flow cytometer after a sample is aspirated and divided into aliquots by the shear valve, as explained below. The drying occurs by an applied vacuum drawing air through the rinsed portions. Each of the three passages 670, 671, 672 is thus clean, dry and ready for use in each subsequent cycle of the instrument.

An axial clearance 678 (also called a dead space) is provided between the valve spool 680 and the housing 679 in order to assure proper seating of the tapered surface of the valve spool. Unlike the axial common port configuration shown in FIG. 66A, this selector valve has the advantage of not exposing the axial clearance 678 to aspirated blood samples, which are instead routed through the radial common port 665. Another significant advantage is that there are no 90° turns which are subject to clogging. The radial common port valve, however, is thought to be more expensive to manufacture than the axial common port valve.

Both of the selector valves 650, 664 require that the spool be indexed accurately with respect to the housing in order to assure that the ports of the spool and the ports of the valve housing are properly aligned. In prior art hematology instruments, this was done using a stepping motor to rotate the spool to precise, indexed positions. The stepper motor and the associated sensor, which monitored the stepping motor shaft position, and the control circuitry, significantly added to the cost of the instrument.

In accordance with the present invention, the selector valve is driven by an inexpensive, non-reversible DC motor coupled to a Geneva mechanism. The Geneva mechanism provides accurate, repeatable mechanical indexing of the valve spool without the necessity of stopping motor rotation at precise angles. Position sensors are used to determine in which one of the several index positions the valve currently rests. However, and advantageously, acceleration and deceleration of the motor need not be finely controlled in the case of the present invention, because the Geneva mechanism converts constant angular velocity of the motor, smoothly accelerates the valve spool from standstill, and leaves the spool in the next position at zero angular velocity, and with a relatively high degree of precision. It also leaves the spool positively locked at the selected index position while the driving cam is moving or stationary, except when the index position is being changed.

Figure 65:
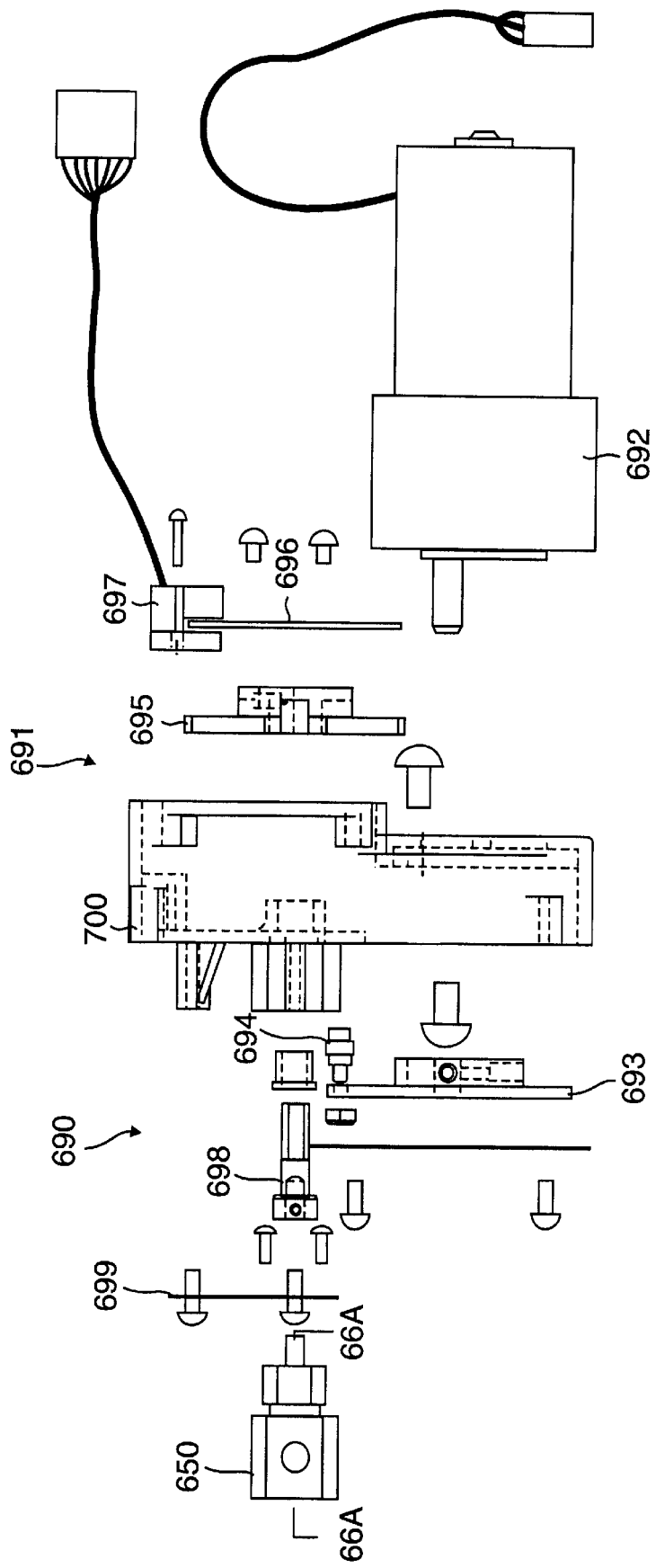
FIG. 65 is an exploded side view of an automatic three-way selector valve of the UFC of FIG. 49.

An exploded elevation view of the selector valve assembly 690, including a selector valve 650 and Geneva mechanism drive 691, is shown in FIG. 65. The drive 691 comprises a DC motor 692 mounted in a housing 700. In a preferred embodiment, the DC motor has an integral speed reducer to produce an output that changes the valve state (position) at the desired rate, e.g., one change per second. Such a motor is also known as a gearmotor in the art.

The motor 692 drives a rotor 693 having an eccentrically mounted cam driver 694. A driven cam 695 rotates on a separate shaft 698 mounted in the housing parallel to the motor 692. The driven cam 695 is intermittently engaged by the cam driver 694 as described below. The shaft 698 turns the spool of valve 650.

The valve 650 is mounted on an adjusting plate 699, which is attached to the housing by screws in slotted holes (not shown). The adjusting plate 699 can be rotated with respect to the housing 700 before tightening the screws. In this way, the rotational position of the valve 650 can be adjusted to match the index positions of the driven cam 695.

Figure 67:
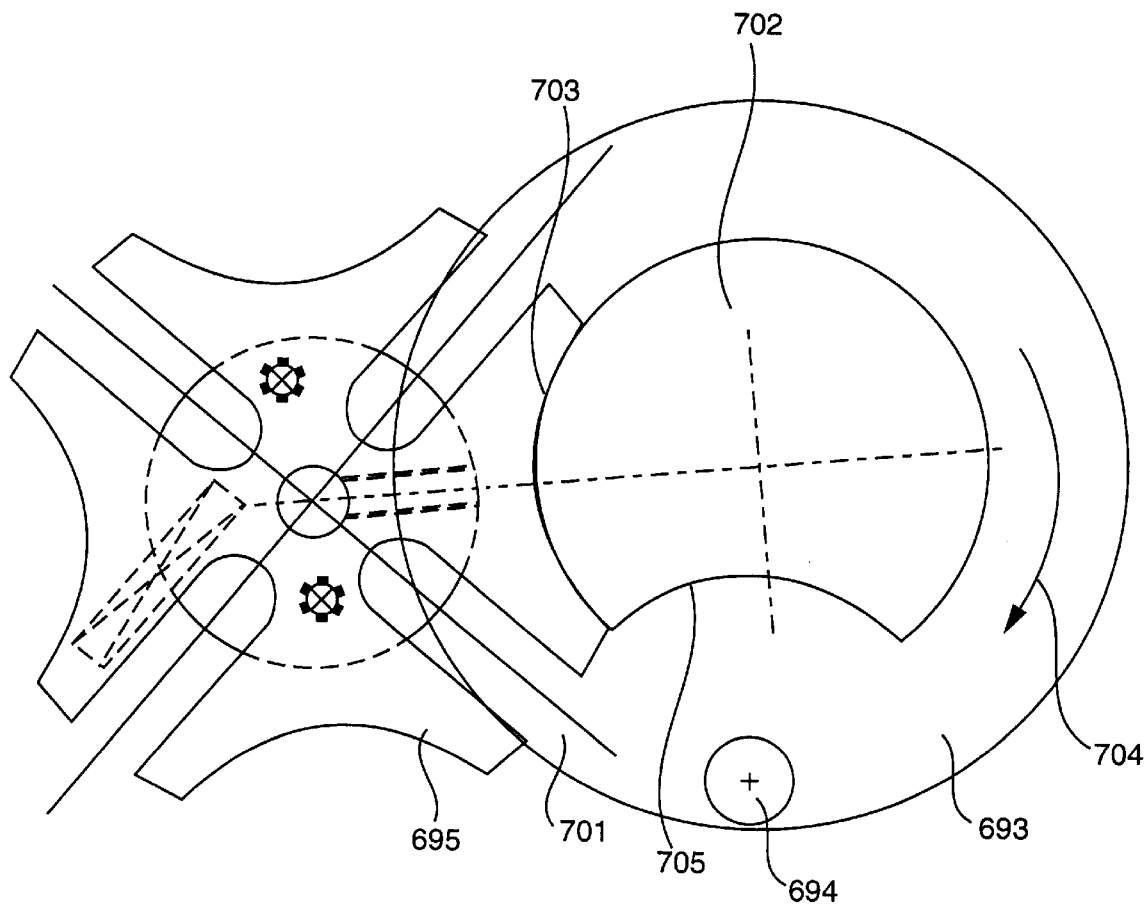
FIGS. 67 and 68 are sectional views of the driven cam and rotor of the Geneva mechanism of FIG. 65 in a locked position and an intermediate position respectively.

The driven cam is shown in FIG. 67 in plan view in one of the indexed positions. The cam driver 694 in this view has not yet engaged the cam slot 701. The hub 702 on the rotor 693 engages the locking radius 703 on the driven cam 695, preventing the driven cam from rotating and locking it in one of the four index positions. The rotor 693 then may rotate through a first range of angular motion, for example, 270° or less, without affecting the position of the driven cam. During this first range, the valve 650 is locked in the given index position. This permits a large angular position tolerance on the motor stop and start positions. Thus, the valve 650 will remain positively locked in the index position whenever and wherever the rotor 693 is in the first range, with the concentric surface 702 in contact with the contacting surface 703.

As the rotor 693 is rotated in the direction of the arrow 704, the cam driver 694 enters the cam slot 701 from a direction in line with the slot, resulting in smooth angular acceleration of the driven cam. A clearance cut-out 705 in the hub 702, defining a second range of angular motion of, e.g., 90° or more, permits the driven cam to rotate from one index position to the next. The first and second angular range preferably add to 360°.

Figure 68:
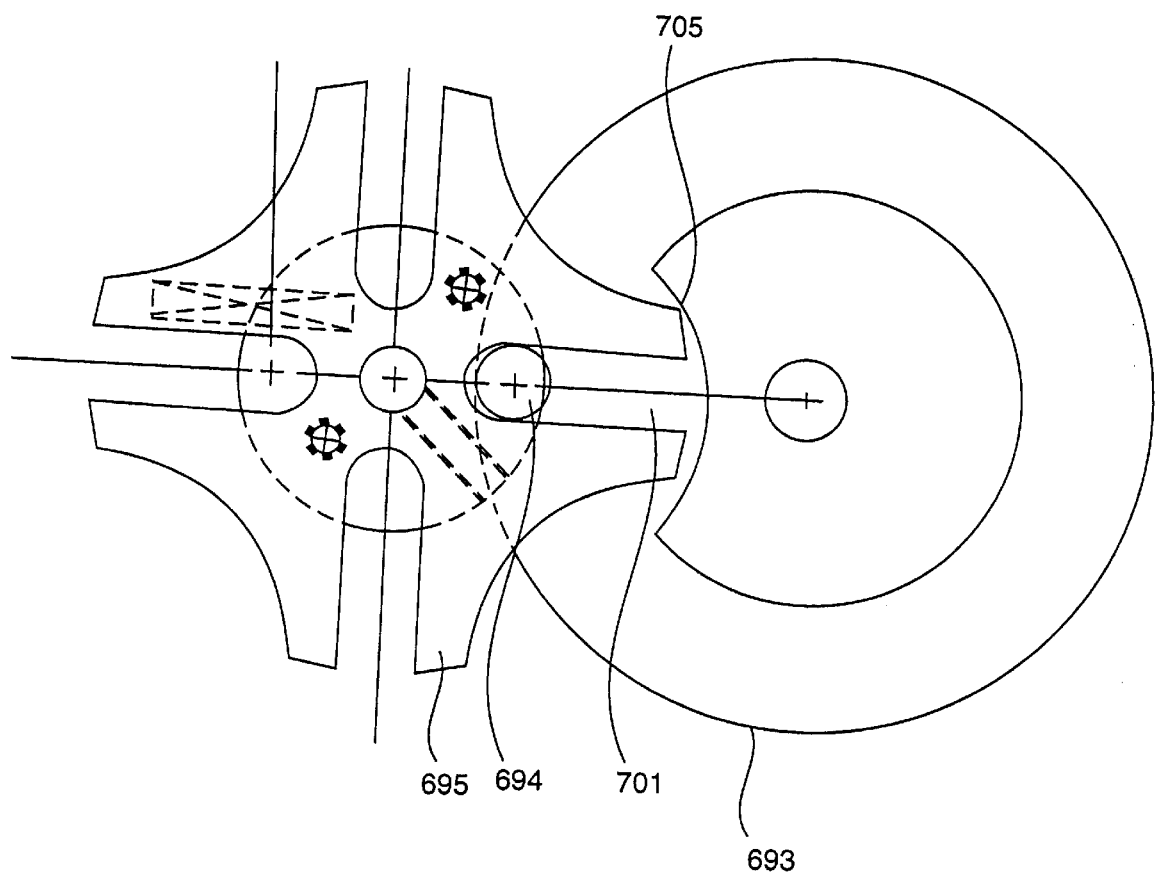

FIG. 68 shows the driven cam in an intermediate position between index positions. The driver 694 is engaged in the slot 701, and the clearance cut-out 705 permits the driven cam 695 to rotate between index positions. The driver 694 exits the slot 701 in a direction in line with the slot, smoothly decelerating the rotation of the driven cam 695.

A rotary position sensor disk 696 (FIG. 65) and first and second position sensors 697 (one is offset from the other) are used to provide valve spool position information to the system. The position sensors are arranged on the sensor disk to sense the four index positions so that only the first sensor is on in a first position, both sensors are on in a second position, only the second sensor is on in a third position, and neither sensor is on in a fourth position. At any intermediate position between the four index positions, neither sensor is on. By having the unused position on the selector valve 650 correspond to the fourth position of the sensor, the system can always drive the motor until at least one of the sensors is on. Preferably, optical rotary position sensors are used which depend on sensing the presence or absence of a light (relative to a threshold), but other types of position sensors could be used.

Because of the precision indexing of the Geneva mechanism, the passageways of the selector valve are accurately aligned in each of its three positions. The motor and associated position sensors, however, need not be so accurate. In the illustrated embodiment, the rotor theoretically has 270° to stop (i.e., the length of the first angular range), after indexing the valve (i.e., passing through at least half of the second angular range), without affecting its position. While a four-position Geneva mechanism driving a three-position valve is disclosed, the invention may be easily practiced using a Geneva mechanism having from three to eight positions, driving a valve having as many or fewer positions. The degree of rotation of the rotor without changing the spool position can be adjusted accordingly. Advantageously, through the use of this simple, reliable and inexpensive Geneva mechanism, it is assured that the valve is precisely engaged in one of its operative positions.

B. Unified Fluid Circuit Assembly

Figure 49:
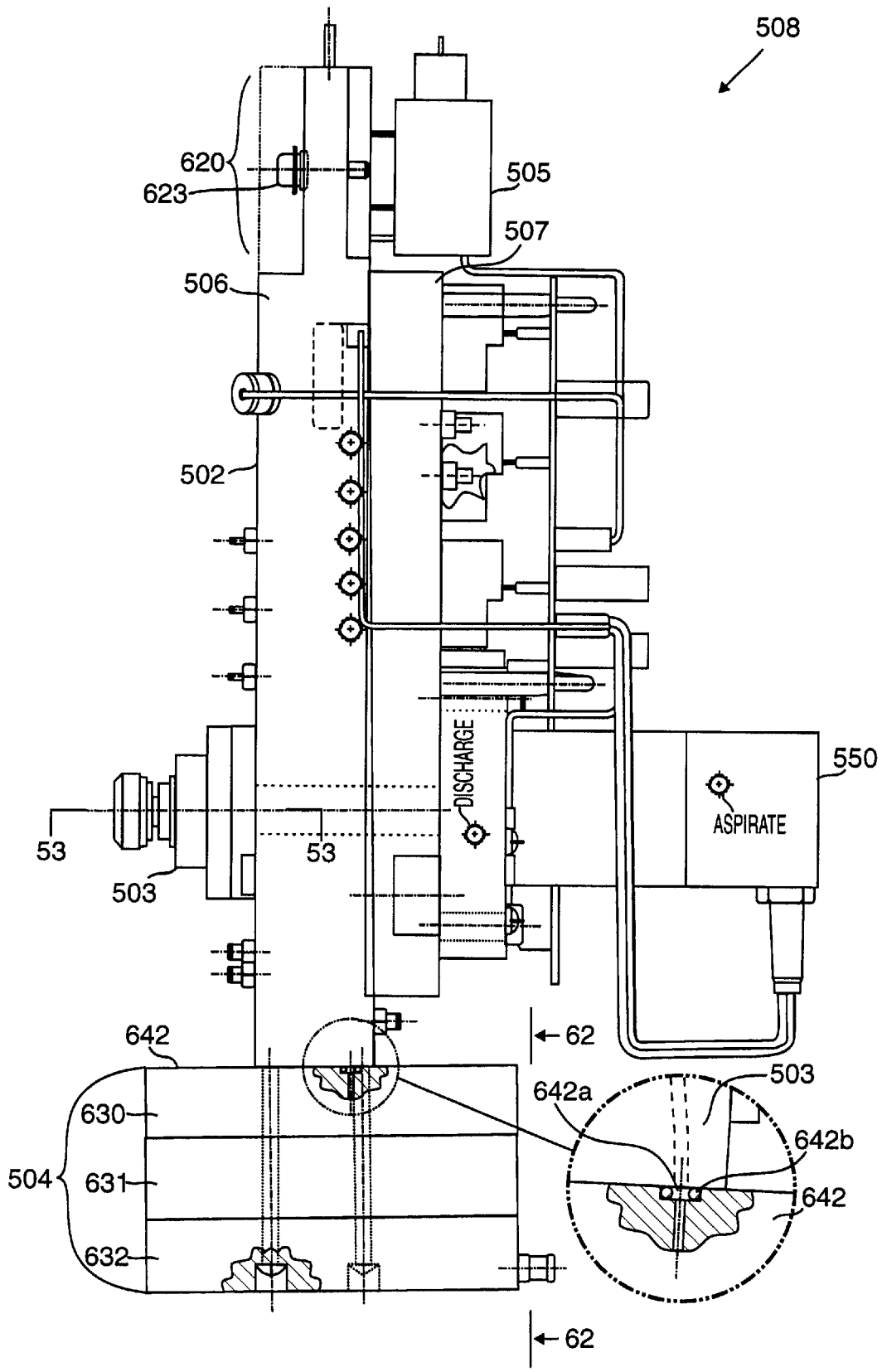
FIG. 49 is a side view of the unified fluid circuit assembly in accordance with a preferred embodiment of the present invention.

The unified fluid circuit assembly 508, shown in FIG. 49, performs many of the hydraulic functions of an analytic instrument, such as the clinical hematology instrument of the preferred embodiment, including receiving the sample from the selected aspirator port, splitting the sample into multiple aliquots, selectively pumping and mixing reagents or other fluid with the sample aliquots, providing reaction chambers for mixing the samples and reagents under appropriate conditions of time and temperature, and providing valves and flow paths for the reacted mixtures to flow to the sample pumps for passing the reaction mixture through a flow cell. More particularly, the assembly 506 contains reaction chambers and a network of flow paths and valves that are controlled in a predetermined manner selectively to pass a given sample and a given reagent (or other fluid) into a reaction chamber where a reaction occurs such that a plurality of reaction mixtures are formed in the different reaction chambers, after which the reaction mixtures are ready for optional analysis as described herein. The network also encompasses various valves and flowpaths that function to direct the reacted mixtures out of the reaction chambers, e.g., to a flow cell or to another output of the unified flow circuit assembly such as to a waste container. As used herein, the terms flow path, passageway, pathways, lines, with or without the modifiers hydraulic or pneumatic, are used interchangeably.

The fluid circuit assembly 508 comprises a unified fluid circuit (UFC) 502, a sample shear valve 503 having a rotary actuator 550 (also referred to herein as a rotary indexer), a reagent pump assembly 504, and a heated PEROX reaction chamber subassembly 505. The unified fluid circuit 502 has a front plate 506 containing the reagent and sample flow paths, and a rear plate 507 containing solenoid air valves and related air flow paths.

1. Reagent Pumps

Figure 62:
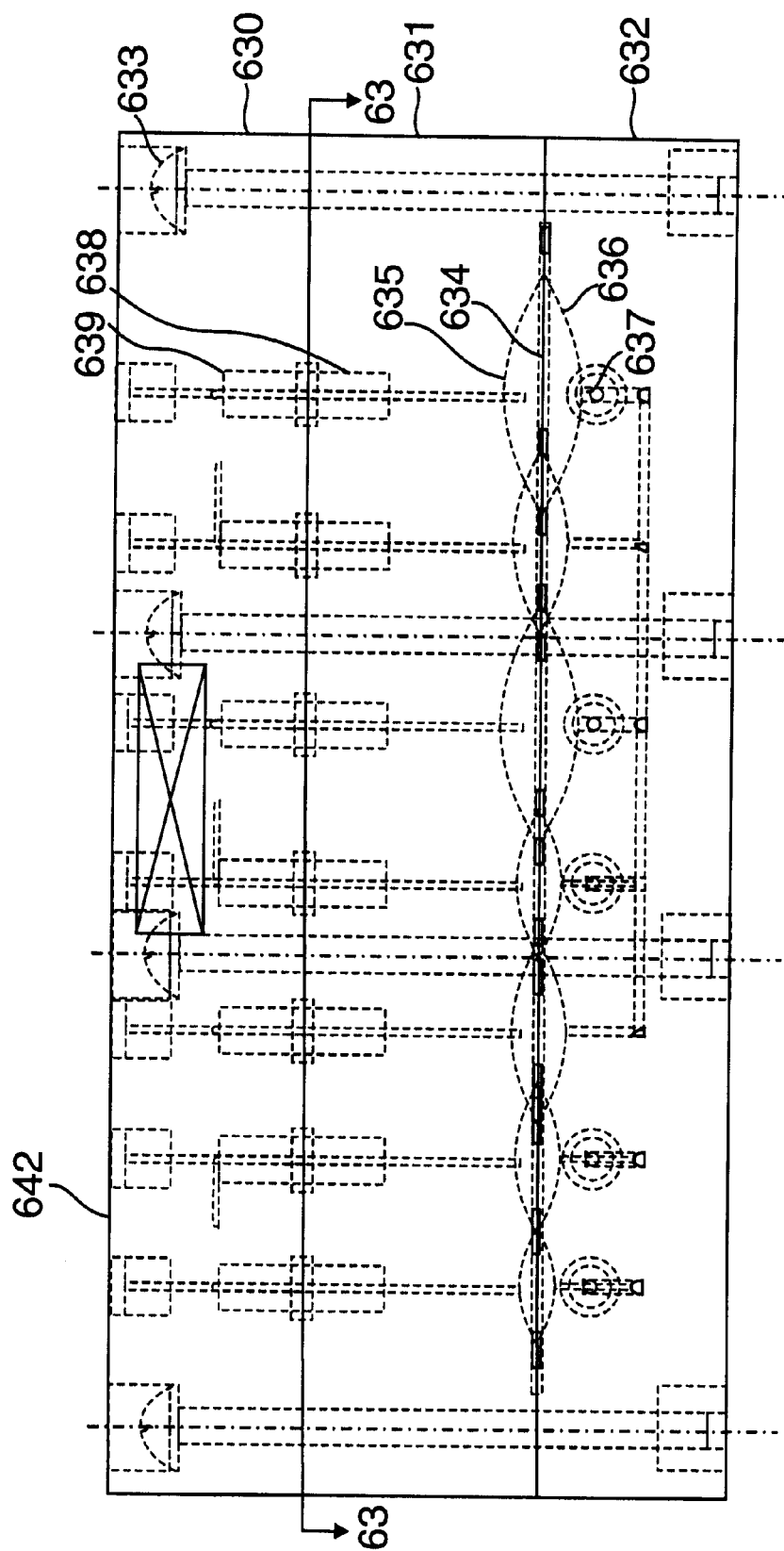
FIG. 62 is a side sectional view of the reagent pump assembly of FIG. 49 taken along line 62—62.
Figure 63:
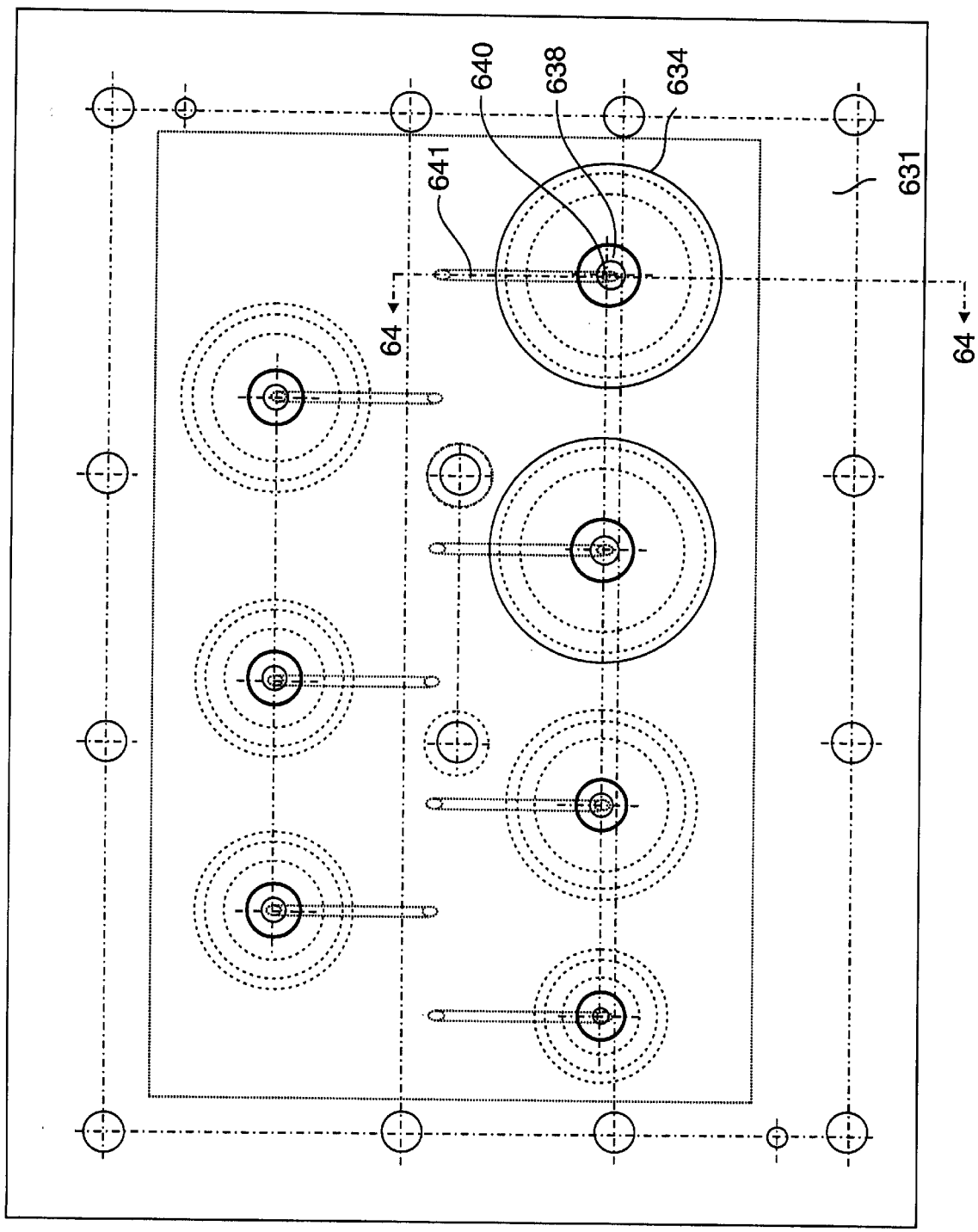
FIG. 63 is a top sectional view taken along line 63—63 of FIG. 62.

Referring to FIGS. 49 and 62–64, the reagent pump assembly 504 comprises a set of diaphragm pumps for independently pumping precise volumes of reagent from the reagent containers (not shown) into the front plate 506 of the UFC, through the shear valve 503, and back into the UFC 502 to one or more of the reaction chambers contained therein. The reagent pump assembly 504 comprises top, inner and bottom acrylic layers 630, 631, 632 respectively, bolted together with bolts (e.g., bolt 633 as shown in FIG. 62). Between the inner and bottom layers 631, 632 are membrane materials such as diaphragm 634, movable between cavities 635, 636 in the inner and lower acrylic layers 631 and 632, respectively. Alternating vacuum and pressure applied from a passage, such as passage 637 in cavity 636 actuates the diaphragm 634 to move between the two positions.

Figure 64:
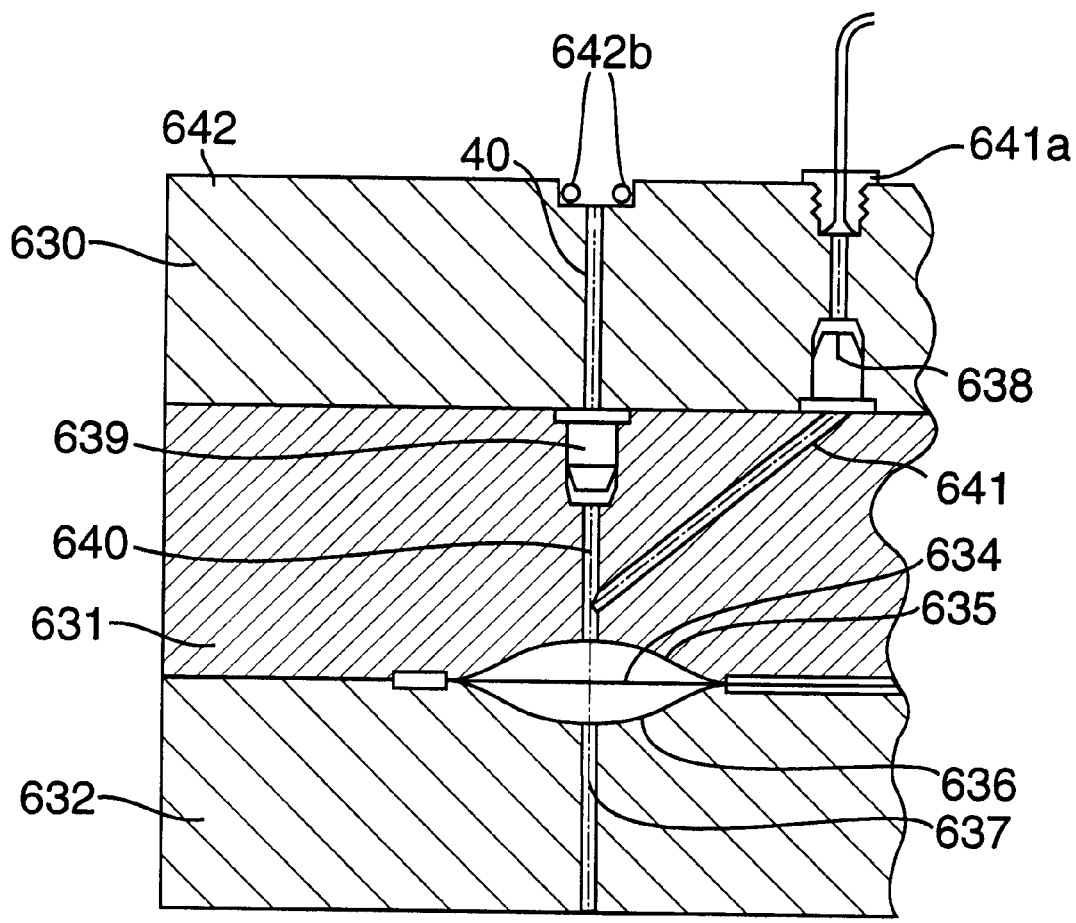
FIG. 64 is a side sectional view taken along line 64—64 of FIG. 63.

Reagent inlet and outlet passages, such as passages 640 and 641 respectively, best shown in FIG. 64, are formed through the inner and top layers 630 and 631, connecting cavity 635 and the top surface 642 of the reagent pump assembly 504. One-way valves 638, 639 are installed in the inlet and outlet passageways between the inner and top layers 630 and 631. In a preferred embodiment, the one way valves 638, 639 are duckbill check valves. A more detailed description of each pump mechanism and operation is found in U.S. patent application Ser. No. 08/549,958 filed Oct. 30, 1995, in the names of James Mahwirt and Bruce E. Behringer, for Integral Valve Diaphragm Pump and Method, which is hereby incorporated herein by reference in its entirety.

In a prototype embodiment of the invention, seven separately operable diaphragm pumps, having pumping capacities ranging from 125–1250 $\mu$l, are incorporated in the reagent pump assembly 504. The pumps are used for pumping seven reagents used in each of the RBC, RETIC, HGB, and White Blood Cell (WBC) tests. The diaphragm pumps are arranged in a staggered pattern in the reagent pump assembly for space minimization, given the area required for the diaphragm material.

The top surface 642 of top layer 630 the reagent pump assembly is bolted directly to the front plate 506 of the UFC. Outlet passages such as passage 641 thus communicate directly with reagent inlet passages in the UFC 502. Preferably, the outlet passages 641 terminate along a longitudinal axis of the top layer 642 for convenient hydraulic coupling to the UFC 502 reagent inlet passages. This obviates the need for lengthy hydraulic tubing between the reagent pumping section 504 and the UFC 502 and greatly improves reliability while minimizing tubing clutter, part count and service requirements. Alternatively, when the reagent pump assembly and the unified flow circuit are made of an acrylic, e.g., a LUCITE brand acrylic, a surface fusion technique may be used to bond directly the two subassemblies.

Figure 40:
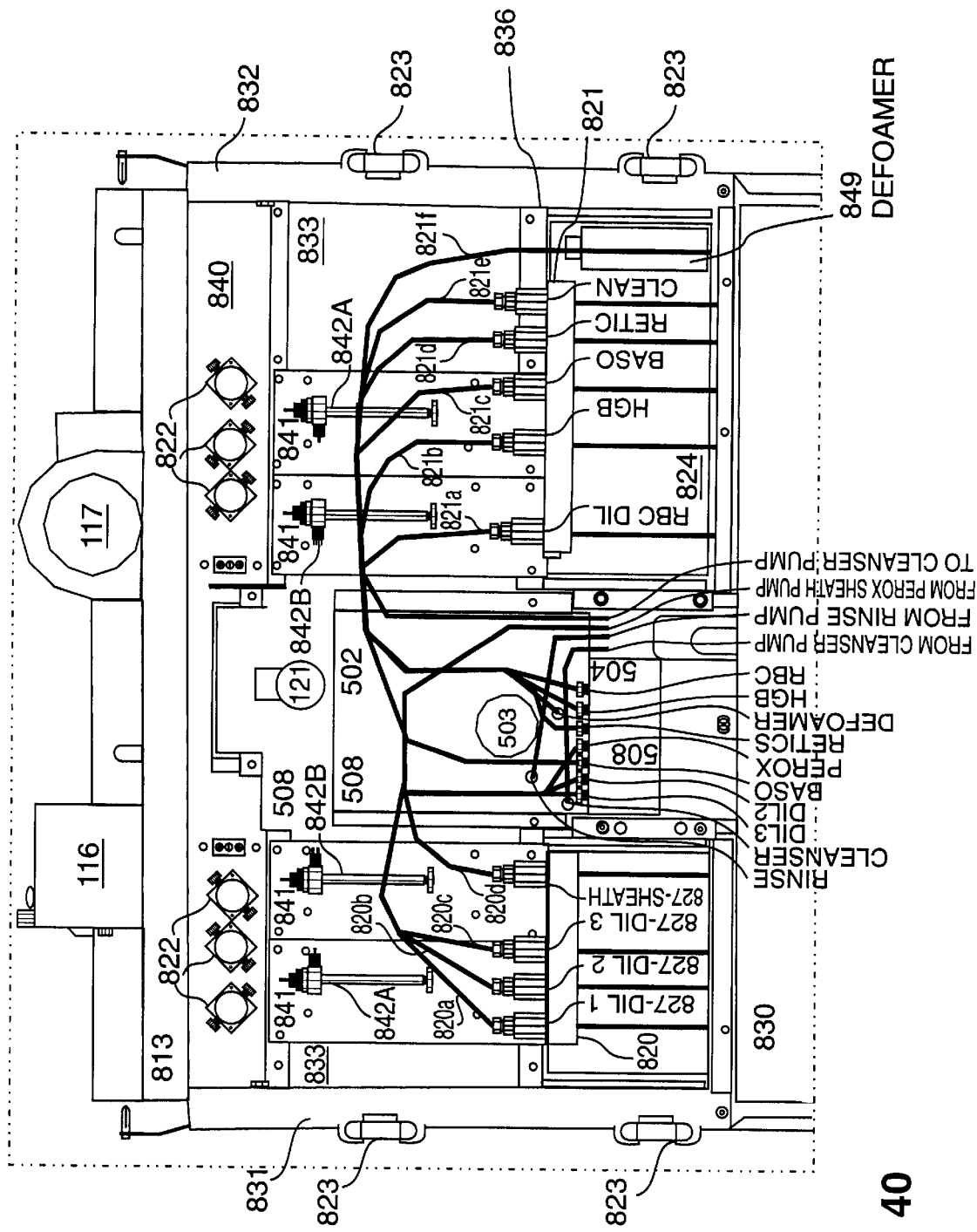

The hydraulic coupling between the pump assembly 504 and the UFC 502 is obtained by a counterbored aperture 642a in the top surface 642, and an O-ring 642b, such that the O-ring 642b forms a fluid tight seal when assembly 504 is flush mounted to UFC 502. The external fluid inputs to the reagent pump assembly 504 (e.g., reagents, rinses, vacuum and pressure) are conventionally provided by pneumatic and hydraulic lines, coupled mechanically to the assembly by threaded couplings 641a that securely screw into the pump assembly block 504 in a conventional manner, as indicated in FIGS. 40 and 64.

The sample shear valve 503 divides the blood sample into as many as five precision aliquots, one for each of the RBC, HGB, BASO, PEROX and RETIC tests. The sample aliquots range in volume from 2 $\mu$l to 12 $\mu$l. The shear valve 503 transfers each of the sample aliquots into precision volume streams of reagents that are pumped into reaction chambers in the front plate 506 of the UFC, as described below. Reagent volumes used in the tests range from 125 µl to 1250 µl.

2. Test Selectivity

In accordance with a preferred embodiment of the invention, the sample shear valve 503 is constructed to permit the instrument operator to select from among all of the available tests which tests to be performed. In this embodiment, the instrument does not pump reagent for the unperformed tests, thereby conserving reagent. In prior art hematology instruments using a single shear valve, all tests were performed on a given sample whether or not each test was requested for that sample. As a result, the unwanted results were either suppressed or also provided. This was done primarily because a reagent in a prior art shear valve would become contaminated by the blood sample, requiring that new reagent be pumped through the valve during each cycle to prevent contamination. Further, some prior art reagent pumps could not be operated independently. Other prior art hematology instruments utilize multiple shear faces to provide a degree of test selectivity. Such a system requires great complexity to offer more than two testing options, and is therefore expensive and unreliable.

In contrast, the single shear valve 503 and UFC assembly 508 of the present invention operate so as not to contaminate reagent from an unperformed test remaining in the shear valve 503. As noted above, the diaphragm reagent pumps of the instrument of the invention can be operated independently. Consequently, in the present invention, new reagent need not be pumped through the valve during each cycle solely to purge the shear valve 503.

Figure 51:
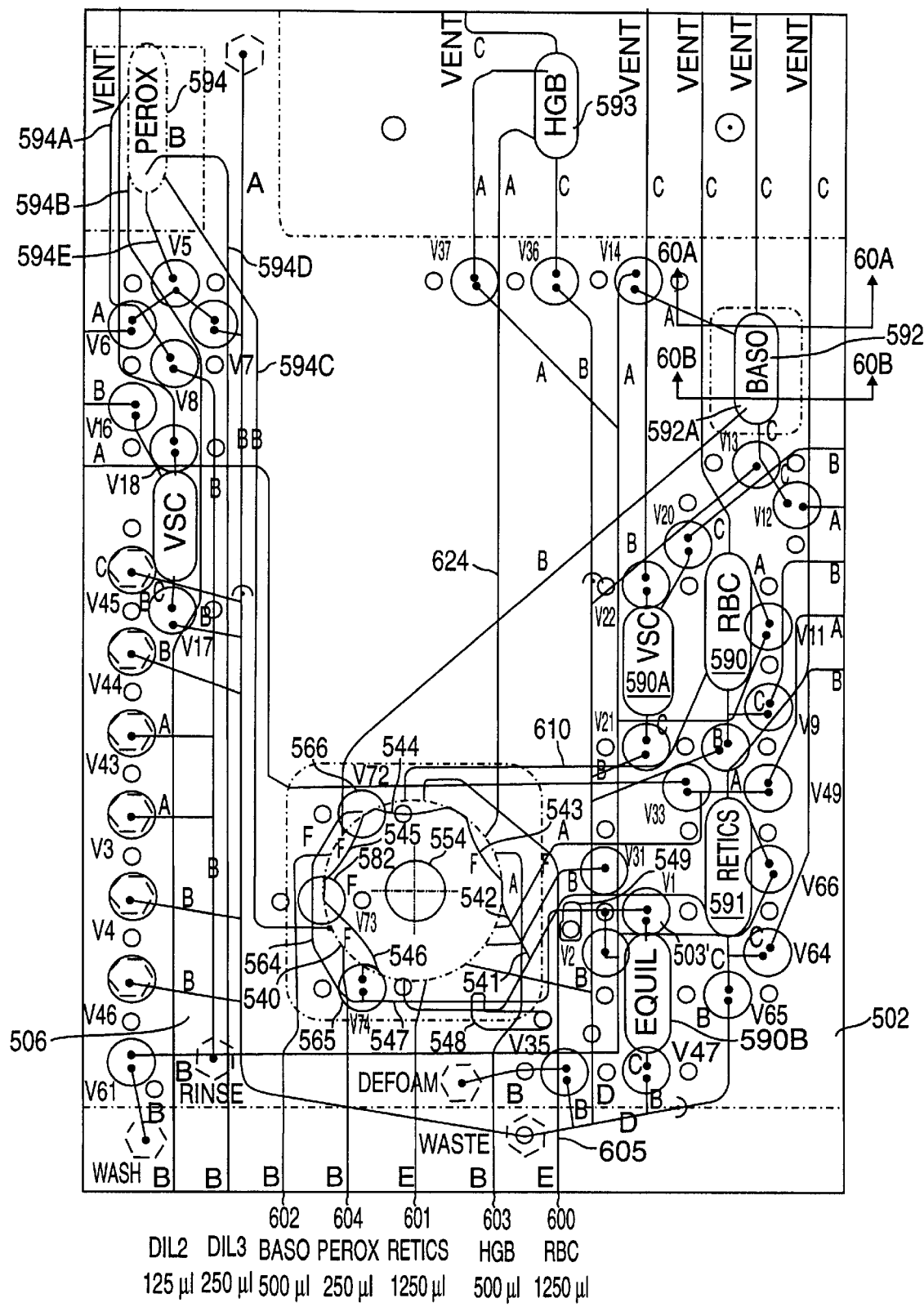
FIG. 51 is a front plane view of the unified fluid circuit (UFC) of the unified fluid circuit assembly of FIG. 49.

Referring to FIG. 51, a plan view of the front plate 506 of the UFC 502 is illustrated, showing a passage hole circle 540 for communication between the sample shear valve 503 (not shown in FIG. 51) and the UFC 502. To aspirate a blood sample from one of the three samplers, a vacuum is applied through a vacuum valve 503' in the UFC 502, through passageway 547, to the shear valve 503. The blood sample enters through an inlet 541 in the front of the front plate 506 of the UFC, through passageway 542, into the shear valve 503. If all of the tests are to be run, the blood sample then passes alternately through the shear valve 503 and through passageways 543–547 in the UFC 502. Aspiration is terminated when the leading edge of the sample stream is detected by a conductivity sensor (discussed below) signaling that the leading edge of the sample stream has passed completely through to fill the shear valve 503. This operates to stop the vacuum and aspiration of the blood sample. Information from the conductivity sensor can also be used to verify that the blood sample meets certain minimum criteria embodied in the hematocrit and measured by concentration and salinity. If the predetermined minimum criteria or criteria range(s) are not met, then the sample may be purged.

Figure 54:
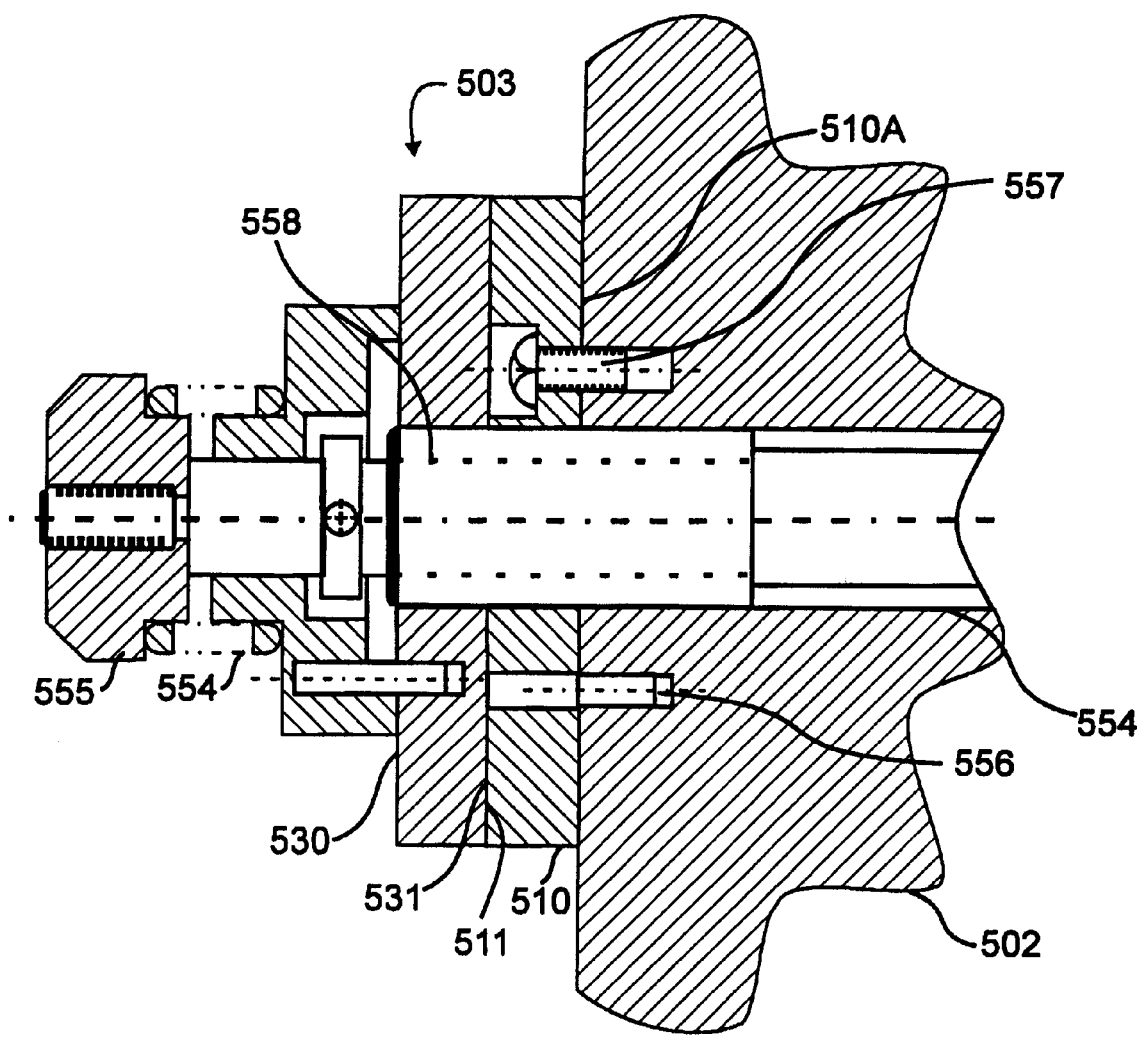
FIG. 54 is a sectional view of the shear valve taken along line 54—54 of FIG. 49.

The shear valve 503, shown in partial sectional view in FIG. 54, comprises a stationary ceramic disk 510 having a shear face 511, and a moving ceramic disk 530 having shear face 531. The shear faces 511, 531 are flat and smooth, maintaining substantially complete contact during relative movement of the disks 510, 530. The moving disk is indexed between a first position for aspirating a sample, and a second position for distributing aliquots of the sample among the various reagents in the network of flow paths.

The stationary ceramic disk 510 is sealably mounted to the front plate 506 of the UFC 502. Sample and reagent inlets and outlets of the shear valve, discussed below, communicate with inlet and outlet holes comprising a communication hole circle 540 in the UFC 502 (FIG. 51). In one preferred embodiment, a thin gasket 510A of silicon rubber is installed between the stationary ceramic disk 510 and the UFC front plate 506, the gasket 510A having a hole aligned with each valve inlet and outlet for permitting communication with the holes of the communication hole circle 540 in the UFC 502. Alignment holes also may be provided in the valve 503, gasket 510A and UFC 502 for installing alignment pins 556 to assure that the ports, holes and flow paths match during assembly. The stationary disk 510 is preferably retained on the UFC 502 using screws 557.

Figure 53C:
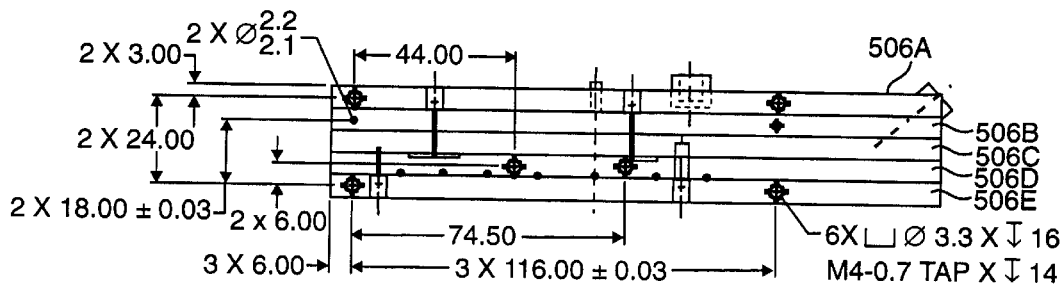
Figure 53B:
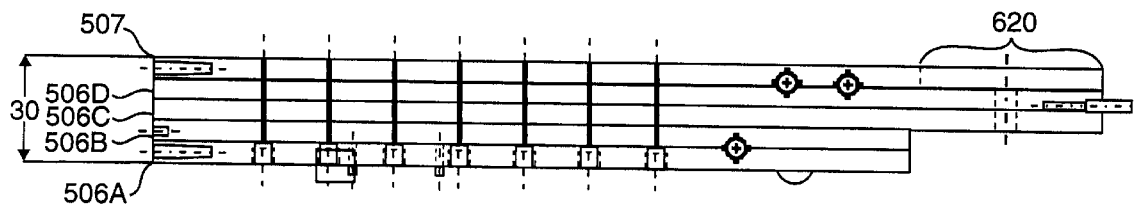
Figure 53A:
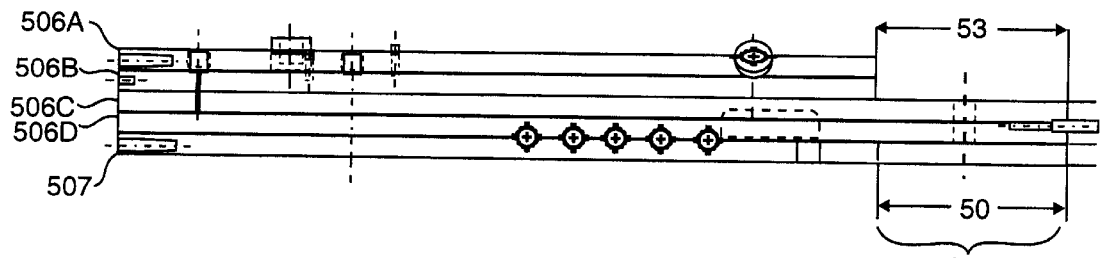

As shown in FIG. 49, a conventional rotary actuator 550 is mounted to the rear plate 507 of the UFC on the side opposite the front plate 506 and the shear valve 503. As best shown in FIG. 53, the shaft 553 passes through a clearance hole 554 in both plates 506 and 507 of the UFC 502, through a bushing 558 that aligns the stationary and moving disks 510, 530, and is attached to the moving disk 530. A compression spring 554 and retaining nut 555 maintain contact between the shear surfaces 511, 531. Actuating the rotary actuator 550 rotates the shaft 553 which indexes the moving disk 530 of the shear valve. In an alternate embodiment the rotary actuator may be a pneumatic cylinder 551 connected to a radius arm 552, which is mounted to a central shaft 553.

Figure 55:
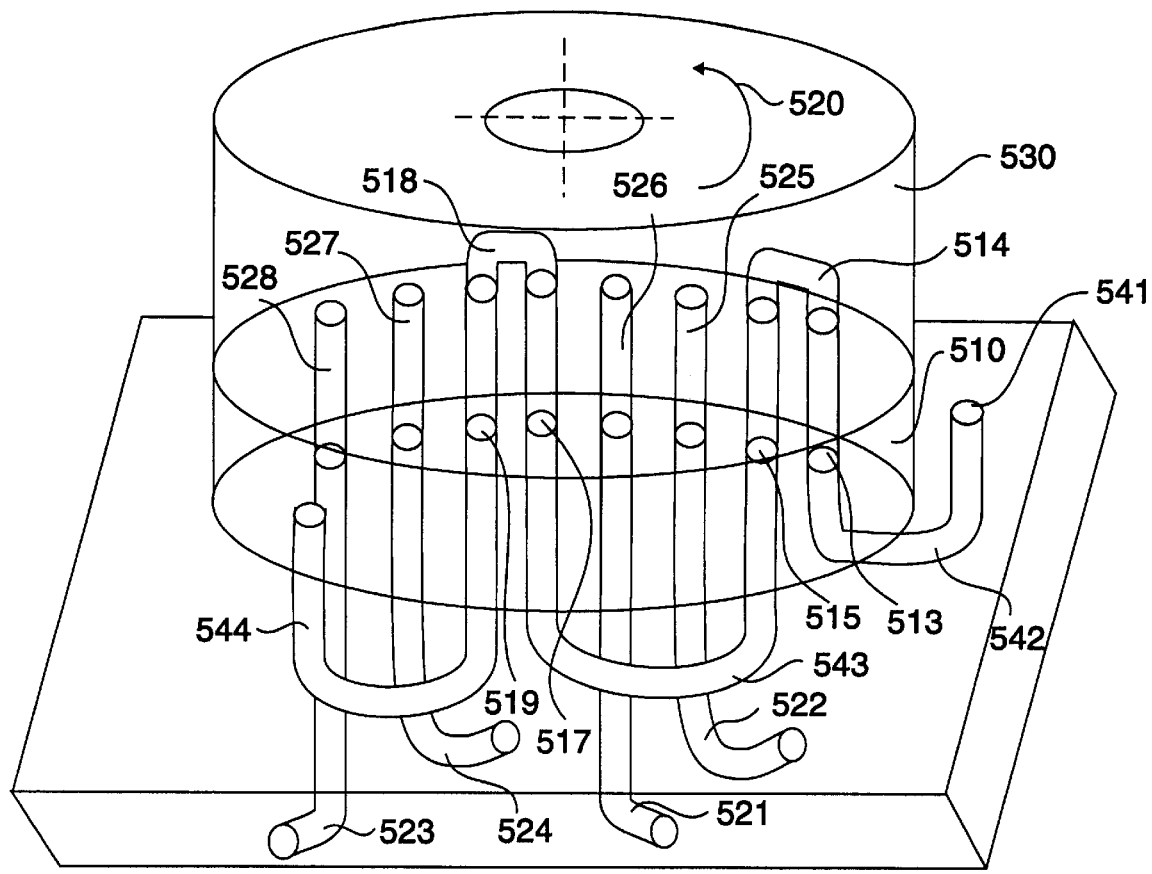
FIG. 55 is an elevated perspective view of the shear valve of FIG. 49.

A perspective view of the shear valve 503 of the invention is shown in FIG. 55. In operation, a sample entering the UFC 502 through port 541 enters the stationary disk 510 through inlet 513. After entering the shear valve, the sample passes through the stationary disk 510 into a first aliquot loop 514 in the moving disk 530, back through the stationary disk 510 and is returned to the UFC 502 through exit port 515. The passage 543 in the UFC 502 then directs the sample to a second entry port 517 in the stationary disk 510. The sample stream then passes again through the stationary disk 510, through a second aliquot loop 518 in the moving disk 530, back through the stationary disk 510, and is returned to the UFC 502 through exit port 519. The sample then continues through passageway 544 in the UFC 502 to fill the remaining aliquot loops (not shown) in the shear valve 503. The sample shear valve 503 thus may be configured with any number of loops depending on the maximum number of tests to be run. In one useful valve design, five aliquot loops, which are connected by sample conduits (See FIG. 57A), are used.

Once the sample has filled the shear valve 503, as verified by the conductivity sensor, the rotary actuator 550 rotates the moving disk 530 in the direction of arrow 520 to the second position. In the second position, the first loop 514 is aligned with reagent passageways 525, 526 in the stationary disk 510, which communicate with a first reagent inlet 521 and a first reagent outlet 522 in the UFC 502. Similarly, the second loop 518 is aligned with reagent passageways 527, 528 which communicate with a second reagent inlet 523 and a second reagent outlet 524 in the UFC. Other loops are similarly aligned with corresponding reagent (or fluid) inlets and outlets. If all tests are to be run during the cycle, all aliquot loops are filled with sample. The reagent passageways, inlets and outlets, contain reagent that was pumped into the valve during a preceding cycle. With each loop aligned with a reagent inlet and outlet, reagent for the tests to be run is pumped through the shear valve to the appropriate reaction chamber, carrying with it the sample aliquot from the loop. This action also purges the valve 503 for the next sample. For the sample lines, valve 503 rotates back to the aspirate position and backflushes the lines with rinse prior to aspirating the next sample.

Figure 56:
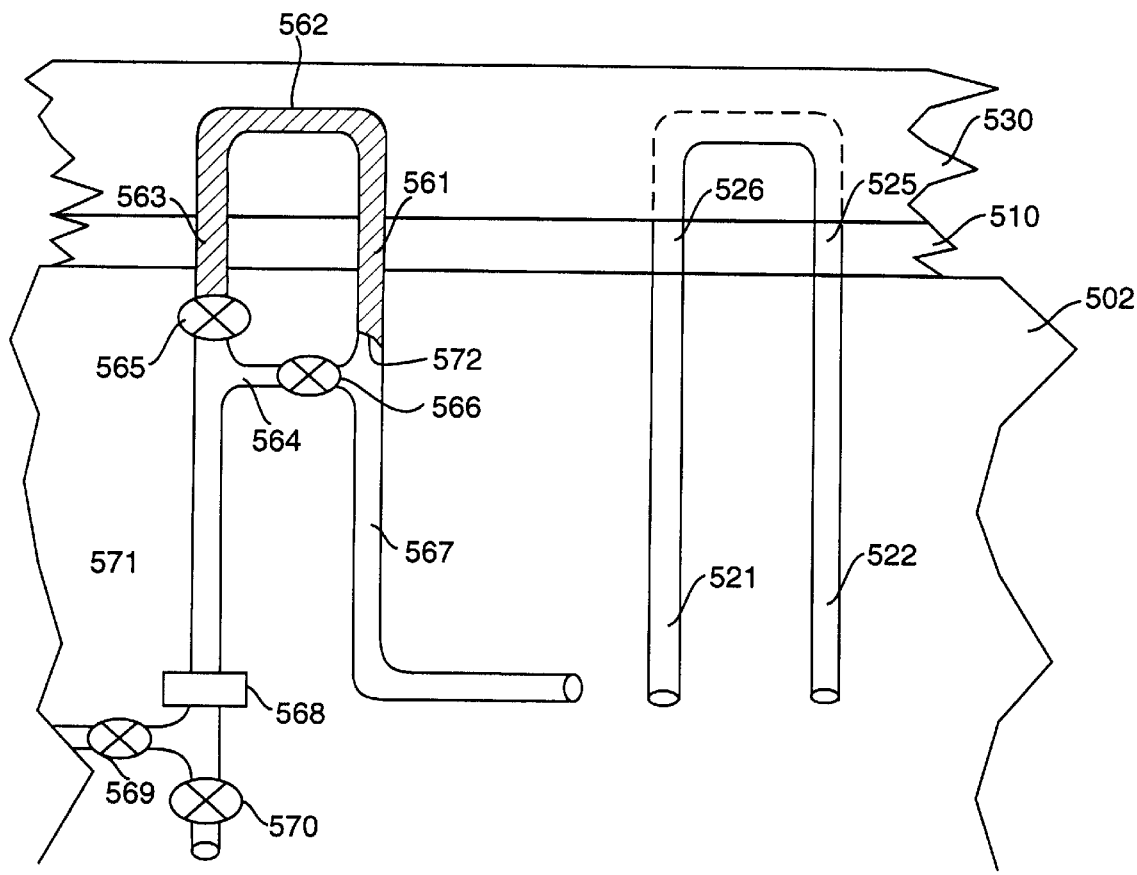
FIG. 56 is a schematic sectional diagram of a shear valve having test selectivity in accordance with a preferred alternate embodiment of the present invention.

As noted above, the instrument of the invention is optionally provided with additional passageways and valves to permit selectively running less than all the available tests, without contaminating the reagent of an unused test for the next sample cycle. FIG. 56 illustrates a schematic view of a single aliquot loop 562 of shear valve having test selectivity capability. The moving disk 530 is shown in its first position, with aliquot loop 562 aligned with sample entry port 561 and sample exit port 563 in the stationary disk 510. The sample entry port 561 connects to passageway 567 in the UFC 502. The blood sample enters passageway 567 either from an adjoining aliquot loop, sample conduit, or directly from the tube sampler. The sample exit port 563 connects to passageway 571 in the UFC 502, passes through the conductivity sensor 568 and connects through a valve 569 to a vacuum source VAC and through a valve 570 to a rinse source RINSE.

The novel positioning of the valves 565, 566, and the bypass passageway 564 in the UFC 502 provides test selectivity for the aliquot loop shown in FIG. 56. After each cycle of the shear valve 503, valve 570 is opened to permit a rinsing liquid to flow through the shear valve, removing contaminants left behind from the previous cycle. As part of a method of using the valve of FIG. 56, a last step in the rinse cycle is to send rinse through the shear valve with valves 569, 566 closed and valves 570, 565 open. Rinse liquid fills the aliquot loop and adjoining portions of the entry and exit ports 561, 563. Passageways 571, 564, 567 are then dried by applying vacuum with valves 566, 569 opened and valves 570, 565 closed, as shown schematically in FIG. 56. Rinse liquid remains in the aliquot loop and adjoining portions of the entry and exit ports, as shown. The rinse liquid is held in that position until it is known which tests are to be run on the next sample.

If the next cycle does not require running the test associated with aliquot loop 562, no additional drying is performed, and the blood sample is aspirated by opening valve 569, applying vacuum to the shear valve. The sample fills passages 567, 564, 571; the rinse liquid in the aliquot loop prevents blood from entering. If there were no rinse in the loop, air in the loop would permit the blood sample to enter when the volume of air decreased as the vacuum pressure was removed. While a portion of the rinse at 572 contacts the sample and is thus contaminated, this point is sufficiently distant from the shear face that it does not contaminate rinse in the loop 562.

The shear valve is then cycled to its second position, indexing the aliquot loop 562, filled with rinse liquid, to a position shown in phantom in FIG. 56, adjoining the reagent ports 525, 526. No reagent is pumped through the passageways 521, 522 for that cycle, and effectively all the rinse remains in the loop. Some rinse may diffuse into the reagent across the reagent/rinse interface existing at the shear face, but the resulting dilution is negligible, given the relatively large volume of reagent pumped for a test, and the nature of the rinse liquid, which is selected for its neutral properties. The shear valve is then returned to the first position, and a rinsing and drying routine is performed as above.

If the next cycle requires that the test associated with the aliquot loop 562 be run, valves 569, 565 are opened and valves 570, 566 are closed, removing rinse from the loop 562 and drying it. A sample is now aspirated with valves 569, 565 opened and valves 570, 566 closed, filling the aliquot loop with blood. After indexing the shear valve to the second position, reagent is pumped through the passageways 521, 522 to a reaction chamber (not shown), carrying the sample aliquot with it.

In a shear valve having multiple loops forming aliquots for multiple tests, requests for several test combinations may be encountered. The apparatus and method described above may be extended to provide several test combinations by connecting the bypass passage 564 to other loops. For example, in a shear valve having five aliquot loops for five tests, FIGS. 57A–F schematically show a test selectivity process and system that can perform either three, four or five tests. For clarity, the figures show the shear face around the circumference of the disks instead of on a surface, as shown in FIG. 55. In one such preferred embodiment of the invention, loop 573 is for RBC tests; loop 574 is for HGB, loop 575 is for BASO, loop 576 is for PEROX, and loop 577 is for RETIC tests. The system can run combinations of either loops 573–575 (CBC test: RBC, HGB & Baso), loops 573–576 (CBC+Diff test: RBC, HGB, BASO & PEROX), or loops 573–577 (CBC+Diff+RETIC test: RBC, HGB, BASO, PEROX & RETIC). The assignee of the present invention has found that these three combinations cover approximately 97% of the test combinations typically requested for blood analysis in the commercial market. Other combinations could be obtained by a straightforward application of the principle of test selectivity described above.

Referring to FIGS. 56 and 57A–57G, the instrument of the invention has a valve 565 in passage 547 of the UFC 502 downstream of the last aliquot loop. A bypass passage 564 in the UFC begins at passage 545 between loops 575, 576 of the shear valve, has a branch 578 connecting to passage 546 between loops 576, 577, and joins passage 547 downstream of the valve 565. Valve 566 is in the bypass passage 564 near where it joins sample conduit passage 545; valve 582 is in the branch 578.

Figure 57A:
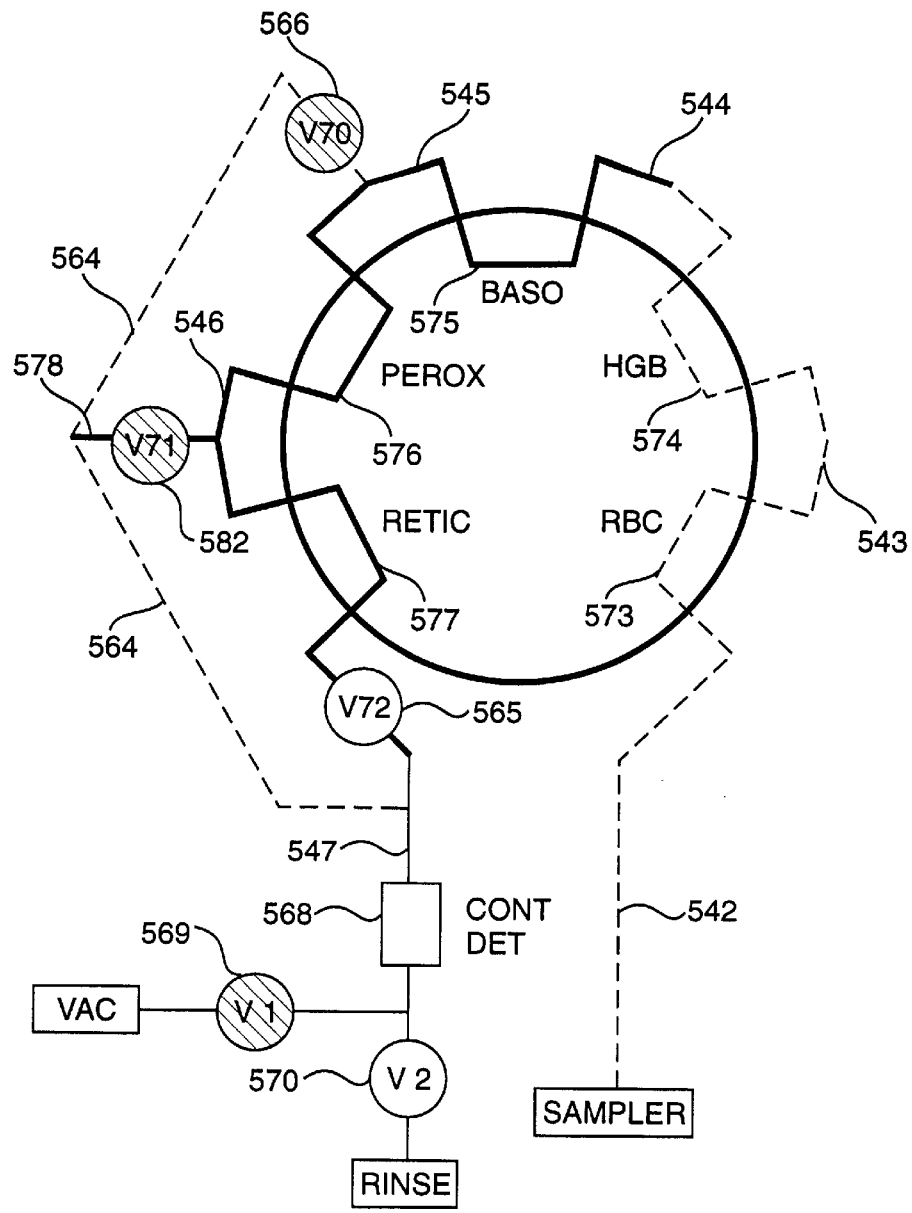
FIGS. 57A–57G are schematic diagrams of a test selectivity process for the shear valve of FIG. 56.
Figure 57B:
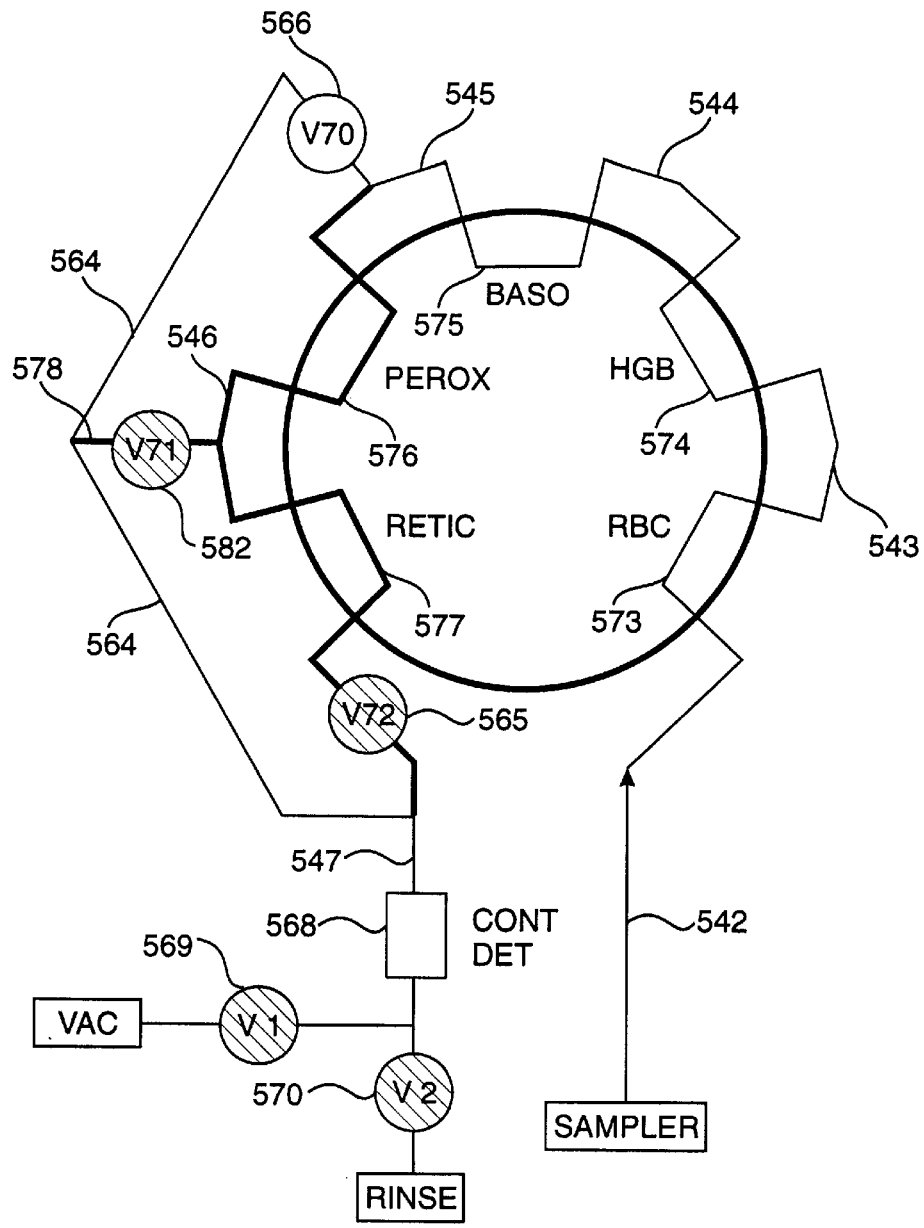

In operation, after each cycle of the instrument, the various flow paths of the shear valve 503 are rinsed. Rinsing of the valves 566, 582, 565, 569, 570 and the bypass passage 564 is not critical, but contamination points must be considered as discussed below. As the last step of the rinse cycle, rinse is sent through the shear valve with valves 566, 582, 569 closed, and valves 566, 569 open, as shown in FIG. 57A. With rinse in the shear valve, valves 570, 582, 565 are closed and valves 566, 569 are opened. The sample probe (not shown), aliquot loops 573, 574, 575, and the bypass passage 564 are dried. Rinse is trapped and held in the loops 576, 577 and adjoining passages, as shown in FIG. 57B. The rinse is held there until the tests to be run on the next sample are known. This is typically when the next sample ID is read by the automated closed tube sampler (autosampler 818) or by an operator input using manual bar code reader 104 (FIG. 11A); however, the instrument may remain idle in this condition if no sample is presented for analysis.

Figure 57C:
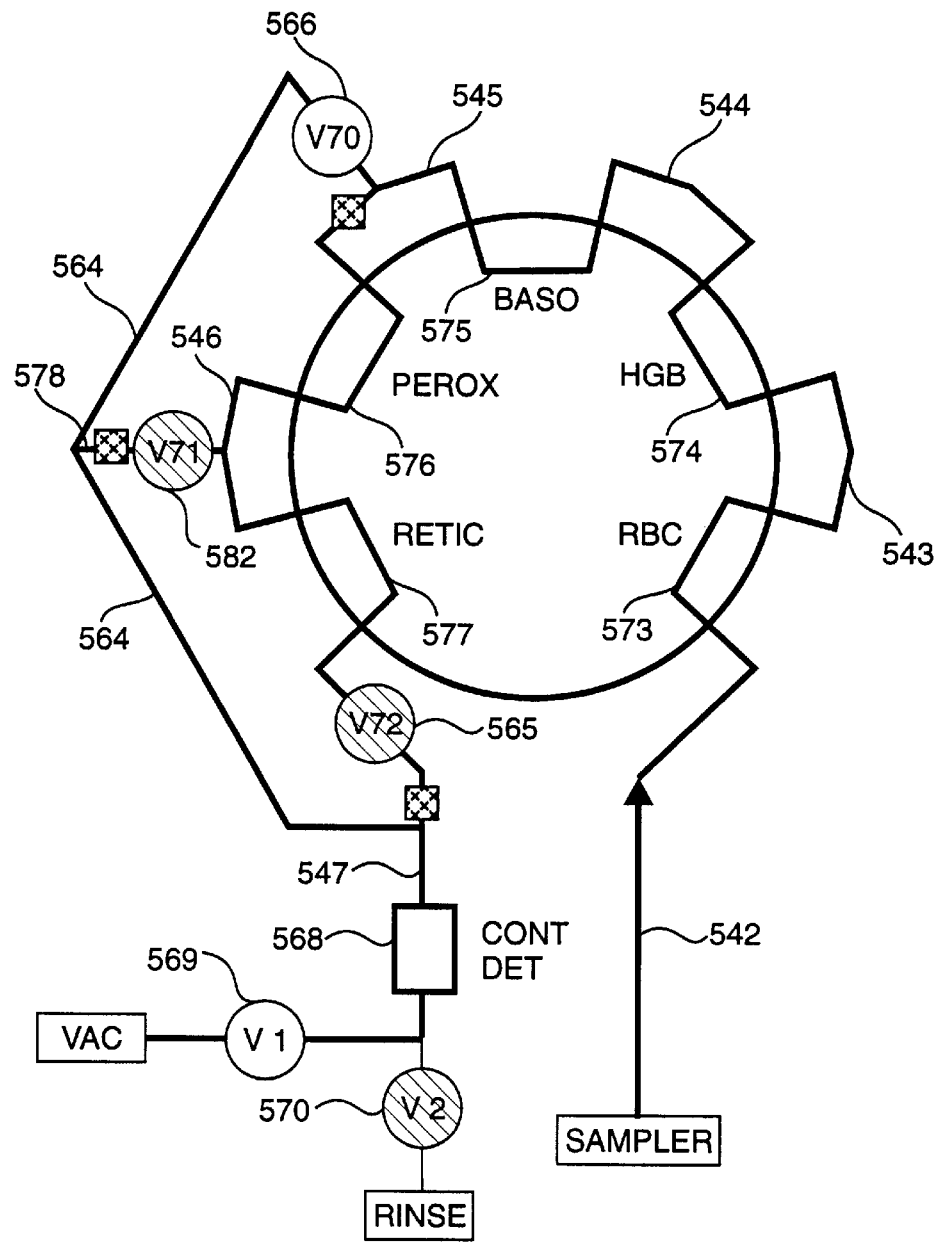

If testing for the next sample requires aliquots from loops 573, 574, 575 only, no additional drying is performed, and the sample is aspirated with valve 566, 569 opened to vacuum, as shown in FIG. 57C. The rinse that is trapped keeps the blood sample from flowing into the aliquot loops 576, 577. As with the valve of FIG. 56, contamination of the rinse is remote from the aliquot loops and does not affect carryover. The rinse remains in loops 576, 577 when the shear valve is indexed, contacting, but not contaminating, reagent in the reagent ports (not shown).

Figure 57D:
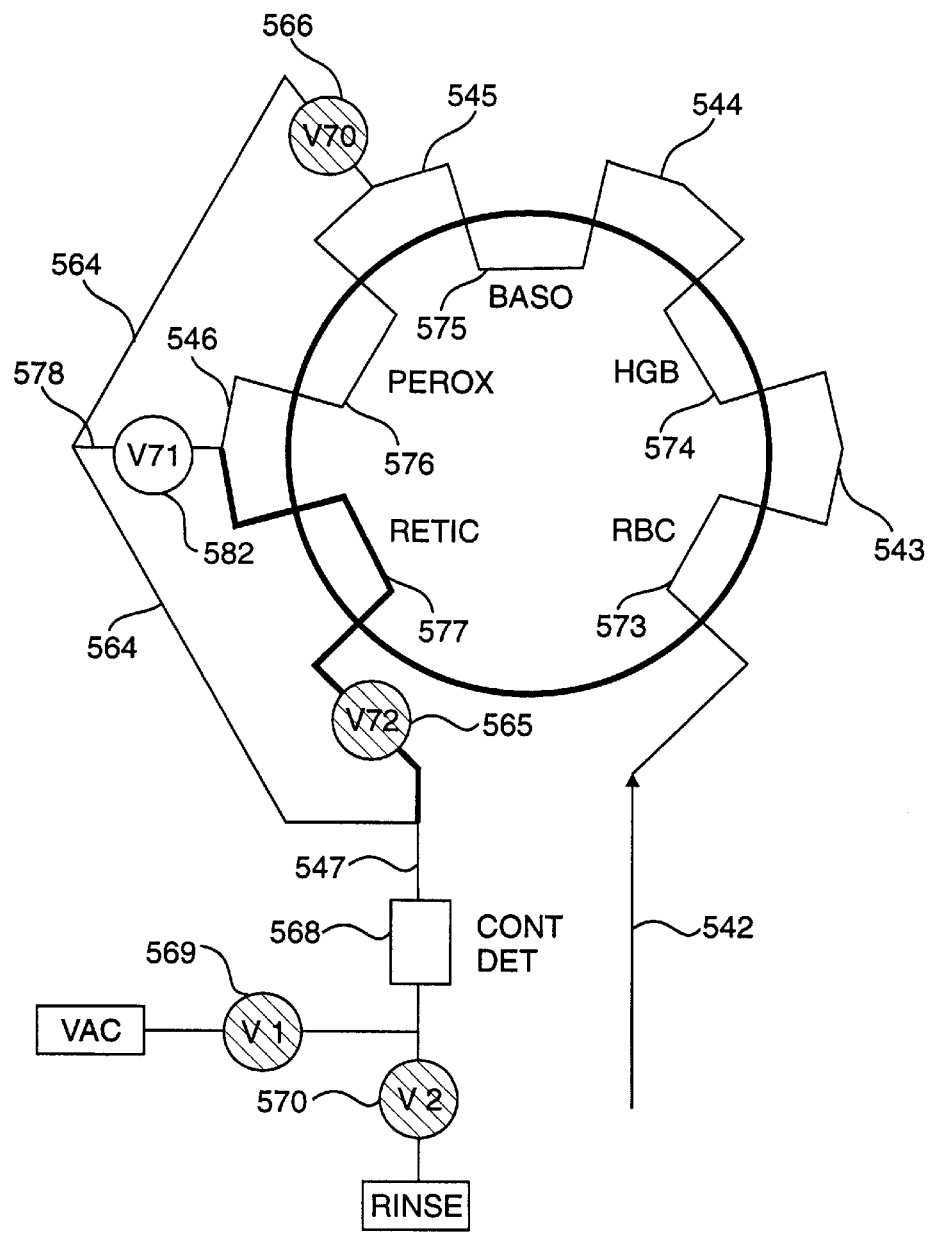
Figure 57E:
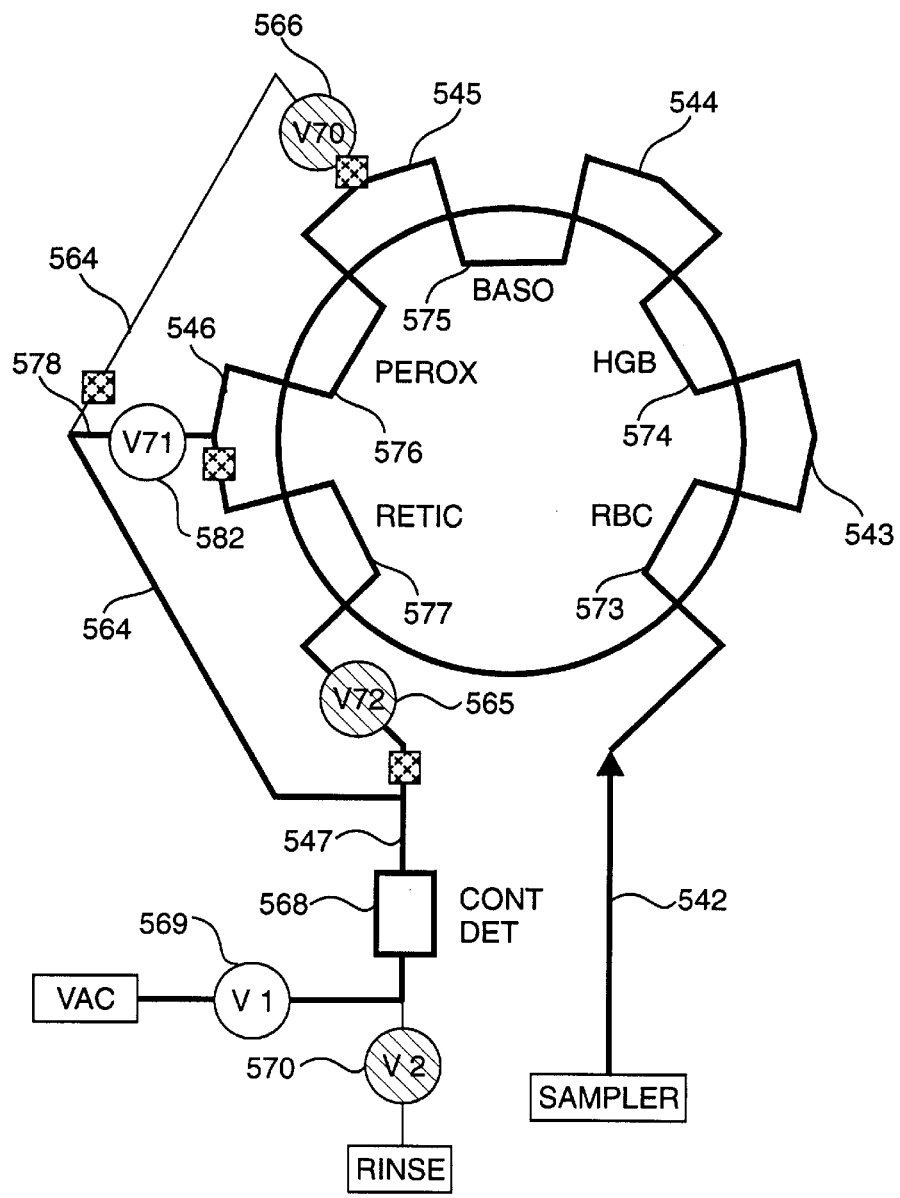

If testing for the next sample requires an aliquot from loop 576 in addition to loops 573–575, the additional loop is first dried with valves 569, 582 open and valves 565, 566, 570 closed. This requires approximately 1 second. The vacuum valve 569 is then closed awaiting sample aspiration, with rinse trapped in loop 577 and adjoining passageways as shown in FIG. 57D. The blood sample is aspirated by reopening valve 569. Rinse trapped in the loop 577 and adjoining passageways prevents blood from flowing into that portion of the shear valve, as shown in FIG. 57E. The rinse remains in loop 577 when the shear valve is indexed, contacting but, not contaminating, reagent in the reagent ports (not shown).

Figure 57F:
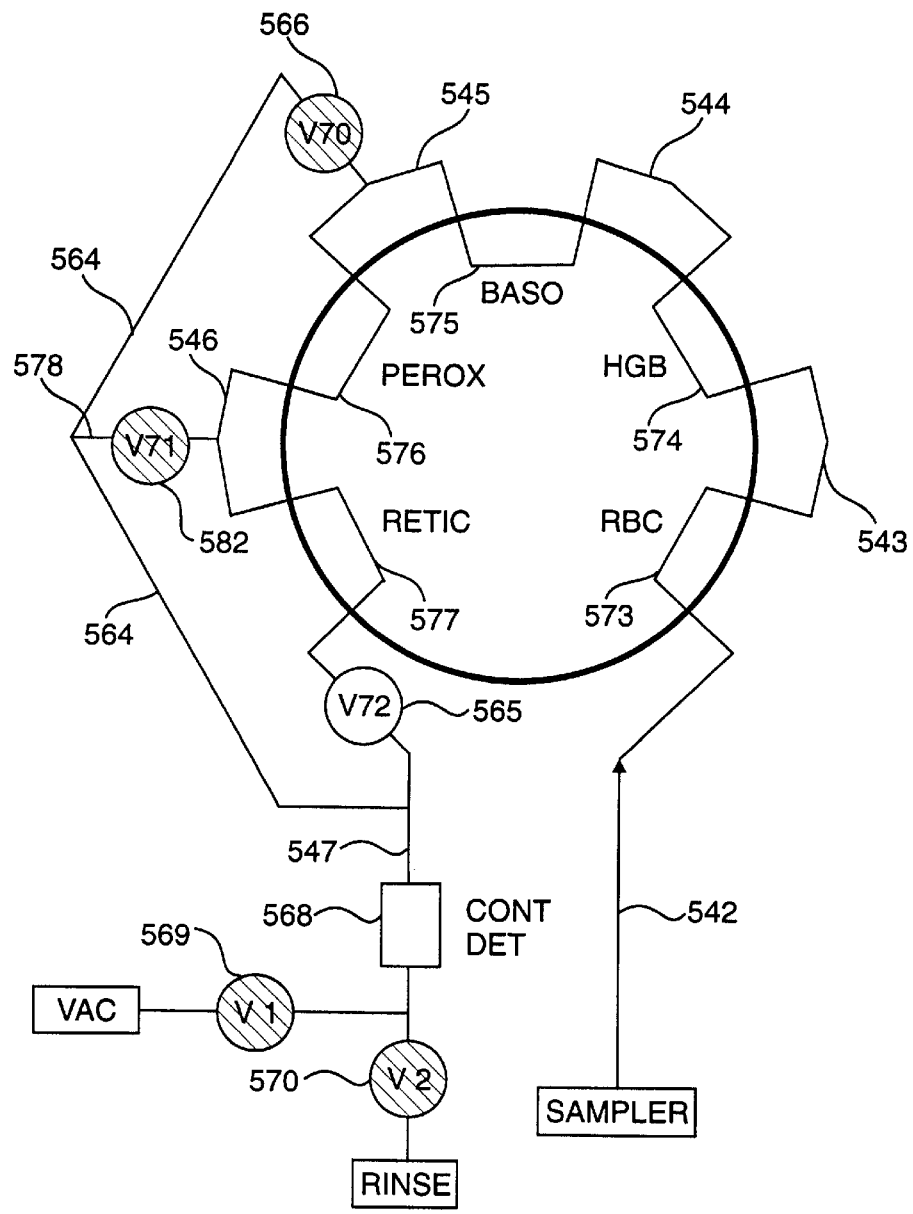
Figure 57G:
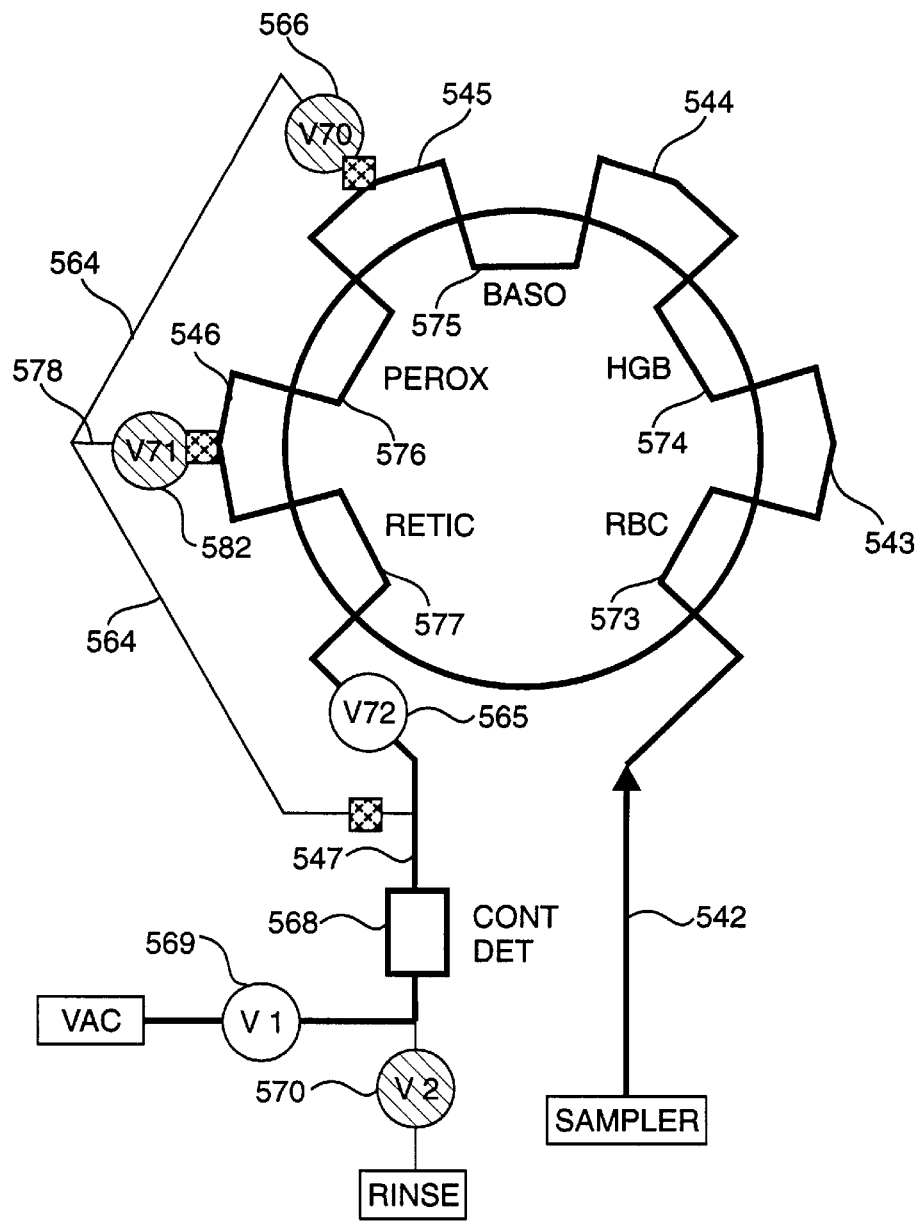

If testing for the next sample requires an aliquot from all of the loops 573–577, the loops 576, 577 are first dried with valves 569, 565 open and valves 566, 582, 570 closed, as shown in FIG. 57F. This requires approximately 1 second. When the sample is ready to be aspirated, the vacuum valve 569 is reopened and sample fills all the aliquot loops, as shown in FIG. 57G.

3. Dome Valves

Figure 52:
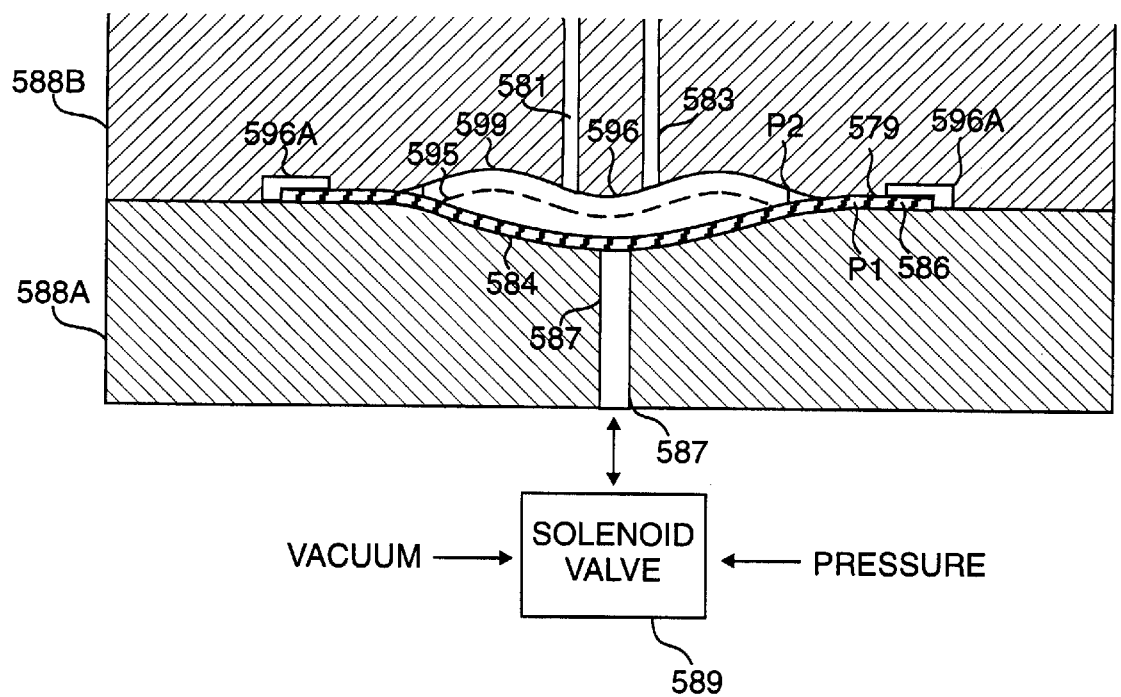
FIG. 52 is a side sectional view of the dome valves of the UFC of FIG. 49.

Referring to FIG. 52, each of the valves 566, 582, 565, 569 and 570 (as well as the other valves in UFC 502) are preferably dome valves of the type illustrated in FIG. 52. Each dome valve, generally indicated by the reference label DV in FIG. 49 (unless designated with a specific reference numeral), has a valve chamber demarcated by a concave surface 584 in the planar surface of a UFC plate 588A and by one surface 585 of a flexible layer 586. The flexible layer 586 is of an elastomeric material such as rubber or silicone sheeting. At least one fluid passageway 587 in the rigid layer 588A opens into the valve chamber at the concave surface 584. The fluid passageway 587 is connected to a solenoid valve 589 which alternately applies vacuum or pressure to the valve chamber to operate the valve.

The dome valve also includes a fluid chamber demarcated by the surface 595 of the flexible layer 586 and a concave-convex surface in the surface of UFC plate 588B, which is opposite the valve chamber. The concave-convex surface has an inner circular convex portion 596 and a concentric annular outer concave portion 599. The convex portion 596 preferably has a dome point at the center thereof and the tangent thereto is coplanar with the surface of the rigid layer 588B. That dome point also is aligned with the center of the concave surface 584.

The surface of plate 588B includes a compression-expansion relief channel 596A which surrounds the dome and the concave-convex surface and defines a compression zone 579 between the dome and the channel 596A. The compression zone compresses the flexible layer 586 and the channel 596A provides for extruded diaphragm material 586. When the rigid layers 588B and 588A are connected together as shown in FIG. 52, the compression zone 579 acts to seal the periphery of the valve and fluid chambers.

In operation, when a vacuum is applied to the valve chamber through passageway 587, the flexible layer flexes into position P1 so that surface 595 is spaced apart from the convex portion 596 and the fluid chamber is open, permitting communication between the hydraulic input 583 and the hydraulic output 581. Conversely, when a pressure is applied to the valve chamber, the flexible layer 586 flexes into the closed position P2 (shown in phantom) so that the surface 595 is tightly against the convex and concave surfaces 594 and 596, preventing communication between the hydraulic input 583 and the hydraulic output 581. The application of pressure and/or vacuum is controlled by the use of solenoid valves, which can be mounted on block 42 or stand-alone.

As a result of the concave-convex surface, there will be equal elastomer stretch deformation in both the open and closed positions P1 and P2, which improves the longevity of the dome valve.

In one embodiment of the present invention, the flexible layer 586 is about 0.01" thick and has a diameter of about 0.375". Channel 596A has an inner diameter of 0.322" and an outer diameter of 0.4" and a height of 0.012". Compression zone 579 has an inner diameter of 0.225" and an outer diameter of 0.322" and the surface is stepped down by 0.009" in the compression zone.

Passageway 587 has a diameter of 0.031" and passageways 581 and 583 have a diameter of 0.02" and a center to center spacing of 0.05". Concave surface 584 has a diameter of 0.156, a spherical radius of 0.1" and a depth of 0.025". Convex portion 599 has an outer diameter of 0.156", an inner diameter of 0.06" and a radius of curvature of 0.02". Concave portion 596 has a diameter of 0.06" and a spherical radius of 0.08". Further details of the dome valves DV are provided in U.S. patent application Ser. No. 08/319,918, filed Oct. 7, 1994, now U.S. Pat. No. 5,496,009, which application is incorporated herein by reference in its entirety and commonly owned.

After the shear valve 503 is indexed to the second position, the aliquots of blood are aligned with the various reagent paths, as described above. For each test to be run, a precise volume of reagent is pumped from the reagent pump assembly 504 (FIG. 49), through the shear valve 503, into one of the reaction chambers, carrying with it the sample aliquot. For example, as shown in FIG. 51, the reagent for the RBC test is pumped into the UFC 502 through port 600 at the bottom of the front block 506 of the UFC 502, and through the passageway 605 to the shear valve communication hole circle 540. The reagent passes through the RBC aliquot loop in the shear valve and returns to the UFC 502 in passageway 610, which directs the reagent and sample aliquot to the RBC reaction chamber 590. Separate, similar paths lead from ports 601–604 to the RETIC reaction chamber 591, BASO reaction chamber 592, HGB reaction chamber 593 and PEROX reaction chamber 594, respectively.

4. Reaction Chambers

Figure 58:
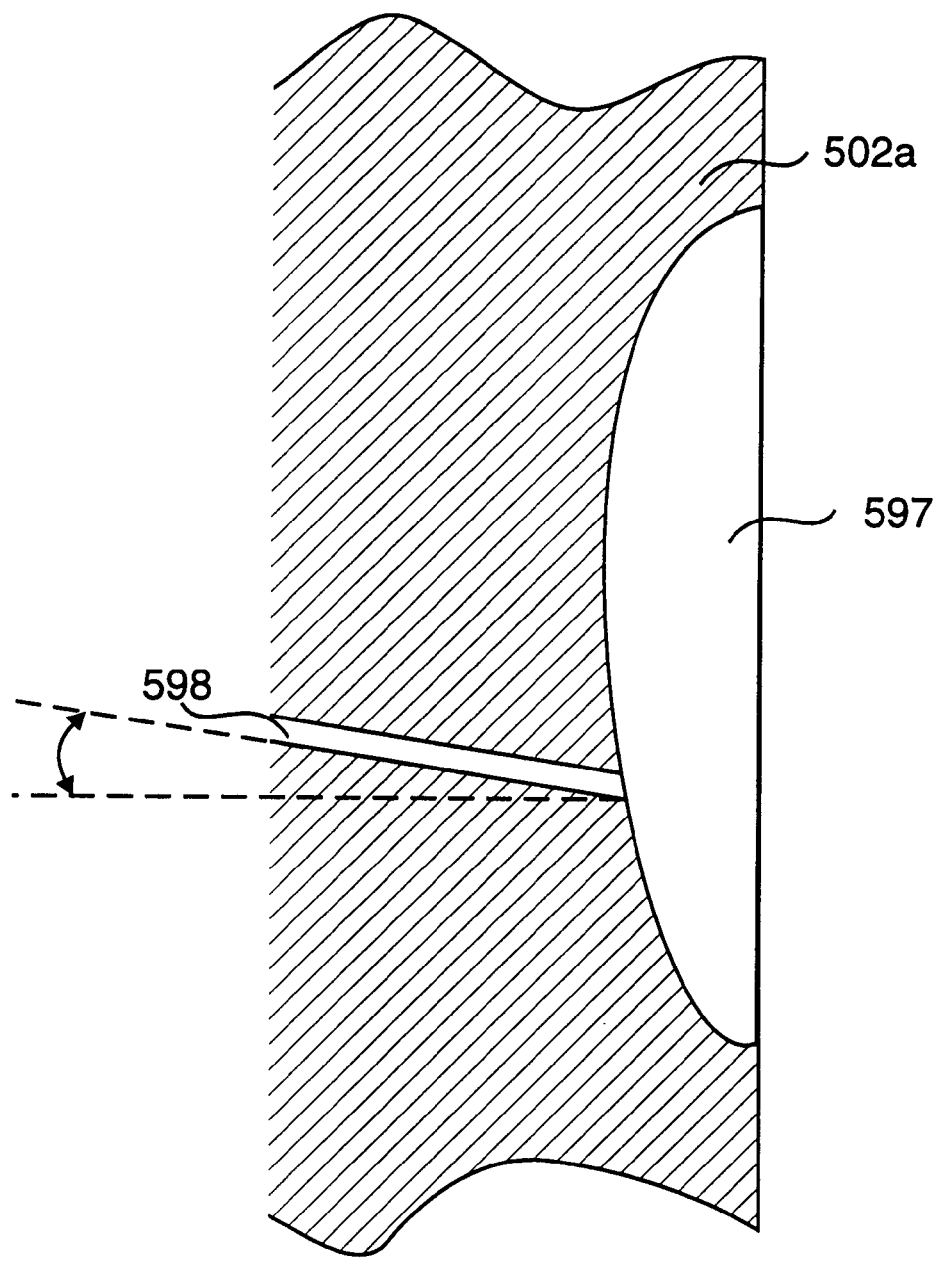
FIG. 58 is a side sectional view of a reaction chamber of the unified fluid circuit (UFC) of FIG. 51.

The RBC and RETIC reaction chambers 590, 591 are formed as an integral part of the front block 506 of the UFC by machining semi-circular cross sections in each of two mating acrylic plates. FIG. 58, for example, shows a semi-circular chamber 597 machined in block 502A of the UFC 502. This chamber matches a similar chamber machined in the mating block (not shown) of the adjacent layer of the UFC 502 to form a reaction chamber. In a preferred embodiment, the RBC and RETIC chambers are 10 mm diameter and 30 mm long. A reagent/sample inlet port 598 is generally shown in FIG. 58 as the terminus of the passageway leading from the shear valve 503 to the reaction chamber; for example, in the case of the RBC reaction chamber, the terminus of passageway 610. The reagent/sample ports for each of the reaction chambers is configured to provide an appropriate amount of mixing as the sample and reagent are pumped into the chamber. In a preferred embodiment, the RBC, PEROX, and RETIC inlet ports are tangent to the chamber side wall on the horizontal (0°) axis, and 0.50 mm in diameter.

It will be appreciated that more than one configuration of the orientation of the terminus of port 598 into the reaction chamber 597 can be used, and that the combination depends on both the reaction chamber shape and the passageway diameter to obtain the desired adequate mixing. It also should be understood that, in view of the multiple layers comprising the UFC 502, different reaction chambers may be located between different layers, and thus the passageways from the shear valve 503 to the reaction chambers may pass through different layers. It is however desirable to have all of the reaction chambers in the same two-layer interface to simplify construction.

Referring now to FIG. 52, the UFC 502 is shown in side view. In this embodiment, UFC 502 front plane 506 comprises four separate sheets of the acrylic material 506A, 506B, 506C, and 506D, which are fused together with sheet 506D fused to the back face sheet plate 507. In one embodiment, the sheets are held in a fixture which heat and pressure are applied to cause fusion. Alternate techniques are known, such as those described in, e.g., U.S. Pat. Nos. 4,875,956, 4,999,069 and 5,041,181, the disclosures of which are hereby incorporated herein by reference.

Although not indicated in FIG. 52, in a preferred embodiment, the RETIC, BASO, HGB, and RBC reaction chambers 591, 592, 593, and 590, the vent ports and lines, are machined in the interface between plates 506C and 506D, the vacuum lines, blood sample input to the shear valve, and waste output lines are machined in the interface between plates 506B and 506C, the reagent input lines to the shear valve 503 are machined in the interface between plates 506D and 507.

As illustrated in FIG. 51, for the BASO, RBC, HGB, RETIC and PEROX chambers, the sample inlet port 598 terminates near the lower end of the chamber at about the location where the radius of the lower end meets the flat cylindrical side of the chamber. The upper and lower bounds are at the top and bottom of FIG. 51 respectively.

Figure 59:
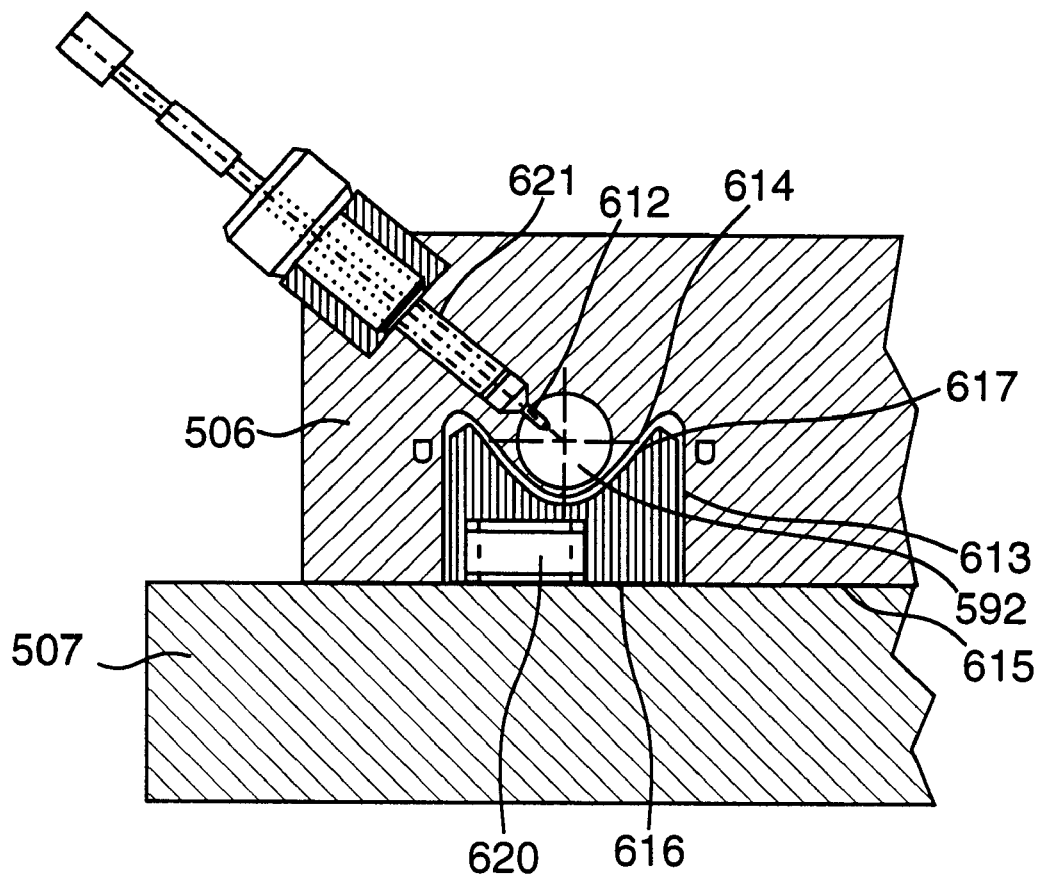
FIG. 59 is a partial sectional view taken along line 59—59 of FIG. 51.
Figure 60:
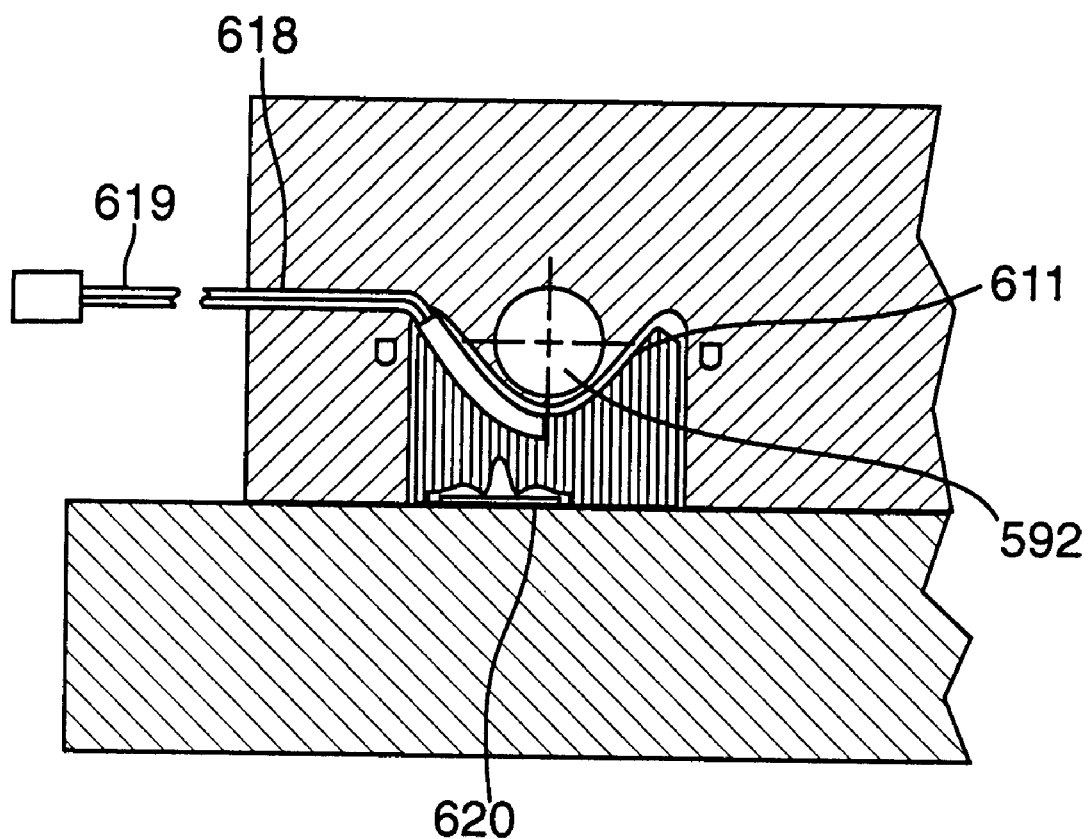
FIG. 60 is a partial sectional view taken along line 60—60 of FIG. 51.

The BASO reaction chamber 592 must be maintained at a temperature of approximately 32° C. for the reagent and sample to react properly. For this purpose, a heater 611 and thermistor probe 612 are provided in the front block 506 of the UFC as shown in FIGS. 59 and 60. The cylindrical reaction chamber 592 is formed in the same manner as reaction chambers 590, 591, by machining semicircular cavities in mating acrylic layers of the UFC front block 506. After the layers (plates) are joined together forming the chamber 592, preferably by fusing, a cavity 613, shown in FIG. 59, is machined from an outside surface 615 of the bonded blocks. The cavity 613 defines a mounting surface 614 for mounting the heater 611. A center portion of the mounting surface 614 curves around the chamber 592, forming a thin wall of acrylic. For thermal efficiency, this wall is as thin as possible while maintaining sufficient strength. In a currently preferred embodiment, the wall between the heater 611 and the chamber 592 is about 0.7 mm thick, but may also be of any thickness that provides thermal transfer to the reaction chamber contents.

The heater 611, shown in cross section in FIG. 60, is a foil-type resistance heater. Such devices are available from various manufacturers. The heater is placed on the surface 614. A spacer block 616 having a concave curved surface 617 conforming to the curve of surface 614 and the thickness of the heater 611 is placed in the cavity 613, with the heater 611 sandwiched between the surface 617 of the spacer block and the surface 614 of the UFC. A passageway 618 is provided in the UFC 502 for heater leads 619. The thermistor probe 612 extending into the reaction chamber 592 is mounted in a passageway 621 in the UFC block.

The spacer block 616 is contained in the cavity 613 by the rear block 507 of the UFC 502, which is bolted through to the front block 506. Two compression springs 616A are placed behind the block 507 in order to maintain contact between the block, the foil heater 611 and the surface 614.

The reagent/sample inlet port 592A (not shown) in FIGS. 59, 60 for the BASO reaction chamber 592 is configured to provide an appropriate amount of mixing as the sample and reagent are pumped into the chamber. In a preferred embodiment, the chamber 592 is 8 mm in diameter and 23 mm in height and the port is angled 15° down and 15° from radial, and is 0.50 mm in diameter.

Figure 61:
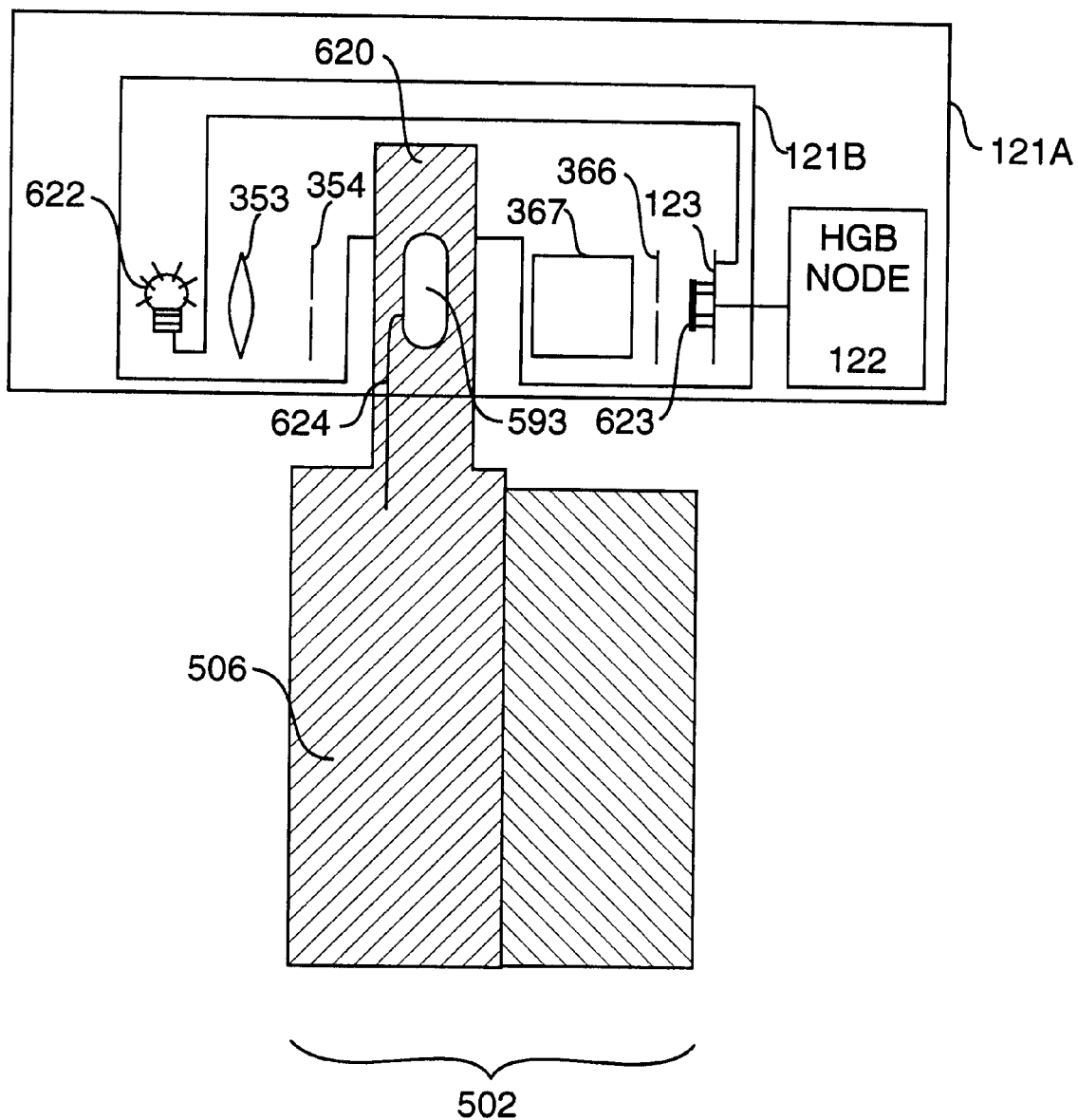
FIG. 61 is a sectional view of the HGB reaction chamber of FIG. 51 and the HGB calorimeter in accordance with an apparatus of the present invention.

The HGB reaction chamber 593 is located in an upper portion 620 of the UFC front block 506, as shown in FIGS. 49, 51 and in section in FIG. 61. The upper portion 620 is reduced in thickness relative to the lower portions of block 506 in order to provide access for the colorimeter 621 used in testing HGB. The cylindrical HGB reaction chamber 593 is formed in the same manner as reaction chambers 590, 591, 592, by machining semicircular cavities in mating acrylic layers of the UFC front block 506. A passageway 624 in the front block connects the HGB loop of the shear valve with the reaction chamber 593. Because the HGB reaction chamber 593 is an integral part of the UFC in the present invention, no separate tubing and valving is required, as was required in prior art instruments.

Figure 11A:
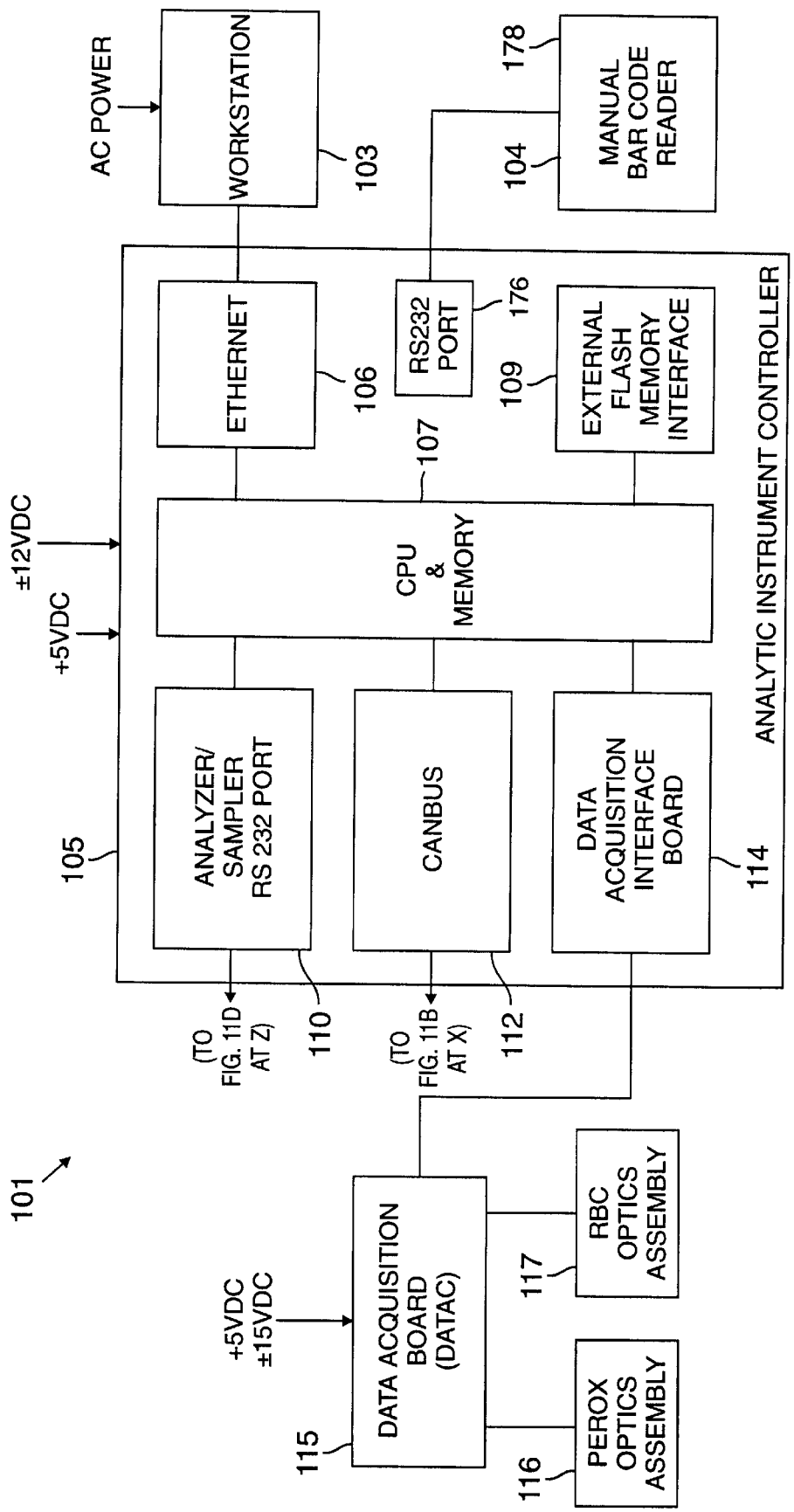
Figure 11B:
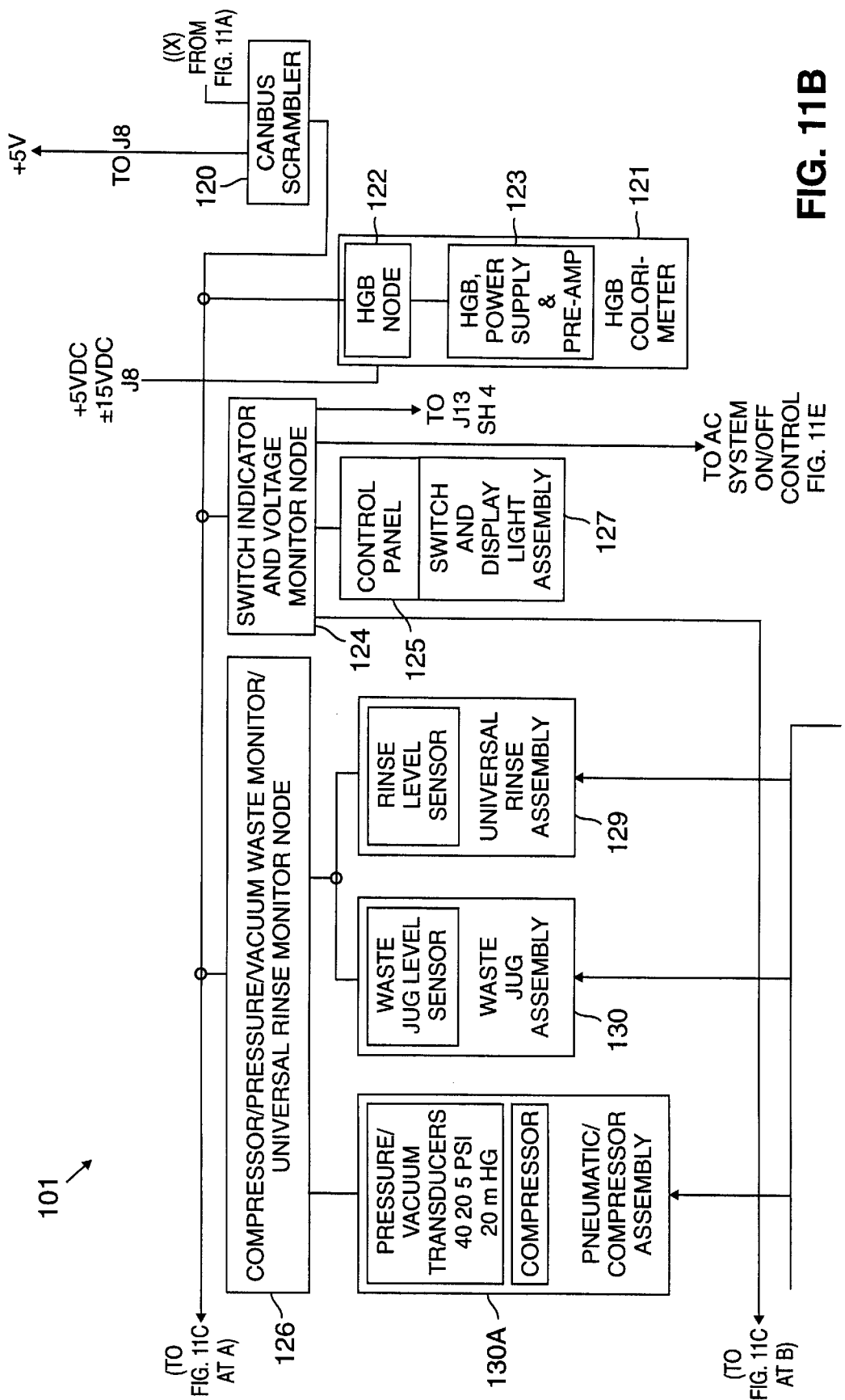

Colorimeter measurements are taken directly through the acrylic block 506 using a calorimeter assembly 121. With reference to FIGS. 11B, 51 and 61 the hemoglobin (HGB) calorimeter assembly 121 is described. The HGB calorimeter includes a reaction chamber 593 in the UFC 502, a light source 622, preferably 3.5 volt tungsten light source, an optical filter 367, and a photodetector 623 mounted on the circuit board 123. The lamp 622 is mounted in a housing 121A, more preferably in a metal casting 121B having fins (not shown) for dissipating heat generated by the lamp 622. The housing 121A is secured to UFC 502, with lamp 622 on one side of reaction chamber 593 and detector 623 on the other side.

Filter 367 is mounted inside housing 350 and operates to filter out effectively all wavelengths except that at approximately 546 nanometers. As a result, the light at 546±0.2 nanometers passes through. The NIST 930D filter set, absorbing 0.5A at 546 nanometers, may be used to provide the filtering operation.

An aperture 366 is interposed between the filter 367 and the photodiode 623. Lamp 622 is mounted so that there is a space 353 between the lamp and the reaction chamber 593. An aperture 354 is provided to limit the amount of light passing into the reaction chamber 593.

As is known in hemoglobin calorimeters, the 3.5 volt light source is driven by a stable 3.5 volt source. This may be achieved by any conventional circuitry, such as a differential amplifier using feedback. The lamp power supply circuit is preferably also on a circuit board 123, although it alternately may be mounted on a separate board also in housing 121A. Almost any stable power supply circuit may be used. One useful circuit uses a zener diode to provide a floating ground reference voltage, at 5.1V±10%, a second zener diode to provide a 2.5V reference at its anode, and a potentiometer to provide an adjustable portion of the 2.5V reference to the positive input of a differential amplifier. The potentiometer is used to set the 3.5 volts across the lamp 622. The output of the differential amplifier then drives the lamp 622 through an emitter-follower transistor.

The lamp voltage is then sensed by a second differential amplifier, referenced to the 2.5 volts source anode with a gain of 0.68, and applied to the negative input of the first differential amplifier via a resistor. The result is that the lamp voltage applied to lamp 622 remains at the level which causes the first differential amplifier inputs to be equal. A current sensing resistor and a transistor, coupled to the emitter follower transistor, are used to limit the output current to drive the lamp 622.

In operation, a blood sample to be analyzed and a reagent are injected in sequence into the reaction chamber. The injection causes mixing of the sequentially injected blood sample and reagent in the chamber. After a time period, which allows the reagent and blood sample to react and bubbles to rise out of the optical pathway, an optical absorption measurement is obtained from the photodetector 623.

The detection circuit on board 123, which preamplifies the photo-sensed signal, may be any circuit to convert the pin photo-diode current to a voltage for signal processing by the HGB node 122. One useful circuit includes a chopper stabilized operational amplifies that is operated in the transconductance made. This provides a low offset voltage and input bias (current, voltage). Using a PNP transistor connected in the emitter-follower configuration in the feedback loop of the operational amplifier will increase the driving capabilities of the operational amplifier. The base-emitter drop of the transistor is compensated for by the close loop again of the operational amplifier.

The output value of the photodetector output is then converted, based on the known lamp intensity at a 3.5 volt input, to a color measurement parameter using a look-up table of values, as is described elsewhere. The sensor 623 and related electronics are calibrated to account for the light transmission properties of the acrylic material of the UFC 502. From time to time a volume of rinse is pumped into the reaction chambers to provide a reference measurement for a HGB baseline reading.

The reagent/sample inlet port 624A (see FIG. 49) for the HGB reaction chamber 593 is configured to provide an appropriate amount of mixing as the sample and reagent are pumped into the chamber. In a preferred embodiment, the chamber 593 is 8 mm in diameter and 23 mm in height and the blood/reagent inlet port is angled 30° down and 10° from radial, and is 0.50 mm in diameter.

5. PEROX Chamber

Figure 50:
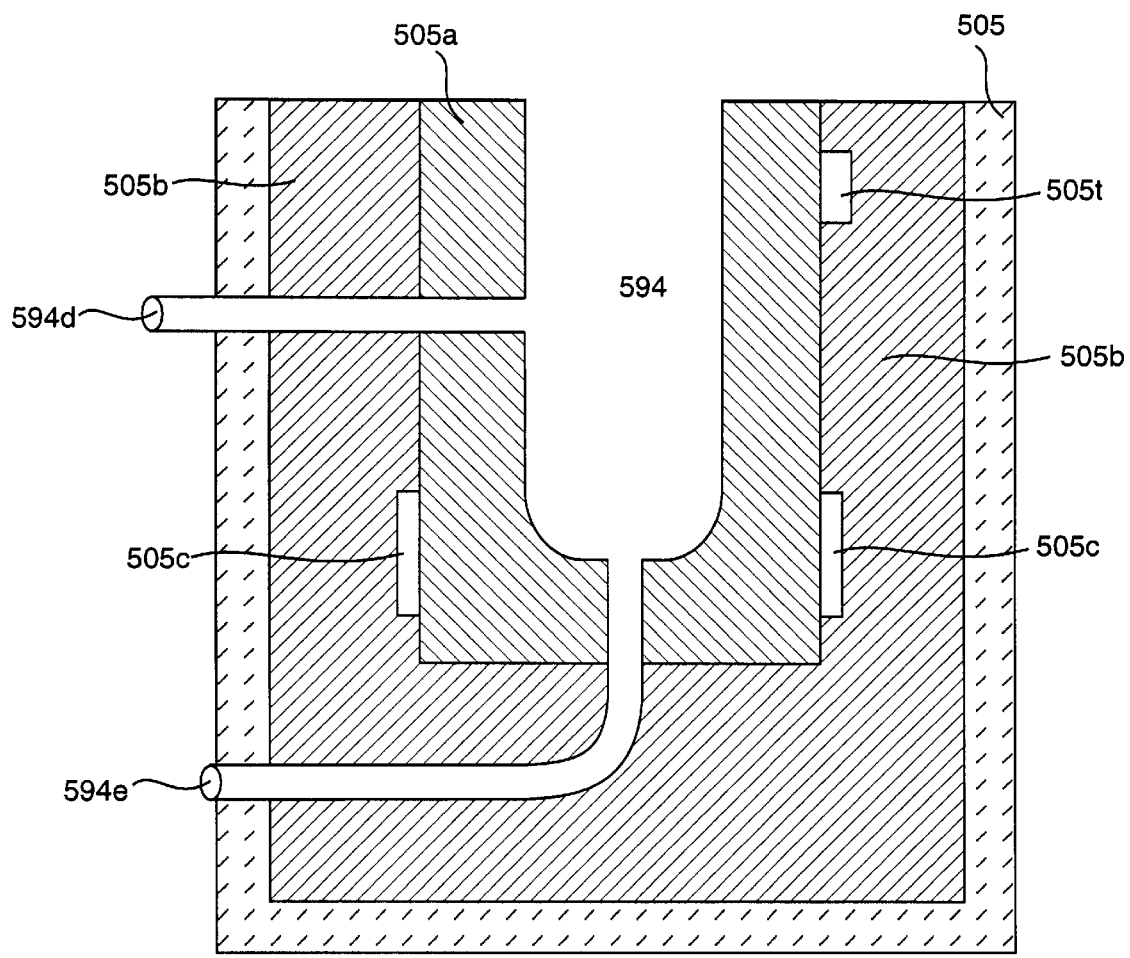
FIG. 50 is a partial cross sectional view of the PEROX reaction chamber of FIG. 49.

The perox reaction chamber 594, in a currently preferred embodiment, shown in FIGS. 49 and 50, is mounted within a separate housing 505 that is coupled to the unified fluid circuit. The reaction chamber 593 is a thermally conductive material 505a, e.g., a 316 stainless steel, around which a wire heater 505c is mounted, and which are secured in a suitably sized insulation material 505b inside housing 505. The perox chamber 594 has three input lines (not all are shown in FIG. 50): 594b for a reagent Dil 2 (125 $\mu$l), 594c for reagent Dil 1 and the blood sample aliquot from the shear valve 503 (250 $\mu$l), and 594d for another reagent Dil 3 (250 $\mu$l). It also has an input line 594a for a rinse, and an output line 594e to deliver the reacted mixture to the syringe pump for pumping through the flow cell 110a. The blood sample and reagents and diluents are thus injected into the stainless steel chamber 505b, and heated to the desired reaction temperature, e.g., atmosphere in the range of 60–75° C., for the time required to react the blood sample and the reagent, e.g., ten to twenty seconds. The perox reaction chamber 594 in housing 505 is mounted at the upper portion 620 of the UFC front plate 506, laterally displaced from the HGB reaction chamber 593. A temperature sensor 505t is used to monitor the temperature of reaction chamber 594.

In operation, the perox reaction chamber 594 can contain a reaction volume of approximately 1500 $\mu$l of which 250 $\mu$l are a first reagent Dil 1 and sample and 375 $\mu$l are the two reagents Dil 2 and Dil 3, forming a reaction mixture volume of 625 $\mu$l. The HGB and BASO reaction chambers 593 and 592 each can contain a reaction volume of approximately 1000 $\mu$l, of which 500 $\mu$l is the reagent and sample volume. The RBC and RETIC reaction chambers each can contain a reaction volume of approximately 2100 $\mu$l, of which 1250 $\mu$l is the combined reagent and sample volume. The total volume of each of the various reaction chambers is an arbitrary volume, selected only to be convenient to manufacture and contain the reaction mixture. One useful guideline is that the chamber volume is about twice the volume of reaction mixture.

Also shown in FIG. 51 are the VSC and EQUIL reaction chambers 590A and 590B. The VSC reaction chamber 590A is used for generating an evacuated chamber which, by selective control of valves, stores a vacuum. The stored vacuum is then used to draw a precise volume of a given reaction mixture, using appropriate valve control, out of a reaction chamber and into the vicinity of a syringe pump 842A. In this way, when the syringe pump 842A is actuated to draw a sample into it, it immediately draws a volume of reaction mixture rather than a rinse or reagent volume. This use of the VSC chamber and a vacuum/pressure storage is believed more accurate and reliable than actuating a valve and air pressure or vacuum directly, since the volume is not critically dependent on pressure, vacuum, or resistance. The VSC reaction chamber 590A has a diameter of 6.0 mm (internal diameter) and a length of 20 mm, and contains a volume of 511 $\mu$l. The EQUIL reaction chamber 590B has a diameter of 10 mm and a length of 27 mm, and contains a volume of 1859 $\mu$l. Thus, in the illustrated embodiment, the VSC chamber 590A is preferably used in connection with the PEROX optic flow cell 110A and the RBC/BASO/RETIC optic flow cell 110.

The EQUIL chamber 590B is used in connection with the closed tube manual sampler to vent closed tube samples, e.g. Becton-Dickinson product VACUTAINERS, as described in Uffenheimer U.S. Pat. Nos. 4,756,201, 4,799,393 and 4,811,611, which are incorporated herein by reference.

Referring again to FIG. 51, each of the lines (also referred to herein as tubes, flow paths, passages, and passageways in the context of pneumatic or hydraulic flow paths for fluids, air pressure or partial vacuum) in the UFC 502 are illustrated with a code letter as follows:

A is a passage having a depth 0.57 mm and a radius of 0.25 mm at the bottom of the passage; B is a passage having a depth 0.86 mm and a radius of 0.40 mm at the bottom of the passage; C is a passage having a diameter of 0.8 mm cut on both sides of the fuse plane; D is a passage having a depth 3.6 mm and a radius of 2.0 mm at the bottom of the passage; E is a passage having a depth 1.4 mm and a radius of 0.5 mm at the bottom of the passage; F is a passage having a depth 0.45 mm and a radius of 0.25 mm at the bottom of the passage; G is a passage having a depth 1.85 mm and a radius of 0.75 mm at the bottom of the passage.

These dimensions are suitable for use in the unified fluid circuit of the present, invention, but are not the only possible suitable dimensions. It is important to use dimensions that provide adequate flow and result in minimal clogging of the lines, and allow adequate mixing of the blood samples and reagents.

In constructing the UFC 502, it is constructed of clear, fully normalized cast acrylic, preferably of the best commercial grade available, such that all of the fluid carrying surfaces are polished to a 0.2 micrometer finish, the area of the HGB reaction chamber 593 is polished optically clear, and the remainder of the surface of the UFC 502 is polished transparently clear. The area proximate to the shear valve 503 is preferably polished to have a flatness of 20 lightband (fringe) and a 0.2 micrometer finish, and the remainder of the UFC is polished to have a flatness of less than 40 lightband (fringe) over a 50 mm×50 mm area.

C. Perox Optical System

Referring to FIGS. 10A, 10B, 11A–11D, 15 and 37, the PEROX Optical System 116 in accordance with the present invention is illustrated. The PEROX optical System is used in what is now a conventional manner to identify five types of white blood cells. The cell types are eosinophils, neutrophils, lymphocytes, monocytes, and large unstained cells.

The PEROX Optical System 116 includes an illuminator assembly 381, a flow cell 110A and an optical detector assembly 394. The illumination assembly 381 includes a light source 379, preferably a 10 watt tungsten halogen lamp operating at a 5 volt, 2 amp level, and beam optics suitable for focusing a portion of the lamp output onto flow cell 110A. The illuminator assembly 381 also includes a housing 395, which filters out extraneous light, and a mounting block 380 at the lamp end for containing some of the beam optic components. Light that is emitted by lamp 379 is passed through, in sequence, a condenser lens 382, a precision slit aperture 383, a precision circular aperture 384a, and a projector lens 384 which focuses the beam onto the flow cell 110A to interrogate the sample (the particulate suspension entrained in a sheath flow) passing through the flow path in the flow cell 110A.

Figure 10A:
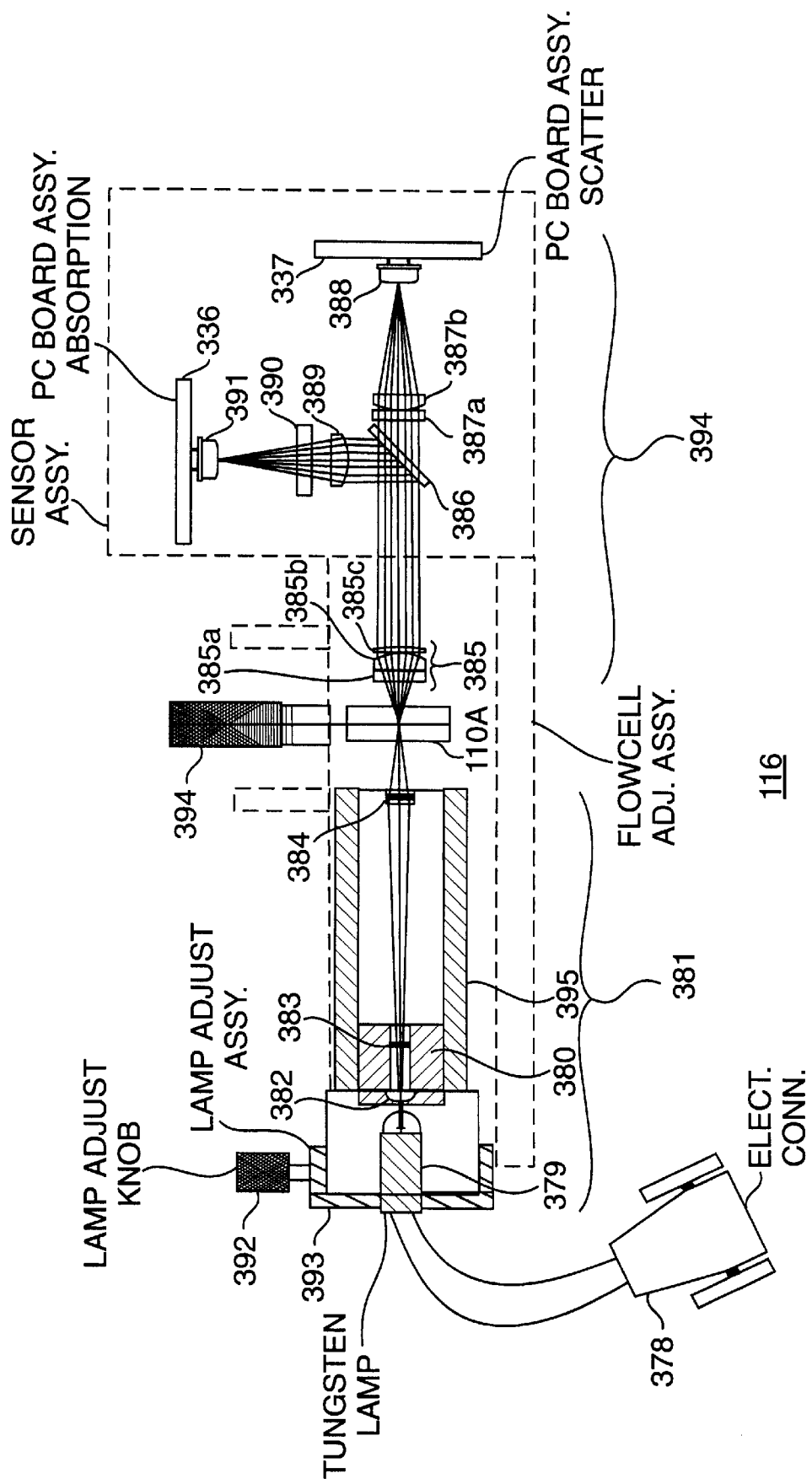
FIGS. 10A and 10B are schematic diagrams of a lamp optical bench and detectors for use in a peroxidase optical channel in a device in accordance with the present invention.
Figure 10B:
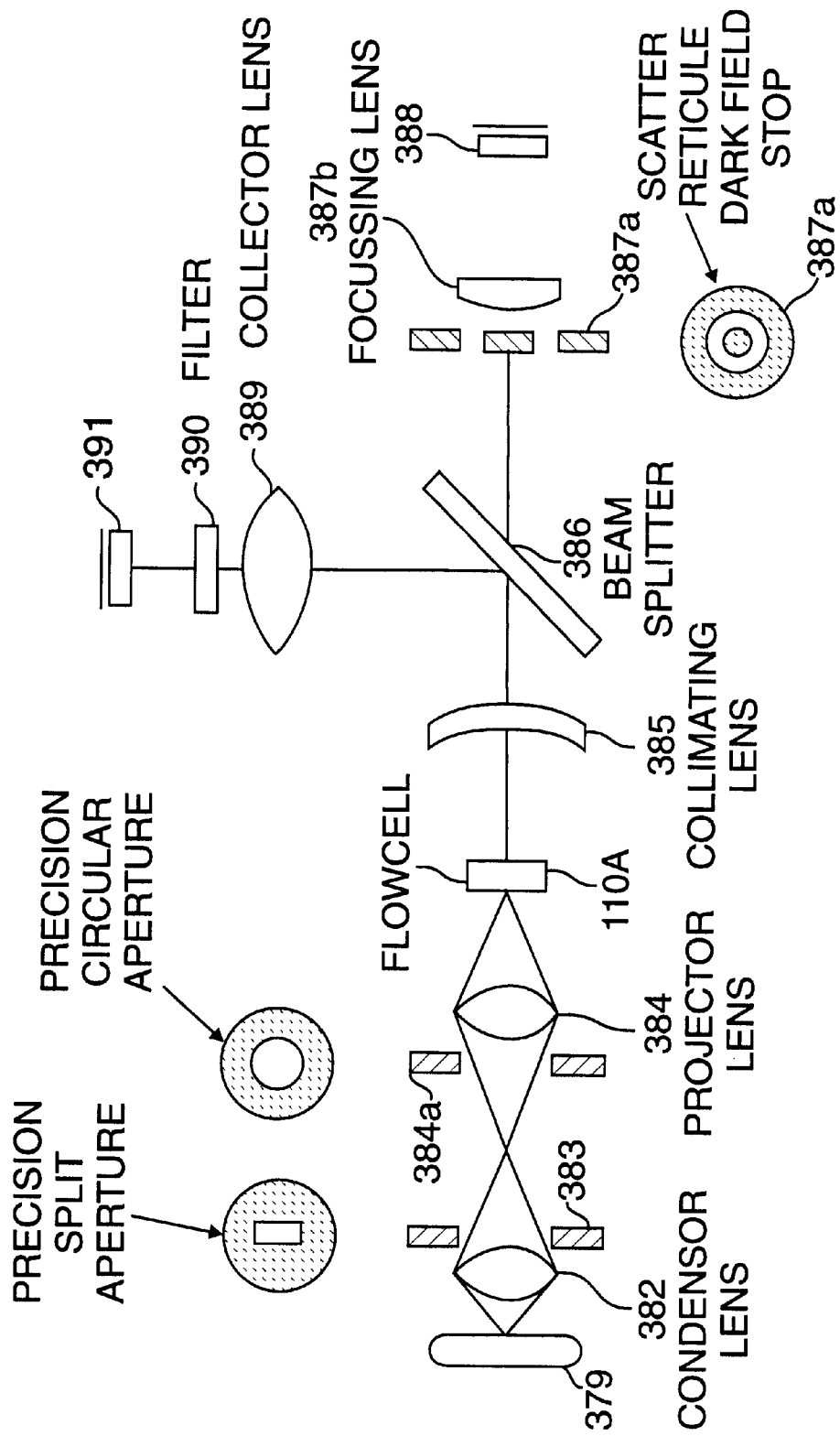

As illustrated in FIG. 10B, the precision slit aperture, which is also shown in an exploded front plan view, is a rectangular slit having a major axis perpendicular to the flow path. The apertures are positioned so as to shape the beam and eliminate extraneous scattered light. Thus, the shaped beam is passed through the flow cell 110A such that the light is scattered and absorbed by cells passing through the flow cell 110A. Flow cell 110A preferably has the same construction as described in connection with flow cell 110 of the RBC/PLT optics 117 below. After passing through the flow cell 11A, the passed light is processed by the detector system 394 to obtain a scatter signal 337 and an absorption signal 336 (See FIG. 15). The detector system 394 includes a collimating lens 385 (preferably a 3 lens system having an objective lens 385a, a collecting lens 385b, and a collimating lens 385c). The collimating lens 385 forms a relatively straight collimated beam which is then divided by a beam splitter 386 into two portions. Beam splitter 386 is preferably a partially reflecting mirror which diverts a portion of the light to an absorption leg and passes the remainder to a scatter leg. The scatter leg includes a transparent reticule having an opaque dark field stop in the center to block the main axis beam and an opaque outer portion leaving a transparent annular aperture through which the scattered light passes through to a focusing lens 387b. The focusing lens 387b focuses the scattered light onto a photodetector 388, preferably a pin current photodiode. The absorption leg receives the beam from the beam splitter 386, passes it through a lens 389, which is then passed through a spectral filter 390 to divide spectrum into two parts and passes only the blue light (smaller than 700 nm), and detected by the photodiode 391, preferably a pin current photodiode. The output of photodiode 388, after low-gain preamplification, is the scatter signal 337. The output of photodiode 391, after low-gain preamplification, is the absorption signal 336. As illustrated in FIGS. 10A and 10B, the absorption photodiode 391 and scatter photodiode 388 are mounted on separate circuit boards.

As illustrated in FIG. 10A, the tungsten lamp 379 is preferably aligned horizontally in a lamp adjust assembly 393, which has an adjusting knob 392 to position the lamp 379 relative to the beam axis of the illumination assembly 381. Because the lamp 379 does not produce a collimated laser beam, as in the case of the laser beam optic system 117, the alignment is not so critical as it is in the other case and micrometer adjustments are not required. Nevertheless, it is necessary to align the several optical components and the flow cell 110A in either the conventional manner, wherein the optical component adjusting mechanisms are permanently mounted to the PEROX Optical System 116, or wherein the component adjusting tools are removably mounted to the PEROX Optic System 116 for alignment at the factory, so that each can be removed when the assembly is installed in a flow cytometer instrument. This latter technique is discussed further below in connection with the REC optics assembly 117.

The electrical connection 378 for lamp 379 is coupled to the Parallel Node 140. Thus, operation of the PEROX Optic system 116, for operating the lamp and providing power to the printed circuit boards on which the photodiodes 391 and 388 are respectively mounted, is controlled through the Parallel Node 140.

Preferably, the same PEROX Optical System that is used in the commercial Bayer Model H*3 Systems clinical hematology instrument may be used in the present invention.

D. Laser Optics and Detection System

The instrument of the present invention includes a laser optical system for use in the RBC, BASO and RETIC methods. A schematic of the laser optical system is shown in FIG. 1. The optical system 100 comprises a flow cell 110 having a channel through which a thin stream of suspended particles, such as blood cells, is passed for analysis, an illuminator assembly 130 (not shown in detail in FIG. 1) for delivering a filtered, collimated and shaped laser beam B to the flow cell 110, and a detector system 164 for measuring light in response to the beam B being scattered and absorbed by the cells.

The flow cell 110 presents suspended cells or other particles essentially one at a time in a stream positioned for optical access by the illuminator assembly 130 and the detector system 164. The cell suspension is introduced through a nozzle into the center of a laminar flow stream of a sheath liquid. The flow velocity of the sheath liquid is controlled to be greater than the velocity of the introduced cell suspension. This causes the cross sectional area of the suspension stream to narrow as it accelerates to the velocity of the sheath liquid, as is well known. The cross section of the cell suspension stream is further narrowed by passing the sheath liquid containing the cell suspension through a gradually reduced cross sectional area. At the point 119 where the laser beam B is impinged on (i.e., intersects to illuminate or interrogate) the cell suspension stream, the diameter of the stream is on the order of the diameter of a cell, so that two cells cannot easily travel side-by-side in the stream.

At least in the region where the laser beam B is impinged on the cell suspension stream, the flow cell 110 is constructed of an optically transmissive material, preferably glass. The sheath liquid must be optically transmissive as well, in order to permit the laser beam B to travel from the illuminator assembly 130 to and through the cell suspension with adequate intensity to permit the scattered and nonscattered laser light to be detected.

Figure 2:
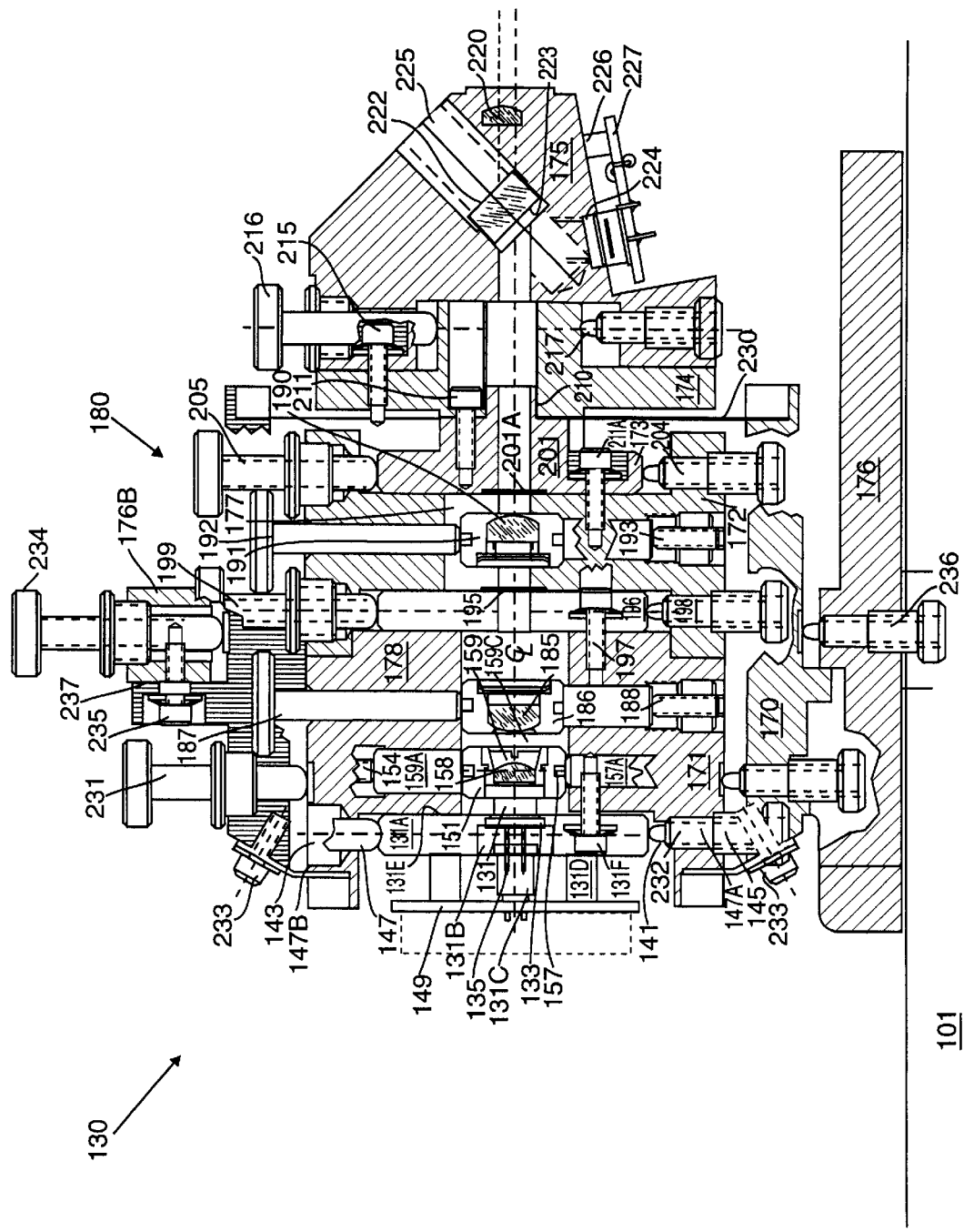
FIG. 2 is a diagram of the illuminator assembly of FIG. 1 in accordance with a first embodiment.

The illuminator assembly 130 of the present invention is shown in FIG. 1 and, in one embodiment, in partial cross section in FIG. 2. It is noted that some of the components used for positioning certain components in a direction perpendicular to the plane of the view of FIG. 2 are illustrated in a position that is rotated 90° from their actual orientation, for clarity of presentation. The illuminator provides a spatially filtered laser image that is focused on the cell stream. The size of the image in a direction parallel to the cell suspension stream is on the order of the diameter of a cell, so that two cells cannot easily pass within the image concurrently.

With reference to the embodiment shown in FIG. 2, the illuminator assembly 130 is constructed in a modular fashion to permit precise, permanent alignment of each optical component as it is installed during assembly. The assembly 130 comprises an illuminator housing 170, and first, second, third, fourth and fifth illuminator optical component carriers 171, 172, 173, 174, 175 mounted as a unit within the illuminator housing. The illuminator housing 170 is mounted within an illuminator mounting ring 176B, which is adjustably mounted to an optical bench 101.

A laser beam source 131 is mounted in a laser source mounting plate 131A. In a preferred embodiment, the laser beam source is a semiconductor laser device, more preferably, a laser diode, such as a 10 mw, 670 nm, InGaAlP laser diode such as Model No. TOLD-9225(S) manufactured by Toshiba. As illustrated in FIG. 2, the laser diode 131 is mounted in a central bore 133 in the mounting plate 131A, and is retained in the plate by a threaded backing plug 131B. Leads 131G pass from the diode 131 through the backing plug 131B and are connected using a connector 131C to the laser diode driver printed circuit board 149 (see FIG. 15 and the related discussion of the laser diode driver circuit). The printed circuit board 149 is bolted to the back of the laser source mounting plate 131A by mount 131D.

The laser source mounting plate 131A is mounted to a plate mounting surface 131E of the first illuminator carrier 171, using locking screws 131F, only one of which is shown. A gap 141 around the periphery of the mounting plate 131A is provided so that the position of the plate 131A can be adjusted by sliding the plate on the mounting surface 131E before tightening the screws 131F.

To further provide for adjustment, holes having extra clearance are provided in the plate 131A for the locking screws 131F. A removable micrometer adjuster 147B, such as a Daedal Cat. # SPDR 1137 micrometer screw, is provided to precisely adjust the location of the plate 131A before tightening the screws 131F. A nut 143 with coarse external threads is first inserted into the threaded hole provided in the first carrier 171. A finely threaded micrometer screw 147 is preinstalled in the nut. A spring-loaded plunger 147A and nut 145 are mounted in a threaded hole opposite the micrometer screw. The micrometer screw 147 and the plunger 144 contact the outer periphery of the laser mounting plate 131A. The position of the plate on the face 131E can be finely adjusted by turning the micrometer screw 147 against the force of the spring loaded plunger 147A, which eliminates back-lash. After the plate 131A is correctly positioned on the mounting surface 131E of carrier 171, the screws 131F are tightened to lock the plate in place. A similar micrometer screw and plunger (not shown) are oriented 90° to the micrometer screw 147 for adjustment in that direction. This achieves an x-y positioning (also called a decentering) of the component relative to a "z" axis which is (or is eventually aligned to be) the optical beam path. The micrometer screw 147 and nut 143, and the spring loaded plunger 147A and nut 145, are removed after tightening the screws 131F. These components may then be reused to assemble another illuminator assembly.

An aspheric collimating lens 158 for collimating the naturally diverging beam emitted by the laser diode 131 is placed in the beam path near the laser diode. The collimating lens 158 is mounted in a bore in a mounting cylinder 151 using a retaining nut 159. The mounting cylinder 151 is placed in a central bore 159C of the first carrier 171. The mounting cylinder 151 fits closely within the central bore 159C so that no further positioning of the collimating lens 158 in the radial direction is required. A focusing tool 157A is placed in another bore provided in the carrier 171 so that an eccentric engaging pin 157 engages a groove in the periphery of the mounting cylinder 151. The axial position (i.e., in the z direction) of the mounting cylinder 151 in the central bore 159C may be adjusted by rotating the focusing tool 157A in the bore, causing the engaging pin 157 to revolve eccentrically in the groove. After the collimating lens 158 is properly positioned, a locking screw 159B is turned to compress a dowel 159A against the mounting cylinder 151, locking it in place in the bore 159C. After tightening the screw 159B, the focusing tool 157A may be removed and reused in assembling another illuminator assembly.

Optionally, a spatial filter 130 is used to remove unwanted spatial frequencies from the now collimated beam, producing a beam with a Gaussian intensity distribution. The spatial filter comprises an objective lens 185, a collimating lens 190, and a filter aperture plate 195 interposed between the objective and collimating lenses. The objective lens 185 is mounted in a bore in a mounting cylinder 186. The mounting cylinder 186 is positioned and locked in the central bore 159C of the first carrier 171 in the same manner as the mounting cylinder 151, using a focusing tool 187 and locking screw 188.

The second carrier 172 is mounted to the first carrier 171 using bolts (not shown). A pilot shoulder 178 is used to align the first and second carriers. The collimating lens 190 is mounted in a bore in a mounting cylinder 191, which is aligned and locked in the central bore 177 of the second carrier 172 in the same manner as the mounting cylinder 151, using a focusing tool 192 and locking screw 193.

The spatial filter aperture plate 195 is preferably a thin metal disk having a non-reflective coating and a central precision aperture, in this example a rectangle that is approximately 14 $\mu$m×32 $\mu$m. The aperture plate 195 is attached to a mounting plate 196 using an adhesive, preferably an epoxy. The mounting plate 196 is mounted to the first carrier 171 using screws 197 (only one shown). The mounting plate 196 is aligned in the x-y direction in the same manner as the laser mounting plate 131A, using two pairs of removable micrometer adjusters 199 and spring loaded plungers 198 (only one pair shown), which are mounted in orthogonal axes in the second carrier 172, and which may be removed after tightening the screws 197.

The laser image is then masked by a beam shaping aperture plate 201A, preferably formed from a thin sheet of metal having a nonreflective coating and an aperture, in this example a rectangle that is approximately 446 $\mu$m×120 $\mu$m. The aperture plate 201A is preferably attached to the third carrier 173 using an adhesive, such as epoxy. The third carrier 173 is mounted to the second carrier 171 using screws 211A (only one shown). The third carrier 173 is aligned in the same manner as the laser mounting plate 131A, using two pairs of removable micrometer adjusters 205 and spring loaded plungers 204 (again, only one pair is shown), which are mounted in the second carrier 172, and which may be removed after tightening the screws 211A. A fourth carrier 174 is aligned to the third carrier 173 using pilot diameter 210, and bolted to the third carrier using bolts 211. Preferably, the spatial filter components are aligned in the x-y directions in an out-of-focus condition. This provides a larger laser beam dimension that makes it easier to align the components than in the case where the spatial filter is focused (adjusted in the z direction) and hence would provide a smaller dimensional beam.

A beam sampler 222 is mounted in an angled bore 225 of the fifth carrier 175. The fifth carrier is mounted to the fourth carrier 174 using screws 215 (only one shown). The fifth carrier 175 is aligned in the same manner as the laser mounting plate 131A, using two pairs of removable micrometer screws 216 and spring loaded plungers 217, which are orthogonally mounted in the fifth carrier 175 (only one pair is shown), and which may be removed after tightening the screws 215 for reuse.

The beam sampler 222 functions to reflect a portion of the laser beam to obtain a reference beam to monitor its intensity for use by a difference circuit in analyzing the blood cells as described below. The beam sampler 222 has a partially reflective surface 223 for reflecting a portion of the beam onto a reference detector 224, such as a photodiode. In a useful embodiment of the invention, 20% of the beam is reflected. The reference detector is mounted on a reference detector preamp board 227, which is attached to the fifth carrier 175 through mounts 226. The reference detector 224 measures random fluctuations in beam strength inherent in the laser source 131. This information is sampled by the reference detector preamp board 227 and is used to compensate measurements of beam absorption made by the detector system 164.

By sampling the beam after it has been filtered by the spatial filter 130 and clipped by the beam shaping aperture plate 201A, only those random power fluctuations affecting the beam as it is imaged in the flow cell 110 are measured. Fluctuations affecting only those portions of the beam that are filtered or masked by the aperture plates 195, 201A are, therefore, ignored by the difference circuit. This results in a more precise compensation for the absorption measurement.

The remaining portion of the beam is transmitted through the beam sampler 222, and is axially shifted slightly by refraction. The beam passes into an illuminator lens 220, which is mounted in a central bore in the fifth carrier 175. The laser beam image is thus focused by the illuminator lens 220 on the cell suspension stream. A third beam shaping aperture 220A is interposed between lens 2.20 and beam sampler 222, to shape the laser beam entering lens 220.

A flexure 230 constructed of sheet metal such as spring steel is mounted between the third and fourth carriers 1.73, 174 and is connected to the illuminator housing 170. The flexure, in conjunction with the micrometer adjuster 231 and spring loaded plunger 232, provide an angular adjustment of the carrier assembly 171–175 with respect to the housing. Turning the micrometer adjuster 231 finely adjusts the angle of the carrier assembly 171–175 as the flexure 230 deflects. After screws 233 are tightened to lock the carrier assembly in place in the housing, the micrometer adjuster 231 and plunger 232 can be removed and reused to assemble another illuminator.

The illuminator housing 170 is mounted to the illuminator mounting ring 176B on an annular face 237. The position of the illuminator housing on the annular face of the illuminator mounting ring is adjusted using micrometer adjuster 234 and plunger 236. The position is locked by screws 235 (one shown), after which the micrometer adjuster and plunger may be removed and reused.

To manufacture the illuminator assembly 130, the optical components are preferably aligned and assembled in the order and manner described above. The micrometer adjusters (and opposing spring plungers) and focusing tools facilitate precise positioning of each component before it is locked in place. After locking in place, micrometer adjusting tools (and plungers) are removed from the assembled structures. It should also be understood that the various micrometers can be adjusted, such that all of the optical components are properly oriented and then locked in place by the mounting screws, after which the micrometers are removed.

The micrometer adjusters, spring loaded plungers and eccentric focusing tools are optimally standardized throughout the illuminator, thereby reducing the number of parts that must be purchased and inventoried for use in the manufacturing process. Because these parts are reused at the factory, extremely high precision tools may be used and yet the materials costs of the illuminator produced are substantially reduced. Moreover, this manufacturing technique yields a reduced cost such that an illuminator installed in a machine requiring service can be more efficiently replaced with a prealigned assembly from the factory and the assembly requiring service can be returned to the factory for service. It should be understood that the term factory as used herein encompassing both original manufacture and a location where out-of-alignment assemblies are realigned, e.g., a service establishment, repair van and the like. It also should be understood that adjusting devices other than eccentric focussing tools may be used to move the components which need to be focussed in the z direction in the beam path, and that the term focussing tools is construed so as to include such devices within its definition. It also should be understood that the terms "micrometer adjusters", "spring plungers" and "focussing tools" as used herein include the various fittings (pushrods, nuts, threaded connections, etc.), which also may be removable, to secure them removably to the components for adjusting the illuminator components.

Figure 2A:
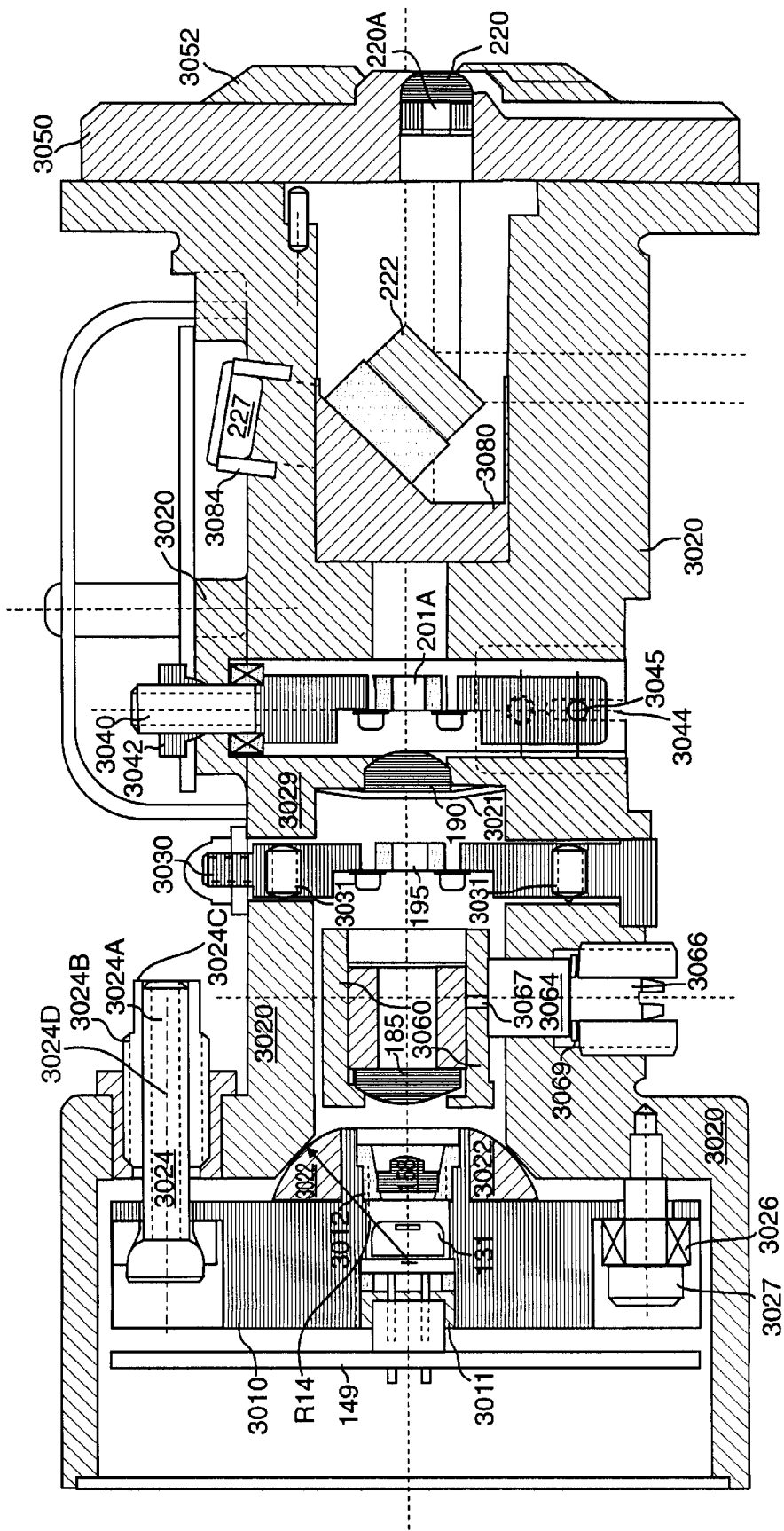
FIG. 2A is a schematic diagram of an illuminator assembly of FIG. 1 in accordance with the second embodiment.

An alternative structure and method of alignment of the illuminator assembly is shown with reference to FIGS. 2A to 2J. In this alternative embodiment, illuminator assembly 130 includes a laser diode subassembly 3010, a housing assembly 3020 and a focusing lens assembly 3050. The housing assembly 3020 also receives a first subassembly 3030 containing the spatial filter aperture 195 and a second subassembly containing the beam shaping aperture 201A. Referring to FIG. 2A the laser diode 131 is mounted on circuit board 149 and mounted to housing 3010 in a spacer member 3011 in a fixed relation. The collimating lens 158 also is mounted to housing 3010 in a retaining ring 3012 precisely spaced from laser diode 131 by a pre-determined distance and orientation so to output a columnated laser beam B. The laser diode 131 and lens 158 are thus pre-focused using a conventional screw arrangement and form an integrated subassembly.

Figure 2B:
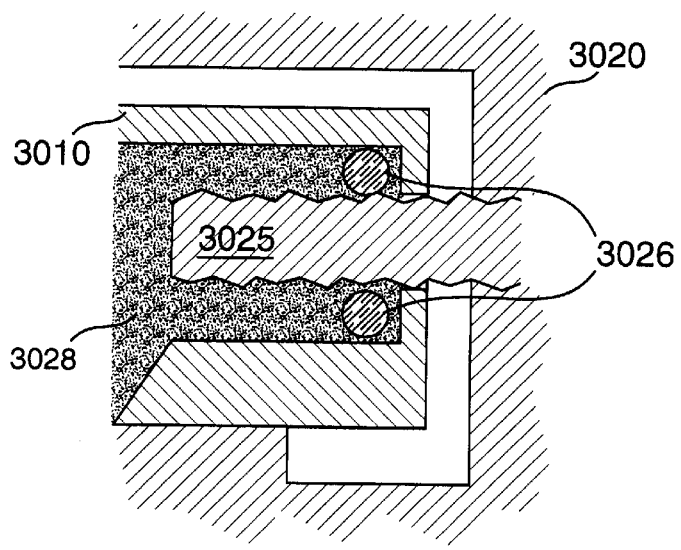
FIG. 2B is a partial side sectional view of the locking screw system of the assembly of FIG. 2A.

Housing 3010 includes a ring 3022 having a spherical segment for contacting a countersunk aperture on housing 3020. This spherical surface is measured from a radius R14, originating approximately from the laser diode 131 as illustrated in FIG. 2A. The precise radius is not significant so long as there is essentially a point (more specifically elliptical) contact with the opposing countersunk (preferably a conical or frustroconical) surface of housing 3020. The laser diode assembly 3010 is then coupled to housing 3020 by a set of two orthogonal differential screws, 3024 which are used to adjust the laser beam axis output from lens 158. The differential screws 3024, of which one is shown in FIG. 2A has two concentric screw threads with pitches 3024A and 3024B that are different from each other. Rotating the differential screw 3024C produces a fine adjustment of the beam axis, whose granularity of adjustment equals the difference between the two threaded pitches 3024A and 3024B. Rotating the mating screw 3024D which engages the inner threaded pitch 3024A of the differential screw 3024 produces a coarse adjustment of the beam axis with a granularity equal to the threaded pitch 3024A. Thus, the tilt of the spherical surface 3022 is adjusted relative to the axis of housing 3020. This is a conventional structure and uses a screw head 3024D for the gross adjustment and a hex head 3024C for the fine adjustment. The two orthogonal differential screws 3024 are thus used to orient the laser diode assembly 3010 to have a common optical axis with the optical components of the illuminator assembly 130. Once the laser diode axis has been appropriately adjusted, a set screw between the housing 3020, and the laser diode assembly housing 3010 as shown in FIG. 2B, and the housing area 3028 is filled with epoxy, e.g., 3M brand epoxy EC2216, to set the laser diode beam axis. An o-ring 3026 is inserted around the set screw 3025 in the area 3028 to form a seal and maintain the set screw potted in the epoxy. Each differential screw 3024 operates against a tension force exerted by a stack of Belleville washers 3026 between a screw 3027 and housing 3020, which serve to maintain a counter force on the differential screw 3024 to maintain the spherical surface 3022 in point contact with housing 3020.

Figure 2C:
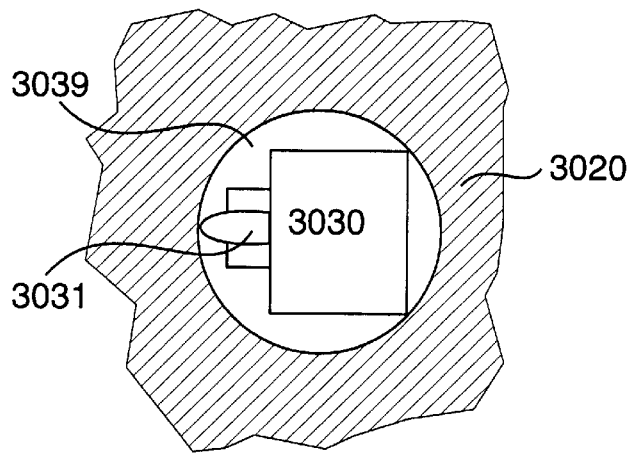
FIG. 2C is a top sectional view of the aperture assembly of the spatial filter of FIG. 2A.

With reference to housing 3020, it includes a cylindrical passageway or bore through its interior, and has a shoulder 3029 against which the collector lens 190 of the spatial filter is urged. The lens 190 is mounted securely and held in place by a spring washer 3021, which may be a Belleville washer or a variation thereof. Lens 190 is mounted in the housing in a fixed orientation, for which there typically is no adjustment. The objective lens 185 of the spatial filter and the aperture 195 of the spatial filter are inserted within housing 3020. The aperture 195 is inserted in a sub-assembly 3030, which is preferably provided with a rectangular cross-section and is inserted into a cylindrical aperture 3039 traversing the housing 3020 and intercepting the beam axis. With reference to FIG. 2C, a top view of the sub-assembly 3030 for the aperture 195 inserted in housing 3020, it is seen that the corners of the aperture assembly 3030 are urged against the cylindrical wall of housing 3020 by a vleer ball spring plunger 3031, which forces the aperture 195 against the bore against which it is inserted. The pair of vleer ball spring plungers 3032 thus serve to seat kinematically sub-assembly 3030 the precision drilled bore in housing 3020.

Figure 2F:
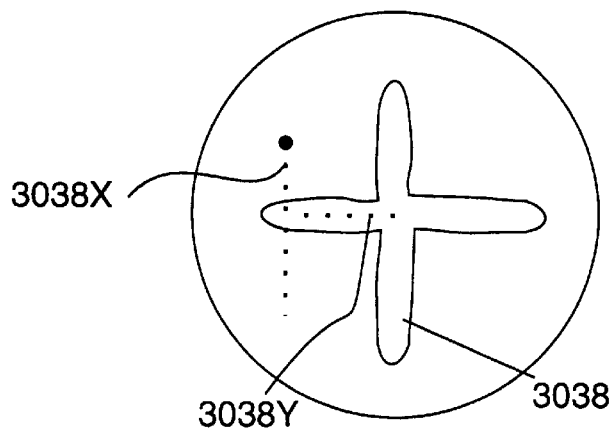
FIG. 2F is a front view of a locating aperture for use in the assembly of FIG. 2A.

The aperture 195 is thus a removable structure which advantageously allows for the insertion of a locator aperture 3038, which is a tool that is temporarily used for purposes of aligning the laser diode beam using the differential screws 3024 as previously discussed and then removed. Referring to FIG. 2F the locator aperture 3038 is illustrated as a cross having a dimension that permits locating the precise center. The aperture 195 has a small hole such that it is difficult to see light passing through the hole, even when it is held up to a bright light. The use of the locator aperture 3038 permits adjusting the beam orientation to traverse one leg of the cross so that the beam passes through and can be detected down stream of the aperture 3038. This is illustrated with a vertical line 3038X on FIG. 2F. Once the beam is centered in the one leg, it then can be translated to the center of the cross, corresponding to the center of aperture 195, as illustrated by the dashed line 3038Y. In this manner, the laser diode beam can be adjusted in two dimensions and the center of aperture 3038 located. This is believed to be easier than simply trying to de-focus the laser beam and locate the center by progressively focusing the laser beam and adjusting the tilt to maintain a beam passing through aperture 195. It is to be noted, however, that this de-focusing technique also may be used in place of inserting a separate locator aperture 3038.

The objective lens 185 of the spatial filter is mounted on a cylinder 3060, which is adapted for moving along the beam axis to focus the laser beam onto the aperture 195. With reference to cylinder 3060, it is machined with a first radius R1 giving it a generally cylindrical structure of which a portion is machined at a second and larger radius R2, off centered from radius R1. The result is an arc 3062 which provides the cylinder 3060 with two line contacts or rails which are engaged against the bore of housing 3020 by an eccentric mechanism. The eccentric mechanism, described below, moves the cylinder 3060 along the rails and hence the beam axis to focus the collector lens 185 of the spacial filter. In this regard, the collector lens 185 is mounted onto cylinder 3060 in a fixed relationship. The cylinder 3060 is provided with a kinematic support in the two line contacts that permit it to translate along the beam axis without wobbling in or about a plane orthogonal to the beam axis.

Figure 2D:
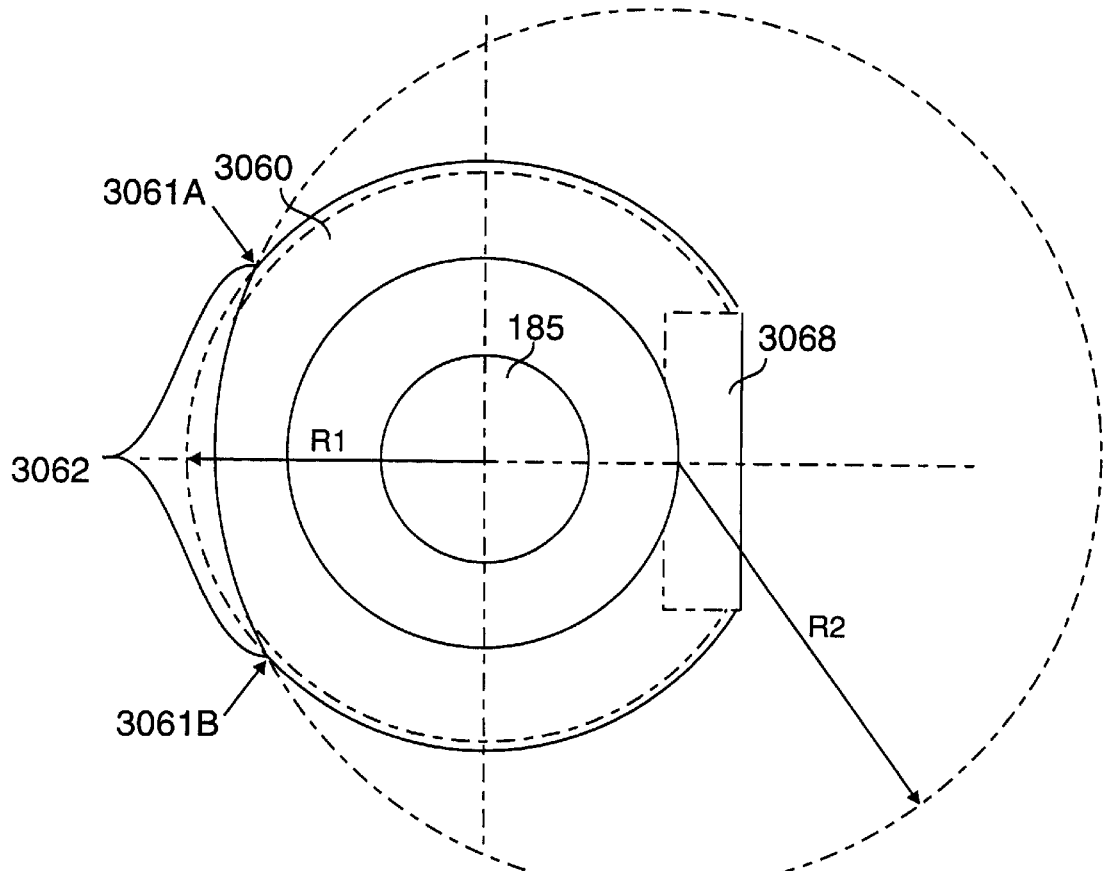
FIGS. 2D and 2E are an end view and a side view of the spatial filter focussing assembly of FIG. 2A.
Figure 2E:
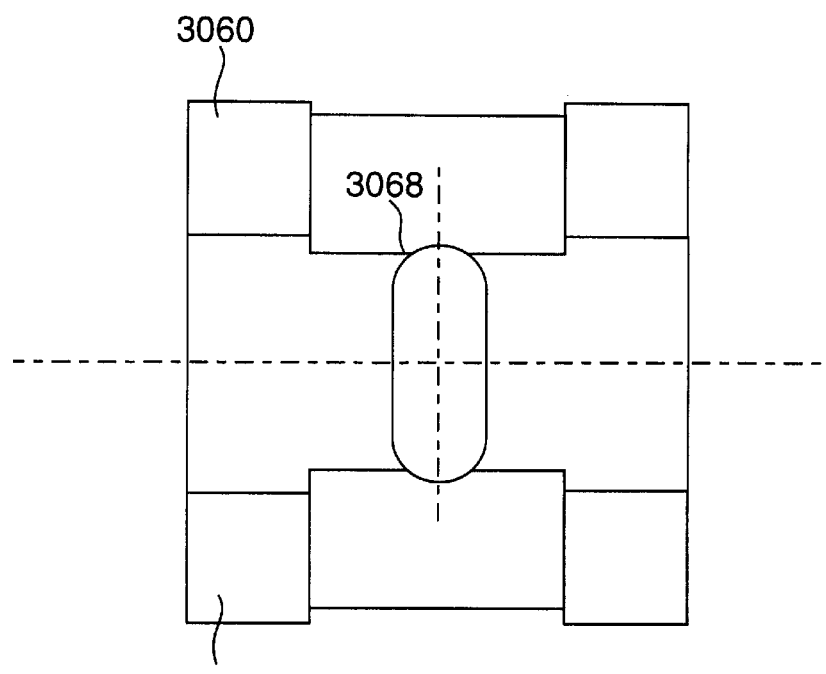

The translation is obtained by an eccentric 3064 which is adjusted by a screw 3066 that rotates a pin 3067 about an axis on the eccentric 3064. Referring to FIGS. 2D and 2E, the pin 3067 is engaged in a slot 3068, such that as the pin 3067 rotates about the eccentric 3064 axis, the pin will move in the slot 3068 and cause the cylinder 3060 to translate linearly along the beam axis. The adjusting screw 3066 is secured in a housing with a Belleville washer 3069 that urges the eccentric 3064 in contact with the cylinder 3060 and maintains the two rails, indicated by arrows 3061A and 3061B on FIG. 2D, against the interior of housing 3060. This provides a smooth action of the housing as the eccentric is rotated and prevents the lens from wobbling, more specifically maintaining the lens in a plane perpendicular to the beam axis as the cylinder 3060 is focused by movement of eccentric 3064 and pin 3067.

Referring to FIG. 2A, beam shaping aperture 201A is mounted securely in an adjustable frame 3040 that is coupled to housing 3020 by means of a oval head screw 3042. The oval head screw has an elastic stop nut 3043. The oval head screw 3042 is mounted against a countersunk aperture in housing 3020 in a way that will permit it, and thus frame 3040, to pivot about in a center in three degrees of freedom. The dome head screw 3042 has a substantially spherical surface to locate against the countersunk hole in housing 3020. The frame or aperture assembly 3040 includes two set screws that are used to control the pivoting of the assembly 3040 about the dome head sphere. Each set screw causes the assembly 3040 to pivot about a small arc so that aperture 201A can be centered on the beam axis. A retaining pin 3045 is used to keep the assembly 3040 from rotating. The pin engages a groove 3044 which allows the assembly 3040 to move, but does not allow it to rotate.

The beam sampler assembly 222 is located in a mount 3080 secured to housing 3020, such that it reflects a portion and refracts the remainder of the laser beam. As a result, the beam passing through sampler 222 is to be offset relative to the beam output by the laser diode as indicated in FIG. 2A.

A reference photodiode 227 is located above beam sampler 222 in a mount 3084 secured to housing 3020. These elements 222 and 227 remain fixed in place.

Regarding the focusing lens 220, it is mounted in an assembly 3050 that is used to focus the laser beam onto a flow cell 110 (shown in FIG. 2A by the mark labeled FC).

Figure 2G:
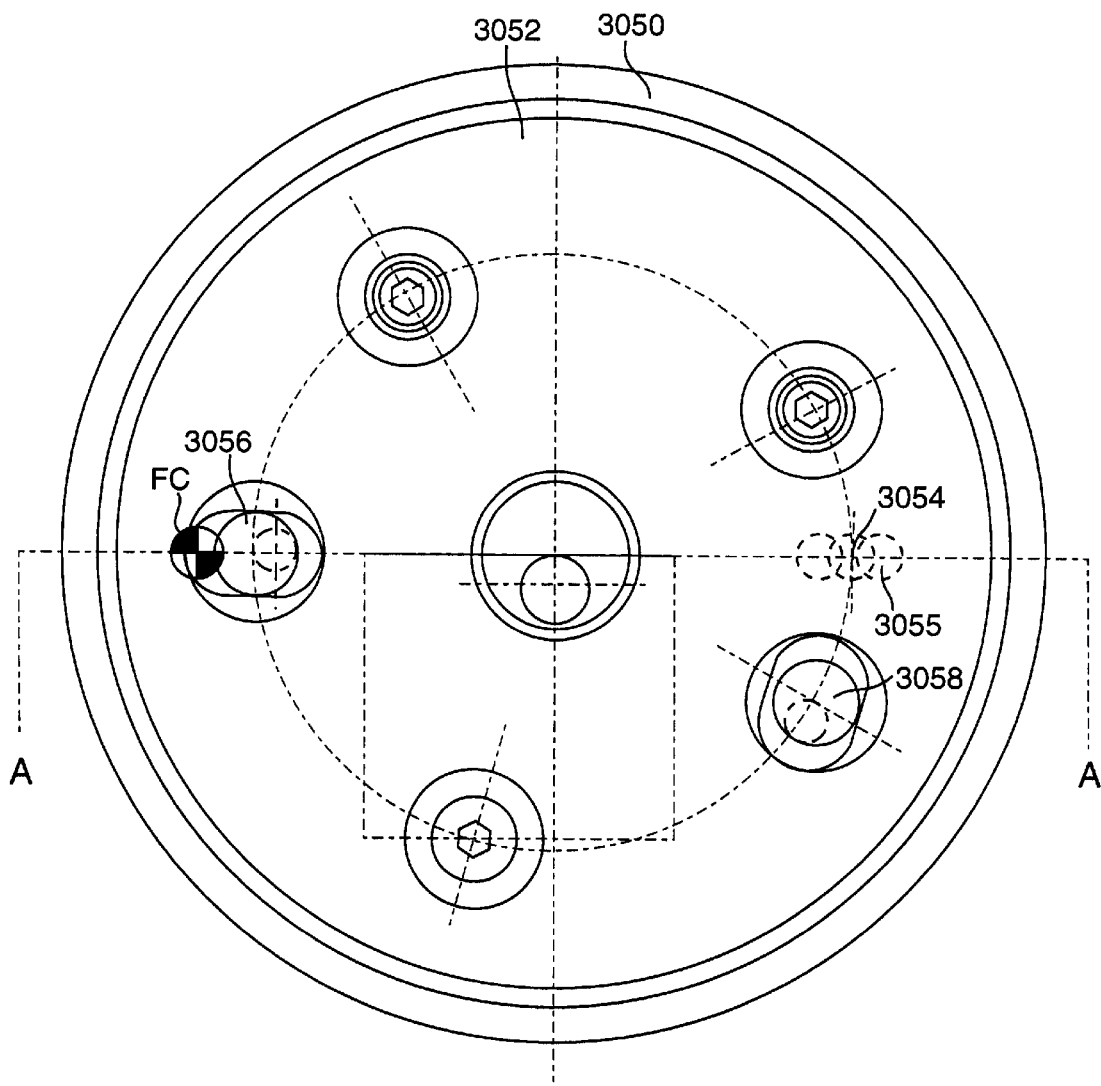
FIG. 2G is a front end view of the focussing lens assembly of FIG. 2A.

Regarding FIG. 2G a side view of the assembly 3050 retaining lens 220 indicates that there are two eccentrics and a fixed pin that are used to locate lens to 220 into the refracted beam path. Lens 220 is mounted securely to a plate 3052 which is adjustably positioned on the assembly 3050. The assembly 3050 is in turn connected to housing 3020 for example, by being bolted together. The plate 3052 has a pin 3054 that is fixed in housing 3050 and slides within a groove 3055 in plate 3052. The first eccentric 3056 causes the plate 3052 to rotate about the pin and thus orients the lens on the beam axis in a up and down position relative to the beam axis. The second eccentric 3058 is used to translate the lens 220 to the left and right on the beam axis and the plate 3052 rotates about pin 3054. Once the lens 220 is centered in the two directions, the plate 3052 is locked down to assembly 3050 by three locking screws and Belleville washers (not shown). It is noted that the focus provided by lens 220 is not particularly critical to the illuminator assembly 130, in as much as the flow cell can be shifted in a tolerance range that is adequate for illuminating the particles under examination.

Figure 2H:
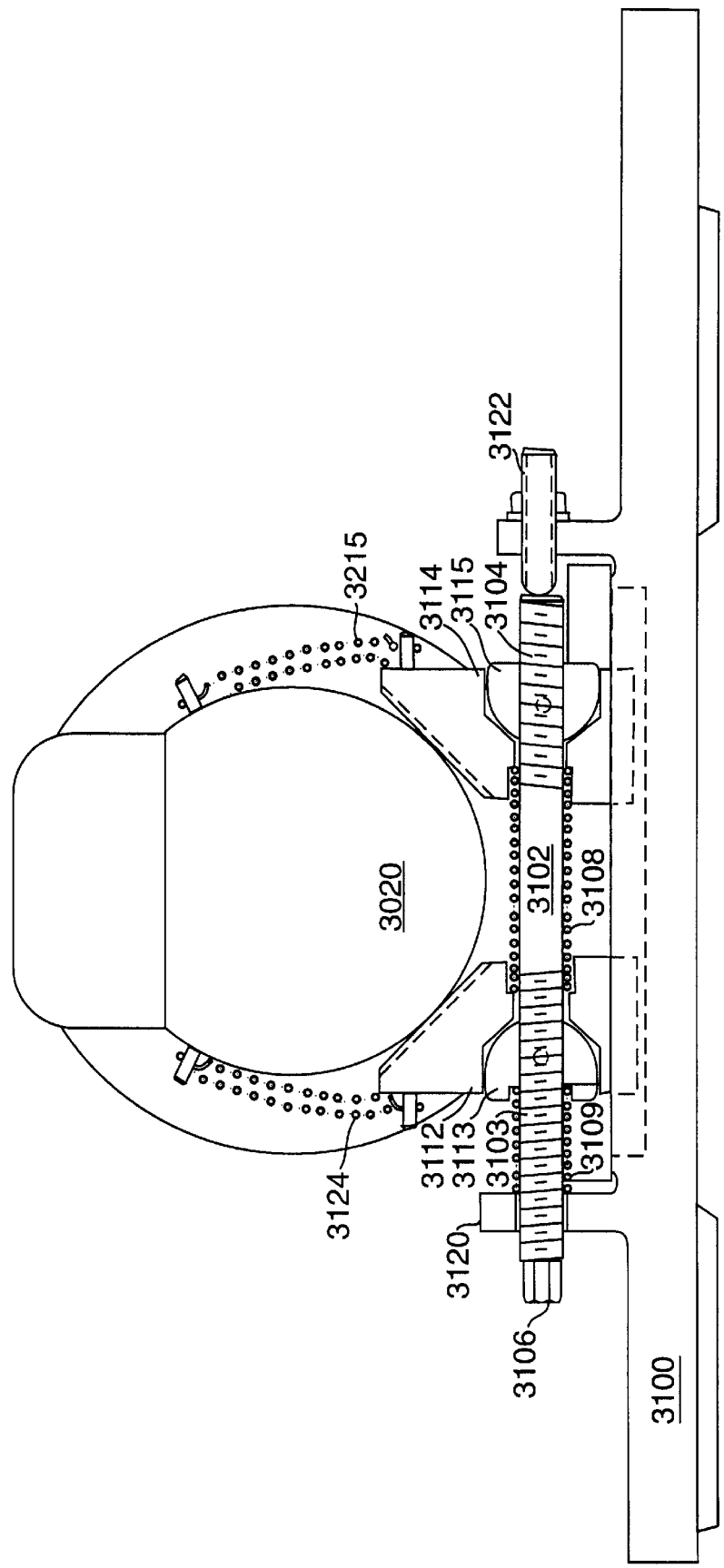
FIG. 2H is a front sectional view of the orientation system for the illuminator assembly of FIG. 2A.
Figure 2I:
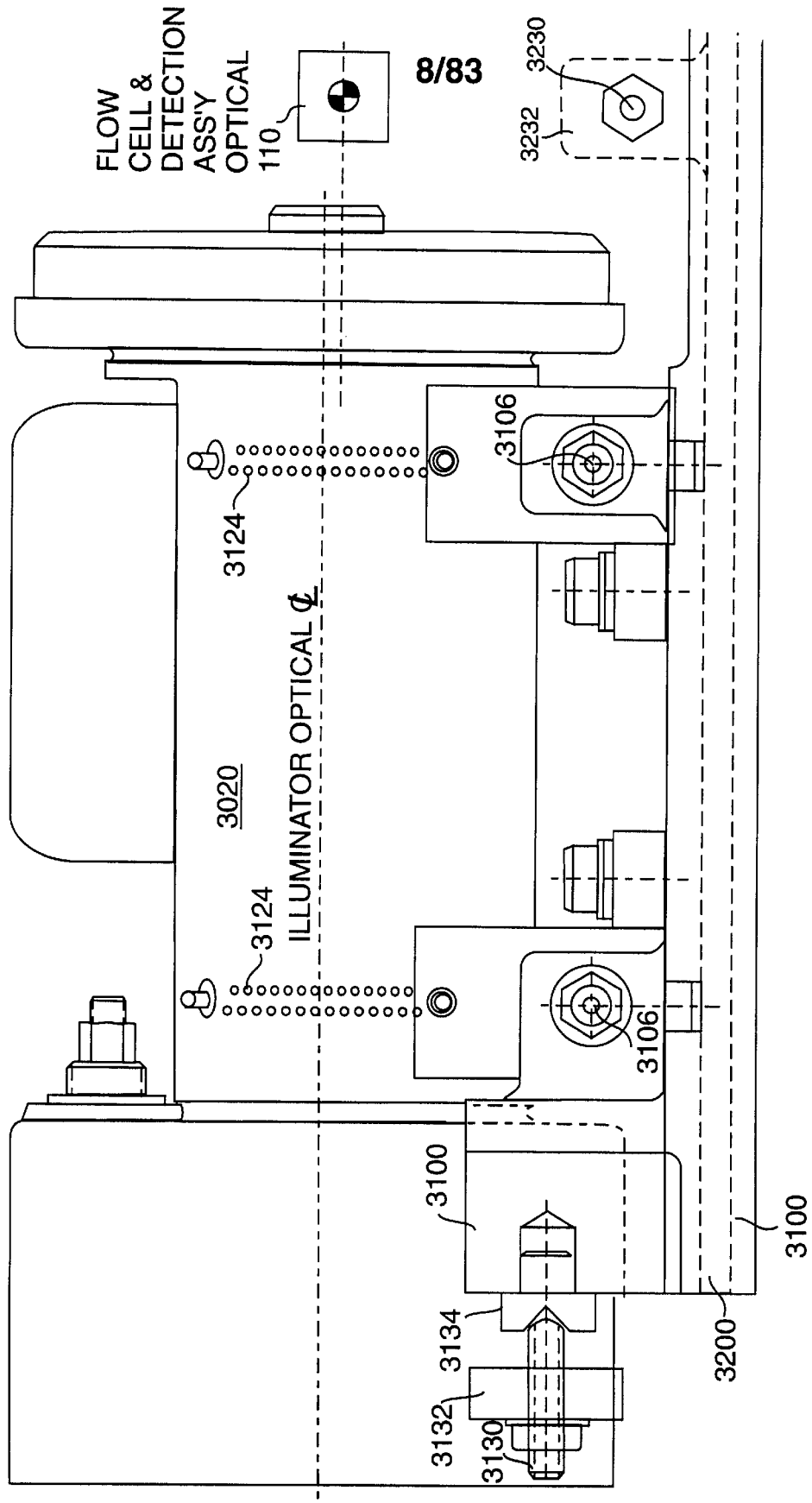
FIG. 2I is a side view of the orientation system of FIG. 2H.

With reference to FIGS. 2H and 2I, the illuminator assembly 130 is mounted on an assembly that is used to orient the laser beam output from lens 220 onto the flow cell. The assembly includes a base 3100 and two turnbuckles 3102 that provides kinematic control over the adjustment of the illuminator assembly 130, and hence the laser beam axis. Each turnbuckle has essentially the same structure of which only one is shown in FIGS. 2H and 2I. Each turnbuckle 3102 has a left handed thread portion 3103 and a right handed thread portion 3104. Respectively mounted on each of the threads is a ball 3113 and 3115 and wedge surfaces 3112 and 3114 which are urged apart by a spring 3108. Each of the wedges 3112 and 3114 are respectively urged in place against balls 3113 and 3115. Spring 3109 is mounted between a boss 3120 and ball 3113 to maintain the turnbuckle 3102 engaged against an dome head screw 3122. Thus, when turnbuckle 3102 is rotated clockwise the balls 3113 and 3115 move outwardly relative to the center of the housing 3020, which lowers the illuminator assembly and tilts laser beam axis. A counterclockwise rotation will operate to raise the portion of the cylinder over the turnbuckle and tilt the laser beam axis the other way.

Figure 2J:
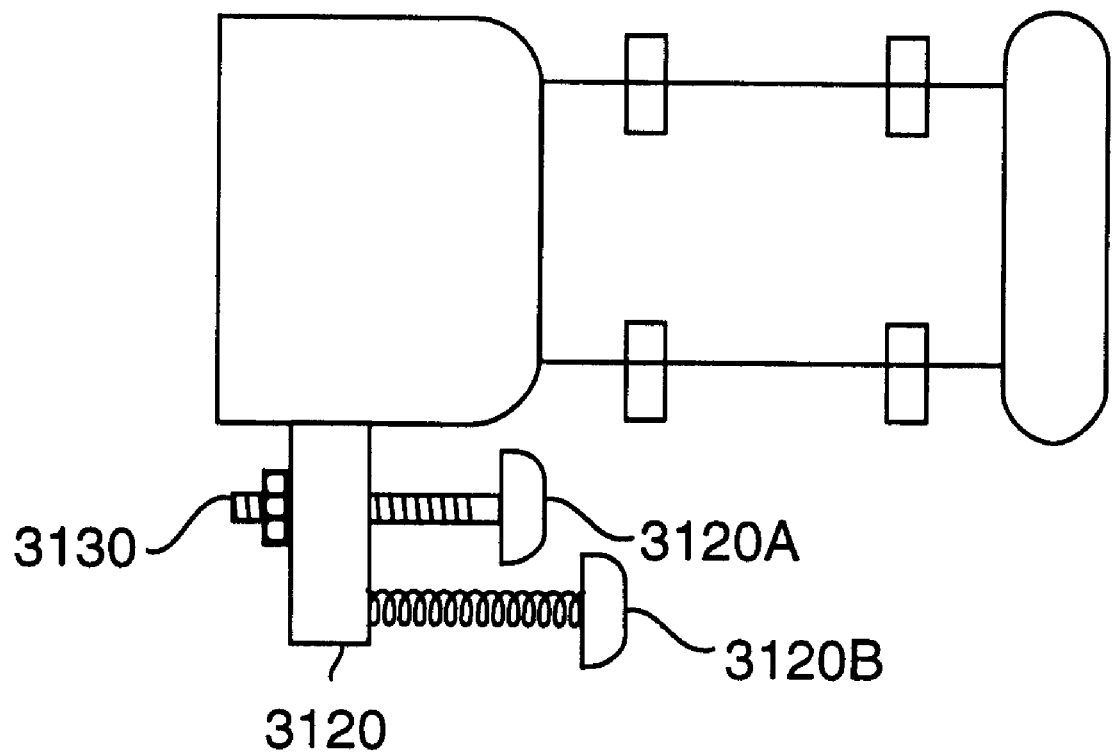
FIG. 2J is a schematic view of the lateral adjustment mechanism of FIG. 2H.

Springs 3124 and 3125 are used to maintain the housing 3020 in contact with the wedged surfaces 3112 and 3114 respectively. The springs 3124 and 3125 do not have a critical tension, but merely keep the housing from falling off. The wedged surfaces 3112 and 3114 are cylindrical, having a curvature that is tangential to the barrel of the illuminator housing 3020 and thus provide a point contact (more accurately an elliptical contact). Thus, with two turnbuckles 3102, the illuminator assembly can be tilted upwardly or downwardly by appropriate adjustment of the respective turnbuckles, and the illuminator assembly translated vertically (while maintaining the angle of tilt constant) by simultaneous action of the two turnbuckles in the same direction. The translation of the illuminator assembly 130 in the x and y directions is obtained by adjusting the dome head screw 3122 to shift the turnbuckle 3102 and its wedge pieces as a unit. Separate adjustment of the turnbuckles by the respective dome head screws will operate to shift the illuminator assembly right and left. Thus, the cylinder of housing 3020 can be moved in two dimensions with four degrees of freedom kinematically. In addition, the foregoing assembly can be provided with a z-axis translation (i.e., along the beam axis) for focus, which is obtained by a separate oval head screw 3130 that is mounted in a boss 3120 and sits against a fixed stop 3134 on the assembly base 3100. Similarly, another plate 3200 (shown in phantom in FIG. 2I) can be interposed between base 3100 and the turnbuckles and used to provide a y-axis translation (i.e., shifting the illuminator assembly and beam axis side to side) of the turnbuckles using an oval head screw 3230 in a boss 3232. One or more appropriate guides or rails (two are shown in FIG. 2J) are used to maintain a precise linear translation, as known to those of ordinary skill in the art. Alternatively, base 3100 could be mounted on to plate 3200 with the appropriate adjustments as between the oval head screws, bosses, and stop member locations. Referring to FIG. 2J, a spring 3230A may be interposed between the boss 3150B and oval head screw 3130 to maintain the assembly boss 3120 in contact with oval head screw 3130. A locknut 3130A may be used to secure the assembly once focus (or shifting) has been achieved.

The force exerted by springs 3109 and 3108 is merely sufficient to overcome the friction. The use of balls 3113 and 3115 is preferred for ease of tolerance in machining of the parts. In this regard, the balls can pivot about their centers to some extent, without involving any change in the position of the wedge surfaces 3112 and 3114.

In this alternative assembly, an accurate and precise alignment of the optical component for the illuminator assembly 130 is obtained, with a minimum number of parts, ease of manufacture and relatively low cost even as compared to the embodiment described in connection with FIG. 2.

As shown in FIG. 1, after exiting the illuminator assembly 130, the laser beam B is directed on the cell suspension stream at point 119 in the flow cell 110. Preferably, the flow cell 110 is tilted at an angle 118 relative to the plane normal to the axis of laser beam B of 3°–5°, preferably 4° (not shown in FIG. 1). The tilt axis is parallel to the long axis of the beam shaping aperture and perpendicular to both the optical axis and the axis of the flow cell.

After leaving the flow cell 110, the scattered beam enters the detector system 164. The detector system 164, shown cut away in FIG. 3, comprises a 2-element, high numeric aperture (NA) lens 301, a beam splitter 310, an absorption detector 315 with an corresponding imaging lens 316, a dark stop 320, a split mirror 330 and scatter detectors 345, 346 with a corresponding imaging lens 347. Each of the elements are mounted in a cylindrical bore of housing 305 in a predetermined and fixed position.

The high NA lens system 301 collects and collimates the scattered light from the flow cell, forming a circular pattern of parallel rays for segregation by the beam splitter 310 and the dark stop 320. It is important that this lens system have a high numerical aperture in order to collect the scattered beam through a maximum included solid angle subtended about the flow cell 110. It has been found by the inventors, however, that some spherical aberration in the pattern of collected light formed by the lens is permissible without significantly degrading the measurement of absorption and scatter. For this reason, a lower cost 2-element high NA lens is useable in the detector system of the invention. High NA lens 301 comprises a first element 302 and a second element 303, and is mounted in the bore of detector housing 305. Lens 302 is held in place by a spring retainer 302A, abutting a spacer member 302B which separates lens 302 and lens 303 by a fixed distance. The spring retainer 302A may be a form of Belleville washer made, e.g., of nylon.

After exiting the second element 303 of the high NA lens 301, the collimated light strikes the beam splitter 310 which is mounted in a fixed angular orientation to the beam axis in a spacer member 310A. A portion of the light is reflected by the beam splitter 310 and passes through an absorption detector imaging lens 316 mounted to the base 305. The imaging lens 316 focuses the light onto an absorption detector 315. In a currently preferred embodiment of the detector, 50% of the light from the high NA lens is reflected by the beam splitter 310 for use by the absorption channel. The beam splitter 310 also has a 0.5° wedge, which is the measured angle between the front optical surface of splitter 310 and rear optical plane of splitter 310 to reduce interference from reflected beams. Alternately, lens 316 may be mounted in spacer member 310A in a fixed position relative to beam splitter 310 to provide for an aligned arrangement.

The absorption detector 315 is preferably a photosensitive diode mounted on a detector circuit board 352, which is described further below.

The absorption detector actually measures the unabsorbed light from the flow cell that is collected by the high NA lens. This measurement is affected by random fluctuations in laser power from the laser diode 131 (FIG. 1). The fluctuations are measured by the reference detector 224 are converted to an oscillating electrical signal in the reference diode preamp board 227, and subtracted from the absorption detector signal by a difference circuit on the DATAC board 115 (FIG. 11A). By eliminating the effect of the random power fluctuations from the laser, a cleaner absorption measurement is obtained. Further, because only the masked portion of the beam utilized in the absorption measurement is sampled by the beam sampler 222, the difference circuit subtracts only those random fluctuations in the laser beam that are likely to affect the absorption measurement. More accurate compensation of the measurement results.

The remaining portion of the light collected by the high NA lens 303 is transmitted through the beam splitter 310 for use in the measurement of high and low angle scatter. Because the light has been collimated, the outer portion of the circular pattern comprises light that was scattered at a high angle in the flow cell; the inner portion of the pattern is light scattered at a low angle. These two portions of the scattered light are segregated by the dark stop 320, which is shown in plan view in FIG. 4. The dark stop is preferably constructed from a thin metallic plate having an opaque, non-reflective coating. The dark stop is preferably mounted in the bore of housing 305 against a shoulder at an angle α (FIG. 3) of about 7½° (7.41°) perpendicular to the beam path, in order to reduce interference from ghost reflections back into the optical system and to minimize aberrations from the optical system. Other angles may be used, e.g., an angle between 5° and 10°. In one embodiment, a screw adjustment may be provided to select the angle of the dark stop 320 relative to the shoulder. The dark stop 320 is held in position by spacer members 310A and 320A and retaining washer 302A.

The opaque coating of the dark stop 320 has a plurality of precision shaped apertures that permit light to pass according to its distance from the center of the light pattern. A first aperture 321 permits high-angle scatter, which is typically light scattered between 5° and 15° in the flow cell, to pass. In a preferred embodiment, the first aperture 321 is a sector-shaped aperture bounded by an inner radius of 3.94 mm, an outer radius of 11.57 mm, and extends through an arc of slightly less than 180°. In the remaining half of the dark stop 320, second and third apertures 322, 323 permit low-angle scatter, which is typically scattered between 2° and 3°, to pass. In a preferred embodiment, the second and third apertures 322, 323 are sector-shaped apertures bounded by an inner radius of 1.58 mm, an outer radius of 2.37 mm, and each extends through an arc of slightly less than 90°. The dark stop thus allows only high-angle scatter to pass in one half of the light pattern, and low-angle scatter to pass in the other half.

For ease of alignment, the center of the dark stop 320 may have a hole to allow a portion of the laser beam to pass therethrough and impinge the reflective split mirror 330 for alignment. Once aligned, the hole is occluded during use by a rod inserted between the dark stop and the collecting lens which blocks the beam portion passing through the alignment hole, but which does not block the shaped apertures.

It should be understood that non-radial apertures in the dark stop may be used for detecting the different scatter (and optionally absorption) optical interactions. Similarly, a non-circular laser beam could be used to impinge on the stream of particles in the flow call 110. In such case, it may be desirable to map empirically the desired scatter range(s) (and absorption) interactions using such non-radial apertures and/or non-circular beams, in view of known scatter and absorption patterns for, e.g., circular laser beams and radial annular sectioned apertures with beam stops (i.e., the conventional configuration for flow cytometers), so that the signals detected can be properly interpreted to identify and enumerate correctly the particles under interrogation.

Figure 3:
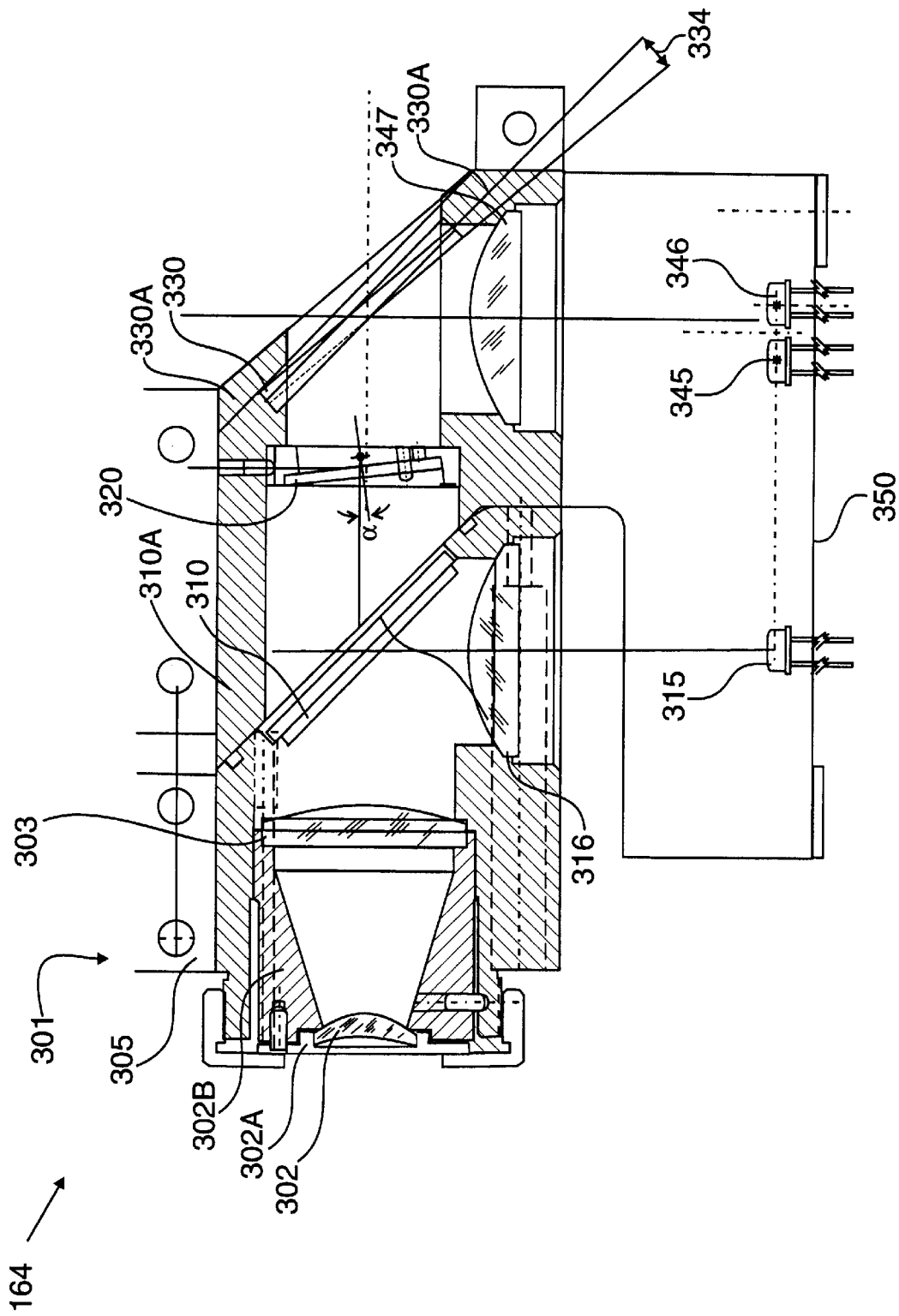
FIG. 3 is a top view of a schematic diagram of the detector system of FIG. 1.
Figure 4:
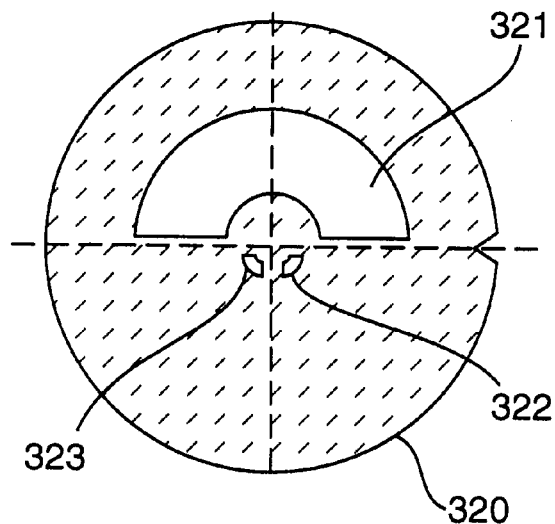
FIG. 4 is a front plane view of the dark stop of FIG. 3.
Figure 5:
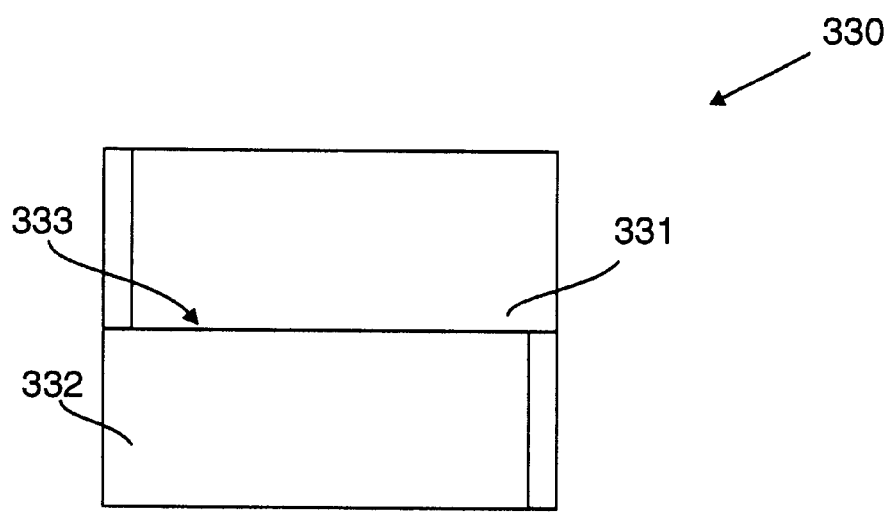
FIG. 5 is a front plane view of the split mirror of FIG. 3.

The light pattern, as masked by the dark stop 320, is transmitted to a split mirror 330 mounted in a housing 330A which is in turn secured (e.g., bolted) to the base 305. The split mirror comprises two optical flats 331, 332, arranged respectively, above and below the optical axis as shown in FIG. 5. The surfaces of the flats 331, 332 are oriented in different planes having a common axis and an angle of tilt 334 between the planes, as best seen in FIG. 3. In a preferred embodiment, the angle 334 (FIG. 3) between the surfaces 331, 332 is 5½°. The split mirror 330 is mounted in the base 305 so that the edge 333 (see FIG. 5) of the surfaces lies between the high-angle scatter portion of the light pattern and the low angle portion of the light pattern. That is, light passing through the first aperture 321 of the dark stop 320 strikes surface 331, while light passing through the second and third apertures 322, 323 of the dark stop strike a surface 332 of a beam splitter element 330 (see FIG. 5). The high and low angle scatter portions of the light pattern are therefore reflected in diverging directions by the split mirror 330. One useful embodiment uses the high angle scatter mirror 331 above the optical axis at an angle of 40.75° relative to the axis, and the low angle scatter mirror 332 below the optical axis at an angle of 46.25° relative to the beam axis.

Figure 6:
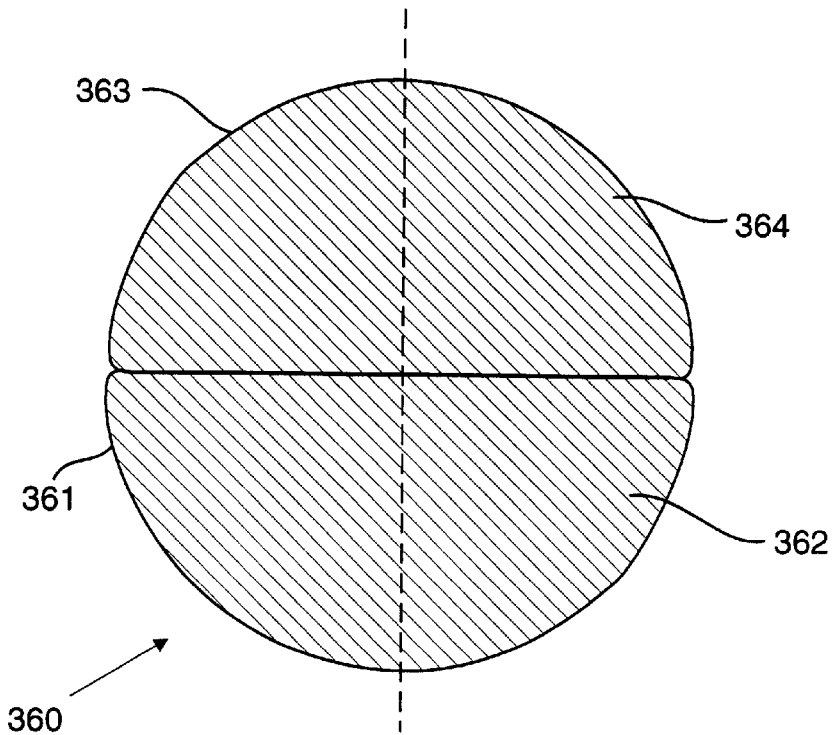
FIGS. 6 and 7 are respectively front and side views of a two-faceted prism for use in an alternate embodiment of the detector system of FIG. 1.
Figure 7:
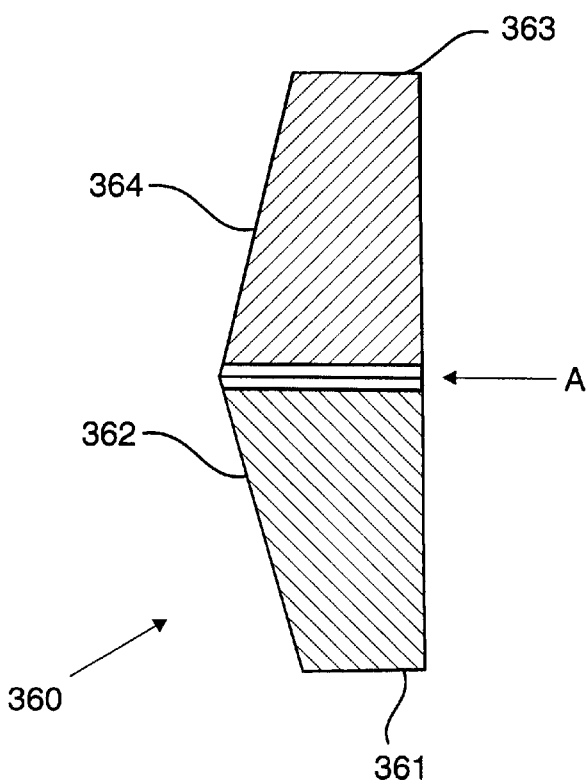

In an alternative embodiment, a faceted prism may be used in place of the split mirror to separate the high and low angle scatter portions of the light pattern. FIGS. 6 and 7 show a two-angle faceted prism 360 comprising first and second sections 361, 363 having first and second facets 362, 364, respectively. The faceted prism 360 is mounted in the detector assembly so that the light pattern is transmitted through the prism in the direction of arrow A. The high-angle scatter portion of the beam from the dark stop 320 strikes the first section 361 of the prism, and the low-angle portion strikes the second section 363. Because the facets 362, 364 have rotated facet angles, the high- and low-angle scatter portions of the light pattern are refracted at different angles.

Figure 8:
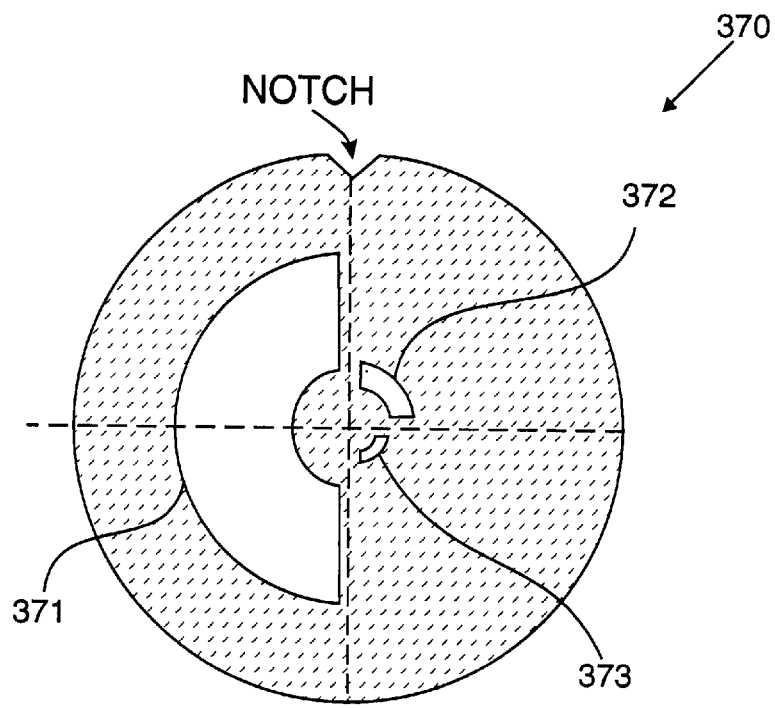
FIGS. 8 and 9 are respectively a front plan view of a dark stop and a three-faceted prism for use in an alternate embodiment of the detector system of FIG. 1.
Figure 9:
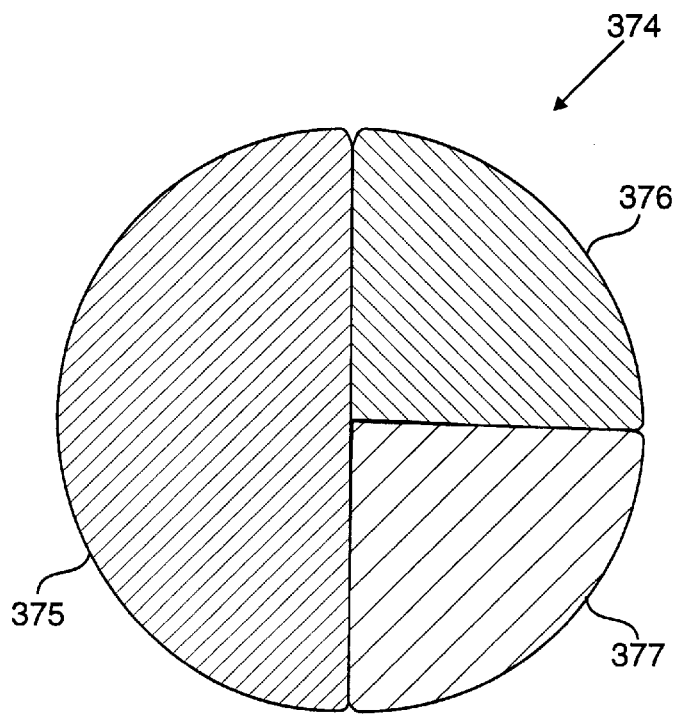

The dark stop and the mirror or prism of the invention could be configured for further resolution of the light scatter pattern into three, four or more ranges of scatter angle. For example, dark stop 370 and prism 374, shown in FIGS. 8 and 9 respectively, are configured for separating the pattern into three portions. The dark stop 370 has three apertures 371, 372, 373 located at three radius ranges from the center of the light pattern. The faceted prism 374 has three corresponding sections 375, 376, 377 for refracting the resulting beam portions onto three detectors (not shown).

Returning to FIG. 3, the high and low angle scatter portions of the light pattern pass through a single scatter detector imaging lens 347. The pattern is focused as two images, one each on a high angle scatter detector 345 and a low angle scatter detector 346. The two portions of the light pattern are sufficiently separated by the split mirror 330 to form two side-by-side images on the two side-by-side detectors 345, 346. This arrangement eliminates an additional imaging lens, beam splitter and dark stop which would otherwise be required to separate the high and low angle scatter portions of the light pattern. Lens 347 also is preferably mounted in housing 330A. The structure of detector assembly 164, using the precision machined bore in housing 305 and spacer members thus provides a low cost and accurately positioned detector assembly.

The absorption detector 315 and the high and low angle scatter detectors 345, 346 are mounted on a common detector circuit board 352. Use of a common printed circuit board reduces cost by reducing part count and simplifying assembly. Furthermore, alignment of the three detectors, which had previously been done separately, can be done in a single operation by adjusting the position of the common board 352. The relative positions of the three detectors on the common printed circuit board can be maintained with sufficient accuracy to each other using standard PC board assembly techniques.

E. Chassis and Assembly of Components

Figure 44:
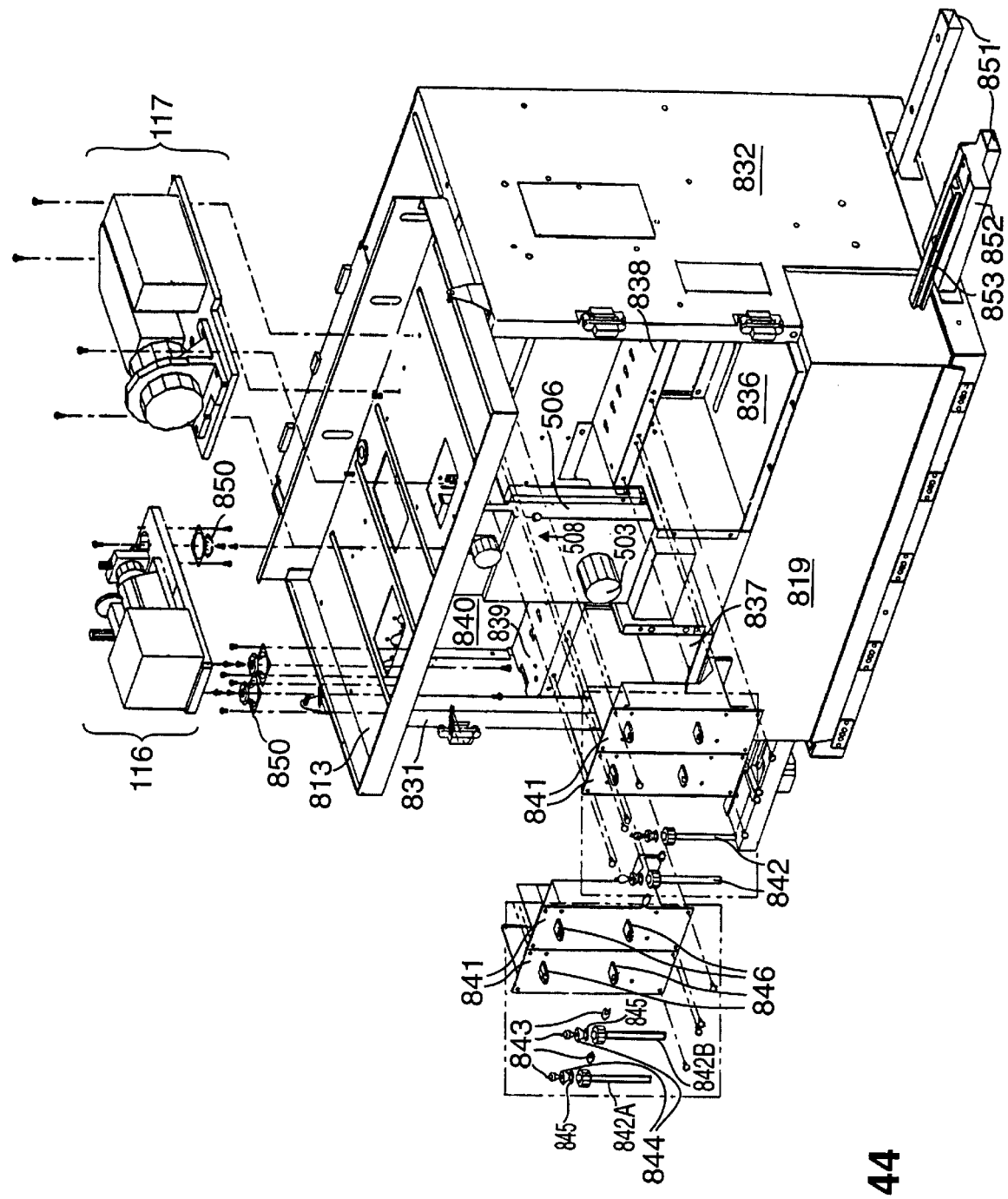
FIG. 44 is a front elevated perspective view of the internal structure of the instrument of FIG. 38.
Figure 45:
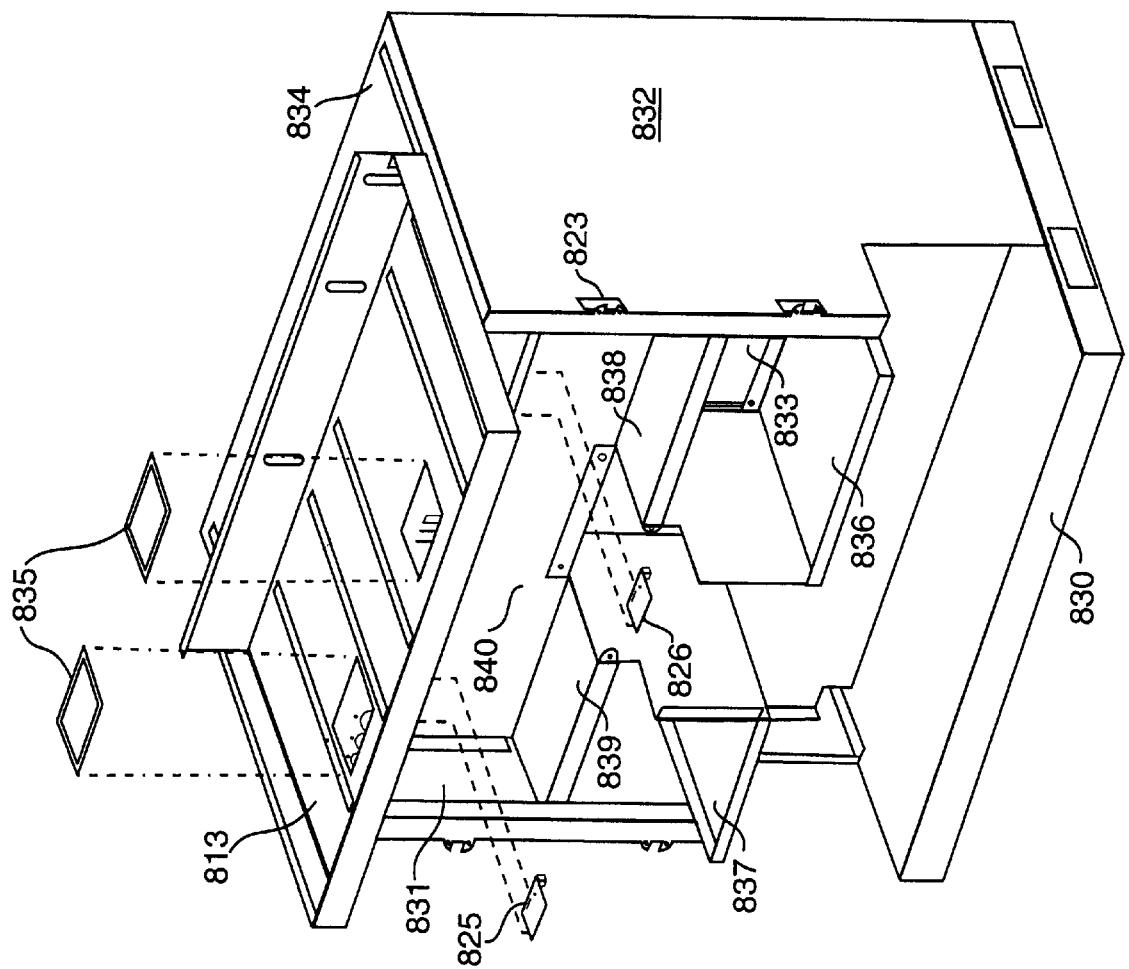
FIG. 45 is a front elevated perspective view of the internal structure of the instrument of FIG. 44.
Figure 47:
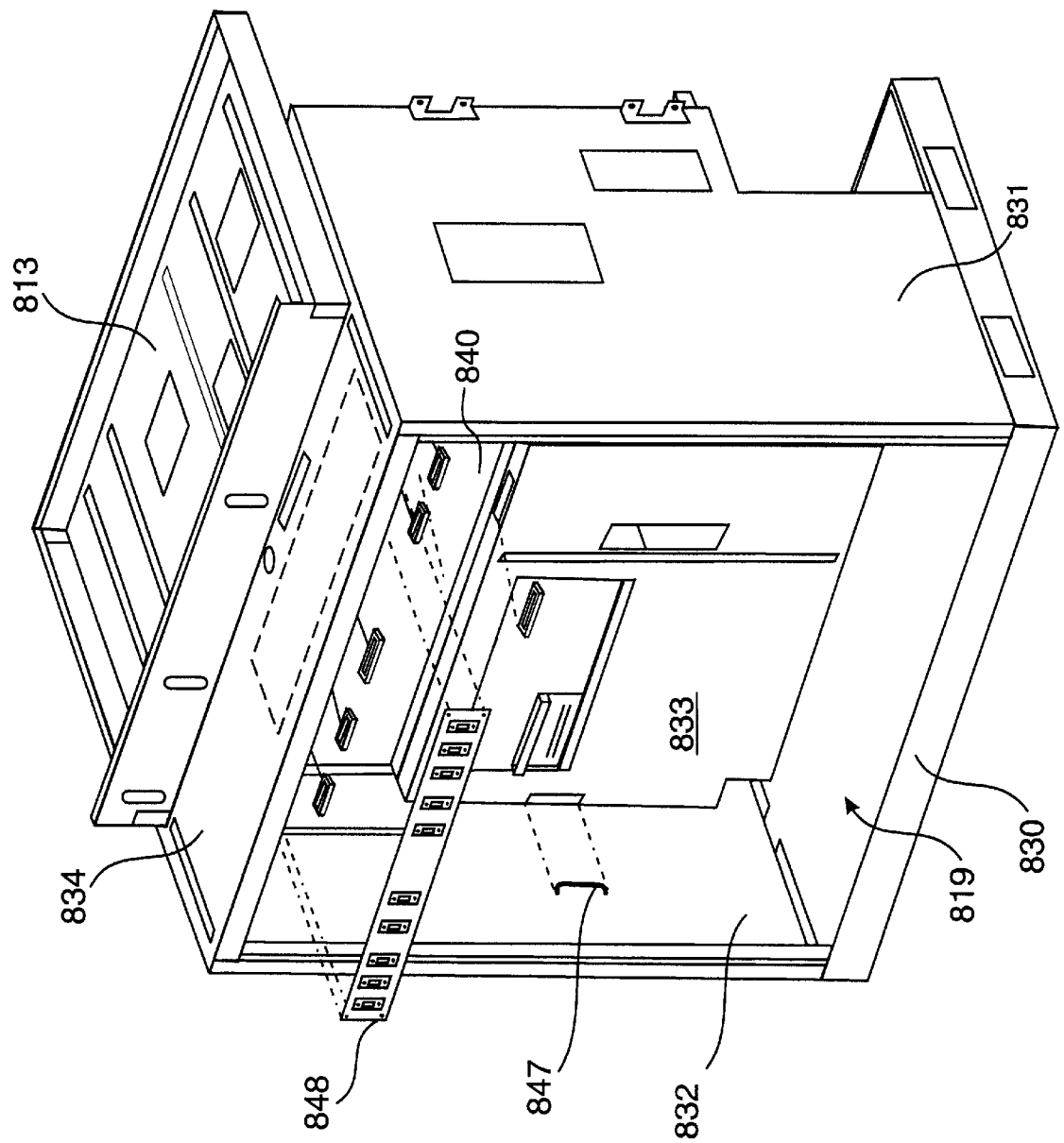
FIG. 47 is a rear elevated perspective view of the internal structure of the instrument of FIG. 44.

The structure of the chassis and assembly of the flow cytometer instrument in accordance with the present invention is shown in FIGS. 37–40, 44 and 45. With reference to FIGS. 45 and 47, the superstructure of the chassis of the flow cytometer instrument includes a base plate 830, left side panel 831, right side panel 832, and a top panel 834 which are secured together, preferably by rivets to minimize distortion and texturing. A top plate 813 is secured on top panel 834 having various apertures (not shown) for passing pneumatic or hydraulic tubing and electronic wiring therethrough, and other apertures (not shown) for mounting various body panels and components using, for example, threaded screws or bolts.

Referring to FIG. 45, viewed from the front, the instrument chassis has top and bottom and left and right internal shelves, formed from top shelf panels 839 and 838, and bottom shelf panels 837 and 836. These panels are secured together and to the respective side panels 831 and 832. Shelves 839, 838, 837, and 836 each contain various apertures (not shown) for passing pneumatic and electrical tubing therethrough. Although not shown in FIG. 45, secured to the underneath side of the top interior shelves 839 and 838 are a plurality of diaphragm pump assemblies as well as various pneumatic manifolds. These conventional structures are used, for example, to control and connect a vacuum line or a pressure line input to the unified flow cell assembly, and to the syringe pumps for the flow cell operation of the network, namely the pneumatic lines and valves for performing the hydraulic flow of the sample processing of reaction mixtures and analysis described herein.

As illustrated in FIGS. 46 and FIG. 11C, the pneumatic control assembly 163 includes 14 valves: three four-way 40 psig/ATM valves, valve V30 for operating the sample shear valve, valve V38 for operating the sample sleeve of the manual open tube sampler, and valve V39 for operating the manual closed tube sampler needle; three three-way 40 psig/Vac valves, including valve V78 for operating the RETIC reagent diaphragm pump, valve V80 for operating the RBC reagent diaphragm pump, valve V77 for operating the PEROX Dil 2 reagent diaphragm pump; six three-way 20 psig/Vac valves, including valve V28 for operating the #1 rinse diaphragm pump, valve V29 for operating the #2 rinse diaphragm pump; valve V60 for operating the Wash rinse diaphragm pump; valve V75 for operating the HGB and BASO reagent diaphragm pump; valve V76 for operating the PEROX Dil 1 diaphragm pump; valve V79 for operating the PEROX Dil 2–3 diaphragm pumps; and two three way 5 psig/VAC valves, including valve V26 for operating the Perox's optics sheath flow diaphragm pump and valve V34 for operating the RBC/BASO/RETIC sheath flow diaphragm pump.

Referring now to FIG. 47, there is a center lateral interior panel 833 that is connected to an upper interior center lateral panel 840 to which the interior shelves 839, 838, 837, and 836 are connected. Strip grommets 847 are mounted to side panels 831 and 832 for supporting a removable module comprising, e.g., the power module/pump assembly module. The CANBUS scrambler 120 is secured to the backside of upper panel 840 for interconnecting the various nodes to the CANBUS as is described below.

Referring to FIG. 45, the printed circuit boards for the PEROX Optic Scrambler 825 and the RBC/BASO/RETIC optic scrambler 826 are shown, with a dotted line connection to their respective positions on interior upper panel 840.

Referring now to FIGS. 37 and 44, it is shown where the PEROX Optics 116 is mounted to the top panel 813 using shock mounts 850. The RBC/BASO/RETIC optic assembly 117 is similarly mounted to the top platform 813. Unified flow circuit assembly 508 is mounted to the space between the left and right interior upper and lower shelves as illustrated in FIG. 38, and 44. The syringe pumps 842A and 840B are between flanges 846 and syringes 843 which are coupled to the syringe pump 842A or 842B using syringe nut 844. As illustrated in FIG. 39, the respective syringe pumps are tubed to respective solenoid valves 822, at coupler 845. The syringes 842B, which inject the volume of reaction mixture to be analyzed into the sheath flow, respectively pump a smaller volume, for example, 50 microliter per stroke, whereas the other pair of syringes 842A, which draw out the sheath flow and reaction mixture from the flow cells pump a larger volume, for example, 1.0 milliliter per stroke.

Figure 42:
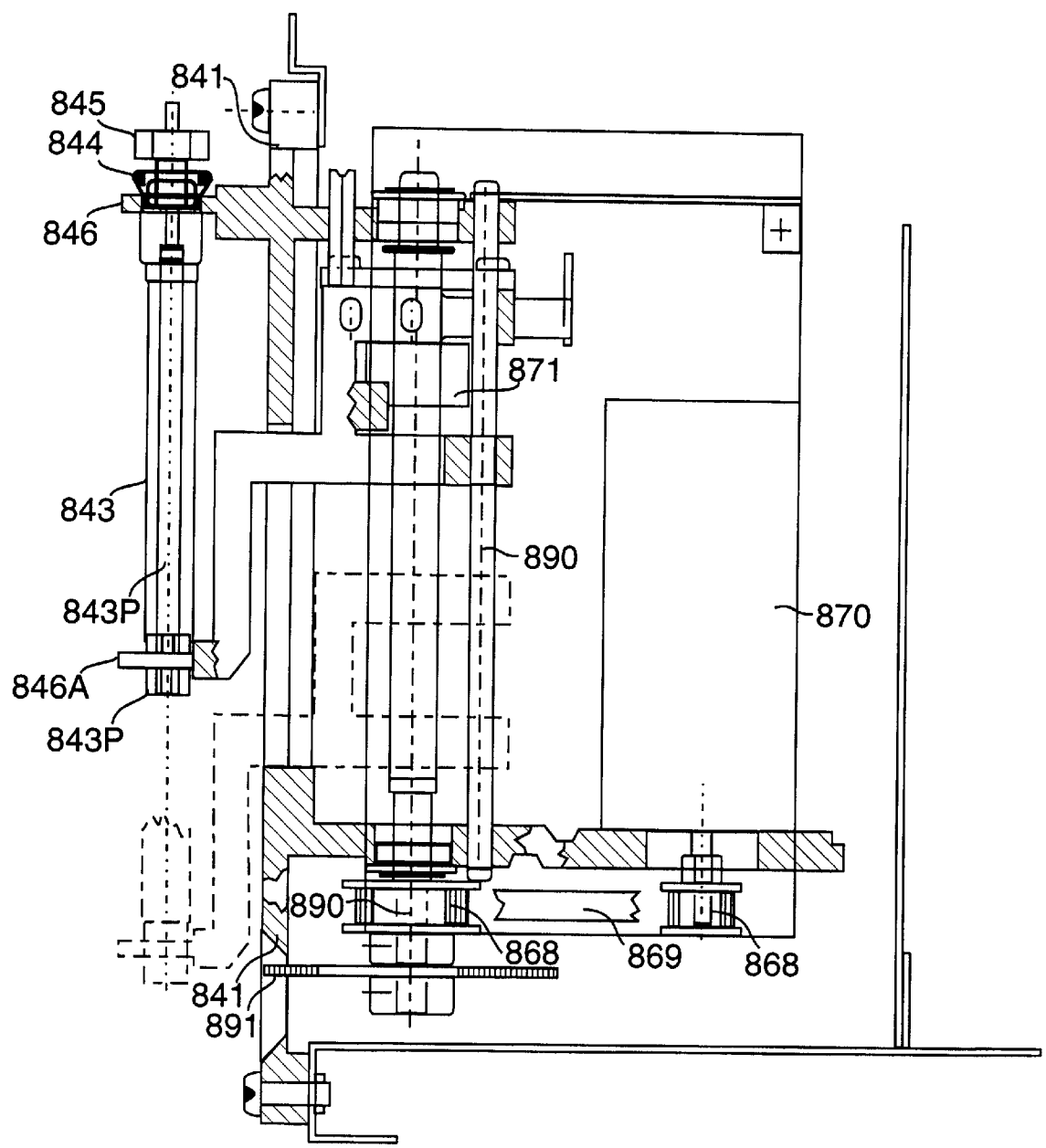
FIGS. 42 and 43 are respectively side sectional and front plan views of a syringe pump of FIG. 38.
Figure 43:
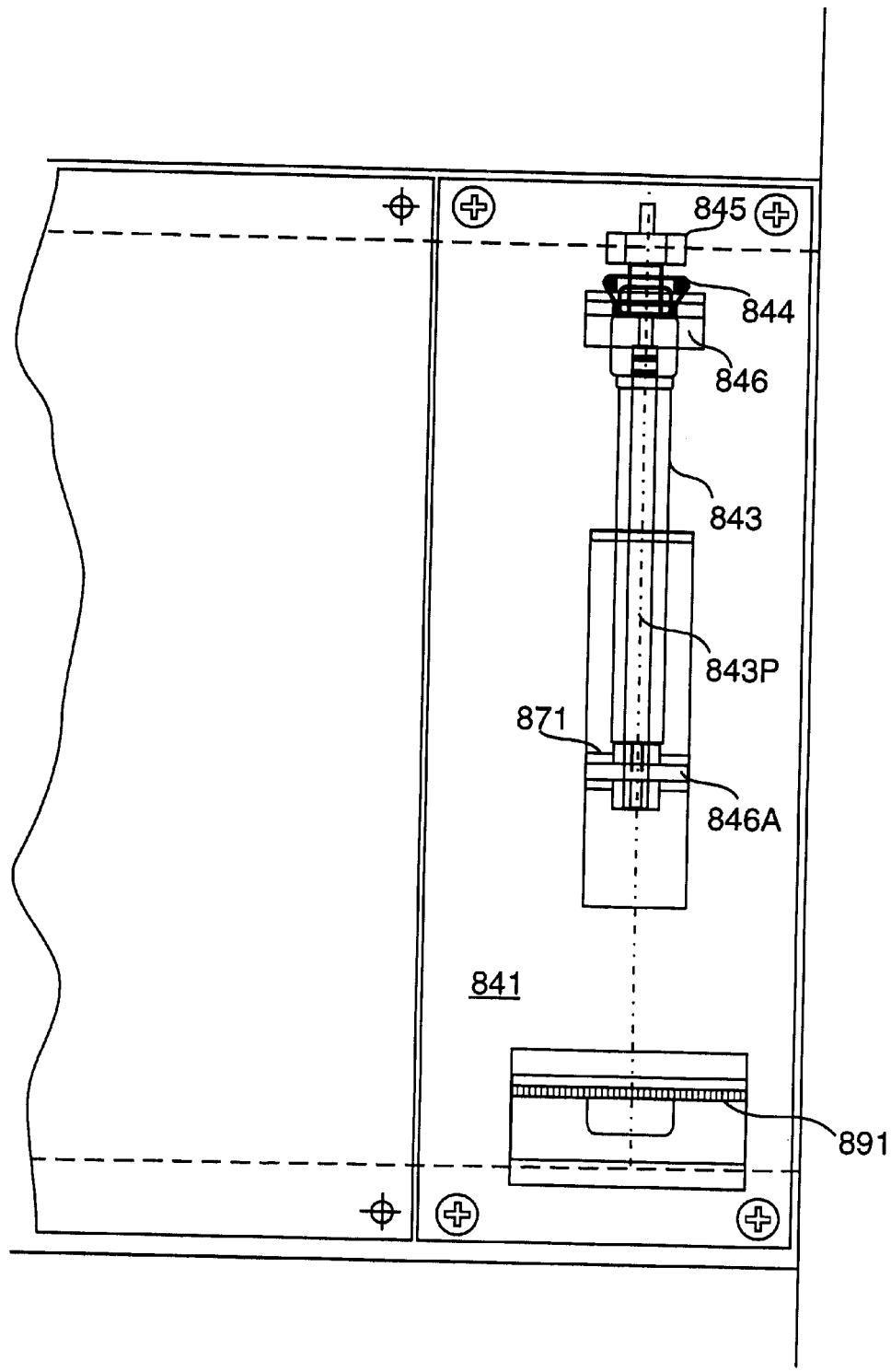

Referring to FIGS. 42 and 43, each syringe pump 841A has a similar construction. It includes a lead screw linear actuator 866 driving a carriage 871 mounted for translation along the threaded lead screw shaft 866. The shaft 866 is turned by motor 870, which is mounted behind plate 841, such that motor 870 is connected to the lead screw 866 by a belt and pulley system designated 868, 869. The syringe piston is moved up and down inside glass cylinder 867. A bar 890 is used to guide carriage 871 as it moves along the lead screw 871. The carriage 866 includes a flange 846A which is coupled to the plunger 843P of the syringe 843. A thumb wheel 891 is provided for manual adjustment of the syringe position.

In operation, the motor 870 is driven according to one of a number of preprogrammed pumping profiles, which are stored in a memory and downloaded into the pump node, which is used to control the syringe pumps 842A and 842B (described below). The downloaded parameters may be any that are useful to control the pump mechanism to be used. The motor could be a stepper or a D.C. motor. In case of a D.C. motor, an encoder whose increments, called steps, is locked to the motor shaft which operates the pump. These "steps" represent the parameters, typically acceleration, and velocity, and total distance, and may include the times when each acceleration segment, velocity segment and deceleration segment start and stop. The times may be provided in the form of a number of steps for each segment or times when the motor is turned on and off and adjusted to run faster, slower or at a constant rate. Alternately, the parameters may include a number of steps per second which rate is increased over time for acceleration segments (and decreased for deceleration segments).

On a downward stroke, syringe pump chamber 867 is filled with a reaction mixture from the selected reaction chamber to be analyzed, in conjunction with the "vac shuttle" port of the UFC 502. For the upstroke, the motor 870 is controlled according the pump profile so that the plunger 843P moves at a calculated rate of acceleration to achieve a desired flow rate of particle suspension and sheath flow through the flow cell in question and then maintain the flow at a given velocity. The upstroke and downstroke profiles may be different and are method (i.e., reagent and sample) dependent.

With reference to FIG. 41, each profile to be used for sampling preferably is essentially trapezoidal in appearance, and typically will have essentially the same acceleration and deceleration time intervals and a uniform flow rate in between, during which the optical measurements are made. The profile should achieve a very stable, and constant, flow rate during the time the absorption and scatter data is acquired. It may be desirable in some embodiments to delay acquiring the optical interaction data until a stable flow rate of particles in the reaction mixture is obtained through the flow cell.

The pump profiles are empirically derived for the particular dimensions and reaction mixture characteristics involved. It is also noted that the pump profiles of the syringe pumps 842A and 842B may be different, given that each pumps a different volume of fluid (two input fluids and one output fluid) during substantially the same amount of time. Suitable pump profiles may be adapted from those found in the Technicon model H*1 system diagnostic instrument formerly sold by Technicon Inc., Tarrytown, N.Y.

Figure 41A:
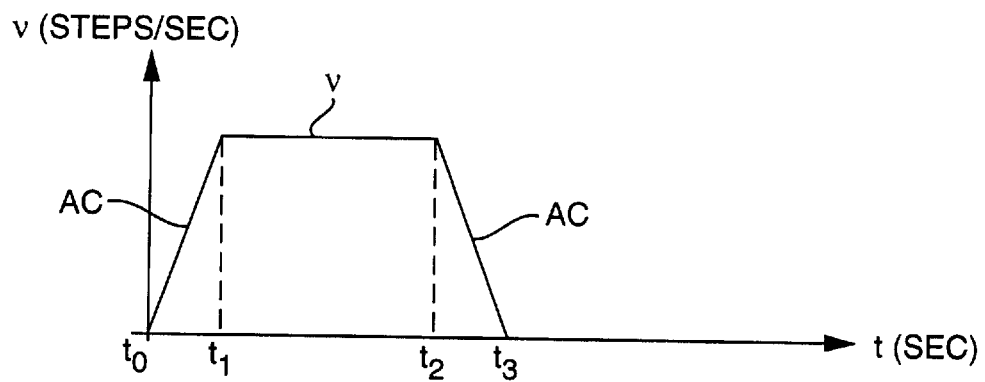
FIGS. 41A–41B are representative pump profiles for the syringe pumps of FIG. 38.
Figure 41B:
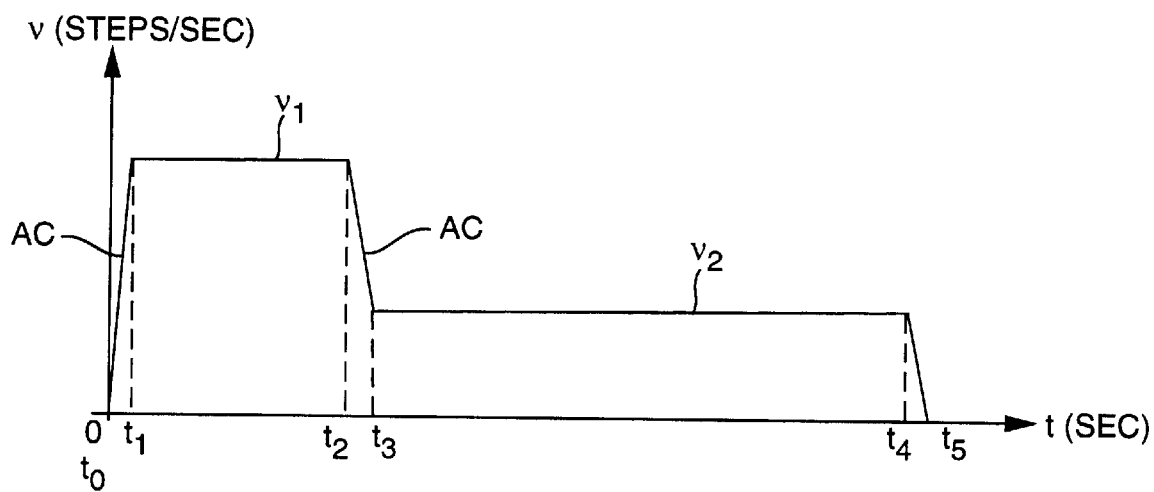

A representative pump profile for various fluid (sheath) and reaction mixture samples is illustrated in FIGS. 41A. Some reaction mixtures, e.g., for the RBC/BASO samples, may advantageously use a first or higher velocity, which is maintained for a first stroke distance of the pump, and which is then decreased to a second or lower velocity for the remainder of the stroke distance. This is illustrated in FIG. 41B. The optical measurements are typically obtained during the second, lower velocity.

With reference to FIGS. 41A and 41B, the time "t" is measured in seconds as a total number of step increments of a step motor 870, the velocity "V" is measured in number of steps per second, and the acceleration "AC" is measured as the number of steps per second squared. For convenience, the pump profile may be defined as a function of velocity which, e.g., starts at zero, progresses through an acceleration stage, reaches a constant, then decelerates and returns to zero.

FIG. 41A represents such a profile suitable for a reaction mixture having an acceleration (and deceleration) AC in the range of from 400,000 steps/sec$^2$ to 1,250,000 steps/sec$^2$, a velocity V on the order of from 10,000 steps/sec to 50,000 steps/sec, with a start to finish duration of between 3 and 15 seconds. The pump profiles for the sheath flow will have at least as great a velocity as the reaction mixture, as is well known, so as to entrain the reaction mixture in the sheath fluid and pass the particles essentially one at a time through the flow cell optical interrogation area.

FIG. 41B illustrates a pump profile of the type which has two constant flow velocity stages, one higher than the other, as discussed. The higher velocity $V_1$ may be, e.g., on the order of between 8000 and 12,250 steps/sec, and the lower velocity $V_2$ on the order of between 1800 and 8000 steps/sec. It is to be understood that the sheath flow will have a higher velocity to entrain adequately the particles. It also may be that the sheath flow velocity will change relatively little, e.g. by 20% or so from the higher to the lower velocity, whereas the reaction mixture flow of the higher velocity may be 3 to 5 times larger than in the lower velocity.

The empirical derivation of a pump profile, which is preferably predetermined for each reaction mixture and sheath, and stored in memory in the form of control parameters appropriate to operate the pump, is straightforward; it depends on the sample size, the portion of the available sample to be optically examined, the time in which it is desired to complete the data acquisition, the time needed to obtain a stable velocity to acquire the data, the size of the particles to be examined, and the size and shape of the flow cell being used. Hence, given the large number of design choices, more than one profile may be suitable for any given reaction mixture. It also should be understood that non uniform, asymmetrical, and non-trapezoidal shaped pump profiles also may be used.

It is to be understood that the solenoid valves 822 are controlled to ensure that the reaction mixture is provided to the flow cell at the appropriate times, and similarly a rinse solution is provided to purge the syringe pumps and the flow cell. Solenoid valves 822C may be used to control the switching of the sheath flow into flow cell 110 and 110A. Solenoid valves 822B operate to control the switching of the reaction mixture and sheath flow through the flow cell, and solenoid valves 822A are used to switch the syringe pumps 842A to the waste system.

Referring to the syringe pumps 842A and 842B on the left side of FIG. 39, they are the pumps used for the Peroxidase analysis conducted in flow cell 110A. Syringe pump 842B is provided with an input having tube 858A coupled to the "shuttle perox output" of UFC 502, and an input tube 858B coupled to the "direct cytometry" output of UFC 502. Syringe pump 842B has an output tube 858C which is connected to an input of the flow cell 110A, illustrated as three-to-one concentric flow module (CFM) 859A. Also coupled to the CFM 859A are tubes 860A from the "vacuum shuttle perox" input to UFC 502 and a tube 861A from solenoid valve 822C. The output of flow cell 110A is coupled to solenoid valve 822B by tube 862A. Tube 862A is coupled to solenoid valve 822B which is coupled to tube 863A which is coupled to the syringe pump 842A.

Referring to the syringe pumps 842A and 842B of the RBC/BASO/RETIC optic assembly, it is shown that they have a similar construction as the syringe valves of the PEROX optic assembly, except that the syringe pump 842B has multiple inputs indicated by tubes 864A–864D respectively connected to the "shuttle baso" output, the "shuttle RBC" output, the "direct cytometry" output, and the "shuttle retics" output of the UFC 502. The other tubing illustrated is used in the same manner as for the perox channel except that the letter designator in the reference numeral is deleted.

F. Pneumatic/Hydraulic Assemblies

The hydraulic connections by tubes 866, 867, and 868, respectively connecting the needle overflow vacuum, the needle vacuum, and the needle rinse lines of the UFC 502 to the Autosampler unit 818, are shown in FIGS. 39 and 40.

Referring now to FIG. 40, the straw assembly connecting the pump assembly 504 of the unified fluid circuit assembly 508 to the various fluids, is shown. The straw assembly includes a DIFF straw assembly 820 including tubings 820A, 820B, 820C, and 820D which are respectively connected to a first reagent (Perox Dil 1), a second reagent (Perox Dil 2), a third reagent (Perox Dil 3), and a sheath fluid, through respective check valves 827 which prevent contamination of the supplies of these fluids. The tubings 820A–820C are respectively input to the inputs labeled PEROX Dil 1, PEROX Dil 2 and PEROX DIL 3, of the diaphragm pump unit 504, and the sheath flow tubing 820D is connected to the PEROX sheath pump.

Regarding the CBC/RETIC straw assembly, tube 821A is connected to a reagent for the RBC test, and is connected to the RBC input of diaphragm pump unit 504. The tubing 821B is coupled to the hemoglobin reagent supply and to the HGB input of diaphragm pump unit 504. Tubing 821C is connected to the supply of reagent for the BASO analysis, which is connected to the BASO input of diaphragm pump 504. Tube 821D is connected to the supply of reagent for the RETIC analysis, and is coupled to the input labeled RETICS on diaphragm pump unit 504. Tubing 821E is connected to a supply of rinse solution located in a separate container, e.g., on the floor and is coupled to a RINSE diaphragm pump.

Tube 821F is coupled to a supply of defoamer 849 and is coupled to a defoamer input of UFC 502.

The part labeled "FROM CLEANSER PUMP", "FROM RINSE PUMP", "FROM PEROX SHEATH PUMP", "TO CLEANSER PUMP", on FIG. 40 refer to solutions that are pumped by the utility diaphragm pumps typically located above the reagent bottles.

Referring now to FIG. 37, it is shown that a top cover 810 is mounted over the top panel 813 to protect the RBC optics assembly 117 and the perox optics assembly 116. Additional cover panels including hinged front covers 811 and 812, 816 and 815, 814, and side panels 817A and 817B are mounted to the chassis. Preferably, the chassis members, except for the covers and other exterior panels, are constructed of galvanized steel to minimize corrosion. The outer body panels are preferably constructed of a durable plastic. The steel construction provides enhanced resistance to EMI. It also provides a stronger structure by a pseudo "unibody" construction, wherein certain components, such as the syringe pump modules, are incorporated into the superstructure and important to the structural integrity of the instrument, which produces a lighter, stronger chassis.

G. Autosampler

Figure 11D:
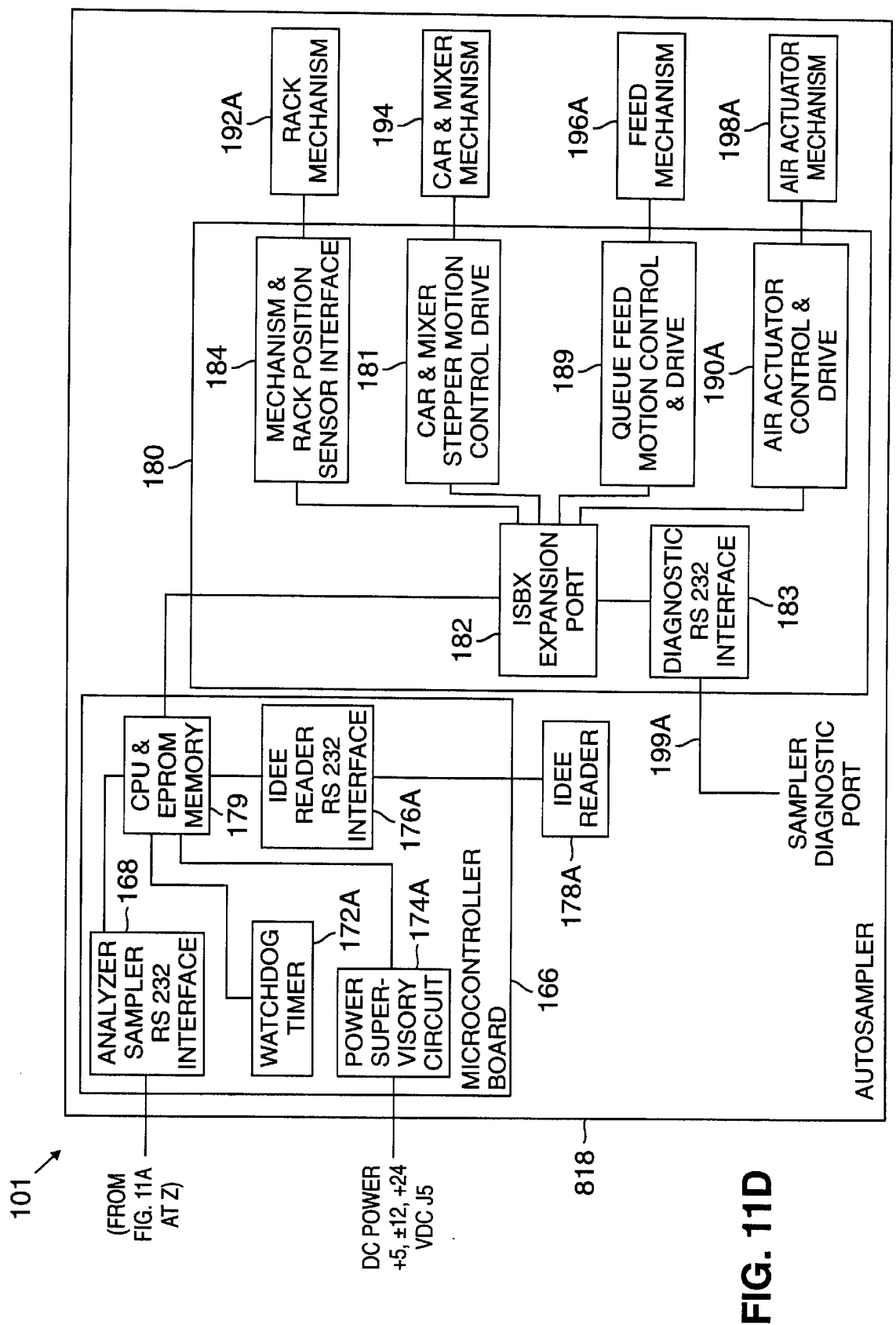
Figure 48:
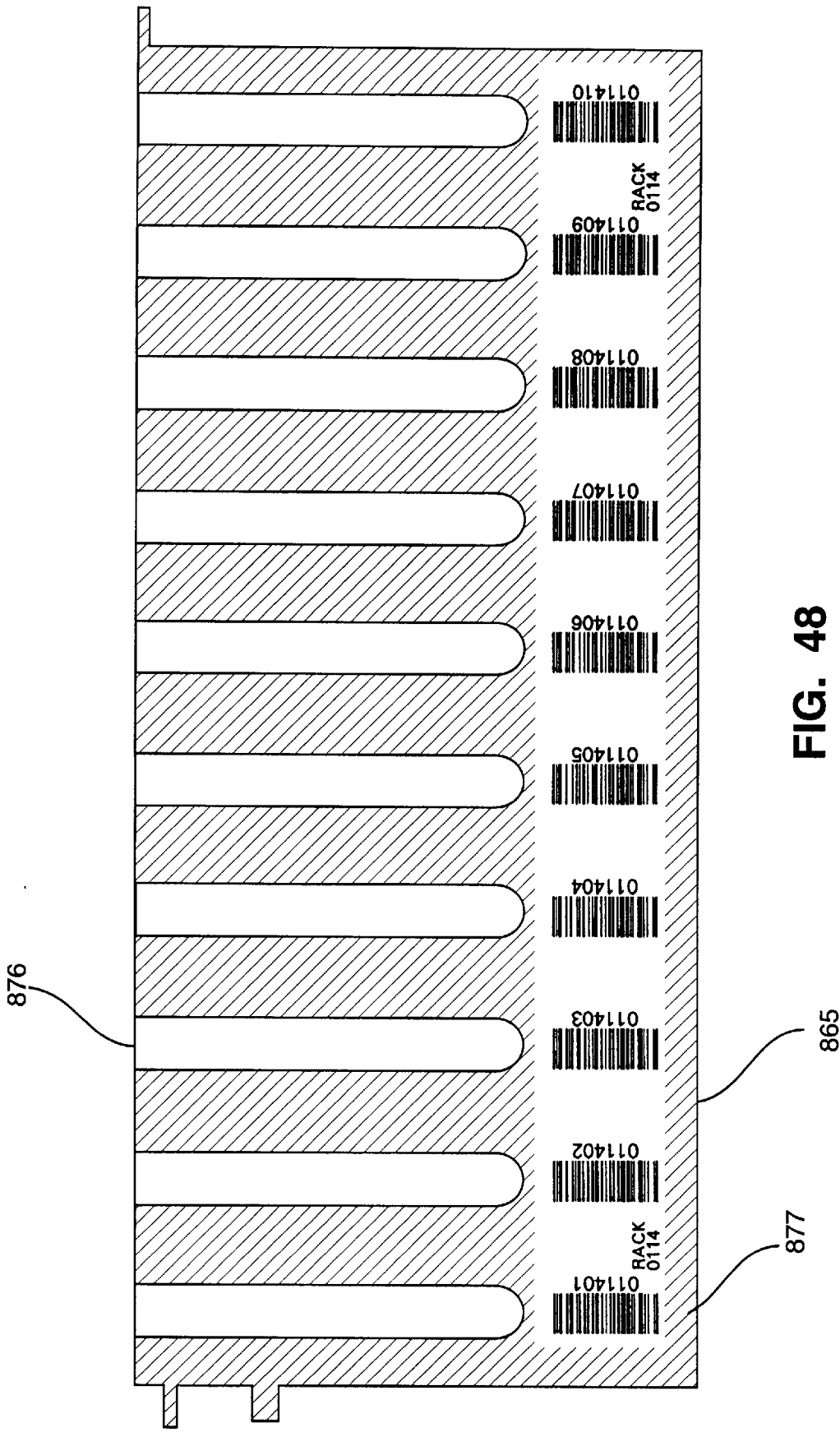
FIG. 48 is a cross sectional view of a cassette suitable for use in the autosampler of FIG. 37.

Referring to FIGS. 11D, 37 and 48, an autosampler assembly 818 which can be used with the present invention is shown. The autosampler 818 comprises an input queue 854, a mixer assembly 880, and an output queue 857. The input queue 854 and output queue 857 are essentially mirror images of each other. Each includes an inner tray 855 for queuing up cassettes 865 (not shown in FIG. 37) wherein each cassette 865 contains a plurality of sample tubes 876, preferably ten (10). A cross section of an exemplary cassette 876 is shown in FIG. 48. Also shown is how each cassette includes ten receptacles which are individually provided with a bar code 877, preferably permanently. Thus, each sample test tube 876 also may be individually bar coded and the bar codes of the sample tubes and the cassette receptacles can be correlated for testing and reporting purposes. The use of ten tubes 876 permits using a "decimal" system for loading a completely full rack. This makes for easy identification by an operator of a tube, for example, from which the autosampler 818 was not able to aspirate a valid blood sample or for which additional tests are required. The operator can then easily locate the tube and perform a test using a manual aspiration port or a separate instrument, as the case may be.

The trays 855 are preferably made of stainless steel and are removable for cleaning. Trays 855 also include one side 855B which is taller than the other side 855A to insure that the cassettes 865, which have corresponding flanges, are loaded into the queue in a proper orientation for passing through the mixer assembly 880. The input queue and output queue are respectively mounted on top of bayonet supports 851 which are rectangular structures secured to the underneath of panel 830 through apertures passing therethrough, and secured to the left and right side using L brackets (not shown). These bayonets 851 serve a dual function of enabling two people to carry the instrument, as well as a support for the input and output queues 854 and 857. A mounting block 852 is used to secure the I-beam rail 853 which protrudes from the input ends of the autosampler mixer assembly 880 to the bayonet 851 and to the input queue 854. The similar arrangement is used on the output queue side. The input and output queues 854 and 857 may be easily removed from the bayonets 851 to facilitate easy transport of the flow cytometer.

The input and output queues each utilize a walking beam design whereby at the input queue, the cassettes are sequentially mechanically urged toward the front of the instrument in close contact with the plurality of cassettes in the queue. Thus, when all of the tubes in a cassette are tested, the next cassette is ready to be inserted, and the just-tested cassette, with all of its sample tubes returned to the cassette, is ejected into a space in the front of the output queue. In one embodiment, two cassettes may be within the mixing assembly at a time. The walking beam design of the output queue walks the tested cassettes to the back of the output queue.

The mixer assembly 880, which does not form any part of the present invention, may be any mechanism suitable for grasping selectively one of the sample tubes 876 from a tubeholding device such as a cassette 865, reading the bar code associated with that selected sample tube, and agitating the selected sample tube 876 and causing the automatic sampler needle 805 to penetrate through the elastomeric seal to aspirate a sample. Alternate autosampler mechanisms also can be used, such as the bandolier system of the Bayer H*3 Systems instrument and the mechanisms used in the Commercial Coulter STKS instrument, and the robotic arm used in the TOA instruments.

It should be understood that the flow cytometer instrument of the present invention is a relatively compact instrument as compared to its prior art devices. It is suitable for use on a table top and it requires only a computer work station electronically coupled to the instrument, and a small space on the floor for a waste container and a bulk supply of sheath fluid. The other fluids that are used in the flow cytometer instrument may be conveniently stored in reagent packs which insert into area 824 of the instrument under the straw assembly (See FIG. 40).

Preferably, the reagent packs have predetermined volumes with a nesting or interfitting design so that they may be banded together, e.g., with a strap of cardboard or plastic, and transported, installed and extracted from the machine at the same time. The predetermined volumes and size of the reagent pack containers are calculated so that, when all of the test capacity of the instrument are used, the supply of reagents will become depleted at approximately the same time. Thus, the operator can conveniently replace a full set of reagent packs with a fresh set of reagents.

In the case that the instrument is provided with test selectivity, as disclosed herein, it may be necessary to provide separate reagent packs corresponding to the combinations of selectable tests, or alternately to separate the reagent packs and use containers that are separately replaceable. In this regard the instrument is provided with an operator input panel which contains various switches and display indicators. These switches enable the operator to commence operation or to interrupt an existing automatic operation to perform a stat sample test. Alternatively, the operator may control operation through a workstation coupled to the instrument, which permits running preprogrammed tests or test sequences automatically.

Having described the mechanical, hydraulic, and assembly of the hardware of the flow cytometer, the following description concerns the electronics and control over the instrument for performing the desired analysis. It should be understood that, although in the preferred mode the instrument is used for analyzing human blood, it also may be used for analyzing blood of other living creatures, as well as non-blood samples having particulates therein which react with particular reagents (fluorescent or non-fluorescent) to obtain unique light absorption and scatter patterns that permit segregating, quantifying, or analyzing one or more subpopulations of the sample, and preferably identifying the particulates therein.

II. ELECTRONICS

A. An Overview

FIGS. 11A–11E are simplified block diagrams which illustrate the electronics architecture 101 of an embodiment of the invention. In FIG. 11A, a workstation 103 is connected to an analytic instrument controller 105 and also may be connected to various other peripherals such as a printer or modem (not shown). The workstation 103 may also be connected to additional instruments controllers and workstations. It is contemplated that the workstation 103 comprises an IBM-compatible personal computer or equivalent (a WINDOWS 95 or WINDOWS NT brand operating system (Microsoft Trademarks) may be used) having a central processing unit at least as powerful as a 486-type microprocessor and adequate memory, a color monitor and a keyboard and mouse for use by an operator. The workstation 103 is preferably connected to an Analytic Instrument Controller 105 via an Ethernet 106.

The Analytic Instrument Controller 105 comprises a 386 CPU and memory 107 connected to the Ethernet 106, to an external flash memory 109, to a manual identification reader device 104, which may be a barcode reader via an RS232 port 176, to an analyzer/sampler RS 232 port 110, to a Control Area Network bus (CANBUS) interface 112, and to a Data Acquisition Interface Board (DATAC IB) 114. The DATAC IB 114 is connected to a Data Acquisition Board ("DATAC") 115 which processes signals generated by the peroxidase (Perox) optics assembly 116 and the RBC optics assembly 117. Power is supplied to the workstation 103, Analytic Instruments Controller 105 and the DATAC 115 from the power supply circuit 200 illustrated in FIG. 11E, which is explained below.

The CANBUS interface 112 of the Analytic Instrument Controller 105 is connected to a CANBUS scrambler 120 shown in FIG. 11B. The CANBUS scrambler 120 provides the cable connections from the Analytic Instrument Controller 105 to the various nodes, which are explained below. Referring to FIGS. 11B and 11C, it can be seen that the CANBUS connects the Analytic Instrument Controller 105 to a plurality of Nodes. In particular, in FIG. 11B, the CANBUS is connected to the hemoglobin node (HGB node) 122, the Switch Indicator Node 124, and the Pressure and Switch Node 126. The HGB node 122 is part of the HGB calorimeter 121 and is connected to a HBG power supply and pre-amplifier circuit board 123. The Switch Indicator Node 124 is connected to a control panel 125 and to the switch and display light assembly 127. The Pressure and Switch Node 126 is connected to the universal rinse assembly 129, the waste jug assembly 128 and the pneumatic/compressor assembly 130A. Power is supplied to the CANBUS scrambler 120, the HBG Colorimeter 121, the Switch Indicator Node 124 and the pneumatic/compressor assembly 130A by the power supply circuit 200 of FIG. 11E.

Referring to FIG. 11C, the CANBUS is connected to Motor Driver Nodes 132, 134, 136 and 138, which are connected to the RBC Optics sample pump 133, RBC Optics sheath pump 135, PEROX sample pump 137 and PEROX sheath pump 139 respectively. The CANBUS is also connected to the Parallel Node 140, which is connected to the Aspirate and Selector Valve assembly 142, the sample Shear Valve assembly 144, the PEROX reaction chamber assembly 146, and the BASO reaction chamber assembly 148. The CANBUS is also connected to two Valve Driver Nodes 150, 160. The first Valve Driver Node (node 1) 150 is connected through a scrambler 151A to the various components comprising the Unified Fluid Circuit (UFC) which is discussed elsewhere, including the sample shear valve 152, the Unified Flow Circuit Assembly 153, the Conductivity Detector 154, the PEROX heater 155 and the BASO heater 156. The second Valve Driver Node (node 2) 160 is connected through scrambler 161A to several valves located in both the RBC Optics assembly 117 and the PEROX Optics assembly 116. In addition, the second valve driver node 160 is connected through scrambler 162 to a plurality of valves in the Pneumatic Control Assembly 163.

Figure 11E:
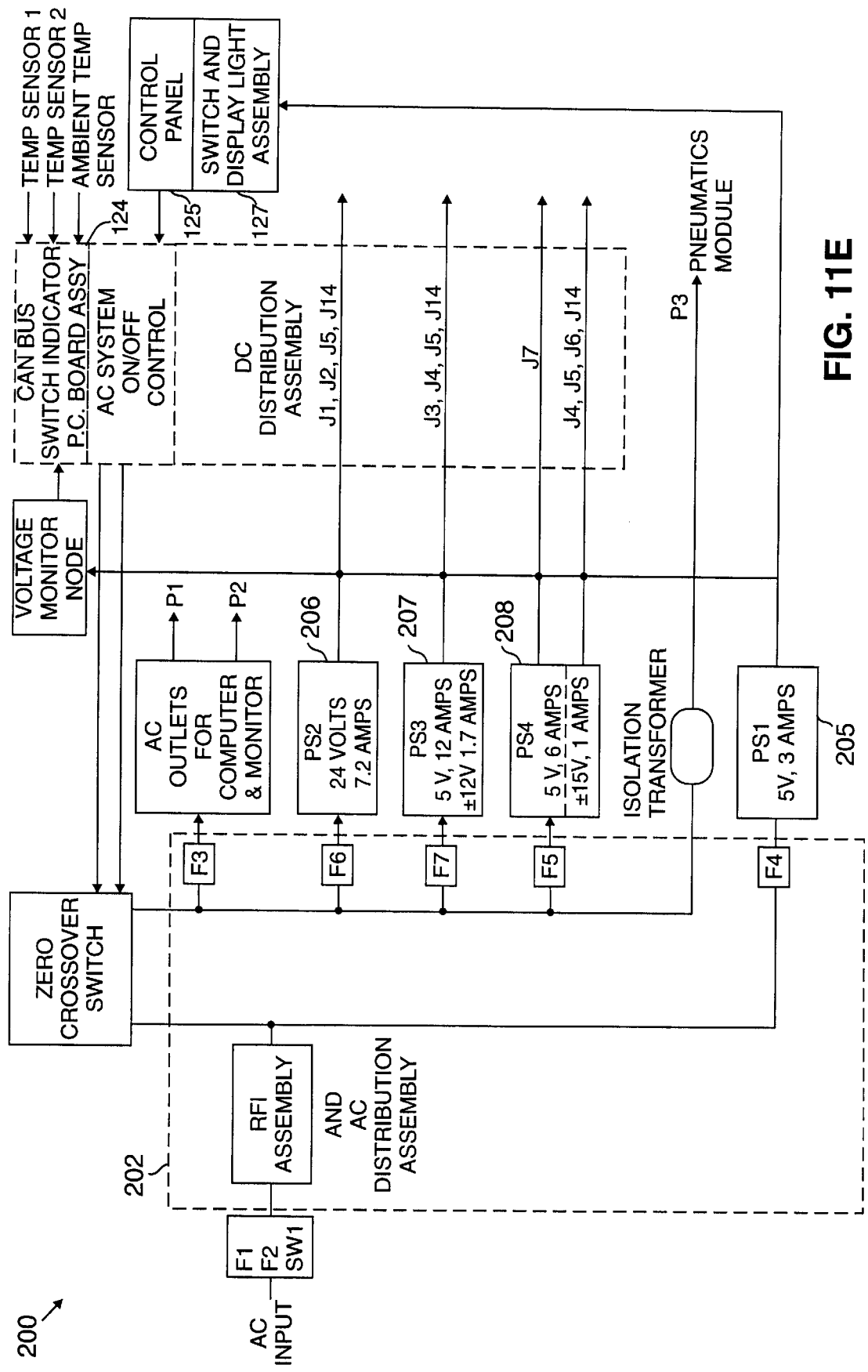

FIG. 11D is a simplified block diagram of the electronic connections for an Autosampler 818 which may be coupled to the flow cytometer of the invention. A Microcontroller Board 166 is connected to the Analytic Instrument Controller 105 of FIG. 11A through an analyzer/sampler RS232 interface 168. A CPU and EPROM memory circuit 179 is connected to the RS232 interface 168, and is connected to a watchdog timer 172A, a power supervisory circuit 174A, and a bar code reader interface 176A which connects the Microcontroller Board 166 to a bar code reader 178A. The Microcontroller Board 166 is further connected to a custom designed Daughter Board 180 via an ISBX Expansion Port 182. The Daughter Board comprises the ISBX Expansion Port 182 connected to a Diagnostic RS232 Interface 183, a Mechanism and Rack Position Sensor Interface 184, a car and Mixer Stepper Motion Control Drive 181, a Queue Feed Motion Control and Drive 189 and an Air Actuator Control and Drive 190A. Connected to the Daughter Board 180 are the Rack Mechanism 192A, the car and Mixer Mechanism 194, the Feed Mechanism 196A, the Air Actuator Mechanism 198A and a Sampler Diagnostic Port 199A. Power is supplied to the Autosampler 818 by the power supply circuit 200 of FIG. 11E FIG. 11E is an embodiment of a power supply circuit 200 suitable for use with the apparatus of the invention. The power supply circuit 200 advantageously utilizes linear power supplies which avoids the use of switched power supplies. Linear supplies are less expensive than switched supplies, and generate less noise in the system. Noise from the power supply must be kept to a minimum so that the signals generated as a result of the optical analysis of the blood samples are not corrupted by such noise. The alternating current (A/C) power comes into a RFI filter assembly 202, which includes fuses F1, F2, and main power interrupting switch S1, and provides the A/C outlets 203 for use by the workstation 103 components, such as the computer and monitor. The RFI assembly 202 provides a system ground and also provides protection from transient voltage spikes, power supply fuses, and voltage selector programming switches (not shown). Zero Crossover Switch 204A is used for turning the system on and off, and an AC to DC linear power supply 205A, provides 5 volts at 3 amps for use by such components as the HGB lamp, front panel switch and other display control components. The Zero Crossover switch 204A is connected to AC to DC convertor power supplies 206, 207 and 208. Power is supplied directly from the Zero Crossover Switch 204A to an isolation transformer which is used to supply the pneumatics module 126 via line J3. The power supply 206 supplies 24 volts DC at 12 amps to the fans, solenoids, heating baths, dryers and motors of the apparatus. The fans (not shown) for the system are mounted below the power supply 200 and the other components comprising the invention, and thus provide forced air cooling for the entire system. The power supply 207 supplies±12 Volts DC at 1.7 amp to the sampler, heater and communication components. The power supply 207 also provides 5 Volts DC at 12 amps for the sampler and system logic processing components. The power supply 208 provides 5 Volts DC at 6 amps for the Peroxidase optics lamp. Power supply 208 also supplies±15 Volts DC at 15 amps for the HGB Colorimeter 121, DATAC 115, reference channel illumination assembly and the RBC Optics assembly 117. Other components, not mentioned immediately above, also receive power from the power supply circuit 200 as needed.

The Switch Indicator and Voltage Node 124 is located in the Power Module 200 and is connected to the system controller 107 (shown in FIG. 11A as including a CPU and associated memory devices). The system controller 107 monitors each power supply through the Switch Indicator Node 124 to ensure that the voltage levels are within preset tolerance limits. If a problem is detected, an alerting signal can be generated for display at the workstation 103 to notify the operator. In addition, temperature sensors monitor Power Module 200 air temperature and the system ambient temperature which can be displayed at the Workstation 103.

Now that an overview of the electronics architecture of the apparatus has been presented, detailed descriptions of certain components follow.

B. The Workstation

Figure 12:
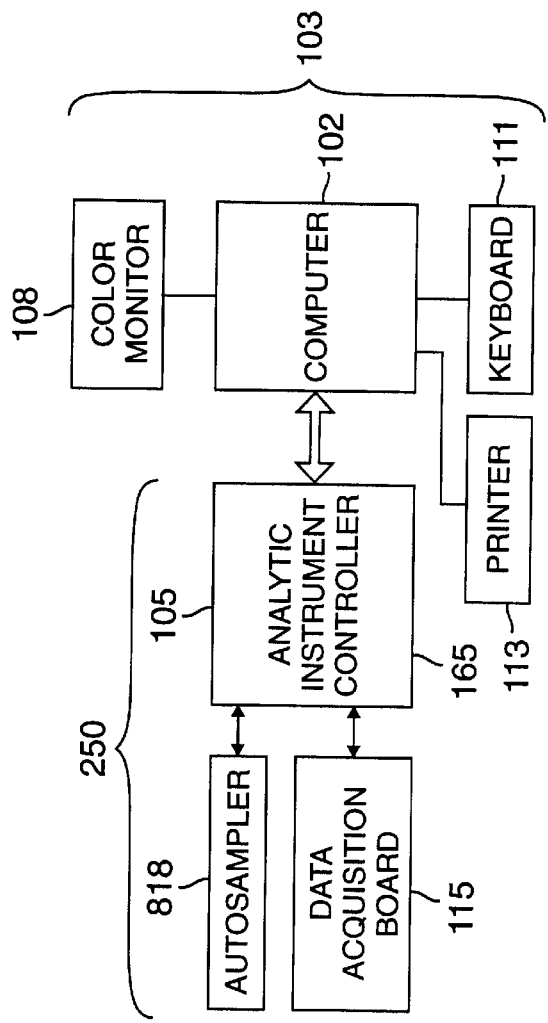
FIG. 12 is a block diagram of the two major computer subsystems of the architecture of FIG. 11A–11E.

FIG. 12 is a simplified block diagram of the two major subsystems of the apparatus in accordance with the present invention, the Analytical Subsystem 250 and the Workstation Subsystem 103. The Workstation 103 comprises an IBM compatible PC 102 having a color monitor 108 and keyboard 111, which is connected to a printer 113 and to the Analytic Instrument Controller 105 via an Ethernet connection using the TCP/IP protocol. The workstation may have floppy, hard disk and CD-ROM drives, and a mouse. The Analytical Subsystem 250 comprises the Analytic Instrument Controller 105, the Autosampler 165 and the Data Acquisition board 115.

The Workstation 103 contains software to initiate testing of blood samples, process the resulting test data and graphically present the results. It also may be coupled to a network for interworkstation communications. The software to enable the electronic circuitry and the electromechanical devices of the submodule 250, to analyze samples and generate test data to be processed, may be downloaded from workstation 103.

Regarding the analytical submodule 250, it is a collection of hardware and software that together control and monitor the hydraulic hardware, the sampler 818 and communicate with an instrument workstation 103. The controller 105 executes a software routine on, e.g., an Intel 386 ex processor. The architecture also includes an Ethernet and control area network (CAN) cards, a PC104 bus, the DATAC board 115 and the "NUCLEUS PLUS" RTOS, which is available from Accelerated Technology Inc. A "loose" coupling mechanism is employed in the analytical submodule software architecture to provide greater maintainability, portability and extensibility. IPC mechanisms are the only coupling between modules. In general, processes will block waiting for input. This input can come from the CANBUS, autosampler 818, the workstation 103, the barcode reader 178, 104, or from the expiration of internal timers.

The workstation 103 does not form a part of the present invention. However, it can be used with the present invention to provide greater user flexibility and enhance the utility of the clinical hematology instrument disclosed herein. For example, some of the conventional functions that might reside in the system controller 105 e.g., reset functions, and responding to operator input selections on the instrument control panel 125 (see FIG. 11B) to run one or a series of tests, can be off loaded to the workstation to minimize the computational burden on the analytic controller 105 CPU 107. Thus, the workstation 103 may be a more powerful machine, such as a 486 DX 66 MHz CPU or a Pentium class CPU. In this context, the workstation PC 103 can be configured to execute a "start-up" procedure which launches all required system-critical processes, initializes key system attributes, presents the main system menus on the workstation display (thus avoiding the need for a dedicated display for the system controller 105), provides a clean system shutdown, allows for the ability to configure system initialization in terms of: (i) on-line (connected to an instrument) or off-line operation (e.g., operating on data on a disk); (ii) selecting the system critical modules to launch at startup; and (iii) selecting other modules to launch at start-up.

The workstation also carries out all processing required on the raw digital data received from the analytic instrument controller 105 DATAC 115, and completes all required data analysis, determined by the sample analytical mode, e.g., CBC, CBC/DIFF, etc. Thus, the workstation 103 stores, preferably in compressed form, the raw data as it was received, issues the analytical results to a "results" storage mechanism (memory, Floppy, paper printout) and issues the analytical results. to a Run Screen (visual display). Preferably, the workstation also contains data management processing software for operating on the acquired data post-acquisition.

Another function that the workstation 103 can perform is as the central arbitration and messages issuing point to the analytic submodule 250. It handles the issuing of message to the submodule 25 as required by other applications/processes and receives back the status of submodule 250. Such a workstation 103 may connect to the submodule 250 over 2 unidirectional "sockets," one for the issuing of control messages and the other for the reception of status and error messages.

Regarding worklists, work-orders and controlling the running of sample tests, the Workstation 103 may be responsible for ensuring that the selectivity (or more correctly the analytical mode) and the header information (ID, date, time, Sample type, Species, etc.) are selected on a per sample basis as required by the user. It can locate the required information from a user-defined Worklist (if one is active), or Run Control user interrupt screen (if it is active and contains the required information), or from a default setting. Thus, the workstation can receive a notification that a sample is about to be processed and react to this by issuing the required analytical mode and header information from the pertinent source; when running in a Bar code reading mode (either via the Manual IDEE Reader 104 or via the AutoSampler bar code reader), receive the Bar Code data and update the Run Control screen accordingly; and when running in a Worklist mode, to issue the pertinent sample data as retrieved from the worklist database to the analytic submodule 250 and to issue this same information to the Run Control user interface.

At the start of a series of tests as initiated by the workstation 103, the System CPU 107 generates the commands to the various Nodes to acquire the raw data from the red blood cell (RBC) and platelet (PLT) (collectively, RBC/PLT), reticulocyte (RETIC), Hemoglobin (HGB), Peroxidase (PEROX) and Basophil (BASO) channels.

As the RBC/PLT and hemoglobin data are acquired they are converted from analog to digital form and loaded into a buffer in the System CPU 107. The raw digitized data are checked for validity and, if valid, transferred to the workstation 103 for processing. At the end of the data acquisition period, the accumulated RBC/PLT and HGB data are analyzed by the workstation by the RBC/PLT, hemoglobin analysis program to calculate the RBC parameters and the platelet PLT and hemoglobin HGB parameters, and to generate the thresholds and graphics for the RBC Cytogram and the graphics for the RBC Volume and PLT histograms.

Similarly, at the end of the perox data acquisition period, the valid perox data transferred to the workstation are analyzed in the workstation by the white blood cell (WBC) analysis program to calculate the WBC parameters, and to generate the thresholds and graphics for the PEROX cytogram. The data from the Basophil channel transmitted to the workstation are analyzed after the peroxidase channel data by the WBC analysis program. As in the other two channels, the Basophil data is calculated and reported. The Lobularity Index is also calculated and reported, and the thresholds and graphics for the Baso/Lobularity cytogram are generated.

Reticulocyte samples also are automatically analyzed after being transmitted to the workstation. As the reticulocyte data are acquired, they are converted from the analog to digital form and loaded into a buffer and, if determined valid, transmitted to the workstation and stored. At the end of the data acquisition period, the reticulocyte data transmitted to the workstation are analyzed by a RETIC analysis program to generate histograms, cytograms and thresholds, which are used to determine the percentage of reticulocytes.

The color monitor 108 used by the system accepts screen data from the workstation 103. The printer 113 is able to print out screen data and graphics, for example, test results, statistical data, and graphics (cytograms, histograms), preferably in multiple colors.

It should be understood that the functions of the workstation could be integrated into the system controller 105, although this is not believed to be desirable given the current state of data processing technology and power.

C. The Data Acquisition Board

The DATAC board 115 shown in FIG. 11A processes signals generated from the flow cytometric light scattering tests to measure red cell count, volume and hemoglobin content, platelet count and volume. As explained briefly below, cell volumes and hemoglobin content are determined using high angle and low angle light scattering techniques. The signals generated from such tests are processed and then may be displayed on a monitor screen of the workstation 103 for review by an operator, or printed out on a printer.

In particular, data are collected by the DATAC 115 for the low angle low gain, high angle low gain, and absorption signals for each of a large number of cells comprising the sample set. A reticulocyte cytogram before pseudo-absorption correction is generated using the high angle scatter and absorption data. An RBC cytogram is generated using the high angle scatter and low angle scatter data.

The Volume (V) and Hemoglobin Concentration (HC) is then calculated cell by cell using the low angle scatter and high angle scatter data. The values found for V and HC are used to calculate the pseudo-absorption for each cell. The new cell data are used to regenerate the reticulocyte cytogram.

The reticulocyte threshold, the upper coincidence threshold and the lower platelet threshold are calculated using high angle and absorption histograms. The RBC, reticulocytes and outliers are separated using software and threshold settings.

The system typically reports only the percentage of reticulocytes. The absolute reticulocyte count is found by matching sample IDEE (i.e., bar code) numbers and multiplying the percent reticulocyte count by the RBC count found in the autocytochemistry results. These calculations are performed by the workstation 103 based on the data provided by DATAC 115.

Figure 13:
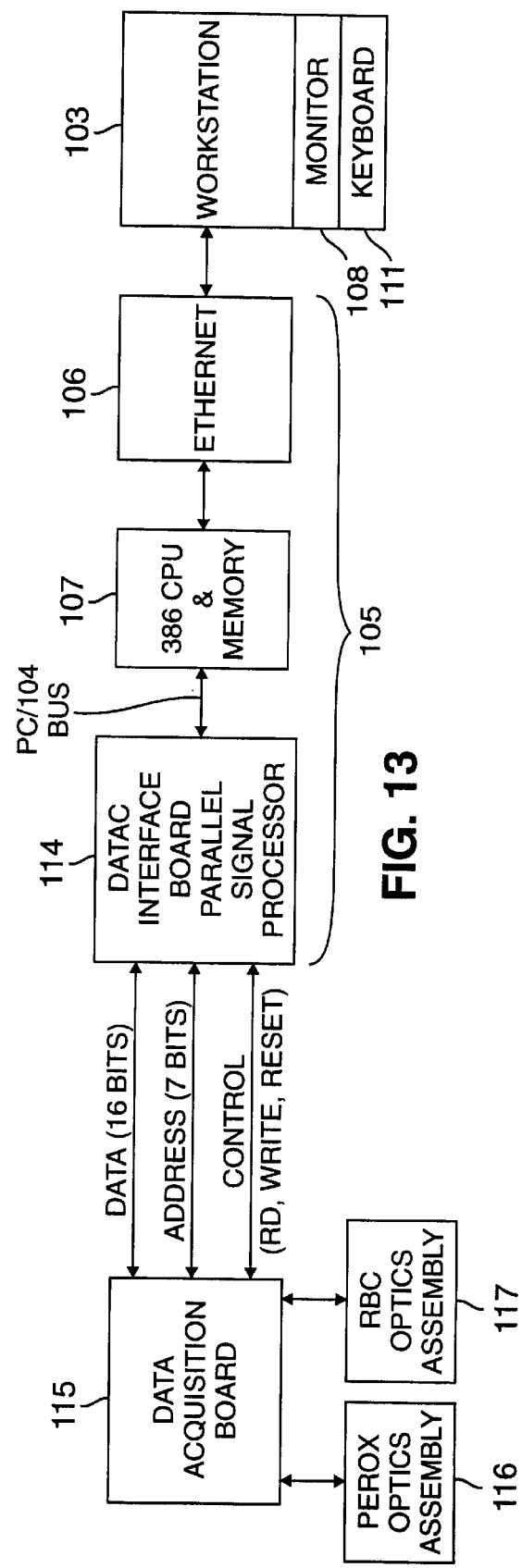
FIG. 13 is a block schematic diagram of the input and output connection of the Data Acquisition Board of FIG. 11A.

FIG. 13 is a simplified block diagram of the input and output connections of the DATAC 115 of the invention. In particular, the DATAC 115 receives blood test data in the form of analog signals from both the Peroxidase Optics assembly 116 and the RBC Optics assembly 117. These analog signals are received at the DATAC 115 where, when appropriate, they are conditioned, amplified, digitized and fed into a buffer for data collection.

The DATAC 115 is connected to the Data Acquisition Interface Board ("DATAC IB") 114 of the Analytic Instrument Controller 105 via a 50 pin ribbon cable. DATAC IB 114 has a PC/104 parallel bus which is compatible with PC/AT system architecture and is mapped into the standard DOS I/O address space (OH-03FFH). Sixteen bi-directional data lines, seven address lines and I/O Read, I/O Write and Reset control lines are provided between the DATAC board 115 and the DATAC IB 114. The typical transfer rate to pass digital cell information to the System CPU 107 via the DATAC IB PC/104 parallel bus is 80K bytes per second.

The DATAC 115 performs signal amplification, analog and digital processing and test or diagnostic functions. The DATAC 115 is preferably embodied in a board utilizing hybrid circuits and field programmable gate arrays (FPGAs) which convert analog signal inputs into digital outputs for further processing. Such circuitry reduces the size of the board by combining discrete digital control circuit functions into single component blocks. In addition, cabling requirements are reduced, and modular testable blocks and test injection ports are provided.

Figure 14:
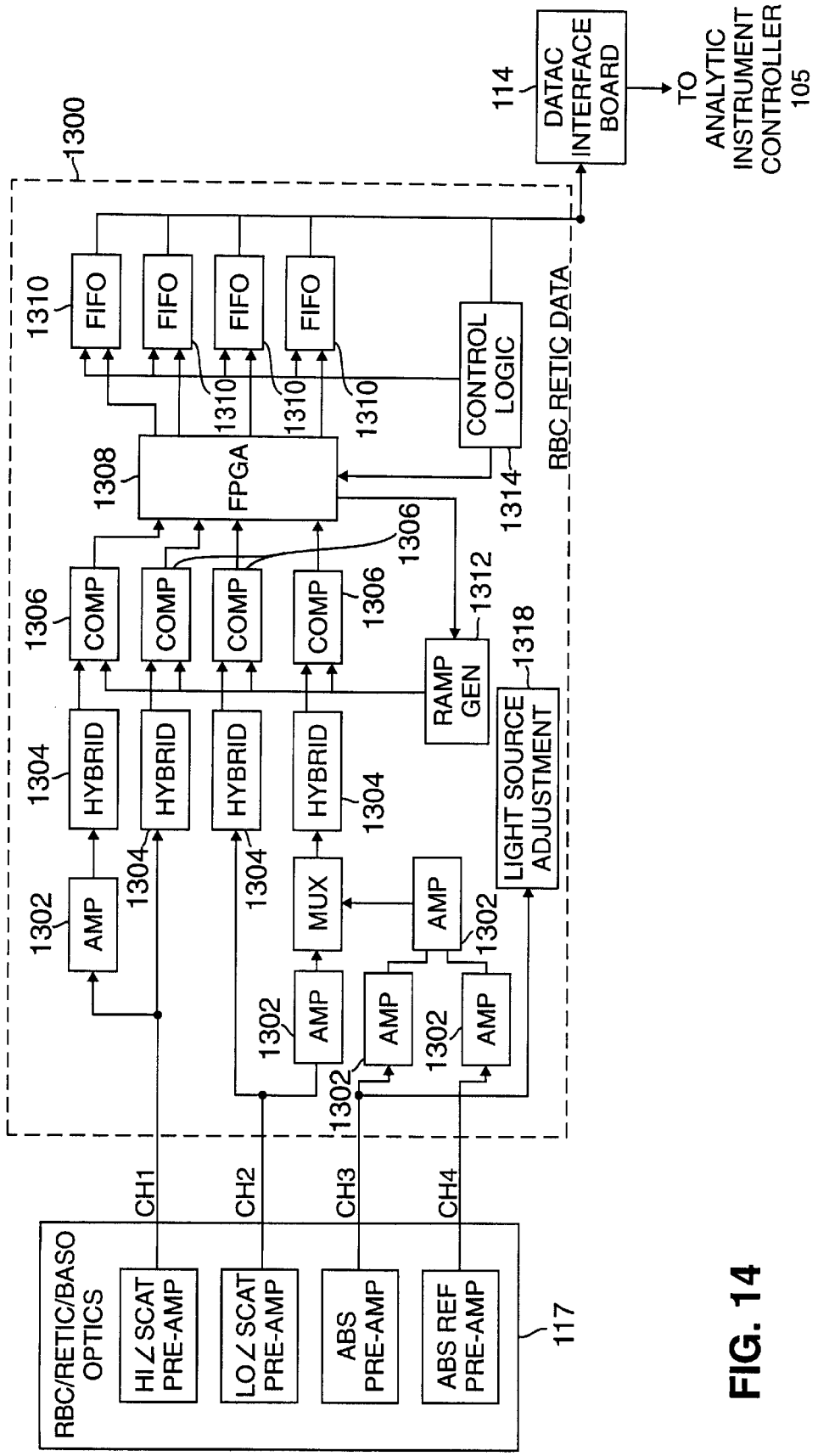
FIG. 14 is a schematic block circuit diagram of the Data Acquisition Board of FIG. 13.

FIG. 14 is a simplified block diagram of a portion of the DATAC 115 circuitry that is used for processing the signals and providing output concerning the RBC/RETIC and BASO blood tests performed by the apparatus. An optical bench 117 provides analog blood test signals from the laser diode 131 not shown in FIG. 14) over four channels. The signal pulses provided by the four channels are, respectively, an Absorption reference (AR) signal (Channel 4), a Scatter Low Angle (SLA) signal (Channel 2), a Scatter High Angle (SHA) signal (Channel 1), and a RETIC Absorption (RA) signal (Channel 3). The circuitry demarcated by dotted line 1300 processes the analog signals from the four channels to produce the RBC and RETIC blood analysis results. The analog signals, which are low gain signals as discussed below, are input to amplifiers 1302, then into hybrid circuits 1304, comparators 1306 and FPGA 1308 for RBC/RETIC blood analysis processing. The hybrid circuits 1304 include analog divider circuitry, analog gain control circuitry, variable gain amplifiers, DC restoration amplifiers and peak-detecting circuitry. The analog gain control circuitry is used in part to nullify variations in the energy of the optical channel illumination source ratiometrically. It should be understood that the hybrids 1304 may actually include the comparator 1306 (shown separately in FIG. 14 for clarity) and perform the digital conversion of the peak-detected analog signed under the control of the. FPGA 1308 and in response to the ramp generator 1312, as described in further detail below. FPGA 1308 includes logic sequencer circuitry, pulse height analyzer circuitry and control is logic circuitry to calculate variables such as cell dead. time and valid cell count. Some general background on the red blood cell (RBC) and reticulocyte (RETIC) blood tests follows immediately below.

Reticulocytes are immature red blood cells that still contain RNA. They are often larger than mature red blood cells (RBCs). In the present invention, reticulocyte samples are chemically treated with a reagent on-line in a RBC channel. The reticulocyte reagent volumetrically spheres all RBCs and then stains the RNA in the reticulocytes. See commonly owned U.S. Pat. No. 5,350,695 (Collella et al.) which describes a suitable reagent and methodology permitting the on-line incubation and which is incorporated herein by reference. Reticulocytes are determined in two phases. Phase one is by measuring the light absorption of the cells and phase two is by software which discriminates between RBCs and reticulocytes.

The RBCs and reticulocytes that pass through the flow cell 110 (not shown in FIG. 14) scatter light at low and high angles, and the stained reticulocytes also absorb a percentage of the light. The scattered light signals are detected by photodiodes on a single printed circuit board. The percentage of light absorbed, and light scattered at too great of an angle for the optics to collect (pseudo-absorption) are detected by an RETIC Absorption photodiode as described elsewhere herein.

Referring again to FIG. 14, the signal amplitude in the scatter low angle low gain channel (channel 2) must be greater than 0.6 volts to be considered a valid cell. If the signal from the low angle low gain channel 2 meets the first criteria for a valid cell, it is checked again in FPGA circuit 308 to determine if the pulse width is between 2–80 microseconds. A ramp generator 1312 provides a ramp signal, as part of the digital conversion process, for ten microseconds to convert simultaneously the four peak detected signals. If the pulse width is within the specified limits, and the first criterion is also true, then the signal is classified as a valid cell signal and the resultant analog signals produced by channels 1, 2, 3 and 4 for the same cell-laser beam interaction are converted to digital words and stored in FIFO buffers 1310. A control logic circuit 1314 controls the release of data from the FIFOs to the analytic instrument controller 105 via the DATAC IB 114 (see FIG. 11A). Light source adjustment circuit 1318 provides a constant gain setting to the denominator of the analog divider inside the hybrids 1304 so that any change in the light source is equally experienced by the numerator and denominator of the hybrid divider(s), and therefore provides a normal cell pulse signal from the dividers. More generally, it provides for computer setting of the automatic gain control voltage to the hybrids 1304. It is one of the achievements of the present invention that the use of potentiometers and other devices requiring manual adjustment for calibration the electronics, which are used in prior art instruments, are avoided.

During the RBC/RETIC testing period, a computer program performs coincidence correction to trim and transform the cytogram data into RBC volume and hemoglobin concentration histograms. The high angle, high gain data are used to form a platelet volume histogram. The histograms are used to calculate cell size parameters. The RBC/RETIC ratio, together with the dead time and valid cell counts, are used to calculate the percent RETIC count and RETIC indices. After the test signals are processed, an operator can view all the blood test results on the monitor of workstation 103.

FIG. 14 also depicts the BASO blood test signal acquisition circuitry which processes the signals from channels 1 and 2. The separation of the baso/lobularity cytogram into distinct clusters is performed by software and fixed thresholds. The Basophils are relatively large and scatter more light in the direction of the low angle scatter detector. The polymorphonuclear (PMNs) separate from the mononuclear (MNs) cells by scattering more light in the direction of high angle scatter detector. The ratio of PMNs and Mns are used in a lobularity index (LI). In particular, the SHA and SLA signals are input to their respective hybrid circuits 1304, and then into comparators 1306 and FPGA 1308 as previously described, but used in this case for the BASO processing. The data from the other channels 3 and 4 are not used in the BASO determination. A feedback signal from FPGA 1308 through ramp generator 1312 is used by the comparators 1306 for the digitization. The signal amplitude of the SHA, scatter high angle gain signal (channel 1), must be greater than 0.6 volts to be considered a valid cell. If the SHA signal from channel 1 meets the first criteria for a valid cell, it is checked again in FPGA 1308 to determine if the pulse width is between 2–80 $\mu$sec. If the pulse width is within the specified limits, and the amplitude is greater than 0.6 volts, then the signal is classified as a valid cell signal and the analog signals are peak-detected and converted to digital words and stored in the corresponding FIFO buffers 1310.

Control logic circuit 1314 controls the release of data from the FIFOs 1310 to the analytical instrument controller 105 via the DATAC IB 114. The data collected from the low and high angle detectors are then used to form a cytogram, which can be viewed by an operator at the workstation 103. Preferably, BASO signal acquisition circuitry is on the same printed circuit board as the RBC/RETIC circuitry 1300. However, a separate circuit board with a parallel set of hybrid and FPGA circuits also could be used.

Figure 16:
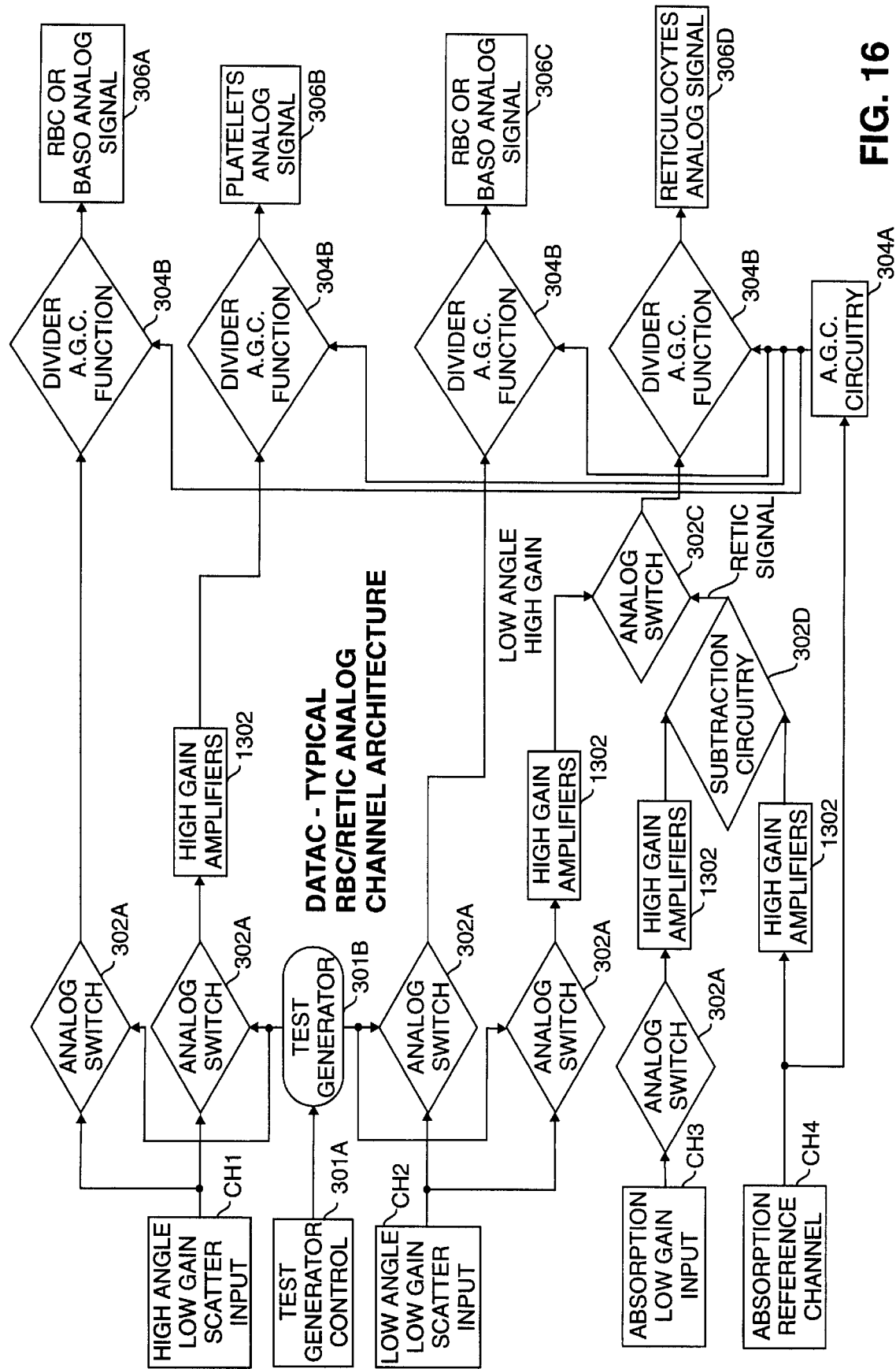
FIG. 16 is a functional schematic diagram of a portion of the Data Acquisition Board of FIG. 14.

Referring to FIG. 16, a functional schematic drawing of the input section of DATAC 115 including the hybrids 1304 of FIG. 14 is shown. Each input channel is provided with an automatic gain control circuit 304b which typically performs a divider operation on the analog signal. The magnitude of the division function is controlled by a master gain control circuit 304a. Other automatic gain control circuits may also be used. The analog switches 302a are used to control the selection and direction of the four possible low gain input signals through DATAC 115 for deriving the different output analog signals to be input to the four comparators 1306, as follows: the high angle scatter RBC or BASO analog signal to comparator 306a, the platelet analog signal to comparator 306b, the low angle scatter RBC or BASO analog signal to comparator 306c and the RETIC analog signal to comparator 306d. Although not shown in FIGS. 14 or 16, a D.C. voltage restoration circuit for each a.c. coupled analog signal is used, preferably at the input to the comparators 1306. See, e.g., the similar circuits in the PEROX signal processing circuits in FIG. 17.

Subtraction circuitry 302d is used to derive the RETIC signal using conventional differential subtraction technigues, as are well known. Analog switch 302c is used to select passage of one of the low angle high gain signal and the RETIC signal through the corresponding divider circuit 304b.

The test generator control circuit 301a is used to operate the test generator circuit 301b, which produces predetermined valid analog signals into the DATAC 115 inputs (bypassing only the photodetectors), to perform diagnostic and troubleshooting tests on the data acquisition and signal processing equipment. This on-board test signal injection uses known pulse width, pulse height and duty cycle signals to test the system integrity and diagnose malfunctions, as well as to calibrate the instrument automatically. For example, the system controller 105 or the workstation 103 can be programmed to perform maintenance checks on the electronics at particular times or time intervals, e.g., start up or reset, to actuate the test generator control circuit 301*a* and appropriate analog switches to verify proper operation. Preferably, it also can be "manually" activated, for example, during a field service inspection or operator initiation. In this regard, the test signal amplitude can be used to conduct unsaturated testing of all analog system components. Further, synchronization of test signals allows digitizing, counting and displaying pulse pairs on a monitor. The test system is disabled during normal operation.

Figure 15:
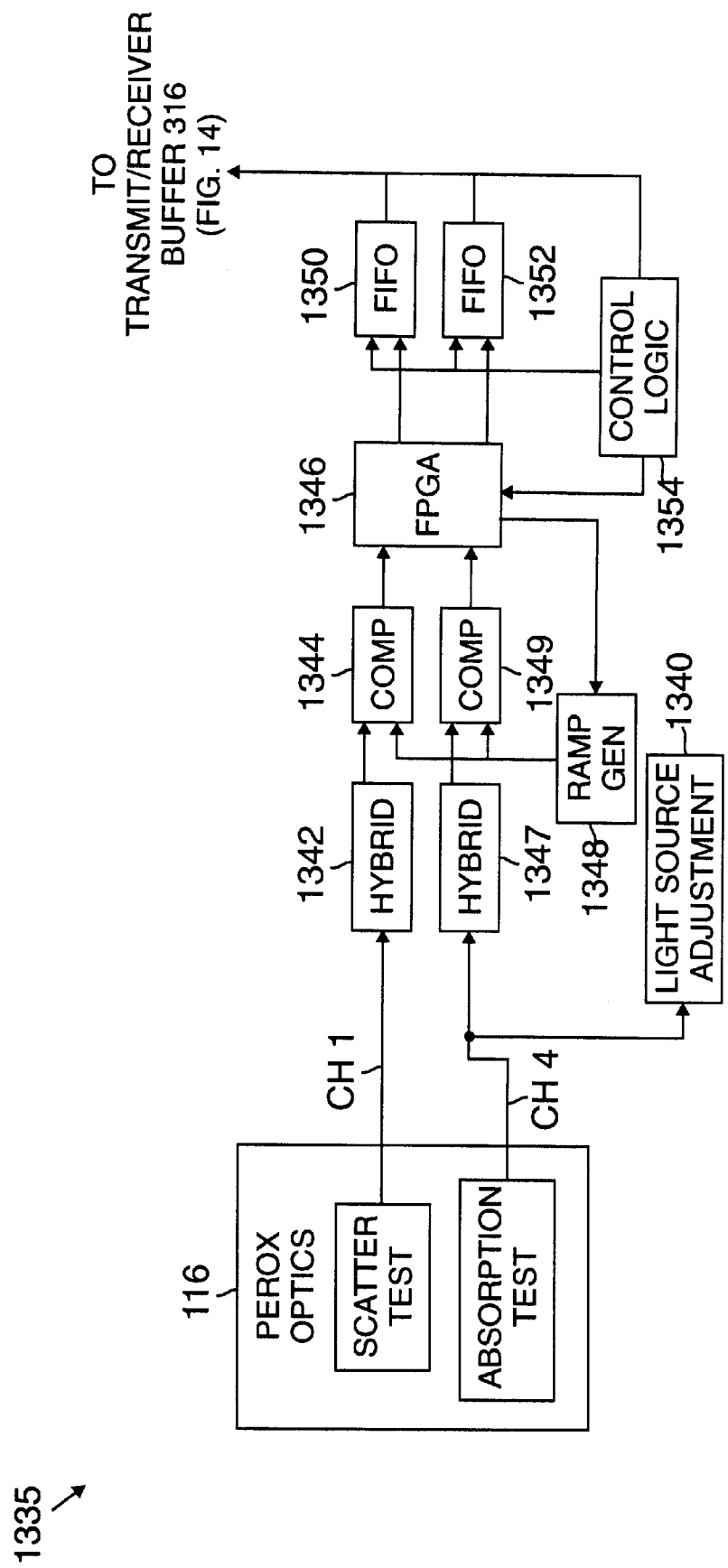
FIG. 15 is a block schematic diagram of the Peroxidase Analog channel of the apparatus of FIG. 13.

FIG. 15 is a simplified block diagram of a Peroxidase Analog channel architecture 1335. The PEROX Optics Assembly 116 generates two signals, a low gain scatter signal CH1 and high gain absorption signal CH4, which are input to hybrids 1342 and 1347, respectively. The high gain scatter signal from channel 1 is fed to a hybrid amplifier 338, is fed to a hybrid circuit 1342, then to comparator 1344 and into FPGA circuit 1346. Similarly, the high gain absorption signal from channel 4 is fed to hybrid circuit 1347, then to comparator 1349 and into FPGA circuit 1346. The comparators 1344 and 1349 each have a second input from ramp generator 1348, which is controlled by the FPGA circuit 1346. During the PEROX analysis period, the signal amplitude in the scatter channel must be greater than 0.6 volts to be considered a valid cell signal. As in the RBC/PLT, RETIC and BASO data acquisition channels, the signal is checked again to determine if it meets the valid cell criteria of a pulse width between 2–80 µsec. If it does, the analog pulses in the scatter and absorption channels (X and Y) are peak-detected, converted into digital words and stored in FIFO buffers 1350 and 1352. The control logic circuit 354 controls the release of the data signals stored in the FIFOs to the analytic instrument controller 105, as shown in FIG. 14, which are then used to form a PEROX cytogram. The signal pulses in the scatter channel are also measured by a dead time counter and the pulse widths are checked to determine if the signals should be counted by the valid cell counter.

Figure 17:
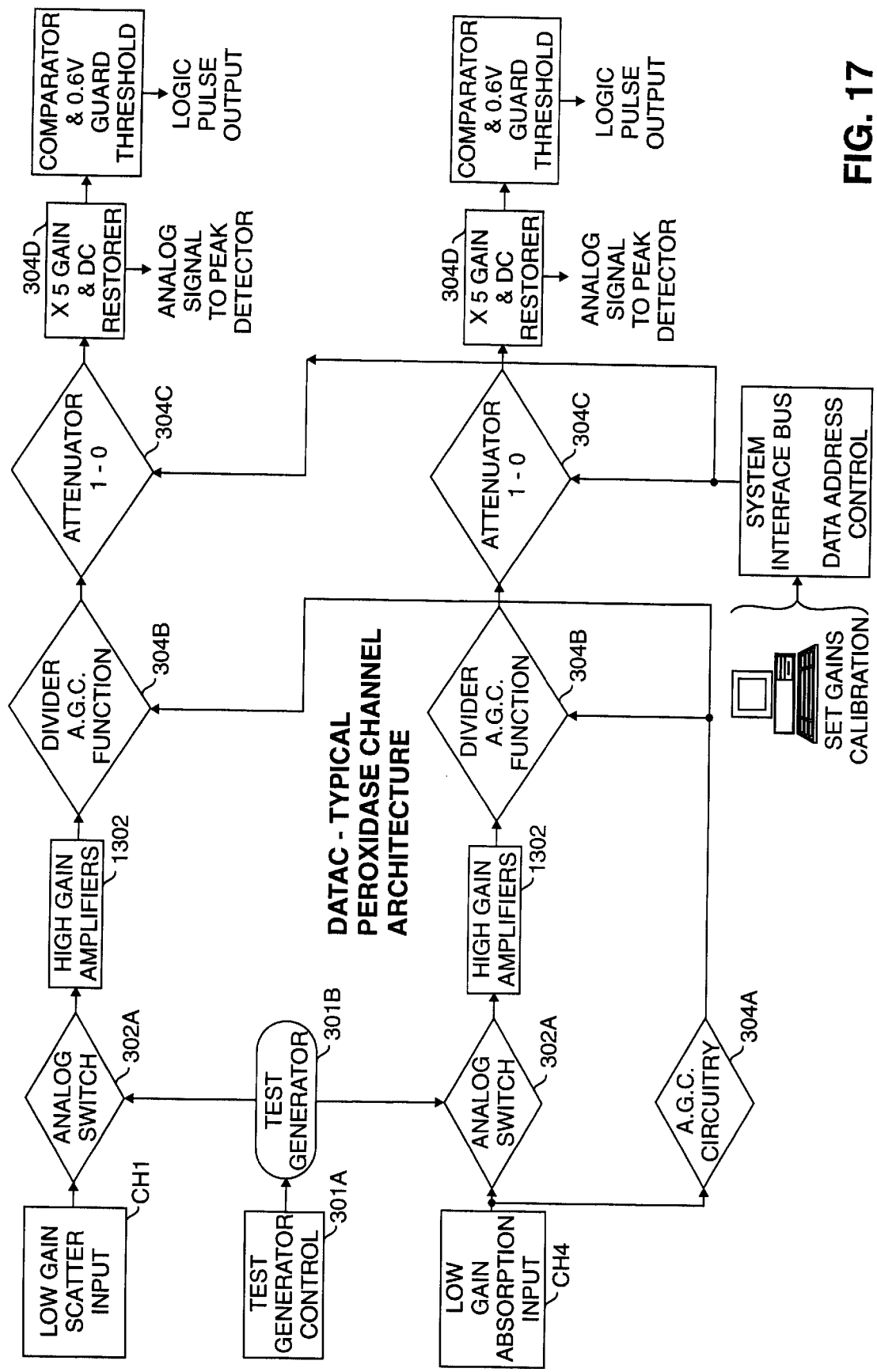
FIG. 17 is a functional schematic diagram of a portion of the Data Acquisition Board of FIG. 15.
Figure 18:
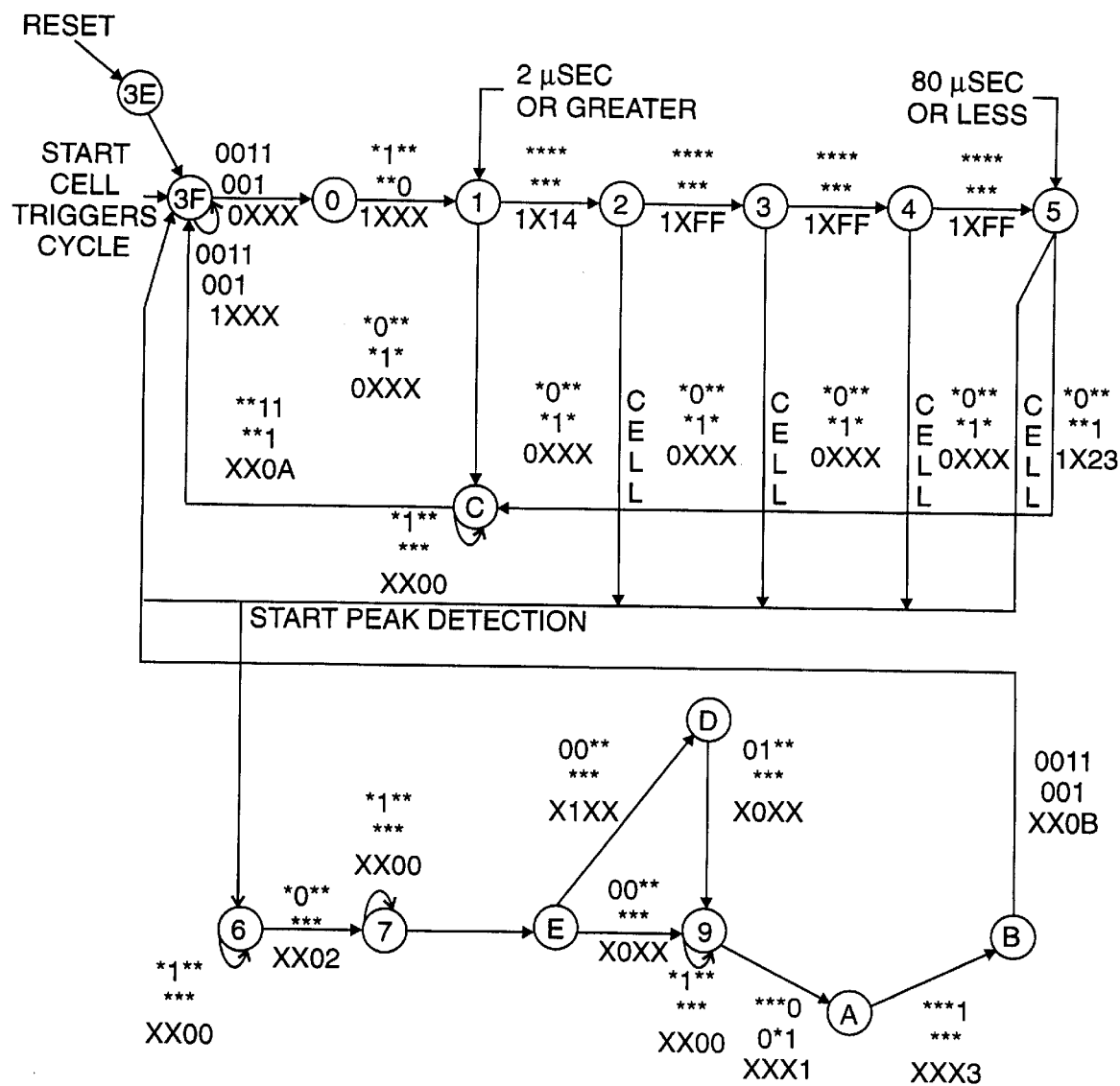
FIG. 18 is a state diagram of the Data Acquisition Board of FIG. 13.

Referring to FIG. 17, further details of portions of the PEROX channel of FIG. 15 are shown. Similar to the RBC/BASO circuit of FIG. 16, the PEROX channel also includes analog switches 302*a*, which in this case can select between on the one hand the high gain scatter input of CH1 and the high gain absorption input of CH4 and on the other hand the test pulses output by test generator 301*b* (under the control of test generator control 301*a*). The PEROX channel also includes automatic gain control circuit 304*a* and the divider circuits 304*b*, which respectively provide automatic gain control for the two analog signal channels CH1 and CH4, using a division functionality. Again, alternate automatic gain control circuits could be used.

At the output of the automatic gain control, the analog signals are input to attenuator circuits 304*c* which provides a programmable gain in the range of from 0 to 1 and to an amplifier circuit 304*d*, which provides a gain of 5 and dc restoration-of the ac coupled analog signals. The attenuator circuits 304*c* are operated by the system controller 107 to select the calibration of the gains in these analog channels. The output of each amplifier circuit 304*d* is provided to peak detection circuitry and separately to the comparator 1344. The comparators 1344 provide the 0.6 v threshold used to discriminate potentially valid pulses as described elsewhere. The peak-detectors acquire the peak value, pending the response to the FPGA 1346 confirming that the signal is from a valid pulse.

It should be understood that the same attenuator and amplifier circuits 304*c* and 304*d* are used, although not shown, in the hybrids 1304 of the RBC/BASO/RETIC circuit illustrated in FIGS. 14 and 16.

Referring now to FIG. 17, a state diagram of the FPGA 1308, the operation of the "sequencer" portion of the FPGA 1308 in the DATAC 115 is now described. The Sequencer has the following defined inputs and outputs:

| INPUTS | DEFINITION/COMMENTS |
| --- | --- |
| I15 RESET | issued by Analytical Instrument Controller 105 |
| I10 CELL | issued by one of the four Hybrids 1304 (software selectable) |
| I9 FIFO FULL | issued by any of the four FIFOs 1310 when one of its memory is full |
| I6 COUNTER MSD | Upper byte of internal 8 bit counter |
| I3 COUNTER LSD | Lower byte of internal 8 bit counter |

| OUTPUTS | DEFINITIONS/COMMENTS |
| --- | --- |
| F0 Dump | used to enable input signal to circuitry inside of Hybrid 1304; the analog input signal in each channel to charge to its peak value |
| F1 Disable | input signal to circuitry inside of Hybrid 1304; used to disable the peak detectors |
| F2 Ramp Enable | input signal to Ramp Gen 1312; used to start the single slope Analog to Digital (A/D) converter |
| F3 FIFO Write | input signal to FIFOs 1310; used to temporary store A/D converter outputs |
| F4 Comparator Clear | input signal to internal circuitry of FPGA 1308; used to clear internal flip-flops in preparation of another A/D converter cycle |
| F5 Counter Load | input signal to internal circuitry of FPGA 1308; used to initialize the counters to zero |
| F6 Counter Enable | input signal to internal circuitry of FPGA 1308; used to enable the internal counter circuitry to start (the counter is incremented every 0.1 microsecond--based upon a free running 10 mega hertz clock cycle) |

The state operation is as follows. Upon "boot-up," the Analytical Instrument Controller 105 issues a reset command and puts the sequencer and its outputs into the RESET STATE(3F). While in the RESET STATE, if the CELL(I10) pulse is low, the sequencer moves to STATE 0 and waits for the leading edge of the CELL(I10) pulse to arrive.

As the leading edge of the CELL(I10) pulse enters the FPGA 1308, a logic 0 Dump (F0) signal is issued to the Hybrids 1304 and a logic 1 Counter Load(F5) signal is issued to the FPGA 1308 internal counter as the sequencer moves to STATE 1. The Dump(F0) signal enables the peak detector stages in each Hybrid 1304 to charge to the peak value of the analog input pulse and the Disable(F5) signal initializes the internal counters to zero.

As the trailing edge of the CELL(I10) enters the FPGA 1308, it is tested to determine if the duration of the signal is greater than 2 microseconds and less than 80 microseconds. This is accomplished in STATE 1 through STATE S. While in STATE 1, if the CELL (I10) pulse goes low (i.e., pulse is less than 2 microseconds) the sequencer moves to STATE C and issues a logic 1 Dump(F0) signal to stop the charging of the peak detected signal. While in STATE C, the counters are initialized back to zero and the sequencer waits for a hexadecimal count of 0A hex (i.e., MSD=0 & LSD=A), which equates to 1 microsecond, before the sequencer moves to the RESET STATE (3F) with its outputs in the known reset condition. If the sequencer moves all the way to STATE 5 and the CELL(I10) pulse has not gone low, then the pulse is greater than 80 µsec and the sequencer moves to STATE C in the aforementioned manner and waits for another CELL(I10) pulse.

If at any time the CELL(I10) pulse goes low between STATES 1 and 5 (i.e., the cell meets the criteria for a valid cell), a logic 1 Disable(F1) and a logic 0 Counter Load(F5) signals are issued, and the sequencer moves to STATE 6.

While in STATE 6, the counters are initialized to zero and a logic 1 Ramp Enable(F2) signal is issued to the Ramp Gen 1312. This signal to the Ramp Gen 1312 starts a 0 to 10 volt linear ramp. After counting for 0.2 $\mu$sec for stabilization of the linear ramp, the sequencer moves to STATE 7 where its counters are again initialized to zero. The linear ramp, which builds at the input of a comparator inside the Hybrid 1304, is compared with the peak amplitude voltage of the analog input signal. Once the ramp slightly exceeds the peak amplitude voltage, the comparator output switches state. It is the duration of the output from the comparator that is equivalent to the peak amplitude analog signal, thereby performing the A/D conversion. During this period that the Ramp is building at the comparator, the counters are clocking its time at 10 MHz, and the value is being latched into its respective internal 8-bit latch inside the FPGA 1308.

After the Ramp has been enabled for 10 $\mu$sec, a logic 1 Counter Enable(F6) is issued to disable the internal counters, a logic 0 Comparator Clear(F4) is issued to the comparator inside the FPGA 1308, and the sequencer moves to STATE E. The Comparator Clear signal is issued simultaneously with the Counter Enable signal to prepare the DATAC 115 for the another A/D converter cycle.

While in STATE E, if any one of the FIFO buffers 1310 memory is filled, the sequencer moves to STATE D, where it disables the internal counters and waits for the Analytical Instrument Controller 105 to start reading the FIFOs. When the FIFO memories are emptied, the sequencer moves to STATE 9 where it can begin to store the latched peak detected amplitude signal into its respective FIFO 310.

When the sequencer moves to STATE E and detects that the FIFO memory is not full, the counters are disabled and the sequencer moves to STATE 9. In STATE 9, the counters are initialized to zero and 0.1 $\mu$sec later the sequencer issues a logic 1 Dump(F0) signal to the Hybrid 1304 to enable the peak detector stages, a logic 0 Ramp Enable(F2) signal to turn off the conversion ramp, a logic 0 FIFO Write(F3) signal to the FIFO 310 which stores the latched converted data inside the FIFO memory, and the sequencer moves to STATE A.

STATE A holds the FIFO Write(F3) signal low for 0.3 $\mu$sec, and then moves to STATE B where it stops writing data to the FIFO 310. While in STATE B, the sequencer waits for the charged peak detected stages output signal to drop to a 0 volt level before returning to the RESET STATE (3F), where the sequencer waits for another CELL(I10) pulse to convert.

As noted, the DATAC 115 board outputs a cell dead time signal, which indicates the amount of time that the signal acquisition circuitry is busy for all signals that exceed the peak-detected 0.6 v threshold, and a valid cell count signal, which is a count of pulses that satisfy the 0.6 v threshold and the 2–80 $\mu$sec pulse width test. DATAC 115 also provides a light power signal, which provides a digital measure of the absorption low gain analog signal and represents average power of the optical source.

It should be understood that the PEROX optics bench 116 can be constructed in the same manner as the RBC/RETIC/BASO optics bench 117, except that fewer optical components are needed and a different light source, namely, a tungsten lamp and illuminator assembly are used. Alternately, the PEROX optics bench used in the commercialized H*3 Systems model clinical hematology instrument can be adapted for use in the present invention. In an alternate embodiment, however, low gain amplifiers incorporating boot strap amplifiers may be used to transmit low gain analog signals over channels 1 and 4 to amplifiers (not shown) which are preferably mounted as part of the DATAC board 115. Indeed, in this construction, the same circuits for processing the high angle scatter and the absorption reference signals of channels 1 and 4 depicted in FIG. 20B can be used, thereby further minimizing the number of circuits required.

The hemoglobin determination, which is discussed in more detail below in connection with the HGB Node, is conventionally performed colorimetrically at 546 nanometers. Although it is not part of the DATAC 115, it is briefly discussed here in the context of optical data acquisition. For each measurement, a signal current that is directly proportional to the light transmitted through the reaction vessel containing the reacted sample, reagent and diluent mixture is produced by a photodiode. The signal current is converted to a voltage and then output to the analog to digital converter on the HGB Node 122 (FIG. 11B). The equivalent digital word is then output to the System CPU 107 in the Analytic Instrument Controller 105 via the CANBUS (FIG. 11A). The CPU 107 determines the hemoglobin concentration by the change in the light transmittance reading of the optical density readings. After each HGB measurement, a baseline reference signal is monitored using a rinse solution in the reaction vessel.

D. Laser Drive and RBC Detection Circuit Architecture

Figure 19:
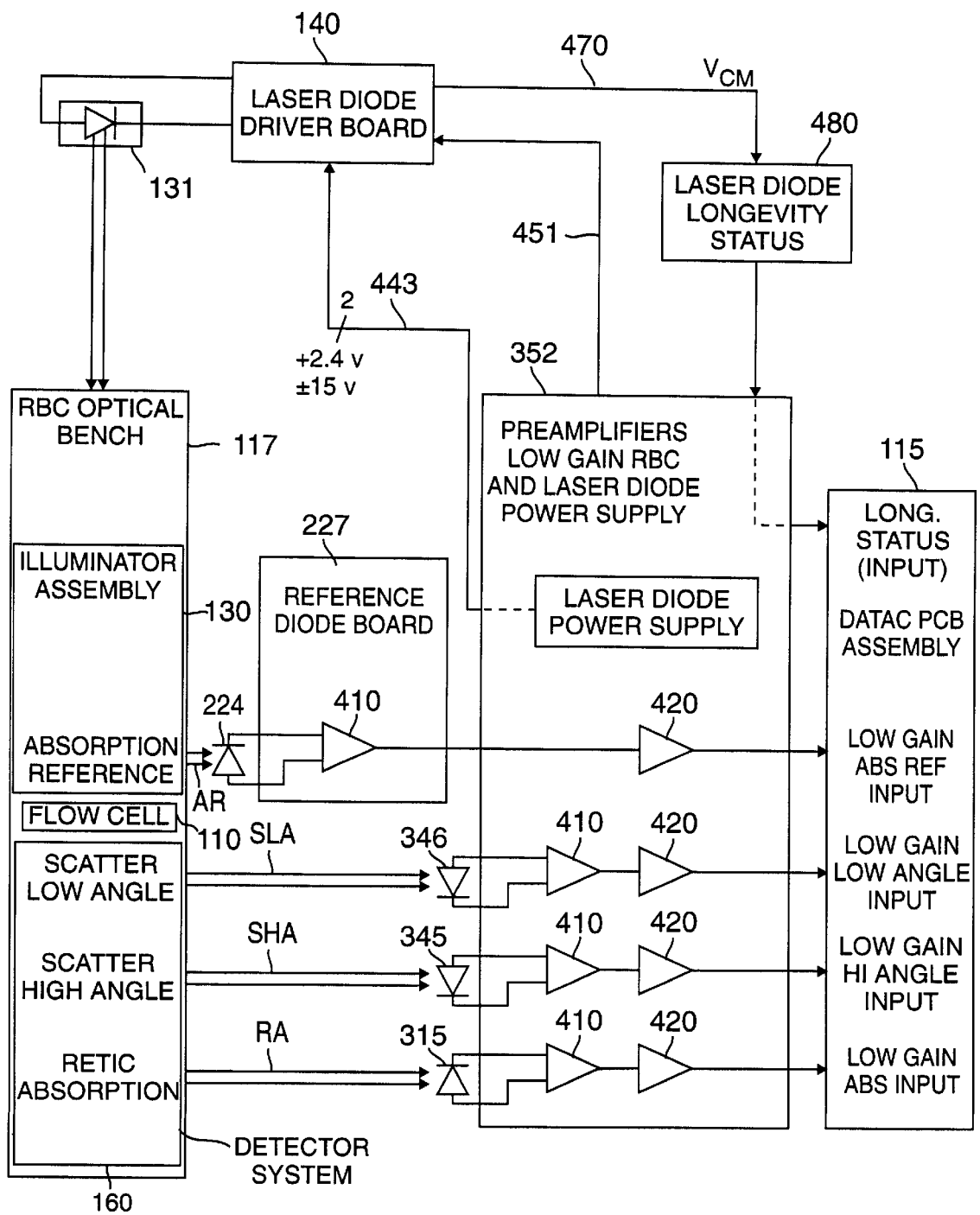
FIG. 19 is a block schematic circuit diagram of the RBC/RETIC/BASO optical bench of FIG. 11A.

Referring to FIG. 19, the circuit structure for controlling the operation of laser diode 131 and detecting the optical outputs provided from the red blood cell ("RBC") optics assembly 117 is illustrated. The optical signals are illustrated by double lines and the electrical connections are conventionally illustrated by single lines. As is illustrated in FIG. 19, the output of the laser diode 131 passes into and through the RBC optics assembly 117 and results in four optical signals coming out of the bench, as are described more specifically elsewhere in the specification. The four optical signals are the absorption reference AR, which is obtained upstream of the sample flow cell 110, and the scatter low angle SLA, the scatter high angle SHA, and the reticulocyte ("RETIC") absorption RA, which are obtained downstream of the flow cell 110. Each of these optical signals is separately detected by a photodetector, depicted as photodiodes 224, 346, 345 and 315, respectively. Each photodetector is preferably a light to current pin diode detector, e.g., Hamamatsu pin silicon photodiode Model 51223-01 (or 618-6081-01) or an equivalent. Each of these detector diodes is coupled across a low gain pre-amplifier 410, in an active bootstrap amplifier configuration and filtered, inverted, and buffered by respective low gain amplifiers 420. The output of each amplifiers 420 is consequently a low gain electronic signal. These four electrical outputs are respectively passed along relatively lengthy cables, e.g., approximately 2 feet long, and input to the DATAC 115, for use in analyzing the blood sample under examination.

In view of an object of the present invention being to improve construction and serviceability, the three detector diodes 346, 345 and 315, along with their respective amplifiers 410 and 420, are mounted on a single printed circuit board 352 with the detector diodes disposed in a fixed prealigned manner with respect to the beam axis of the three optical signals SLA, SHA and RA. This avoids the problem of aligning three separate circuit boards, as was done in prior art devices. It also is advantageous because it reduces part count, simplifies the interconnection of circuit board to the machine chassis, allows the use of more economical multiple discrete component integrated circuit packages, and reduces real estate, cabling and power consumption requirements.

Because the absorption reference optical signal AR is obtained upstream of the flow cell 110 at the other end of the RBC optics assembly 117, it is more convenient to locate detector 224 and its pre-amplifier 410 on a separate printed circuit board 227, mounted directly to the optics assembly base. However, as an alternative, it is possible to mount detector 224 and its amplifier 410 on printed circuit board 352 and use an optical fiber or mirrors (not shown) to conduct the optical signal AR to detector 224. Indeed, optical fibers could be used to couple light from each of the optical inputs to the pin diode photo-detectors conveniently mounted on a common printed circuit board.

Another advantage of the present invention is the omission of high gain amplifiers in the detector circuits (boards 227 and 352) such that only relatively low gain electronic signals are passed along any significant circuit length to high gain amplifiers. This structure avoids cross-talk interference, which was a significant problem in the prior art devices, which had high gain signals transmitted over relatively long cables from the detector circuits to the signal processing board. It also aids in obtaining a higher bandwidth for the electronics.

Figure 20:
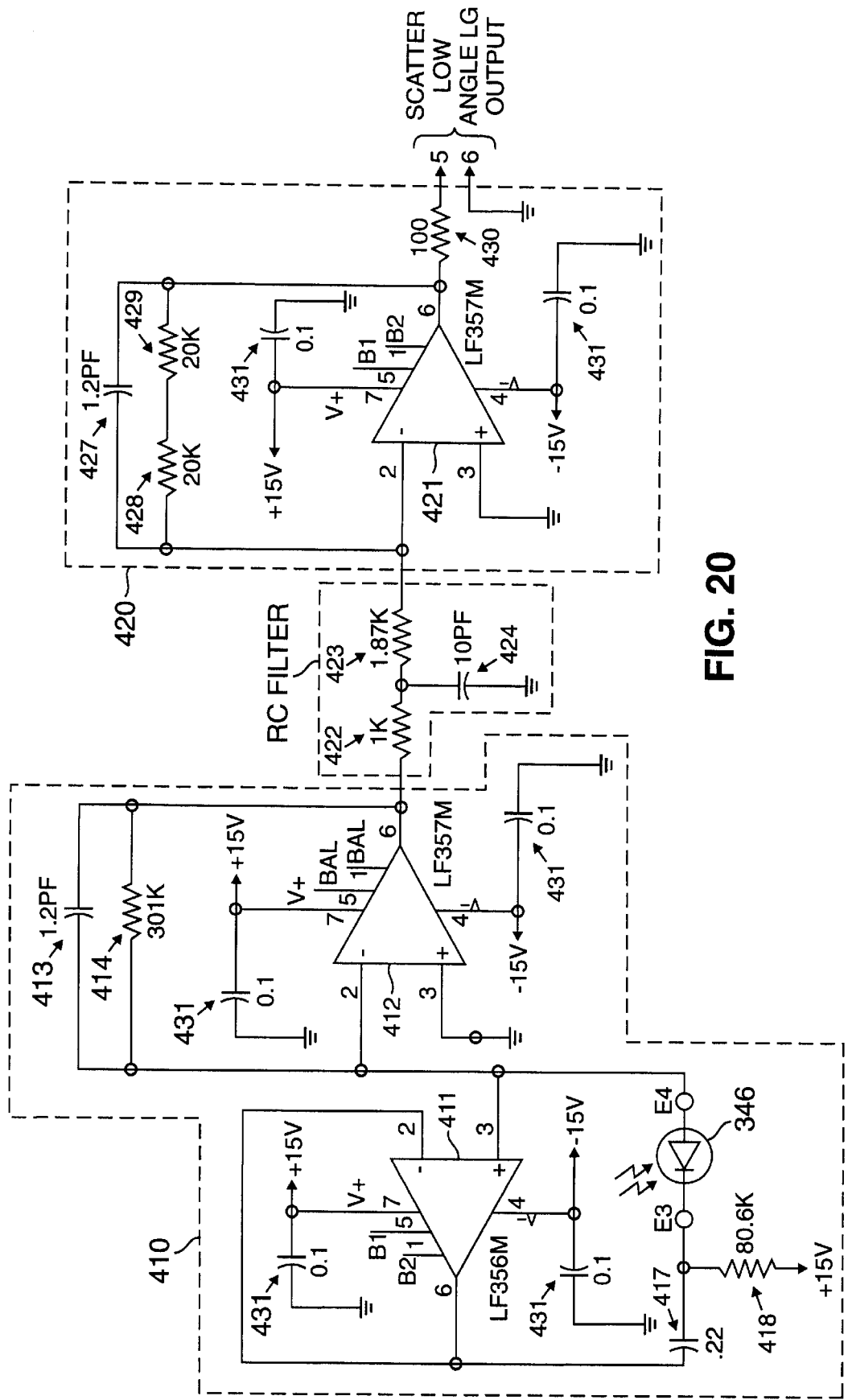
FIG. 20 is a circuit schematic diagram of the analog signal channel of FIG. 19.

Referring now to FIGS. 19 and 20, a preferred embodiment of amplifiers 410 and 420 is illustrated for the scatter low angle detection circuit (channel 2). In this embodiment, amplifier 410 comprises two operational amplifiers 411 and 412. Amplifier 411 is preferably a type 356 operational amplifier configured as a voltage follower for the photodiode 346, having a unity gain. The photodetector 346 is connected in series with a capacitor 417, between the output and the noninverting input of amplifier 411. Capacitor 417 is, e.g., a 0.22 µf capacitor. A resistor 418 is connected between a +15 volt supply and the junction between detector 346 and capacitor 417. Resistor 418 is preferably 80.6 KΩ. Amplifier 412 is preferably a model 357 operational amplifier having the inverting input connected to the anode of detector 346 and the noninverting input connected to ground. Amplifier 412 has a feedback loop including capacitor 413 and resistor 414 connected in parallel. The capacitor 413 is preferably 1.2 picofarad and resistor 414 is preferably 301 KΩ.

The output of amplifier 412 is passed across an RC filter network (not shown in FIG. 19) to the inverting input of amplifier 420, illustrated in FIG. 20 as amplifier 421. The RC filter includes resistors 422 and 423 and capacitor 424, preferably having values of 1 KΩ, 1.87 KΩ and 10 pf, respectively.

Amplifier 421 is preferably a model 357 operational amplifier and has a feedback loop including capacitor 427 in parallel with two series resistors 428 and 429. Capacitor 427 is preferably 1.2 pf, and resistors 428 and 429 are each 20 KΩ. The output of amplifier 421 is then passed across a 100Ω resistor 430, which provides the electrical scatter low angle output signal, which is passed to the DATAC 115. This output signal can be passed over a cable a distance of approximately 2 feet, without suffering any significant degradation due to crosstalk from other signals in the instrument. Each of the amplifiers 411, 412 and 421 are provided with ±15 volt bias voltages, which are also coupled to ground across 0.1 µf capacitors 431 as illustrated in FIG. 20.

The circuit for detecting the scatter high angle signal differs from the scatter low angle circuit detector only in that there is only one 20 KΩg resistor in the feedback loop of amplifier 420.

The circuits for detecting the absorption and reference signals AR and RA are the same as the circuit for the scatter high angle detection circuit except that the ±15 volt supply coupled to the voltage follower amplifier is changed to −15 volts, the polarity of the pin photodiode is reversed, and the RC filter network between amplifiers 411 and 412 is replaced with a variable resistance RC network such that, with reference to FIG. 21B, capacitor 424 is replaced with a 1.0 pf capacitor, resistor 422 is replaced with a 10 KΩ resistor, and resistor 423 is replaced with a 50 KΩ potentiometer. The difference in the polarity of the voltage supply is to account for the fact that the scatter low and high angle detect dark field absorption, whereas the absorption and reference detectors detect bright (light) field absorption. The 50 KΩ potentiometer is used to provide a variable gain to the preamplifier 420 for the bright field absorption signals.

The structure of the detection circuits is to provide a pulse height output corresponding to the detection of a particle, such that low and high angle scatter produces a positive pulse of from 0.5 to 1.5 volts peak amplitude, and a signal pulse width of, for example, 10 microseconds (assuming a nominal flow of cells through the flow cell 110 at a rate of approximately 2 meters per second). In contrast, the absorption reference and RETIC absorption have an adjustable gain to produce positive going pulse of approximately 1.5 volts peak amplitude at a nominal pulse width of 5–7 µsec.

Figure 21:
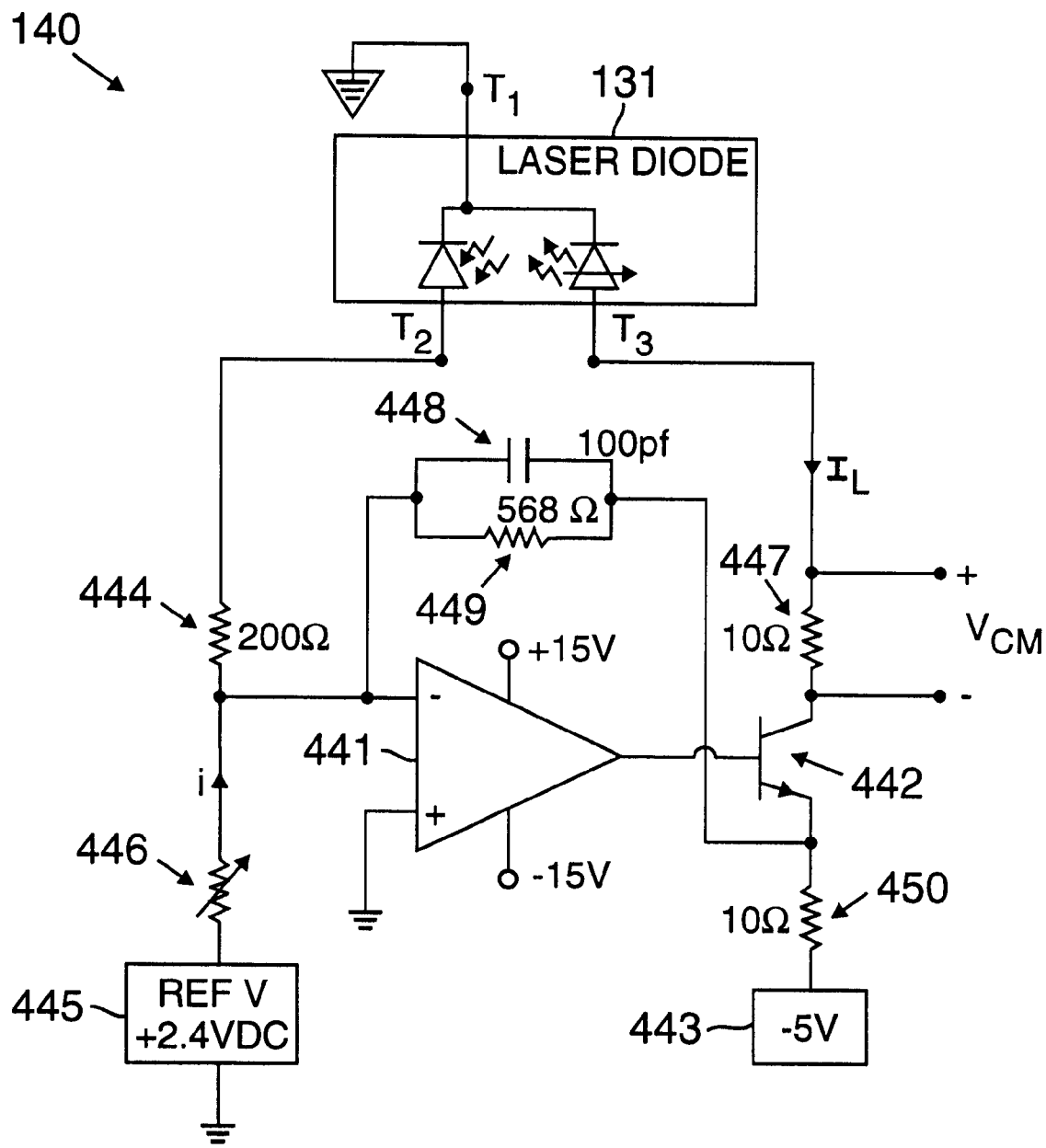
FIGS. 21 and 22 are circuit schematic diagrams of the laser diode driver and power supply circuits of FIG. 19.

A circuit for driving a laser diode 131 depicted in FIG. 19 as board 140 is shown in detail in FIG. 21. The laser diode 131 has a case terminal $T_1$ which is connected to the common ground return, a current output terminal $T_2$, and a drive current output terminal $T_3$. The driver circuit is connected between terminals $T_2$ and $T_3$. A suitable laser diode 131 is the Toshiba Model No. TOLD9225(S).

The laser diode driver circuit includes operational amplifier 441, a transistor 442, a regulated −5 volt source 443, a +2.4 volt reference 445, and ±15 volt reference voltage supplies. The amplifier 441 is preferably a model 356 operational amplifier having at its inverting input the sum of three signals: first, a signal from terminal $T_2$ of laser diode LD passed across a resistor 444, a 200 ohm resistor; second, a feedback signal from the amplifier 441 output; and third, a signal from a reference voltage 445 which is passed across a potentiometer 446. Preferably, the potentiometer 446 provides a 300Ω to 600Ω resistance range, and the reference voltage 445 is ±2.4 volts DC. The non-inverting input of amplifier 441 is connected to ground.

The output of amplifier 441 is input to the base of transistor 442 which is preferably a model 2222A transistor. The collector of transistor 442 is coupled to the drive current output terminal $T_3$ of laser diode 131 across a 10Ω resistor 447. The voltage $V_{CM}$ sensed across resistor 447 is a voltage that is a proportional to the laser diode drive current $I_L$. The emitter of transistor 442 is coupled to the inverting input of amplifier 441 across a timing circuit, preferably an R-C network including capacitor 448 and resistor 449 connected in parallel. The timing circuit provides the amplifier with a fast response time, for example, a maximum of one microsecond. This response time corresponds to a minimum bandwidth of at least 350 Khz so as to reduce the sensitivity of the RBC channel parameters to the velocity of the sheath flow in the flow cell, and to provide increase sampling throughput capabilities. In a preferred embodiment, the values of capacitor 448 and resistor 449 are selected to be 100 pf and 568Ω, respectively.

The emitter of transistor 442 also is connected to a drive voltage source 443 of −5 volts across a resistor 450. Resister 450 is, for example, 10Ω. The resistors used in the circuit are preferably well-matched, thermally tracking resistors having a 1% accuracy limit.

In accordance with the present invention, the power output of the laser diode 131 can be easily controlled by varying the potentiometer 446 to adjust the laser diode current $I_L$. As noted, the diode current $I_L$ is monitored by tracking the voltage $V_{CM}$ across the resistor 447 in the collector of transistor 442. The diode current is then controlled by transistor 442, the output of which is fed back to the inverting input of amplifier 441. Advantageously, because the transistor 442 is in the feedback loop of the operational amplifier 441, it operates independent of the driver circuit component variations and is controlled by the operational amplifier output. Relative to the known prior art designs, the laser diode driver circuit of the present invention provides improved longevity (discussed below) and response time (bandwidth), namely faster control over the operation of the laser. Advantageously, the laser driver circuit 149 also uses a minimal number of parts and provides an extremely stable operation in a linear mode. As a result, there is substantially no saturation or non-linear operation of the transistor 442. The driver circuit also provides improved balance control because it operates in a fixed linear mode, and provides bandwidth control by selecting the time constant of the values of resistor 449 and capacitor 448 of the RC network in the feedback loop. This results in a greater sample throughput potential.

The laser diode driver circuit 149 and the laser diode 131 can be advantageously mounted on a single printed circuit board, which provides three basic functions. One is to provide a steady state current to drive the laser diode 131. A second function is to generate a dynamic feedback loop to maintain the laser diode 131 in a constant power mode. The third function is to detect, and to indicate, the status of the upper limit of the laser diode current $I_L$ by monitoring a voltage $V_{CM}$ representative of the current $I_L$. Preferably, adjusts are provided on the printed circuit board 149 for setting the laser diode drive current $I_L$ by adjusting potentiometer 446, and a similar potentiometer (not shown in FIG. 21) for setting the threshold for the drive current $I_L$ upper limit for use in monitoring the voltage (not shown in FIG. 19). Although a manually adjustable potentiometer 446 is shown as an exemplary device, a digitally controlled variable resistance device could also be used so that the resistance can be controlled by a microprocessor executing suitable software instructions. Advantageously, the circuit illustrated in FIG. 21 can be constructed using surface mount components and potentiometer installed on one side of a 1.5"×1.5" printed circuit board.

Figure 22:
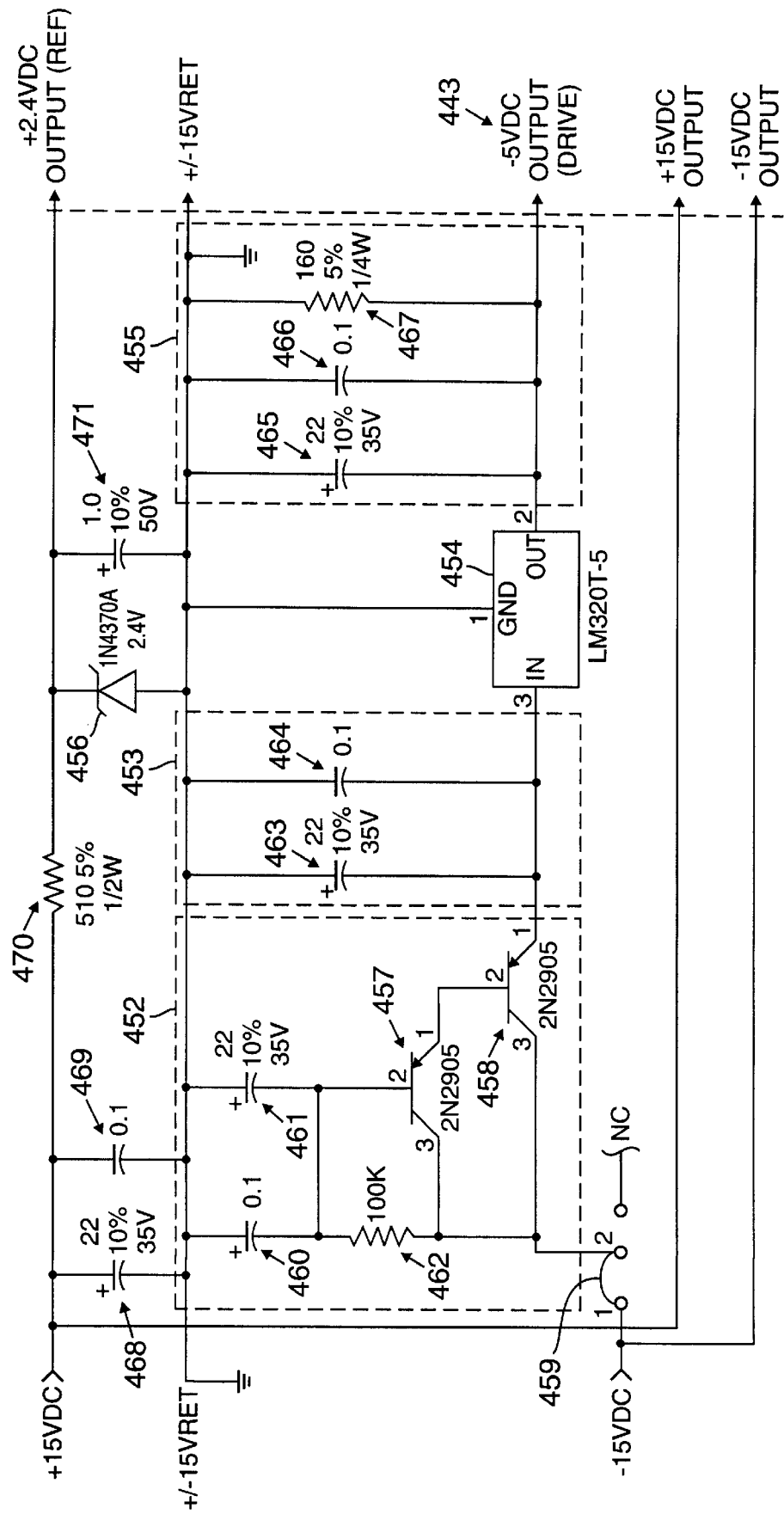

Considering FIGS. 21 and 22, the laser driver circuit and its power supplies operate in a manner to protect the laser diode 131 from turning on during current transients. Accordingly, the laser diode drive voltage source 443 is provided with a turn-on, soft-start delay time of, for example, 0.5 to 1.0 second, relative to the other dc supply voltages powering the diode driver circuit, namely, the +15, −15 and +2.4 volt supplies. Such operation improves the longevity of the laser diode 131.

Referring to FIG. 22, the turn-on, soft start delayed −5 volt reference voltage 443 is obtained using a conversion circuit coupled to the +15 and −15 volt supplies. This conversion circuit includes a soft start circuit 452, a filter circuit 453, a 5 volt regulator 454, and a filter circuit 455. The output of filter circuit 455 is the −5 volt supply 443 that is turn-on, soft-start delayed. The turn-on delay is typically set at 0.5 to 1.0 second, relative to the other DC supply and reference voltages. Other times may be used.

The soft start circuit 452 is preferably a circuit that delays the provision of the input signal to the voltage regulator 454. The circuit includes two cascaded transistors 457 and 458, each a model 2N2905 transistor, such that the −15 volt supply, when switched into the circuit at switch 459, operates to turn on transistors 457 and 458 with a delay caused by the RC network of capacitor 460 in parallel with capacitor 461 and in series with resistor 462. Resistor 462 is connected between the base and collector of transistor 457. The other end of the capacitors 460 and 461 are connected to the common ground return. Capacitor 460 may be 0.1 μf, capacitor 461 may be 2.2 μf (10%, 35 v rated), and resistor 462 may be 100 KΩ. The RC network provides a time constant of 0.5 to 1 second, at the end of which the −15 volt supply becomes fully coupled to the input of voltage regulator 454 through transistor 458. When this occurs, i.e., after the delay, the voltage regulator turns on and provides a regulated −5 volt output (443). During this delay, the +15, −15 and +2.4 volt supplies are directly passed to the laser diode driver circuit board 149 as indicated by line 451 in FIG. 19. The voltage regulator is preferably a model LM320T-5 available from distributors such as National Semiconductor having external heat sinks.

Filter 453 comprises two capacitors 463 and 464 in parallel between the common ground return and the voltage regulator input, and is utilized for input noise filtering. Filter 455 has a parallel capacitor construction 465, 466 and a parallel resistor 467. The capacitors 465 and 466 provide output noise filtering and improved voltage regulation. Resistor 467 is used for minimally loading the voltage regulator 454. Capacitors 463 and 465 are preferably 22 μf (10%, 35 w rated) capacitors 464 and 466 are 0.1 μf, and resistor 467 is 160Ω (5%, ¼ watt rated).

Referring again to FIG. 22, the +15 V supply also is passed across a conversion circuit including a 2.4 v Zener diode 456 (a model IN4370A device) to produce a +2.4 reference signal. The +15 supply is passed across a filter including parallel capacitors 468 (22 μf, 10%, 35 w), and 469 (0.1 μf) and resistor 470 (510Ω, 5%, ½ watt) in parallel with the Zener diode 456. A capacitor 471 (1.0 μf, 10%, 50 v) is connected in parallel with the Zener diode 456 and produces the +2.4 volt signal.

In a typical operation, the laser diode drive current $I_L$ is set at 70 milliamps nominal, and 80 milliamps maximum, such that the value is continuously adjustable between 60 and 80 milliamps. Regarding the Toshiba model TOLD9225(S) laser diode, which includes an internally packaged detector, the monitored current is typically 1.5 milliamps, and 3.0 milliamps maximum, with a 0.5 milliamps minimum at an output of 10 milliwatts.

The sensed voltage $V_{CM}$ representing the laser diode drive current $I_L$ is advantageously used to generate a "longevity" ("LONG.") signal, which has a logical level output, for the laser diode 131. In this regard, a logic HIGH signal (1) is indicated when the laser diode current $I_L$ is greater than or equal to a preset reference value, e.g., corresponding to 80 milliamps. A logic LOW (0) signal is used to indicate normal laser diode operation.

Figure 23:
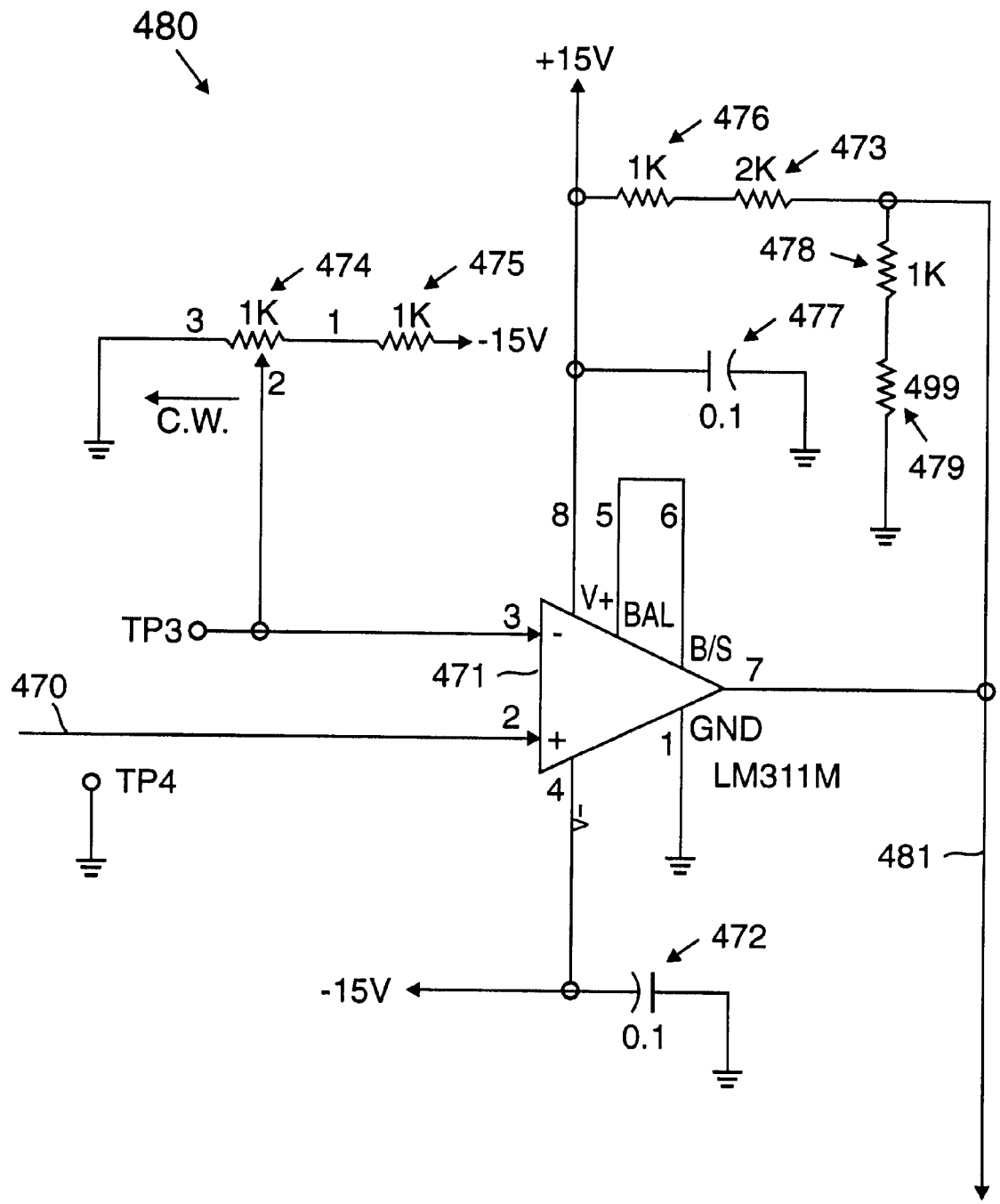
FIG. 23 is a circuit schematic diagram of a laser diode longevity status circuit of FIG. 19.

FIG. 23 is a schematic diagram of an embodiment of a laser diode longevity status circuit 480, also shown in FIG. 19. The laser diode driver board 149 provides the input line 470 to the status circuit 480. The status circuit 480 includes a comparator 471, and ±15 volt reference voltage supplies. The comparator 471 is preferably a model LM311M, having at its inverting input the sum of two signals: first, a signal from a −15 volt source passed through a voltage divider comprising a 1 KΩ potentiometer 474 and a 1 KΩ resistor 475; and second, a signal from terminal TP3 of the laser diode 131. The non-inverting input of comparator 471 is connected to the input line 470 from the laser diode driver board 149 to input voltage $V_{CM}$.

The comparator 471 is biased by a −15 volt source connected in parallel with a 0.1 µf capacitor, and by a +15V source. The output of comparator 471 is connected to the +15 volt source through a 2 KΩ resistor 473 and a 1 KΩ resistor 476. The +15 volt source is also connected in parallel with a 0.1 µf capacitor 477 and the resistors 473, 476 and 1 KΩ resistor 478 and 499Ω resistor 479. The output signal on line 481 provides an indication of the amount of power the laser diode is utilizing to produce the required light intensity. In particular, the potentiometer circuitry at 474, 475 is adjusted to set a threshold level which is compared by comparator 471 to the laser diode power signal on line 470. If the threshold level is exceeded, a TTL compatible output signal corresponding to a 1 logic level is generated on line 481 indicating that the laser diode 131 is using too much power and thus may need replacement. If the threshold level is not exceeded, then a TTL compatible output signal corresponding to a 0 logic level is generated on line 481, meaning that the laser diode 131 is operating normally.

E. The CANBUS

Figure 24:
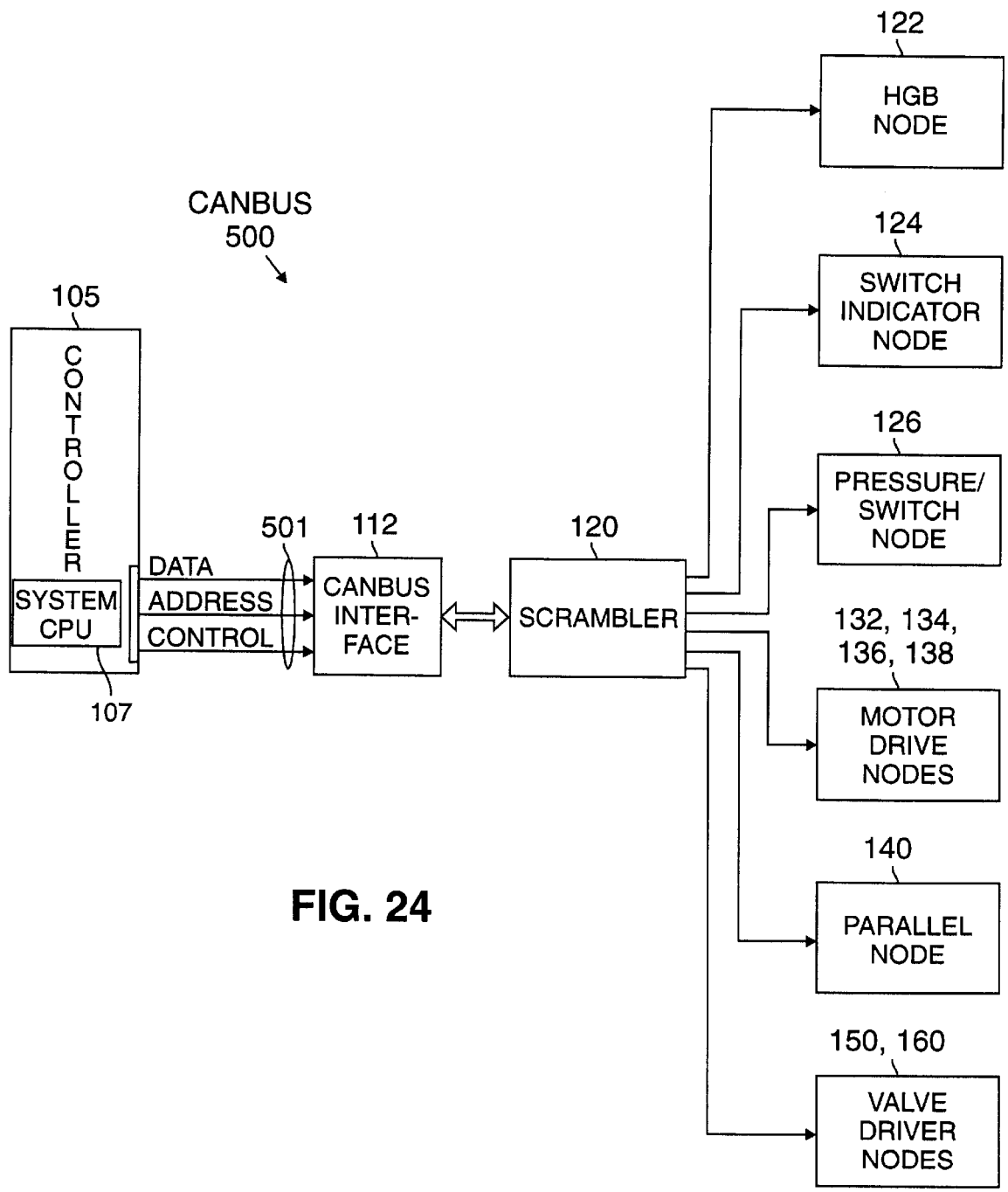
FIG. 24 is a block diagram of the CANBUS architecture of FIGS. 11A–11E.

FIG. 24 is a simplified block diagram of the CANBUS architecture 500 according to an embodiment of the present invention. In particular, the CANBUS interface 112 is connected to the system CPU 107 via a PC 104 Bus having data, address and control lines, generally designated as PC 104 bus 501. The CANBUS interface 112 is also connected through the CANBUS scrambler 120 to the system nodes comprising the HGB node 122, the Switch indicator node 124, the Pressure and Switch Node 126, the motor drive nodes 132, 134, 136, 138, the Parallel node 140 and the Valve Driver nodes 150, 160. Each node is a "smart" node, and thus contain a resident microprocessor to receive, process and send data, address and control signals on the CANBUS 500. The use of the CANBUS permits distributed logic to be implemented in the system.

The CANBUS interface 112 is an interface that is the transmitter and receiver of all communications between the Analytic Instrument Controller 105 (see FIG. 11A) and all the attached nodes. The Analytic Instrument Controller 105, e.g., an Intel series 386Ex CPU, communicates via a serial link which is part of a CAN protocol. The CANBUS interface 112 is preferably connected to the analytic instrument controller 105 by bus 501 using input by bus 501 output connections according to the PC 104 standard. The design may be based on the Intel model 82527 serial communications controller with the CPU InterLace Logic using a 16 bit multiplexed architecture mode.

The CANBUS interface 112 is preferably optically isolated from the CANBUS 500 connected to it and the various nodes. A conventional 9 pin D-type connector (not shown) including a bus high line pin, a bus low line pin, a +5 v input power pin, and ground pins, is used to couple each node to the CANBUS scrambler 120 to the CANBUS 500.

Figure 25:
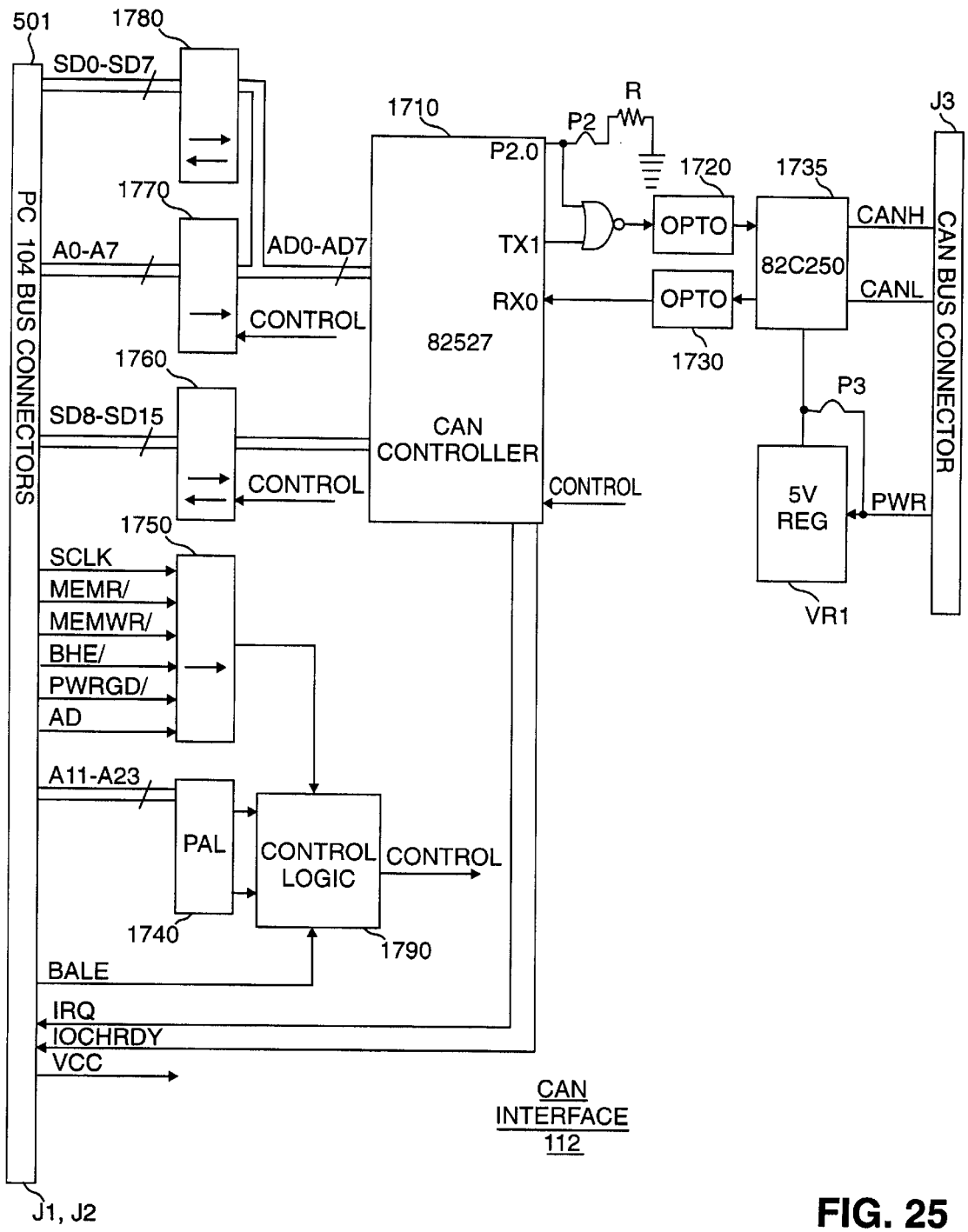
FIG. 25 is a block schematic circuit diagram of the CAN interface circuit of FIG. 24.

Referring to FIGS. 24 and 25, the major components of the CANBUS interface 112 and the CANBUS scrambler 120 are shown. CANBUS interface 112 includes a CAN controller, 1710 two opto-isolators 1720 and 1730, which couple interface 112 to CANBUS scrambler 120, a programmable array logic (PAL) device 1740, a buffer circuit 1750, a database transceiver circuit 1760, an address buffer circuit 1770, a data transceiver circuit 1780, and a control logic circuit 1790.

CAN controller 1710, preferably an Intel device model No. 82527 controller, is a serial communications controller that performs communications according to the CAN protocol. The CAN protocol uses a multi-master bus configuration for the transfer of message objects between nodes on the network. The CAN controller 1710 performs all serial communication functions, such as transmission and reception of messages, message filtering, transmit search and interrupt search, with minimal interaction from the host CPU 107.

A communications object consists of an identifier along with control data segments. The control segment contains all the information needed to transfer the message A transmitting node broadcasts its message to all other nodes on the network, and an acceptance filter at each node decides whether to receive that message.

CAN controller 1710 not only manages the transmission and reception of messages, but also manages the error handling, without any burden on the CPU 107. CAN controller 1710 features several error detection mechanisms including Cyclical Redundancy Check and bit coding rules. If a message was corrupted, it is not accepted by the receiving node. The controller 1710 monitors transmission status and an automatic retransmission of data is initiated in the case of error. Preferably, controller 1710 can distinguish permanent hardware failures from soft errors and defective nodes are switched off the bus.

In a preferred embodiment, the controller 1710 is configured in the conventional Intel 16 bit multiplexed mode, which allows data transfers from the CPU in 8 bit bytes or 16 bit words. The controller 1710 thus appears to the CPU as a block of 256 bytes of RAM, which is divided between control and message registers. An 8 bit general purpose I/O port is provided by the controller 1710, bit 0 of which is used to force a system reset over the CANBUS 500. The clock for the controller 1710 is the 8 MHz clock signal BCLK, from the PC 104 Bus 501. More detailed information on the Intel part 82527 is available on the Intel data sheet, which is incorporated herein by reference.

The CANBUS interface (driver/receiver), preferably a Philips model 82C250 device, provides the physical interface to the CANBUS scrambler 120 of CANBUS 500 on a connector J3 (the 9 pin D-type connector) and thence to the complimentary CAN interface device and CAN controller microprocessors of each of the Nodes coupled to CANBUS 500. These node elements are described further below. The CANBUS states are defined as follows:

| TxD | CANH | CANL | BUS STATE | RxD |
|---|---|---|---|---|
| 0 | High | Low | dominant | 0 |
| 1 or float | float | float | recessive | 1 |

A resistor is used to control the slope of the CANBUS signal. The output of the CAN connector J3, has the following pin definitions:

J3-1 no connection
J3-2 CANL
J3-3 Power Return
J3-4 Power Return
J3-5 Power Input
J3-6 no connection
J3-7 CANH
J3-8 Power Return
J3-9 Power Input A CANBUS terminator jumper (not shown) may be inserted to provide a CANBUS termination of 118 ohms, or not used to provide no CANBUS termination.

In addition, a power supply jumper P3 is used to control in part the power supplied on the CANBUS 500. The circuitry requires 5 volts, however, an on board regulator VR1 is provided which allows operation from an 8–12 volt supply. Jumper P3 selects power source, and is inserted for use with 5 volt supply that is available from the CANBUS 500, and is removed for use with higher supply voltages.

Opto-isolators 1720 and 1730 isolate the CAN driver/receiver 1735 and the CANBUS 500 from the remainder of the circuitry of CANBUS interface 112 and the system controller 105. The circuitry on the CANBUS controller 1710 side of the isolators is powered from the PC104 bus 501.

CANBUS interface 112 interfaces to the CPU 107 board through a PC104 bus 501. The PC 104 bus 501 is similar to the standard ISA (P966), but modified with connectors better suited to embedded applications. The board is memory mapped with a 16 bit interface. This allows both 8 bit and 16 bit transfers and allows the board to occupy memory space above 1 meg. The following pin definitions in connector J1 are used:

| 2  | 5VRET   | 40 | BCLK  |
|----|---------|----|-------|
| 3  | SD7     | 41 | A10   |
| 4  | PWRGD/  | 42 | IRQ7  |
| 5  | SD6     | 43 | A9    |
| 6  | +5 V    | 44 | IRQ6  |
| 7  | SD5     | 45 | A8    |
| 8  | IRQ9    | 46 | IRQ5  |
| 9  | SD4     | 47 | A7    |
| 11 | SD3     | 49 | A6    |
| 13 | SD2     | 51 | A5    |
| 15 | SD1     | 53 | A4    |
| 17 | SD0     | 55 | A3    |
| 19 | IOCHRDY | 56 | BALE  |
| 20 | 5VRET   | 57 | A2    |
| 29 | A16     | 58 | +5 V  |
| 31 | A15     | 59 | A1    |
| 33 | A14     | 61 | BLE   |
| 35 | A13     | 62 | 5VRET |
| 37 | A12     | 63 | 5VRET |
| 39 | A11     | 64 | 5VRET |

The following pin definitions in connector J2 are used:

| 1  | GND      | 22 | MEMW/ |
|----|----------|----|-------|
| 2  | GND      | 24 | SD8   |
| 3  | MEMCS16/ | 26 | SD9   |
| 4  | BHE/     | 28 | SD10  |
| 6  | A23      | 30 | SD11  |
| 8  | A22      | 32 | SD12  |
| 10 | A21      | 34 | SD13  |
| 12 | A20      | 36 | SD14  |
| 14 | A19      | 38 | SD15  |
| 15 | IRQ14    | 33 | VCC   |
| 16 | A18      | 37 | GND   |
| 18 | A17      | 39 | GND   |
| 20 | MEMR/    | 40 | GND   |

The PAL device 1740 operates to decode the PC104 address lines A11–A23 to enable CPU communication to the CANBUS interface 112. The equations which define the PAL are as follows:

$$CS/ = MCS16L // *A16/*A15/*A14/*A13/*A12/*A11/*$$
$$E1 + MCS16L // *A16*A15/*A14/*A13/*A12/*$$
$$A11/*E1/*E0 + MCS16L // *A16/*A15/*A14/*$$
$$A13/*A12/*A11/*E1/*E0$$

$$MCS16 = A23*A22*A21*A20*A19*A18*A17*E1*E0 +$$
$$A23/*A22/*A21/*A20/*A19*A18*A17*E1*E0 +$$
$$A23/*A22/*A21/*A20/*A19*A18*A17/*E1/$$

E0 = P4-1   E1 = P4-3

Jumpers are used to select the base address of the board.

| Base Add | P4 1-2 | P4 3-4 |
|----------|--------|--------|
| 0C0000h  | X      | X      |
| 0D000h   | X      | open   |
| 0E0000h  | open   | X      |
| FE0000h  | open   | open   |

CAN controller 1710 I/O port P2.0 controls the CANBUS reset function. To initiate a reset over the CANBUS 500, I/O P2.0 must be held high for at least 130 μsec. This forces the CANBUS 500 into the dominant state for this time, a condition which activates the reset function of each node on the bus. A Jumper P2 is used to control the initial state of the reset circuit at power up. With the jumper P2 removed, the board forces a CAN reset upon power up and port P2.0 must be programmed to a low state to release the reset. When jumper P2 is inserted, no reset occurs on power up until the software forces port P2.0 high.

The CANBUS protocol used in the invention allows for MASTER/SLAVE along with SLAVE/SLAVE communications. The term MASTER refers to the initiating device, and the term SLAVE refers to the device receiving a command. The SLAVE will respond and/or execute the command. The system controller CPU 107 in the Analytic Instrument Controller 105 is known as the HOST, and any NODE can be the MASTER for specific commands, such as querying another device for its status. The HOST is responsible for transmitting commands and status inquiries to the various nodes, and for processing data received from the nodes for the workstation 103 (see FIG. 11A).

The CAN protocol utilizes an 11 bit identifier field for the Message Identifier (MID). Messages are prioritized by the MID value such that the lower the MID the higher the priority. Thus, the CAN interface and controller hardware arbitrates the bus using the MID. Along with the MID, there are 8 data bytes that are used to transfer from 0 to 8 bytes of data. A four-bit Device CLASS field is used in the MID to define fifteen different device classes plus one broadcast class. Since the priority of the message is based on the value of the MID, the classes are defined based on system timing requirements. Certain devices, such as the valves controlled by the Valve Driver Nodes 150, 160, typically require a higher degree of accuracy for command execution. By having a lower CLASS value, e.g., value (1), this helps decrease command latency for control of the valves due to CANBUS arbitration.

Other CLASS definitions may be allocated as follows. CLASS (0) for Broadcast, which is used to speak with all devices on the bus, and is usually given the highest priority. Commands used are those such as Stop, Reset, Request a device on bus, etc. Most all nodes will hear and process these commands (e.g., certain pump devices may ignore these commands). CLASS (1), for valves and other activities, such as shutters. CLASS (2), for pump control of host to node information, and CLASS (10), for pump node to host information (these classes uses different drivers and communications than other device classes and does not necessarily respond to Broadcast commands). CLASS (3), for Servo mechanisms and samplers for sample aspiration, CLASS(6) for Stepper motor devices and transport mechanisms. CLASS (7) for pumps. CLASS (8) for AC motors, e.g., in operating sample aspiration and the autosampler. CLASS (9) for sensors, e.g., to determine the fill levels of containers, positions of components, temperature of elements and the like. CLASS (11) for ID Readers to read bar codes for sample data tracking. CLASS (12) for the serial or parallel input/output communications. CLASS (15) for the instrument controller. Of course, other classes could be used and the assigned CLASS priorities modified as appropriate for a given instrument.

In the described system, bits 0–2 define the Frame type which identifies the type of message being sent. Bits 3–6 of the 11 bit MID identify the Device ID. Bits 7–10 identify the Destination device CLASS. The Frame type of messages include: "O" an acknowledgement from a slave to master, which is returned to the initiating master device; "1" a single Frame or an end of a multiframe sequence, which is sent from the master to the slave; "3" multiframe start, which is sent from the master to the slave; "4" multiframe data, sent from the master to the slave; "6" Query sent from master to slave and requesting slave status; and "7", FAULT/NAK, which is sent from the slave to the master in response to a command or an unsolicited FAULT indication from the device. Frame type 5 is not used and Frame type 2 is used for the pumps as explained below.

The first data byte (byte 0) provides the sender identifier MID. The next seven data-bytes (bytes 1–7) provide the data (command or other information).

In the case of the pumps, a different communication format is used. In the 11 bit MID identified field, bit 10 is set to 0 to indicate it is a Host to Pump message and set to 1 to indicate a Pump to Host response. Bits 7–9 are used to distinguish between class (10) and class (2) as described. Bits 3–6 are used to identify the device IDs for 0–15. Bits 0–2 provides the Frame type. The same frame types are used as set forth above except that frame types 0 and 7 are not used, frame type 1 is an Action frame, and frame type 2 is a common command frame.

The CANBUS also includes a DOWNLOAD mode, during which time parameters and/or new software code can be downloaded from the Host to the device.

Such a system permits communications between all nodes in a known, modular fashion, and importantly permits the use of a node from the present apparatus to be used in other devices. A suitable CAN protocol for the 11 bit identifier is described in BOSCH CAN Specification Version 2.0, part A. The term CANBUS stands for Control Area Network Bus.

Different types of CAN controllers can be used at either end of the CANBUS, which offer various degrees of MID filtering. The Intel model 82527 device preferably used in the CANBUS interface 112 offers ten filters. However the described embodiment of the present invention utilizes in each node a Philip model P87C592 microcontroller, distributed by the Phillips Electronics Company, which offers only one filter. This may create a problem if multiple types of CLASS information, such as a BROADCAST or a MULTICAST signal, is required to be received. In general a device (node) does not want to hear all the messages on the bus, and thus an acceptance filter may be programmed to only generate an interrupt for that specific node. The device will then not be capable of receiving a BROADCAST or MULTICAST message if it is set to filter its own CLASS and DEVICE ID. However, another problem arises when it is desired to perform functions like downloading firmware to an entire CLASS at once. Therefore, the devices also incorporate a set of commands that removes all the filtering, enables BROADCAST filtering, enables MULTICAST filtering and enables the original filter.

As will become clear in the following discussion, each of the Nodes preferably include the same basic hardware (CAN interface and microcontroller) to couple to the CAN bus, although each microcontroller will have its own programming and other related circuitry to perform the distributed logic and control functions of the Node.

1. HGB Colorimeter Node

Figure 34:
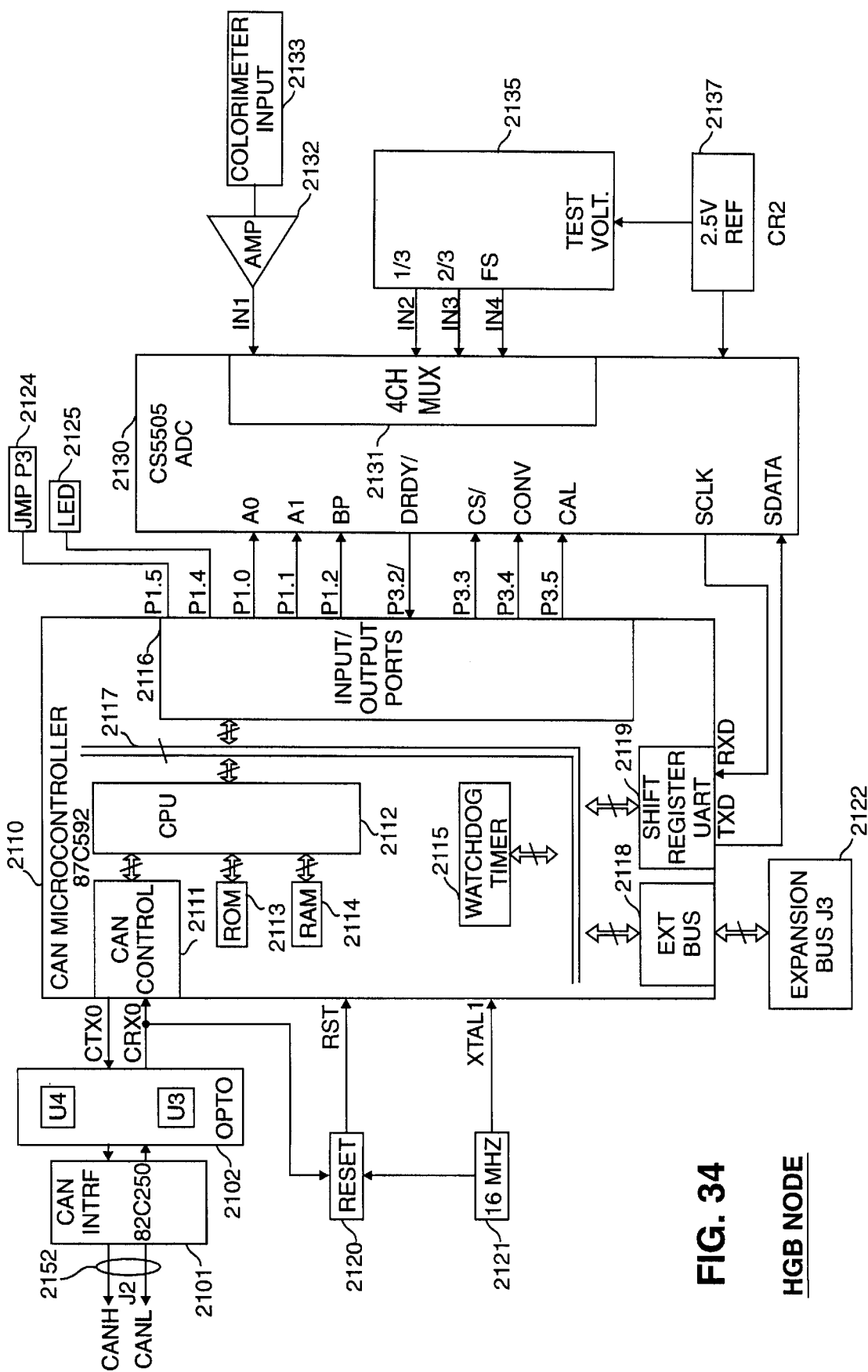
FIG. 34 is a block diagram of the HGB Node of FIG. 11B.

The function of the HGB Node 122 is to sense and convert the voltage signal from the HGB Colorimeter 621 to digital data which can be transferred to the Analytical Controller 105 via a CANBUS 500. Referring to FIGS. 34, 51 and 61, regarding the HGB node 122, a power and preamplifier assembly board 123 is used to supply power to the incandescent lamp 622 and to produce a preamplified signal from the pin-current silicon photodiode detector 623 (FIG. 61). The HGB reaction chamber 593 is interposed in the light path and the detected light is filtered to pas the light wavelength 546±2.0 nanometers to obtain the HGB color measurement. The preamplifier 2132 converts the detector signal. As illustrated in FIG. 61, the lamp assembly, the PC board 123, and the photodiode assembly are mounted in a casting 121B which aligns the lamp 622 and the photodiode 623 in a straight line through the reaction chamber number 593, within a housing 121A secured to the unified flow circuit.

The HGB Node 122 is part of the HGB Colorimeter assembly 161 and preferably is mounted to the HGB Power Supply/Pre-Amp Board 123 (FIG. 61) piggyback style within housing 121A. The HGB Node 122 operates a micro-controller which executes a software routine program to acquire and digitize a value indicative of the color measurement.

Referring to FIG. 34, the HGB Node microcontroller 2110 is preferably a Model No. P87C592 microcontroller, available from Philips. (It is noted that all circuit model numbers of commercial devices are those available from Philips Electronics, Inc., unless otherwise indicated). The microcontroller 2110 includes a CPU 2112, preferably a model 80C51 core with an integrated CAN controller 2111, digital and analog ports 2116, a shift register, serial UART port 2119, ROM 2113, RAM 2114 and watch-dog timer 2115.

Data is transferred from the discrete internal analog-to-digital converter (ADC) 2130 serially using the internal UART port 2119. Since the ADC 2130 transfers the most significant bit of data first and the UART port 2119 receives the least significant bit of data first, it is necessary for the controller 2111 to swap bits around to obtain valid data.

The ADC 2130 port assignments, using the conventional pin numbering, are set forth as follows:

| P1.0 | A0 | ADC address |
| P1.1 | A1 | ADC address |

-continued

| P1.2 | BP | Bipolar/Unipolar select |
| P1.4 | | Option LED 2125 |
| P1.5 | | Option Jumper P3 2124 |
| P1.6 | TxD | CAN Transmit |
| P3.0 | SDATA | Serial data in from ADC |
| P3.1 | SCLK | Serial data clock to ADC |
| P3.2 | DRDY/ | Data ready from ADC |
| P3.3 | CS/ | Chip select to ADC |
| P3.4 | CONV | Convert signal to ADC |
| P3.5 | CAL | Calibrate signal to ADC |

The Philips model 87C592 micro-controller includes all hardware modules necessary to implement the transfer layer which represents the kernel of the CAN protocol. The watchdog timer 2115 is reloaded periodically by the application software. The timer increments every 1.5 ms. If the processor CPU 2112 suffers a software/hardware malfunction, the software fails to reload the timer and an overflow occurs, which forces a reset of microcontroller 2110.

Preferably, the ROM 2113 is a device which contains 16 kbytes of PROM and the RAM 2114 is a device which contains 512 bytes. It should be understood that the ROM also may be a different programmable memory device, e.g., EPROM, FLASH memory or other programmable (magnetic or optical) memory as appropriate.

A more complete description of the Philips model 87C592 device is available in the Philips data sheet, which is publically available and incorporated herein by reference.

The CAN interface 2101, is preferably a Philips model 82C250 device, and provides the physical interface between the CANBUS 500 on connector J1 and the CAN controller 2111 of the microcontroller 2110. The connector J1 is the aforementioned nine pin D-type connector used to couple each node to the CANBUS scrambler 120. It is noted that CAN interface 2101 may alternatively be the same as the CAN interface 1735 described previously, and must in any event be compatible with the defined CANBUS states and protocol. A resistor (not shown) may be used to control the slope of the CANBUS signal and for EMI control. Further details of the model 82C250 CAN interface are available in the Philips data sheet, which is publically available and incorporated herein by reference.

The HGB Node 122 is powered by the ±15 volts power supply, which is regulated down to 5 volts by an on-board voltage regulator. The CAN interface 2101 (not shown) is powered by the CANBUS; 5 volts is required, and a regulator allows operation from 8–12 volts. This is similar to the operation of CAN interface 1735 previously described.

The reset circuit 2120 monitors the state of the CANBUS. Upon receiving a dominant bit condition on the CANBUS for a predetermined number of oscillator periods, e.g., 2048 oscillator periods (corresponding to 128 $\mu$s), a reset to the microcontroller 2110 is initiated. The dominant state should be maintained for at least 24 (1.5 $\mu$s) oscillator periods to complete the reset cycle. An RC circuit (not shown) may be used to hold the clear line of a flip flop in the reset circuit 2120 low as power is brought up insuring power up reset.

An oscillator (not shown in FIG. 34, shown in FIG. 35) is provided for clocking microcontroller 2110 and the reset circuit 2120. The oscillator frequency is preferably 16 Mhz (±0.01%).

The analog-to-digital converter (ADC) 2130 is provided to digitize voltages from 0 to 2.5 volts in unipolar mode or −2.5 to 2.5 volts in bipolar mode. The mode is selected by microcontroller 2110 port P1.2. This ADC 2130 provides 16 bits of resolution with a linearity error of less than 0.0030% full scale. An internal digital filter provides a 50, 60 Hz (line frequency) rejection of 120 dB when operating at a digitization clock frequency of 32,768 Hz. At this frequency, up to 20 conversions per second may occur. Preferably, the ADC 2130 is a model CS5505 device which includes an integrated four channel multiplexer 2131 having analog inputs 1N1, 1N2, 1N3 and 1N4.

The analog input of ADC 2130 will accept voltages of 0 to −2.5 volts in unipolar mode, or −2.5 to 2.5 volts in bipolar mode. The HGB calorimeter preamp board 123 (not shown in FIG. 34, see FIG. 61) presents a DC voltage of −1.1 to −4.0 volts at box 2133, as the preamplified photodetector output from circuit board 123. This corresponds to absorbencies of 0 to 0.53 O.D. with a 4 volt baseline. The input signal at 2133 is first buffered by an inverting, low offset, low noise op-amp 2132 and reduced by half using precision voltage divider coupled to the amplifier output (not shown) before being fed to the analog to digital converter 2130 at input IN1.

The digitized data is transferred to the microcontroller 2110 at UART port 2119 serially, MSB first with the microcontroller 2110 supplying the data clock.

An input on ADC 2130 input pin CONV initiates a conversion on a low to high transition if the signal on the pin CAL is low or a calibrate cycle if CAL is high. If the signal at the pin CAL is high during a low to high transition at the CONV input, a calibrate cycle occurs, which includes calibration of the ADC 2130 offset and gain scale factor.

The ADC 2130 inputs A0, A1 are used to select which input channel is used for the input signal. These signals are latched by a low to high transition at the CONV input. The ADC 2130 BP/UP input selects a bipolar mode if the signal is set high and a unipolar mode if the signal is set low. The ADC 2130 DRDY/ pin is a Data Ready signal that goes low at the end of the analog to digital conversion cycle, to signal to the microcontroller 2110 that data is available on the UART serial port 2119. It returns high after all bits have been shifted out or two clock cycles before new data becomes available if pin CS/ is high. The CS/port allows access to serial port when set low. The SDATA port is a Serial data line on which data is shifted out MSB first. The SCLK port is a Serial data clock supplied by the microcontroller 2110. Preferably data changes on the falling edge of the clock. It is noted that other Nodes may utilize the internal 10 bit ADC of the Philips Model 87C597 device for digitizing data, but a different ADC may be used when greater (or less) resolution is desired, as in the HGB Node 122.

Conventional voltage regulators (not shown) are used to convert the ±15 volt input to the required voltage for HGB Node 122 operation. The following supplies are typically provided: a +5V digital supply; a ±10 volt supply for the op-amp 213-2; and ±5V analog supply for the ADC 2130.

HGB Colorimeter measurements are derived from a ratio of a sample voltage measurement and a baseline voltage measurement made within a 15 second time period. Scaling errors such as the voltage reference tolerance are factored out in making the ratio. Only linearity, offset, noise and drift errors effect results.

The total accuracy for the board in making voltage ratio measurements in the voltage range of 1 to 4 volts is 0.1%. This voltage range corresponds to calorimeter absorbencies of 0 to 0.53 O.D. and a baseline voltage of 4 volts.

2. The Pressure and Switch Node

Figure 26:
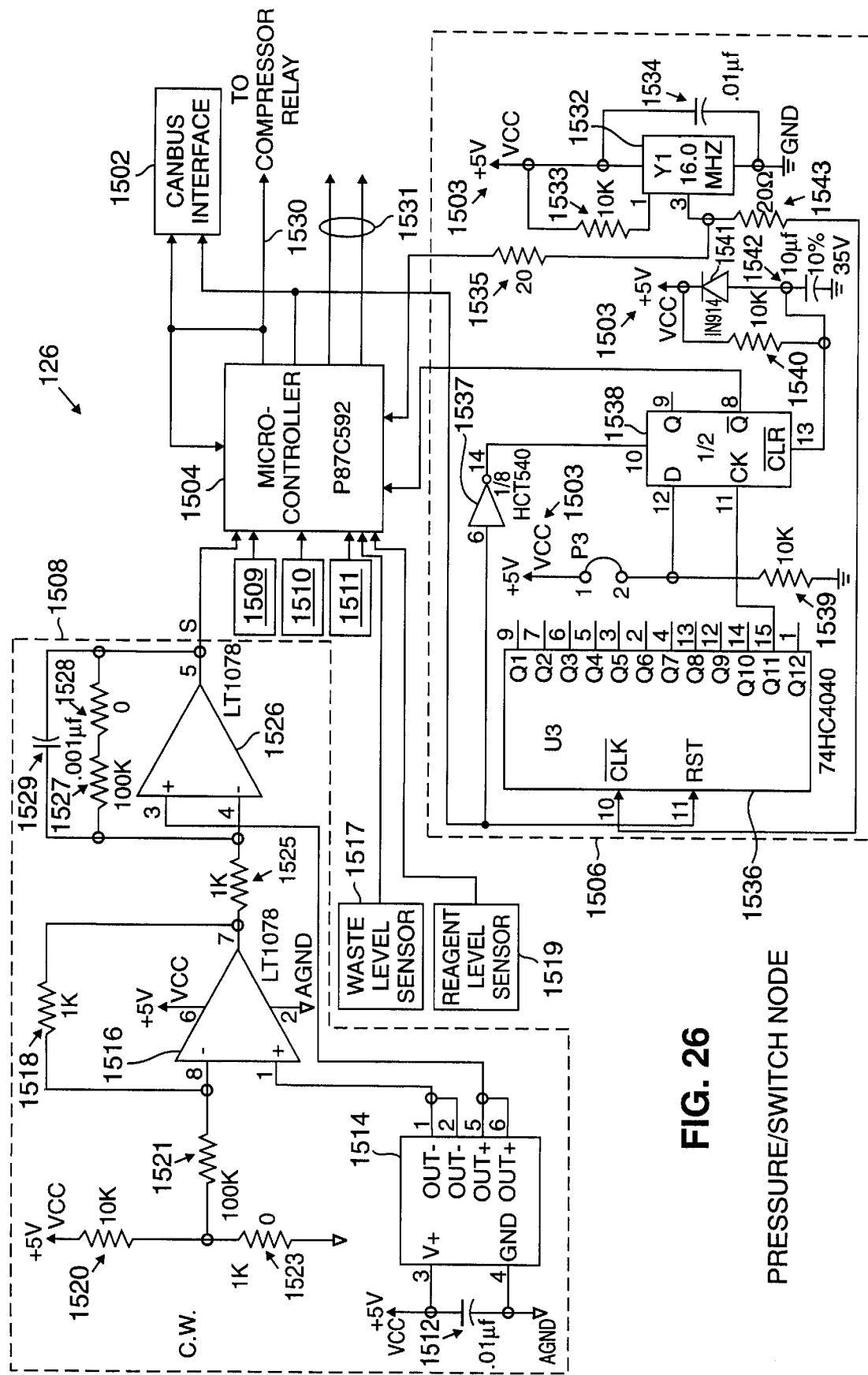
FIG. 26 is a block circuit diagram of the Pressure and Switch node of FIG. 11B.

FIG. 26 is a simplified schematic diagram of the Pressure and Switch Node 126, which is the interface between the analytic Instrument Controller 105 and the pneumatics assembly 129, 128, 130A. The pneumatics assembly is shown in block form in FIG. 11B, and comprises the pneumatic/compressor assembly 130A, the waste jug assembly 128 and the universal rinse assembly 129. The Pressure and Switch Node 126 controls the power to the compressor, dryer and monitors the state of the level sensors for the waste and reagent containers, and monitors the pressure and vacuum lines of the system. Each of the various components of the Pressure and Switch Node is supplied with power from a single 5 Volt source 1503.

Each node, including the Pressure and Switch Node 126, has a CANBUS interface circuit 1502 which links the data on the CANBUS 500 from the other nodes and/or from the system CPU 107 to a node microcontroller such as the Switch Node microcontroller 1504. The Switch Node microcontroller 1504 is thus connected to the system CPU 107 and the other nodes through the CANBUS interface 1502. The CAN interface 1502 is preferably constructed in the same manner and operation as the CAN interface circuits described above (e.g., circuit 2101 in FIG. 34, or alternately circuit 1735 in FIG. 25) and similarly microcontroller 1504 is the same as the above-described node microcontroller device (e.g., microcontroller 2110 in FIG. 34). These devices operate in the same manner as those devices with respect to connecting the Pressure and Switch Node 126 to, and communications on, the CANBUS 500.

In the Pressure and Switch Node 126, the microcontroller 1504 has inputs 1508, 1509, 1510 and 1511 from three pressure transducers and one vacuum transducer, respectively. The microcontroller 1504 also receives input from a reset circuit 1506, and from a waste level sensor 1517 and a reagent level sensor 1519. The level sensors may be magnetically activated reed switches. The microcontroller 1504 may output commands to the compressor relay on line 1530, and may send data to the CANBUS, as required. The relay may be a solid state relay. Further, the microcontroller 1504 may generate a plurality of output signals on data lines 1531 as required for diagnostic or other purposes.

The pneumatic/compressor assembly 130A provides the system with three pressures of 5, 20 and 40 pounds per square inch (PSI), and a vacuum of 20" Hg. Four different electronic transducer circuits 1508, 1509, 1510 and 1511, which are configured in the same manner, monitor the various pressure and vacuum lines (generally referred to as a "pneumatic" or "hydraulic" line) and generate output signals. The four sensors preferably use pre-calibrated pressure transducers, three of which have a maximum sensing capability of 60, 30, and 5 psi for measuring the 40, 20 and 5 psig, operating pressures respectively, and the fourth of which has a maximum capability of 15 psi, but which is installed with its output polarity reversed so as to measure the vacuum. The system microcontroller 107 in the Analytic Instrument Controller 105 selects which of the pressure or vacuum lines to be monitored, and ensures that the pressure measurements stay within a plus or minus 5 percent tolerance band. The tolerance band incorporates any transducer, amplifier and analog-to-digital converter errors that may occur. The analog to digital conversion integral to microcontroller 1504 typically converts the analog pressure and vacuum signals with a ten bit resolution for transfer on the CANBUS. Use of the transducers permits the pneumatics system to be monitored in real time.

Referring to FIG. 26, one of the transducer circuits 1508 is shown in detail. The transducer circuitry utilizes low-offset operational amplifiers in addition to a pressure sensor to monitor the system in real time and is capable of generating a signal if the pressure (or vacuum) is not within a preset tolerance band. Referring to transducer circuit 1508, a 5 Volt power supply 1503 is connected to the inputs of a pre-calibrated pressure sensor 1514 across a 0.01 microfarad capacitor 1512. The negative outputs of the sensor 1514 are fed to the non-inverting input of operational amplifier 1516. The output of amplifier 1518 is fed back to its inverting input through 1 KΩ resistor 1518. In addition, the 5 Volt power supply is connected to the inverting input of amplifier 1516 through a voltage divider circuit comprising resistors 1520, 1521 and 1522 in parallel with resistor 1523. Optionally a 0–1 KΩ potentiometer may be in parallel with resistor 1523. The output of amplifier 1516 is also input through 1 KΩ resistor 1525 to the inverting input of operational amplifier 1526. The positive outputs of pressure sensor 1514 are fed to the non-inverting input of amplifier 1526. The output of amplifier 1526 is fed back to its inverting input through circuitry comprising 100 KΩ and optionally, resistors 1527 and 1528 in parallel with a 0.001 microfarad capacitor 1529. The output signal generated by the amplifier 1526 is fed to microcontroller 1504 for transmission to the CANBUS. The circuits are thus configured as instrumentation amplifiers. Each pressure transducer is connected to provide a 25 mV output at full scale with a 5 V supply. The circuit components illustrated that lack values are optional components intended for providing possible gain and offset adjustments.

Again referring to FIG. 26, a node reset circuit 1506 is shown in detail. Each node in the system contains such a reset circuit, and it functions to reset the node when a dominant signal generated by the CANBUS goes low for a period longer than a preset maximum time period. The reset circuit 1506 contains a 16 MHZ oscillator 1532 (or at least the clock signal from such an oscillator), connected to a 5 Volt source 1503 through a 10 KΩ resistor 1533. The 5 Volt source is also connected to ground through 0.01 microfarad capacitor 1534. The output of oscillator 1532 is connected to the microcontroller 1504 through a 20Ω resistor 1535, and to the clock input of integrated circuit 1536. Through a 20Ω resistor 1543, circuit 1536 is a counter that divides the clock frequency by 2048. The reset input line of the integrated circuit (sensor) 1536 is connected to the CANBUS interface 112, which is also connected through inverter 1537 to flip-flop circuit 1538. The first input of flip-flop 1538 is connected to the 5 Volt source through a jumper P3 (to disable the CANBUS reset function), which is also connected to ground through 10 KΩ resistor 1539. The second input of flip-flop 1538 is connected to the output of the integrated circuit 1536. The "clear" input of flip-flop 1538 is connected to the 5 Volt source through 10 KΩ resistor 1540, and the 5 Volt source is also connected to ground through a circuit comprising resistor 1540 in parallel with diode 1541 and a 10 microfarad capacitor 1542. The oscillator 1532 of reset circuit 1506 enables sensor 1536 to determine when the dominant signal of the CANBUS remains low for a period of time exceeding a preset maximum period (e.g., 2048 clock pulses), and to generate a signal from flip-flop 1538 on line 1544 to the microcontroller 1504 to reset the node where such a situation occurs.

Also input to the internal ADC of microcontroller 1504 is a bank of four analog inputs to monitor voltages from four test volt sources, namely full scale test voltage, ⅔ scale test voltage, ⅓ scale test voltage, and 0 test voltage. The ADC provides a 10 bit analog to digital conversion. The reference voltage for the ADC is the 5 volt power supply which also is the input voltage for the four transducer circuits 1508, 1509, 1510 and 1511, so that the measurement made is ratiometric and not affected by power supply variations.

3. Puma Node—Puma Profile

Figure 35:
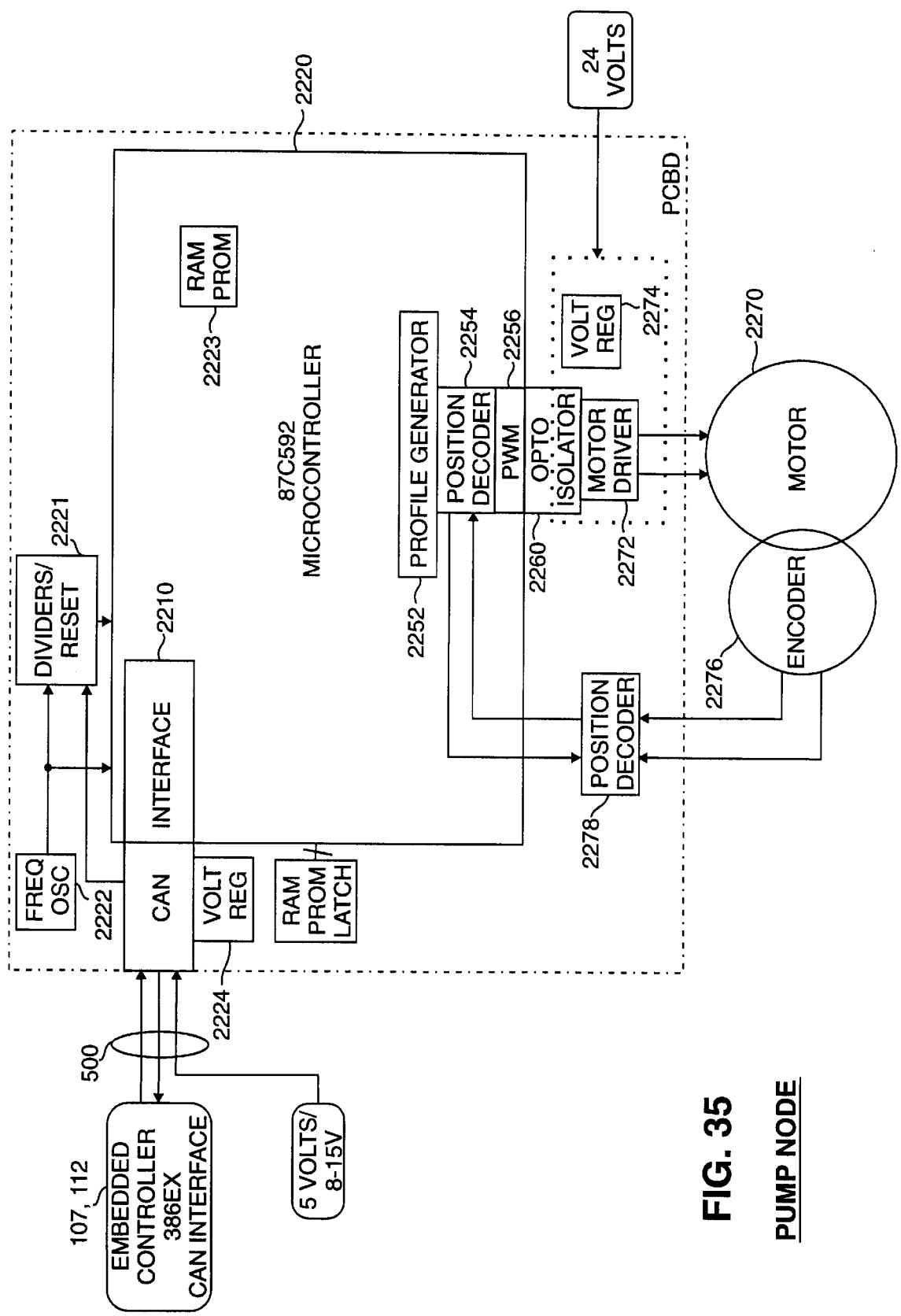
FIG. 35 is a block diagram of the Pump Node of FIG. 11B.

Referring to FIG. 35, generally, the pump node is a small printed circuit board that mounts on the pump itself and monitors the pump utilizing an encoder. The node microcontroller controls the speed of the motor by generating a pulse width modulated signal and varies the duty cycle. The Pump Nodes 132, 134, 136, and 138 each operate the servo motor unit for the syringe pumps 867 for pumping the sheath and the reaction mixture through the flow cells 110 and 110A for making the optical measurements. Taking as an example the Pump Node 138, it functions to control its associated syringe within a specified time according to a predetermined pump profile, which avoids erratic movement and has a substantially constant velocity during the flowcell read time. Each of the pump nodes operates in substantially the same manner, and therefore only one will be described.

The Pump Node 132 includes a CAN interface circuit 2210, a microcontroller 2220, a voltage regulator 2224, a reset circuit 2221, an oscillator 2222, RAM and PROM memory 2223, all having the same essential construction and operation with respect to communications between the Node 132 and the CANBUS 500 and system CPU 107 as the other nodes and as previously described. In addition, Node 132 includes a profile generator 2252, a position detector 2254 and a pulse width modulator circuit 2256 which is coupled to an opto-isolator 2260. The pulse width modulated signal produced by microcontroller 2220, which implements the pump profile to be obtained, is transmitted over opto-isolator bridge 2260 to control the motor driver circuit 2272. This motor driver circuit 2272 in turn drives motor 2270 to operate the associated syringe pump 867 according to the programmed profile. The profile, more specifically the constants needed to determine the profile, is downloaded from the system controller 105 over the CANBUS 500 and stored in the profile generator 2252. The constants may be, for example, an initial condition, an acceleration slope (counts per sec$^2$) and duration (counts), constant velocity (counts per sec) and duration (counts), and deceleration (counts per sec$^2$) and a duration (counts)

The motor 870 (FIGS. 42 and 43) has a corresponding encoder circuit 2276 which produces an encoded signal representative of the position of the syringe pump motor. This encoded signal is then decoded by position decoder circuit 2254, and compared to the profile using profile generator 2252, thereby to provide feedback control of the pump motion according to the desired profile. The feedback is provided by the encoder 2276 of the motor, and the quadrature decoder 2278, e.g., devices model Nos. HEDS-9120 and HCTL-2016, available from Hewlett Packard. In the event that the pump motor cannot be corrected to follow the desired profile, then the microcontroller 2220 can generate the appropriate fault signal and transmit it to the host CPU on the CANBUS 500. The motor driver circuits may be provided with a 24 volt supply separately from the CANBUS 5 volt supply or the on board voltage regulator 2224, to generate the power necessary to operate the motor 2270. Hence, the opto isolation is desired and used. A preferred motor driver circuit is a model LMD18200 device available from National Semiconductor Corp., Santa Clara, Calif. 95052.

These circuit elements are preferably mounted on a single printed circuit board which is in turn connected adjacent the motor for operating the syringe pumps., in the pump modules as discussed below.

4. Valve Node

Figure 31:
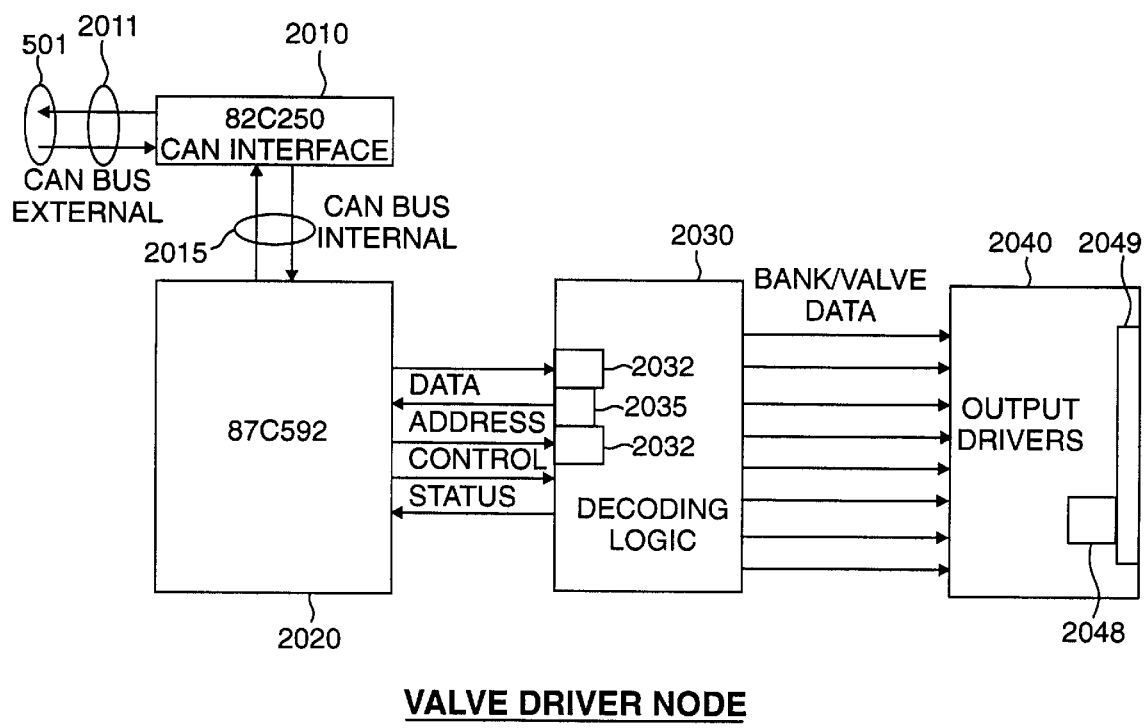
FIGS. 31, 32 and 33 are block diagrams of the Pneumatic Valve Driver Node of FIG. 11C.

Referring to FIG. 31, the Valve Driver Node 160 is the interface between the analytic Instrument Controller 105 and its CPU 107 and the system valving hardware. The valve driver node 160 controls the applicable system solenoid (pneumatic) valves V26, V28, V29, V30, V34, V31, V75, V76, V77, V78, V79, V39, V60 and V80 (see FIG. 52). It also contains fault indicating circuitry for valve shorts and open circuit conditions.

The Node 160 is made intelligent via an on board microcontroller 2020 and a CANBUS interface 2010 which is queried by the host CPU 107 via the CANBUS 500 to handle valve selection, timing and to report valve status. Valve node 160 is preferably formed as a printed circuit board assembly, based on the MICREL Semiconductor integrated circuit MIC 59P50, 8 Bit Parallel Input Protected Latched Driver circuit for driving the valves.

The valve driver node 160 is preferably able to power 40 low current (50–60 MA) dome or diaphragm valves, which may be arranged in a bank of 5×8 valves. The valve driver node 160 also is preferably able to power 6 high current (200 MA) solenoid valves, which may be arranged in two banks of 1×2 and 1×4, and a combination of the above. The valve drivers are collectively represented by output driver circuit 2040.

The microcontroller 2020 the CAN Interface 2010 are similarly configured as in the other nodes, having a reset circuit 2021, an oscillator 2022 at 16.0 Mhz, RAM and PROM memory 2023, and an on-board voltage regulator 2024 to perform data and control functions transfer between the Instrument Controller 105 and the node 160 except that the inputs and outputs of the microcontroller and its data processing functions are different to perform the dedicated node 160 functions.

Figure 32:
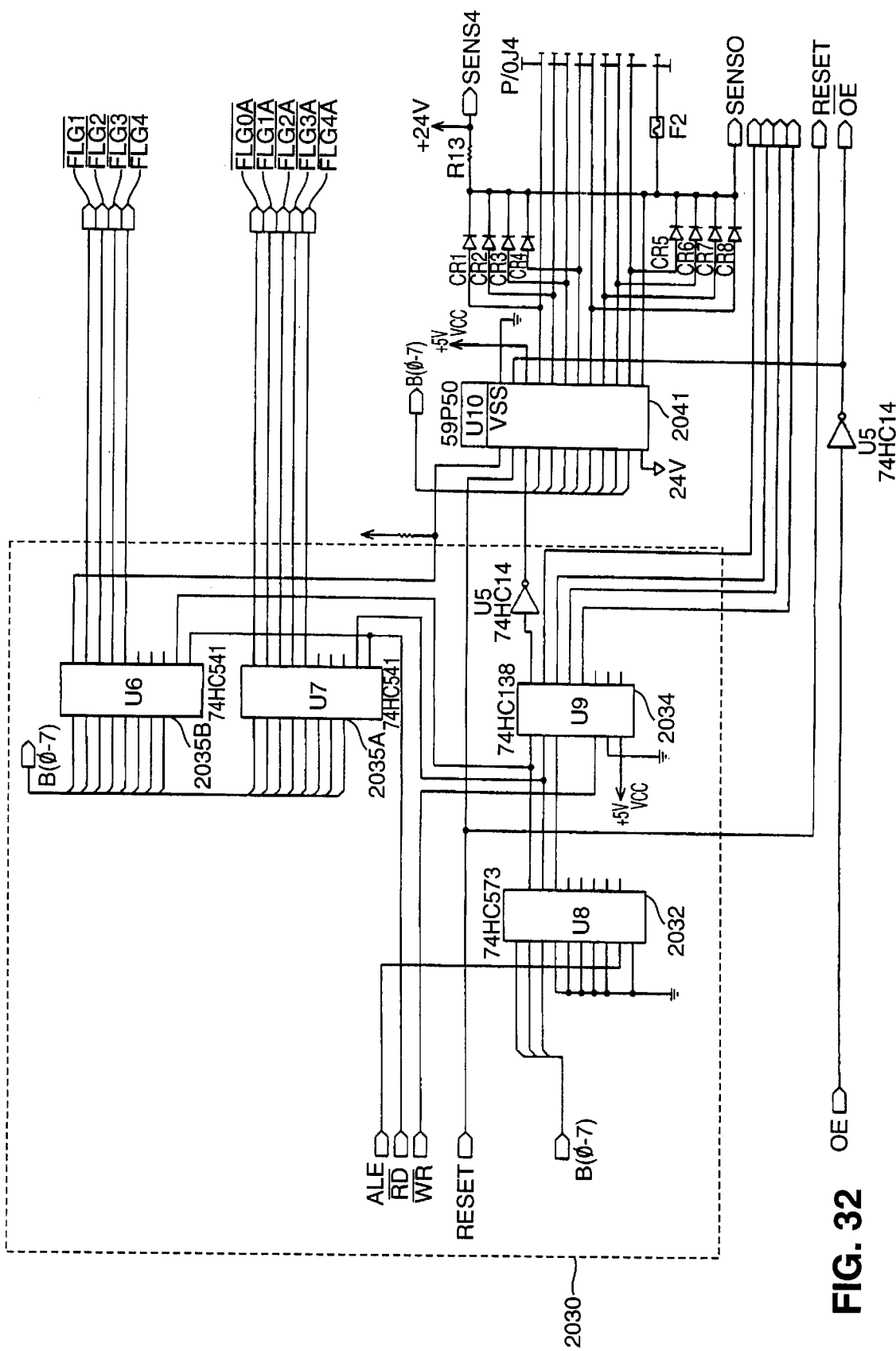

Referring to FIG. 32 the decoding logic circuitry 2030 include circuits to decode the valve driver stobe from system CPU 107. Circuit 2032, preferably a model 74HC573 latch, latches the least three significant address bits via an ALE/ signal to select which driver integrated circuit is to receive new data. Circuit 2034, preferably a model 74HC138, is a 3 to 8 line decoder which receives the stored data bits and processes them at the appropriate time by the arrival of a WR/ signal. Decoded strobes are than routed to the various power output drivers 2040 to control the identified valve accordingly. Octal Tri-State Buffers 2035A and 2035B are used to steer valve fault flags to the on-board microcontroller 2020 by decoding Data bits D0, D1 and the RD/signal.

The output valve driving circuitry 2040 comprises integrated driver circuits 2041, 2042, 2043 and 2045, each preferably the MICREL model 59P50 device, having a +5 volt supply and a 24 v ground return. Each driver output pin is protected by a transient diode tied up to the power rail (not shown). Also incorporated on all driver outputs is a wired or series current sensing resistor (not shown), e.g., 1.0 ohms 5% (3 watts) connected in a differential mode to the sense comparator circuitry 2048 and 2049. The sense comparator circuitry 2048 and 2049 (e.g., preferably an Allegro model ULN2454 device) are used in decoding logic 2030 to sense the voltage drop across the sense resistor as the software turns on each valve individually. If no voltage is sensed, then the valve or wiring is assumed to be open circuit. This is then reported to the system controller 105.

Timing for the driver circuitry 2040 is obtained in accordance with the truth table below.

TRUTH TABLE

| Data In | Strobe | Clear | OE | O(t − 1) | O(t) | Note: |
|---|---|---|---|---|---|---|
| 0 | 1 | 0 | 0 | x | off | x = Irrelevant |

-continued

TRUTH TABLE

| Data In | Strobe | Clear | OE | O(t − 1) | O(t) | Note: |
|---|---|---|---|---|---|---|
| 1 | 1 | 0 | 0 | x | on | t − 1 = previous output state |
| x | x | 1 | x | x | off | t = present output state |
| x | x | x | 1 | x | off | |
| x | 0 | 0 | 0 | on | on | |
| x | 0 | 0 | 0 | off | off | |

Optionally, one or more of the output driver circuits may be provided with output parallel wiring that allows each output driver to be used in parallel. These output drivers may be used for delivering a high current drive.

The microcontroller 2020 is preferably the Philips model P87c592-EFA device having an 80c51 core with an array of various I/O capability as previously described. In a preferred embodiment of the Valve Driver Node 160, the microcontroller 2020 port assignment using the conventional pin assignments is as follows: Port P0.0–0.7 is used for the internal data bus I/O 2015, Port P1.0 and Port 1.5 are used to port decode the Node 160 identity, Port P1.2 is used for board Reset, Port P1.3 and P1.4 are status indicators, Port P3.6 is used for board WR/ command, Port P3.7 is used for board RD/ command, and Port 3.2 is used for board Output Enable command.

The valve driver node 2 shown on FIG. 1K has the same construction as valve driver node 1.

5. Parallel Node

Figure 27:
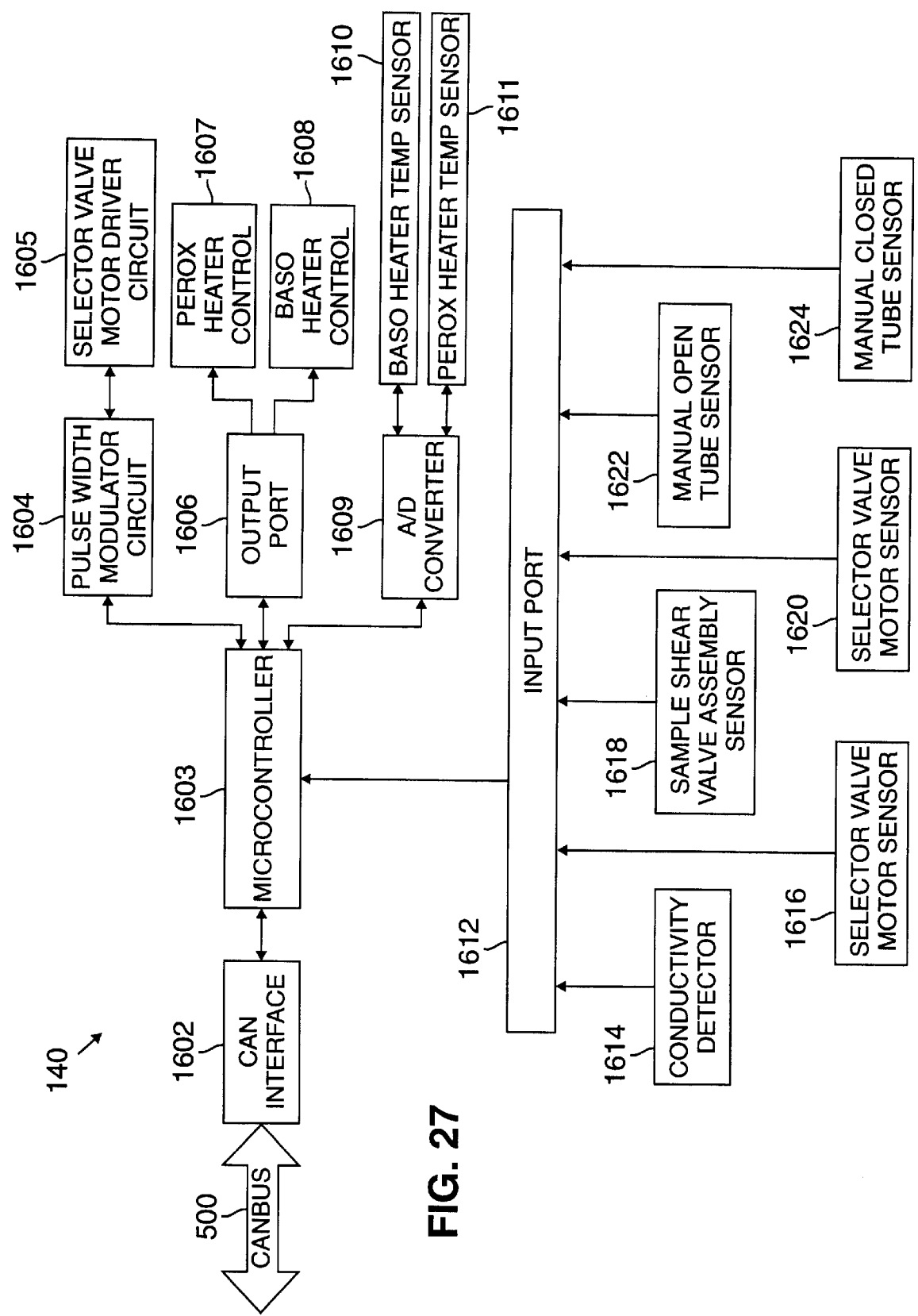
FIG. 27 is a block diagram of the Parallel Node of FIG. 11C.

FIG. 27 is a simplified block diagram of the architecture of the Parallel Node 140. A CANBUS Interface 1602 connects the CANBUS to the Parallel Node microcontroller 1603 which is in turn connected to various sensors, heaters and motors associated with the BASO, PEROX, Sample Shear Valve and the Aspirate and Selector Valve Assemblies, as shown in FIGS. 11A and 11C. The CANBUS interface 1602 is essentially the same as interface 2011 in the Valve Driver Node 160. Similarly, microcontroller 1603 is the same as microcontroller 2020 (although programmed differently) and the same internal bus between interface 1602 and microcontroller 1603 is used as was described in the Valve Driver Node 160 and the other Nodes.

The microcontroller 1603 is connected via a pulse width modulator circuit 1604 to the selector valve motor drive circuit 1605 for controlling the operation of the circuit. The microcontroller 1603 is also connected to the PEROX and BASO heater controls 1607 and 1608 via an output port 1606, and to PEROX and BASO temperature sensors 1610 and 1611 via Analog to Digital converter 1609. In addition, a conductivity sensor 1614, a first selector valve motor sensor 1616, a sample shear valve assembly sensor 1618, a second selector valve motor sensor 1620, a manual open tube sensor 1622, and a manual closed tube sensor 1624 are each connected to the microcontroller 1603 via input port 1612.

The Parallel Node 140 also controls the PEROX and BASO heaters utilizing CMOS control logic, wherein a "high" level enable signal turns the heaters ON, and a "low" level signal turns the heaters OFF. The Parallel Node also monitors the analog temperature in the BASO and PEROX chambers, and converts the analog voltages representing the temperature readings to digital values using the A/D converter 1609. A minimum resolution of 10 bits is preferred.

The Node 140 provides a pulse width modulated signal utilizing circuit 1604 to control an FET transistor in the selector valve motor drive circuit 1605 to drive the selector valve motor when the System Controller 107 issues commands to operate the selector valve motor. The Node 140 preferably is able to drive a DC motor with a current of 3.0 amps, and to provide a 3.0 amp signal to each of the heaters. The Parallel Node also provides an input port for the six sensors shown in FIG. 27, namely the conductivity detector 1614, the first selector valve motor sensor 1616, sample shear valve assembly sensor 1618, the second selector valve motor sensor 1620, manual open tube sensor 1622, and manual closed tube sensor 1624. These inputs are used to determine, among other things, the location of a sample to be aspirated, whereupon the selector valve motor is actuated to be in the position to aspirate the located sample.

Each of the sensor signals is input to a buffer circuit comprising a Hex Inverting Schmitt Trigger in input port 1612. Capacitors are preferably used to decouple the analog inputs from transients.

Figure 28:
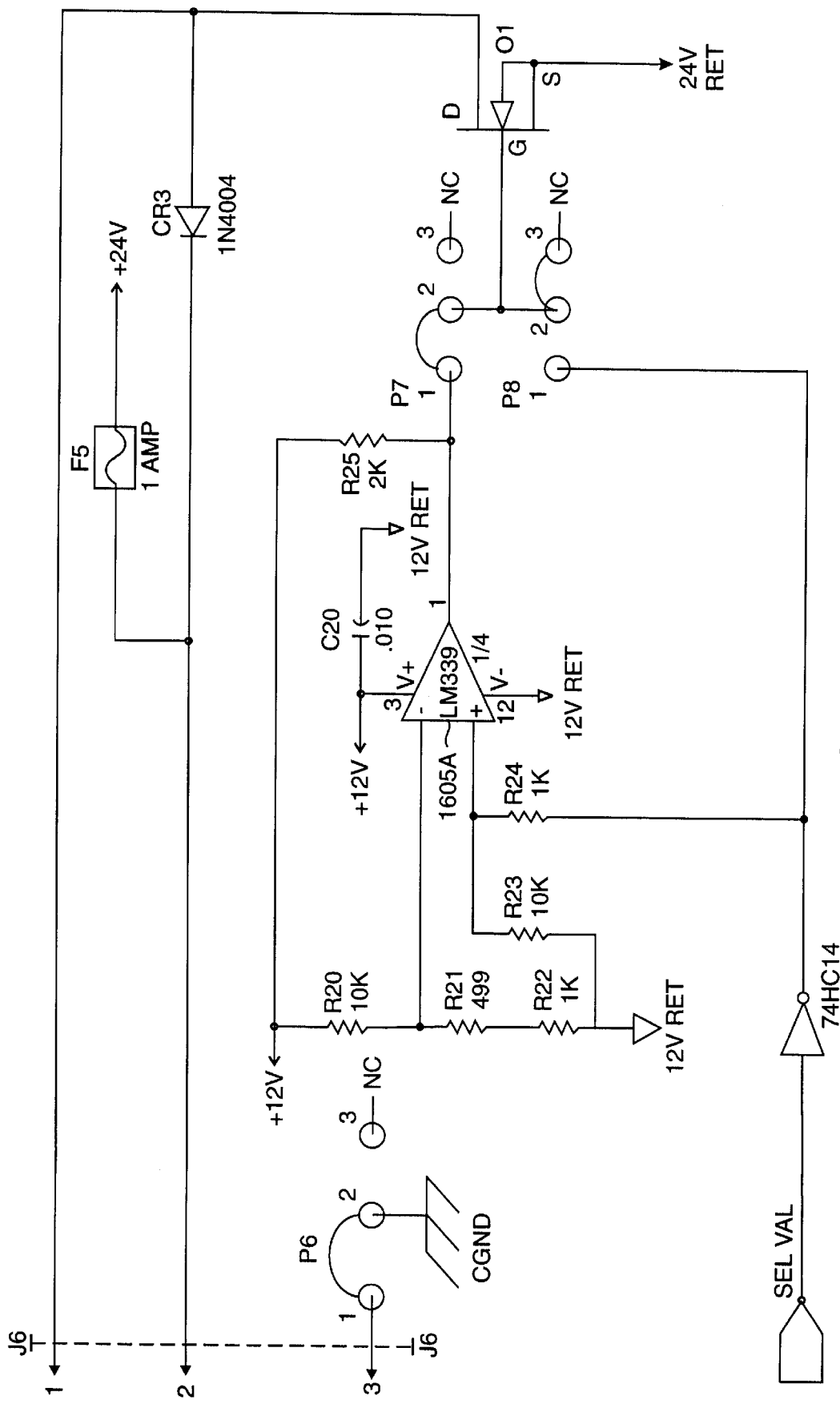
FIG. 28 is a circuit diagram of the selector valve motor driver circuit of FIG. 27.

An opto-isolator is used in the selector valve motor driver circuit 1605 to isolate the shear face actuator signal delivered to the selector valve motor (not shown). The Selector Valve Motor Driver Circuit 1605, shown in FIG. 28, includes a voltage comparator 1605A preferably a model LM399 device having a ±12 volt bias voltages applied, and related circuit components to produce a 50% duty cycle chopper circuit. This output drives a +12 volt DC motor via a power MOSFET Q1 through connector J6. The comparator 1605A is provided with a threshold voltage of +1.56 volts (±15%), and is compared to the incoming select valve logic signal SEL VAL via input port 1612 (FIG. 32). When the threshold is exceeded, then the power MOSFET Q1 is turned on. The Selector Valve Driver Circuit 1605 has three outputs, a Motor Output, a +24 volt supply, and a ground CGND terminating in Connector J6.

The analog input signals from each heater sensed at sensors 1610 and 1611 is analogous to the temperature sensed. These signals are converted by analog-to-digital converter 1609 which is preferably a part of on-Node Microcontroller 1603. A description of the microcontroller 1603 and the operation of its analog-to-digital converter 1609 is provided above. The transfer function for the PEROX analog input is 0 volts for an equivalent +50 degrees Centigrade and +5 volts DC for an equivalent +90 degrees Centigrade. Therefore the function is 8 degrees/1 volt above +50 degrees Centigrade. The transfer function for the BASO analog input is 0 volts for an equivalent 14 degrees Centigrade and +5 volts DC for an equivalent +40 degrees Centigrade. Therefore the function is 5 degrees/1 volt above +40 degrees Centigrade. The BASO heater preferably also has an open sensor input (not shown) monitored by the microcontroller 1603.

Figure 33:
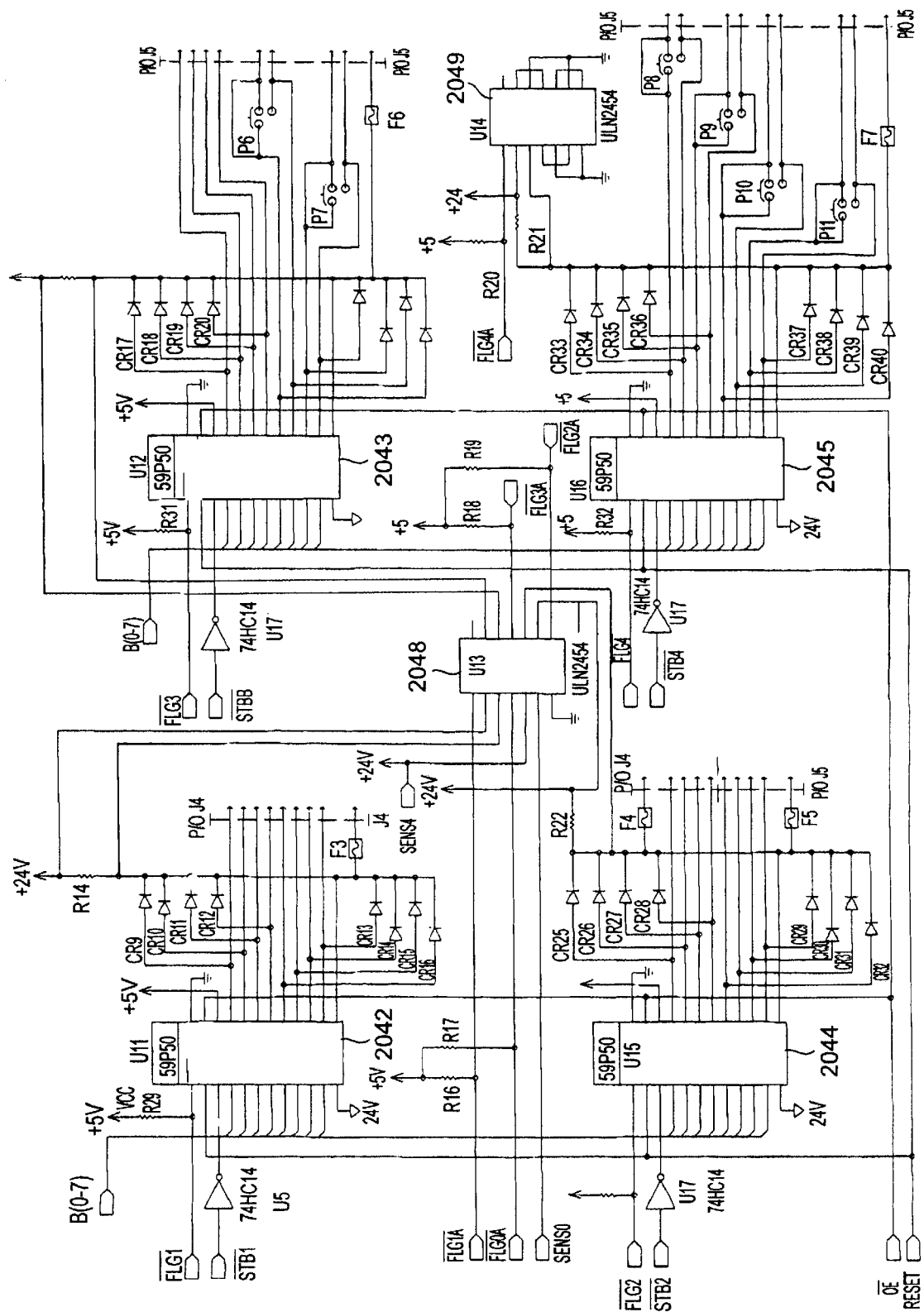

FIGS. 32 and 33 are detailed schematic diagrams of an embodiment of a conductivity detector 1614 for use in the blood analysis system of the present invention. The sensing plates 1628 and 1630 of the conductivity detector 154 are physically connected inside the UFC Valve Assembly 153 (see FIG. 11C) in a manner to contact fluids under analysis, whether stationary or more preferably in motion. In particular, fluids such as water, blood, reagents and other test material flow in the UFC Valve assembly at certain times during the test cycles. The purpose of the conductivity detector 1614 is to determine whether or not a fluid sample, for example, a blood sample, falls within a predetermined conductivity range corresponding to a range of acceptable values for the blood sample. If so, then the sample is considered to be a valid blood sample which should be tested in the normal manner. If not, then no blood analysis tests should be run because a sample that falls outside the range indicates a problem with the sample being a valid blood sample.

Referring to FIG. 32, a signal generator circuit 1625 produces a signal of known frequency and amplitude which is injected, preferably at all times, into a fluid via plate 1628 as described above. The signal is generated under control of the generator 1625. The signal is then sensed by the pick-up plate 1630 and input to an amplifier circuit 1632, which amplifies the signal before sending it on to a rectifier circuit 1634. The output of the rectifier circuit 1634 is connected to an integrator circuit 1636. Referring to FIG. 33, the integrated signal is then presented to the input of an adjustable output circuit 1638. The ultimate output signal is generated when a blood sample (or other conductive fluid of interest) is present in the UFC Assembly by the conductivity sensor 1614 and is indicative of the conductivity of the solution that was sensed between plates 1628 and 1630. In particular, if the conductivity level falls within a predetermined range corresponding to an acceptable blood sample, then a digital zero signal will be generated. However, if the conductivity level is outside the range, then a digital one signal is generated to indicate an unacceptable blood sample is present. It should be understood that unacceptable blood samples can be analyzed when desired, based on the sample having a conductivity value within an appropriate predetermined conductivity range for the analysis to be performed.

The term hematocrit is defined as the volumetric percent concentration of red cells in blood and typically ranges from 30 to 50. In this regard, blood has two major components, red cells and plasma. The red cells are not considered electrically conductive, whereas the conductivity of the blood is due to salts ($Na^+$ and $Cl^-$). The presence of red blood cells can reduce the conductivity relative to plasma.

At some very high hematocrit, which makes blood very viscous, the conductivity sensor may "time outs" due to the conductivity or viscosity and indicate an unacceptable sample. However, it should be understood that such a time-out event actually indicates detection of an acceptable sample for test purposes, although the hematocrit value may not fall in an acceptable range of values for conducting a test. For reliability, a time-out event is typically treated as not detecting an acceptable sample such that an analysis is not done.

In detail, generator circuit 1626 comprises an operational amplifier 1640 connected to a ±12 Volt source through 0.01 microfarad capacitors 1641 and 1642. The inverting and non-inverting inputs of the amplifier 1640 are connected in a feedback path from the output through 100 KΩ resistor 1643 and 2610 KΩ resistor 1644, respectively. In addition, the inverting input of amplifier 1640 is connected to a -12 Volt reference through a 3300 picofarad capacitor 1645, and the non-inverting input is connected to the -12 Volt reference through a 2260 KΩ resistor 1646. The output of the amplifier 1640 is connected to a circuit comprising a 2 KΩ resistor 1647, a 0.47 microfarad capacitor 1648, a 100 KΩ resistor 1649 and diodes 1650, 1651, to produce a square wave signal having a frequency of 1.4 Khz and an amplitude of ±0.5 Volts. The square wave signal is fed to plate 1628, injected into a blood sample and sensed by plate 1630. The sensed signal is fed to the inverting input of amplifier 1654 through a 560Ω resistor 1655 along with a feedback signal that flows through a parallel circuit comprising a 0.001 microfarad capacitor 1656 and an 82 KΩ resistor 1657. The non-inverting input of amplifier 1654 is connected to a 12 Volt reference. The output signal of the amplifier circuit 1632 is fed to the input of rectifier circuit 1634, which comprises a 10 KΩ resistor 1659 connected to the inverting input of amplifier 1660, which also has input from a feedback path which comprises a 15 KΩ resistor 1661, a diode 1662 and a 100 KΩ resistor 1663 in parallel with a 0.0015 microfarad capacitor 1664. The non-inverting input of amplifier 1660 is connected to a 12 Volt reference. The output of the rectifier circuit 1634 is then fed to an integrator circuit 1636, which comprises a 100 KΩ resistor 1665 connected to the inverting input of amplifier 1666, which also has input from a feedback path comprising a 120 KΩ resistor 1667 in parallel with a 0.022 microfarad capacitor 1668. The non-inverting input of amplifier 1666 is connected to a 12 Volt reference. The output of the integrator circuit 1636 is connected to an adjustable output circuit 1638, which comprises a 100 KΩ resistor connected to the inverting input of amplifier 1671 in parallel with a variable resistance circuit comprising a 100 KΩ resistor 1672 and a potentiometer 1673 connected to a 6.81 KΩ resistor 1674 in parallel with a 20 KΩ resistor 1675, which are connected to a +12 Volt reference. The amplifier 1671 is connected to ±12 Volt reference voltages through 0.01 microfarad capacitors 1676 and 1677. The non-inverting input of amplifier 1671 is connected in a feedback path through a 30 KΩ resistor 1768 and to a 12 Volt reference through a 499Ω resistor 1679 in parallel with a 1 KΩ resistor 1680. The output of amplifier 1671 is also connected to inverter 1684 through a 68.1 KΩ resistor 1681 in parallel with a 20 KΩ resistor 1682, and to a 12 Volt reference through a 6.81 KΩ resistor 1683. The output signal from the inverter 1684 is indicative of whether or not the blood sample falls within an acceptable hematocrit range to permit further testing. In the output circuit 1638, the potentiometer 1673 can be adjusted to select the desired hematic range.

Figure 29:
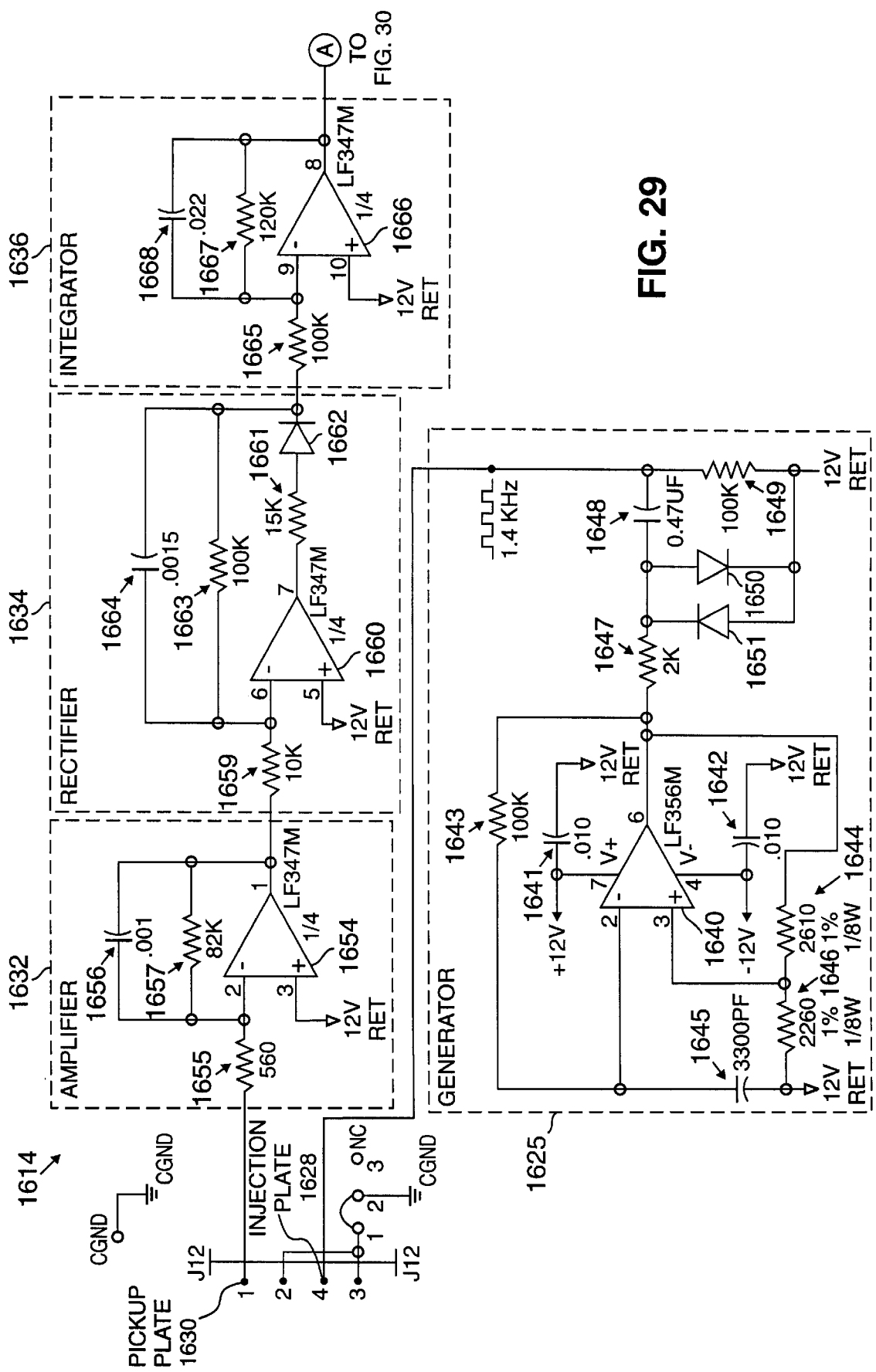
FIG. 29 is circuit schematic diagram of the conductivity sensor of FIG. 27.
Figure 30:
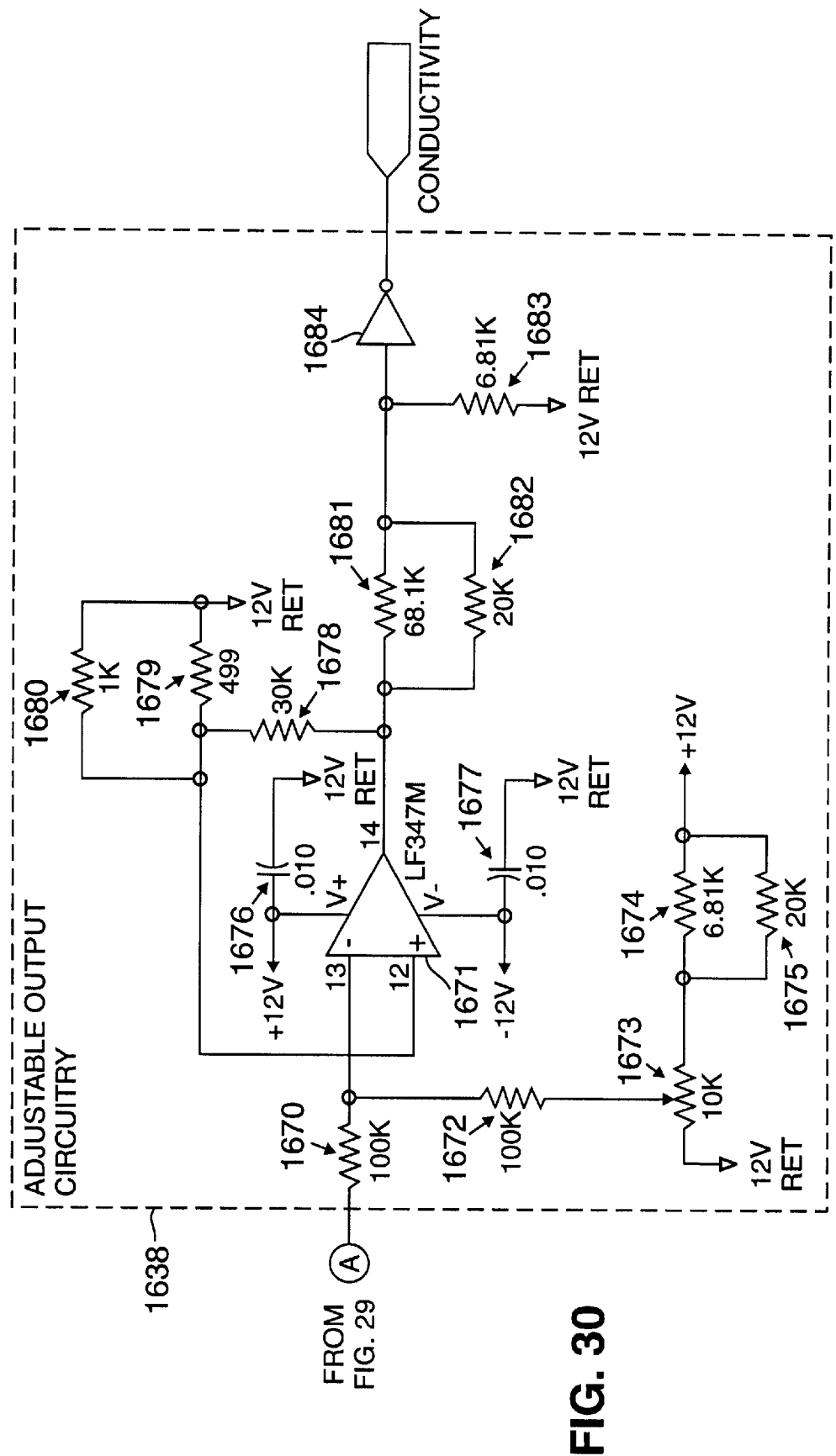
FIG. 30 is a schematic circuit diagram of an adjustable output circuit of the parallel node of FIG. 27.

Although the described conductivity detector 1614 of FIG. 29 utilizes one amplifier, one rectifier and one integrator, it is to be understood that various other circuit combinations, such as using two or more amplifier circuits, could be utilized to perform the required signal processing functions. One of skill in the art would also recognize that multiple pairs of plates could be used to increase detector capabilities, and that the sensed signals could be processed in any of a number of ways to obtain useful data. For example, each output signal from the conductivity detector circuit could be processed by the system microcontroller CPU 107 to produce data concerning the amount of impurities or the like in the blood sample. Thus, any combination of usable data signals could be generated to obtain information concerning the constitution of the blood sample so that only those samples which fall within a predetermined range or ranges will be tested. This permits conservation of reagents used in the blood analysis and minimizes the amount of biological wastes that must be processed for disposal. For non-blood sample analysis, it would similarly minimize usage of the analytic reagents that would otherwise be used.

6. Switch Indicator Node

Figure 36:
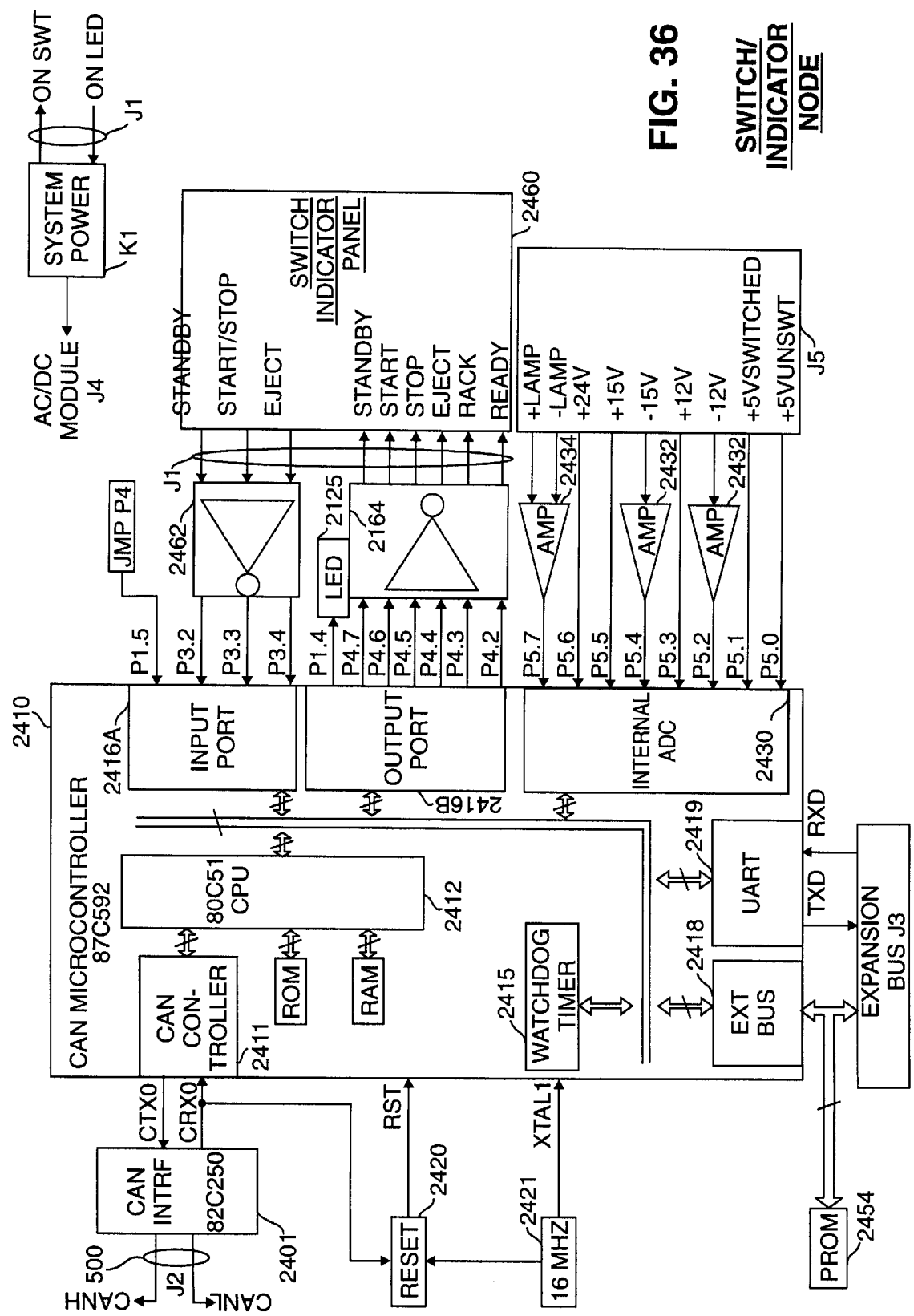
FIG. 36 is a block diagram of the Switch/Indicator Node of FIG. 11B.

Referring to FIG. 36, the switch indicator node 124 monitors the front panel switches and controls the status LEDs on the front panel 2460 over a ribbon connector J1, optionally monitors the power supply voltages over connector J5, and interfaces with CPU 107 over the CANBUS 500.

The Node 124 includes a CAN Interface 2401, a CAN microcontroller 2410, a reset circuit 2420 and an oscillator 2421, all configured as previously described for the other Nodes for communication with the CANBUS 500. The CAN Interface 2401 is preferably the Philips Model 82C250 device, and the CAN microcontroller 2410 is preferably the Philips Model 87C592 device. The reader is referred to the description of microcontroller 2110 of the HGB Node (FIG. 34), except for the analog-to-digital converter portions, wherein the reference numerals X4XX used in FIG. 37 refers to the same device having reference numerals X1XX in FIG. 34.

In this Switch Indicator Node 124, the Port P5 of the microcontroller 2410 is configured as inputs to the on-board ten bit ADC 2430 of the controller 2410. ADC 2430 is thus used to monitor, by analog to digital conversion, the voltages from eight power supplies. The reference voltage for ADC 2430 is 2.5±0.4 volts.

The Port Assignments of microcontroller 2410 are as follows:

| | |
|---|---|
| P1.4 | Option LED |
| P1.5 | Option Jumper P4 |
| P1.7 | Power supply over-temperature sensor |
| P3.2 | Standby switch |
| P3.3 | Start/Stop switch |
| P3.4 | Eject switch |
| P3.5 | Spare |
| P4.0 | Standby LED display |
| P4.1 | Start LED display |
| P4.2 | Stop LED display |
| P4.3 | Eject LED display |
| P4.4 | Rack LED display |
| P4.5 | Ready LED display |
| P4.6 | DRST/OE/ - reset/output enable/ for LED driver |
| P4.7 | Flag - over-current flag for LED driver |
| P5.0 | +5 volt unswitched power supply |
| P5.1 | +5 volt switched power supply |
| P5.2 | −12 volt power supply |
| P5.3 | +12 volt power supply |
| P5.4 | −15 volt power supply |
| P5.5 | +15 volt power supply |
| P5.6 | +24 volt power supply |
| P5.7 | +5 volt lamp supply |

The power supply voltages are brought to the Switch/Indicator Node 124 on connector J5. All voltages are scaled by voltage dividers (not shown) to fit the 2.5 volt range of the ADC 2430. The negative voltages are inverted by amplifiers. The isolated lamp supply is buffered by differential amplifier 2435.

The transfer function for each channel is thus defined as follows:

$$V = N/1024 \times V_{fs}$$

where V is the measured voltage, N is the recorded count on the ADC and $V_{fs}$ is the full scale voltage of the channel.

The connector J5 to the voltage supplies has the following pin definitions:

| Pin | Port | Function | $V_{fs}$ | |
|---|---|---|---|---|
| J5-6 | P5.0 | +5 volts unswt | 7.500 volts | |
| J5-5 | P5.1 | +5 volts switched | 7.500 volts | |
| J5-8 | P5.2 | −12 volts | −25.000 volts | |
| J5-2 | P5.3 | +12 volts | +27.000 volts | |
| J5-4 | P5.4 | −15 volts | −25.000 volts | |
| J5-7 | P5.5 | +15 volts | +27.500 volts | |
| J5-1 | P5.6 | +24 volts | +27.500 volts | |
| J5-3 | | AGND | | |
| J5-12 | P5.7 | +5 volts lamp (+) | +6.2375 volts | 2.5% |
| | | lamp (−) | | |
| J5-11 | | lamp (−) | | |
| J5-9 | P1.7 | Temp | | |

High temperatures in the power supply assembly are preferably sensed using an over temperature switch (or similar temperature sensing device) and the output of which comparison is passed to port P1.7. Thus, a high signal on the port indicates a high temperature condition.

The switch closures on the Control Panel 2460 are independently detected on microcontroller ports P3.2–P3.4. Input pins on connector J1 coupling Node 124 to panel 2460 are normally set high and pulled low by a switch closure to ground. These levels are inverted by inverting amplifier 2462 before going to port P3. Switch resistances of less than 380 ohms constitute a switch closure.

The Control Panel LEDs are visual display indicators controlled by microcontroller port pins P4.0–P4.3 and driven by driver circuit 2164, preferably a MICREL Model 59P50 device through connector J1. Each LED is driven at 15 ma. The FLAG pin on the MIC59P50 device is connected to microcontroller 2410 port P4.7 and signals an over-current or over-temperature fault. The OE/Reset pin of the MIC59P50 device is connected to port P4.6. Port P4.6 must be low to enable the LED drivers, while a high disables the drivers and/or resets a fault condition. Connector J1 may be fused to protect its 5V output. The connector J1 to the control Panel interface pin definitions are as follows:

| Pin | Design | Micro-Controller Port | Port states |
|---|---|---|---|
| J1-1 | Standby Swt | P3.2 | Hi = Swt closed |
| J1-2 | Gnd | | |
| J1-3 | Start/Stop Swt | P3.3 | Hi = Swt closed |
| J1-4 | Gnd | | |
| J1-5 | Eject Swt | P3.4 | Hi = Swt closed |
| J1-6 | Gnd | | |
| J1-7 | Standby Led | P4.0 | Hi = LED on |
| J1-8 | AGnd | | |
| J1-9 | Start Led | P4.1 | Hi = LED on |
| J1-10 | AGnd | | |
| J1-11 | Stop Led | P4.2 | HI = LED on |
| J1-12 | AGnd | | |
| J1-13 | Eject Led | P4.3 | Hi = LED on |
| J1-14 | AGnd | | |
| J1-15 | Rack Led | P4.4 | Hi - LED on |
| J1-16 | Off Swt | | |
| J1-17 | On Led | | |
| J1-18 | On Swt | | |
| J1-19 | On/Off Swt | | |
| J1-20 | +5 V | | |

The connector J6 to the LED interface pin definitions are:

| Pin | Design | Micro-Controller Port | Port states |
|---|---|---|---|
| J6-1 | Ready | P4.5 | hi = LED on |
| J6-2 | 5 V(100 ohm) | | |
| J6-3 | CGND | | |

A relay K1 controls system power. This circuit is powered by the unswitched 5 volt power supply, which is always on. Pressing the ON switch of the Control Panel 2460 energizes and latches relay K1, which then applies power to the solid state relay of the Power Supply assembly through AC/DC module connector J4. Pressing the OFF button interrupts current to the relay K1 and hence turns the system off.

The Power control port connector J4 pin Definitions are as follows:

| Pin | Desig |
|---|---|
| J4-1 | 15VUNSWT |
| J4-2 | 5VURET |
| J4-3 | SS PWR RLY |
| J4-4 | CGNC |

Memory 2465 is an optional external memory device, e.g., a Philips model 27C256 PROM. When a jumper (not shown) is in the appropriate position, the microcontroller 2410 will execute its program from this PROM 2465 instead of its internal PROM. Otherwise, the internal PROM is the program source.

One skilled in the art will appreciate that the present invention can be practiced by other than the described embodiments, which are presented for purposes of illustration and not of limitation.

We claim:

1. A reagent pump assembly for an analytical instrument in which precise amounts of reagents are to be mixed with precise sample volumes for analysis of a sample, comprising:
   a top layer having a top surface and a bottom surface;
   a middle layer having a top surface and a bottom surface;
   a bottom layer having a top surface and a bottom surface;
   a plurality of diaphragm pumps formed at a plurality of locations in an interface between the middle layer bottom surface and the bottom layer top surface, each diaphragm pump having a valve chamber and a pump chamber demarcated by a flexible membrane, each diaphragm valve having a first state corresponding to a filled pump containing a predetermined precision volume and a second state corresponding to an empty pump containing substantially no volume;
   a plurality of pressure control lines in said bottom layer, each pressure control line extending through said bottom layer to control the state of the diaphragm pump between said first and second states;
   a plurality of fluid input lines connecting said plurality of pump chambers to a like plurality of fluid supplies, wherein each fluid input line further comprises a first passage through said top layer, a second passage through said middle layer, and a first one-way valve interposed between said first and second passages, wherein the first and second passages and first one-way valve provide for flow of one of said fluid supplies into said pump chamber in response to the diaphragm pump changing from said second state to said first state, and no flow from said pump chamber to said fluid supply in response to the diaphragm pump changing from the first state to the second state, each diaphragm pump having an input line; and
   a plurality of fluid output lines connecting said plurality of pump chambers to a like plurality of output ports, wherein, for a given diaphragm pump, each fluid outlet line further comprises a third passage extending through said top layer, a fourth passage extending from the top of the middle layer and connecting to said second passage between said first one-way valve and said pump chamber and a second one-way valve interposed between said third and fourth passages, wherein the third and fourth passages and second one-way valve provide for flow of a precise fluid volume in said pump chamber to said output port in response to the diaphragm pump changing from said first state to said second state, and no flow from said pump chamber to said outlet port in response to the diaphragm pump changing from the second state to the first state.

2. The reagent pump assembly of claim 1 wherein said bottom layer top surface further comprises a plurality of receptacles wherein the plurality of first one-way check valves are inserted in said plurality of receptacles.

3. The reagent pump assembly of claim 1 wherein said middle layer bottom surface further comprises a plurality of receptacles wherein the plurality of second one-way valves are inserted in said plurality of receptacles.

4. The reagent pump assembly of claim 1 wherein the top, middle, and bottom layers are fused together so that the opposing top and bottom surfaces are molecularly bonded together.

5. The reagent pump assembly of claim 1 wherein the top, middle, and bottom layers are bolted together.

6. A unified flow circuit assembly for use in an analytical instrument comprising:
   a reagent pump assembly in which precise amounts of reagents are to be mixed with precise sample volumes for analysis of a sample, comprising:
   a top layer having a top surface and a bottom surface;
   a middle layer having a top surface and a bottom surface;
   a bottom layer having a top surface and a bottom surface,
   a plurality of diaphragm pumps formed at a plurality of locations in an interface between the middle layer bottom surface and the bottom layer top surface, each diaphragm pump having a valve chamber and a pump chamber demarcated by a flexible membrane, each diaphragm valve having a first state corresponding to a filled pump containing a predetermined precision volume and a second state corresponding to an empty pump containing substantially no volume;
   a plurality of pressure control lines in said bottom layer, each pressure control line extending through said bottom layer to control the state of the diaphragm pump between said first and second states;
   a plurality of fluid input lines connecting said plurality of pump chambers to a like plurality of fluid supplies, wherein each fluid input line further comprises a first passage through said top layer, a second passage through said middle layer, and a first one-way valve interposed between said first and second passages, wherein the first and second passages and first one-way valve provide for flow of one of said fluid supplies into said pump chamber in response to the diaphragm pump changing from said second state to said first state, and no flow from said pump chamber to said fluid supply in response to the diaphragm pump changing from the first state to the second state, each diaphragm pump having an input line; and
   a plurality of fluid output lines connecting said plurality of pump chambers to a like plurality of output ports, wherein, for a given diaphragm pump, each fluid outlet line further comprises a third passage extending through said top layer, a fourth passage extending from the top of the middle layer and connecting to said second passage between said first one-way valve and said pump chamber and a second one-way valve interposed between said third and fourth passages, wherein the third and fourth passages and second one-way valve provide for flow of a precise fluid volume in said pump chamber to said output port in response to the diaphragm pump changing from said first state to said second state, and no flow from said pump chamber to said outlet port in response to the diaphragm pump changing from the second state to the first state; and a unified flow circuit comprising a second plurality of acrylic plates secured together into the unified flow circuit, said second plurality of plates having therein:

a plurality of reaction chambers, each chamber having a predetermined size, at least one inlet, a first plurality of sample inlet passages corresponding to a first number of sample aliquots; and a second plurality of fluid inlet passages corresponding to a second number of fluids;

a third plurality of outlet passages;

a plurality of vent passages;

a network of diaphragm valves and pneumatic lines connecting said sample inlets, fluid inlets, reaction chamber inlets and outlets, vent passages, and outlet passages, each of said diaphragm valves having an open state and a closed state in response to an application of one of pressure and vacuum, wherein the network is operable to control the flow of selected ones of said sample aliquots and selected ones of said number of fluids through said unified flow circuit to form reaction mixtures in selected ones of said plurality of reaction chambers;

wherein the plurality of fluid output lines of said reagent pump assembly are respectively coupled to different ones of said second plurality of fluid inlet passages in the unified flow circuit.

7. The assembly of claim 6 further comprising:

a shear valve having a sample inlet, a plurality of sample outlets, each sample outlet providing an aliquot of an input sample;

wherein said plurality of fluid supplies further comprise a plurality of reagent fluids; and wherein the plurality of fluid output lines are respectively coupled to said plurality of sample outlets, whereby the plurality of diaphragm pumps operate to interpose a precise volume of reagent in a fluid flow adjacent an aliquot of said input sample.

* * * * *